US010253329B2

(12) United States Patent
Wang et al.

(10) Patent No.: US 10,253,329 B2
(45) Date of Patent: Apr. 9, 2019

(54) SOURCES OF APHID RESISTANCE IN SOYBEAN PLANTS

(71) Applicant: Board of Trustees of Michigan State University, East Lansing, MI (US)

(72) Inventors: Dechun Wang, Okemos, MI (US); Carmille Bales-Arcelo, East Lansing, MI (US); Zhongnan Zhang, Zionsville, IN (US); Cuihua Gu, East Lansing, MI (US); Christina D. DiFonzo, Williamston, MI (US); Guorong Zhang, East Lansing, MI (US); Zhenyu Yang, Jilin Province (CN); Menghan Liu, Okemos, MI (US); Clarice Mensah, Ankeny, IA (US)

(73) Assignee: Board of Trustees of Michigan State University, East Lansing, MI (US)

( * ) Notice: Subject to any disclaimer, the term of this patent is extended or adjusted under 35 U.S.C. 154(b) by 934 days.

(21) Appl. No.: 14/099,469

(22) Filed: Dec. 6, 2013

(65) Prior Publication Data

US 2014/0196167 A1    Jul. 10, 2014

Related U.S. Application Data

(60) Provisional application No. 61/734,068, filed on Jan. 4, 2013.

(51) Int. Cl.
*A01H 5/10*    (2018.01)
*C12N 15/82*   (2006.01)

(52) U.S. Cl.
CPC .......... *C12N 15/8286* (2013.01); *A01H 5/10* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,940,835 A | 7/1990 | Shah et al. |
| 4,940,838 A | 7/1990 | Schilperoort et al. |
| 4,945,050 A | 7/1990 | Sanford et al. |
| 4,965,188 A | 10/1990 | Mullis et al. |
| 5,015,580 A | 5/1991 | Christou et al. |
| 5,057,422 A | 10/1991 | Bol et al. |
| 5,173,410 A | 12/1992 | Ahlquist |
| 5,187,267 A | 2/1993 | Comai et al. |
| 5,352,605 A | 10/1994 | Fraley et al. |
| 5,380,831 A | 1/1995 | Adang et al. |
| 5,385,835 A | 1/1995 | Helentjaris et al. |
| 5,416,011 A | 5/1995 | Hinchee et al. |
| 5,451,513 A | 9/1995 | Maliga et al. |
| 5,476,524 A | 12/1995 | Leon et al. |
| 5,491,081 A | 2/1996 | Webb |
| 5,492,547 A | 2/1996 | Johnson |
| 5,500,360 A | 3/1996 | Ahlquist et al. |
| 5,501,967 A | 3/1996 | Offringa et al. |
| 5,536,901 A | 7/1996 | Greaves et al. |
| 5,545,817 A | 8/1996 | McBride et al. |
| 5,545,818 A | 8/1996 | McBride et al. |
| 5,567,862 A | 10/1996 | Adang et al. |
| 5,569,834 A | 10/1996 | Hinchee et al. |
| 5,574,210 A | 11/1996 | Saghai-Maroof et al. |
| 5,584,807 A | 12/1996 | McCabe |
| 5,596,131 A | 1/1997 | Horn et al. |
| 5,606,823 A | 3/1997 | Souza et al. |
| 5,612,191 A | 3/1997 | Briggs et al. |
| 5,763,241 A | 6/1998 | Fischhoff et al. |
| 5,824,877 A | 10/1998 | Hinchee et al. |

(Continued)

FOREIGN PATENT DOCUMENTS

| | | |
|---|---|---|
| EP | 0116718 A1 | 8/1984 |
| EP | 0301749 A2 | 2/1989 |

(Continued)

OTHER PUBLICATIONS

Jun et al., 2012, Theor. Appl. Genet. 124: 13-22, published online Sep. 13, 2011.*
Funke et al., 1993, Plant Molecular Biology 22: 437-446.*
"U.S. Appl. No. 13/567,884, Final Office Action dated Nov. 26, 2014", 13 pgs.
"U.S. Appl. No. 13/567,884, Non Final Office Action dated May 9, 2014", 13 pgs.
"U.S. Appl. No. 13/567,884, Preliminary Amendment filed Jan. 28, 2013", 14 pgs.
"U.S. Appl. No. 13/567,884, Response filed Sep. 9, 2014 to Non Final Office Action dated May 9, 2014", 26 pgs.
"U.S. Appl. No. 13/567,884, Supplemental Preliminary Amendment filed Sep. 6, 2013", 6 pgs.

(Continued)

*Primary Examiner* — Bratislav Stankovic
(74) *Attorney, Agent, or Firm* — Schwegman Lundberg & Woessner, P.A.

(57) ABSTRACT

The present invention relates to compositions and methods for identifying and using new germplasm providing aphid resistant in soybean plants, particularly for use in breeding soybean plant lines and cultivars representing specific set(s) of germplasm. In particular, aphid resistant soybean plants comprising new sources of germplasm and stacked germplasm/genes conferring enhanced aphid resistance are provided. These enhanced aphid resistant plants find use in breeding soybean plant lines (cultivars) including lines having superior aphid resistance. Further, the inventions relate to providing new aphid resistant germplasm identified by markers associated with plants having decreased damage from aphid feeding, as well as plants having enhanced tolerance to aphid infestation. Even further, the invention relates to compositions and methods for using genetic markers in breeding methods for producing plants and plant cultivars having increased resistance to aphid damage and increased tolerance to aphids, while retaining and acquiring desired agronomic traits.

2 Claims, 23 Drawing Sheets
Specification includes a Sequence Listing.

(56) References Cited

U.S. PATENT DOCUMENTS

| | | | |
|---|---|---|---|
| 5,846,795 | A | 12/1998 | Ahlquist et al. |
| 5,861,543 | A | 1/1999 | Lambert et al. |
| 5,866,785 | A | 2/1999 | Donson et al. |
| 5,965,794 | A | 10/1999 | Turpen |
| 5,977,438 | A | 11/1999 | Turpen et al. |
| 5,981,839 | A | 11/1999 | Knauf et al. |
| 5,981,840 | A | 11/1999 | Zhao et al. |
| 6,051,757 | A | 4/2000 | Barton et al. |
| 6,096,944 | A | 8/2000 | Vierling |
| 6,143,550 | A | 11/2000 | Lambert |
| 6,384,301 | B1 | 5/2002 | Martinell et al. |
| 6,538,175 | B1 | 3/2003 | Webb |
| 6,541,448 | B2 | 4/2003 | Isaac |
| 6,593,293 | B1 | 7/2003 | Baum et al. |
| 7,435,873 | B2 | 10/2008 | St Martin et al. |
| 7,781,648 | B2 | 8/2010 | Wang et al. |
| 7,994,389 | B2 | 8/2011 | Hill et al. |
| 8,227,662 | B2 | 7/2012 | Wang et al. |
| 8,237,022 | B2 | 8/2012 | Wang et al. |
| 9,133,475 | B2 | 9/2015 | Wang et al. |
| 2002/0103362 | A1 | 8/2002 | Isaac |
| 2002/0133852 | A1 | 9/2002 | Hauge et al. |
| 2002/0144310 | A1 | 10/2002 | Lightfoot et al. |
| 2002/0151709 | A1 | 10/2002 | Abad et al. |
| 2002/0157139 | A1 | 10/2002 | Martinell et al. |
| 2003/0005491 | A1 | 1/2003 | Hauge et al. |
| 2003/0177528 | A1 | 9/2003 | Abad et al. |
| 2003/0229919 | A1 | 12/2003 | Isaac et al. |
| 2003/0237111 | A1 | 12/2003 | Baum et al. |
| 2004/0091505 | A1 | 5/2004 | Abad et al. |
| 2005/0138685 | A1 | 6/2005 | Flannagan et al. |
| 2005/0261188 | A1 | 11/2005 | Abad et al. |
| 2005/0261483 | A1 | 11/2005 | Abad et al. |
| 2006/0005276 | A1 | 1/2006 | Falco et al. |
| 2006/0015964 | A1 | 1/2006 | Hill et al. |
| 2006/0041951 | A1 | 2/2006 | Sebastian et al. |
| 2006/0041954 | A1 | 2/2006 | Lu et al. |
| 2006/0059580 | A1 | 3/2006 | Han et al. |
| 2006/0095987 | A1 | 5/2006 | Niblett |
| 2009/0241214 | A1 | 9/2009 | Wang et al. |
| 2010/0024073 | A1 | 1/2010 | Wang et al. |
| 2014/0007304 | A1 | 1/2014 | Wang et al. |

FOREIGN PATENT DOCUMENTS

| | | | |
|---|---|---|---|
| EP | 0332581 | A2 | 8/1989 |
| WO | WO-84/02913 | A1 | 8/1984 |
| WO | WO-84/02919 | A1 | 8/1984 |
| WO | WO-84/02920 | A1 | 8/1984 |
| WO | WO-93/07278 | A1 | 4/1993 |
| WO | WO-93/19181 | A1 | 9/1993 |
| WO | WO-94/13822 | A2 | 6/1994 |
| WO | WO-95/14098 | A1 | 5/1995 |
| WO | WO-95/16783 | A1 | 6/1995 |
| WO | WO-96/30517 | A1 | 10/1996 |
| WO | WO-2006125065 | A2 | 11/2006 |

OTHER PUBLICATIONS

"Canadian Application Serial No. 2,608,717, Office Action dated Apr. 11, 2014", 2 pgs.
"Canadian Application Serial No. 2,608,717, Response filed Oct. 10, 2014 to Office Action dated Apr. 11, 2014", 15 pgs.
"Canadian Application Serial No. 2,836,403, Office Action dated May 29, 2014", 2 pgs.
"International Application Serial No. PCT/US06/19200, International Preliminary Report on Patentability dated Mar. 24, 2009", 4 pgs.
"International Application Serial No. PCT/US06/19200, International Search Report dated May 8, 2008", 2 pgs.
"International Application Serial No. PCT/US06/19200, Written Opinion dated May 8, 2008", 3 pgs.
Kim, Ki-Seung, et al., "Fine mapping the soybean aphid resistance gene Rag1 in soybean", Theor Appl Genet (2010) 120:1063-1071 DOI 10.1007/s00122-009-1234-8, (2010), 1063-1071.
Wang, Dagang, et al., "Fine mapping and analyses of RSC8 resistance candidate genes to soybean mosaic virus in soybean", Theor Appl Genet (2011) 122:555-565 DOI 10.1007/s00122-010-1469-4, (2011), 555-565.
"U.S. Appl. No. 13/567,884, 312 Amendment filed Jul. 7, 2015", 5 pgs.
"U.S. Appl. No. 13/567,884, Notice of Allowance dated Apr. 8, 2015", 8 pgs.
"U.S. Appl. No. 13/567,884, Response filed Feb. 26, 2015 to Final Office Action dated Nov. 26, 2014", 15 pgs.
"Canadian Application Serial No. 2,608,717, Office Action dated Jun. 1, 2015", 5 pgs.
"Canadian Application Serial No. 2,823,249, Voluntary Amendment filed Nov. 6, 2013", 231 pgs.
"Canadian Application Serial No. 2836,403, Response filed Aug. 18, 2014", 10 pgs.
Song, Qijian, et al., "Abundance of SSR Motifs and Development of Candidate Polymorphic SSR Markers (BARCSOYSSR_1.0) in Soybean", www.crops.org Crop Science, vol. 50, Sep.-Oct. 2010, (Oct. 1, 2010), 1950-1960.
Song, Qijian, et al., "Development and Evaluation of SoySNP50K, a High-Density Genotyping Array for Soybean", www.plosone.org Jan. 2013 | vol. 8 | Issue 1 | e54985, (Jan. 1, 2013), 12 pgs.
"Canadian Application Serial No. 2,608,717, Office Action dated Nov. 20, 2017", 5 pgs.
"Aphids discovered in Wisconsin", Plant Health Initiative, Soybean Aphids Research Update from the North Central Soybean Research Program (NCSRP) published online by the Plant Health Initiative, (2004), 1 pg.
"U.S. Appl. No. 11/436,262, 312 Amendment filed May 25, 2010", 16 pgs.
"U.S. Appl. No. 11/436,262, Advisory Action dated May 13, 2009", 3 pgs.
"U.S. Appl. No. 11/436,262, Amendment and Response filed Mar. 19, 2009 to Final Office Action dated Jan. 26, 2009", 6 pgs.
"U.S. Appl. No. 11/436,262, Amendment and Response filed Oct. 28, 2008 to Non Final Office Action dated May 28, 2008", 28 pgs.
"U.S. Appl. No. 11/436,262, Final Office Action dated Jan. 26, 2009", 10 pgs.
"U.S. Appl. No. 11/436,262, Non Final Office Action dated May 28, 2008", 14 pgs.
"U.S. Appl. No. 11/436,262, Non Final Office Action dated Jun. 22, 2009", 11 pgs.
"U.S. Appl. No. 11/436,262, Notice of Allowance dated Mar. 22, 2010", 7 pgs.
"U.S. Appl. No. 11/436,262, Preliminary Amendment filed Aug. 9, 2006", 3 pgs.
"U.S. Appl. No. 11/436,262, Response filed Mar. 13, 2008 to Restriction Requirement dated Jan. 23, 2008", 14 pgs.
"U.S. Appl. No. 11/436,262, Response filed May 26, 2009 to Advisory Action dated May 13, 2009", 2 pgs.
"U.S. Appl. No. 11/436,262, Response filed Oct. 22, 2009 to Non Final Office Action dated Jun. 22, 2009", 15 pgs.
"U.S. Appl. No. 11/436,262, Restriction Requirement dated Jan. 23, 2008", 5 pgs.
"U.S. Appl. No. 12/261,951, Non Final Office Action dated Jul. 15, 2011", 12 pgs.
"U.S. Appl. No. 12/261,951, Notice of Allowance dated Mar. 23, 2012", 8 pgs.
"U.S. Appl. No. 12/261,951, Notice of Allowance dated May 4, 2012", 4 pgs.
"U.S. Appl. No. 12/261,951, Response filed Jan. 17, 2012 to Non Final Office Action dated Jul. 15, 2011", 41 pgs.
"U.S. Appl. No. 12/261,951, Response filed May 11, 2011 to Restriction Requirement dated Mar. 17, 2011", 7 pgs.
"U.S. Appl. No. 12/261,951, Restriction Requirement dated Mar. 17, 2011", 7 pgs.
"U.S. Appl. No. 12/324,331, 312 Amendment filed Jun. 6, 2012", 3 pgs.

(56) References Cited

OTHER PUBLICATIONS

"U.S. Appl. No. 12/324,331, Amendment and Response filed Aug. 2, 2011 to Final Office Action dated Jun. 2, 2011", 6 pgs.
"U.S. Appl. No. 12/324,331, Final Office Action dated Jun. 2, 2011", 9 pgs.
"U.S. Appl. No. 12/324,331, Non Final Office Action dated Aug. 16, 2010", 13 pgs.
"U.S. Appl. No. 12/324,331, Non Final Office Action dated Aug. 19, 2011", 7 pgs.
"U.S. Appl. No. 12/324,331, Notice of Allowance dated Mar. 28, 2012", 7 pgs.
"U.S. Appl. No. 12/324,331, Preliminary Amendment filed Nov. 26, 2008", 15 pgs.
"U.S. Appl. No. 12/324,331, Response filed Jan. 31, 2012 to Non Final Office Action dated Aug. 19, 2011", 4 pgs.
"U.S. Appl. No. 12/324,331, Response filed Mar. 22, 2011 to Non Final Office Action dated Aug. 16, 2010", 18 pgs.
"U.S. Appl. No. 12/324,331, Response to 312 Amendment dated Jun. 14, 2012", 2 pgs.
"Canadian Application Serial No. 2,608,717, Office Action dated Mar. 8, 2010", 3 pgs.
"Canadian Application Serial No. 2,608,717, Office Action dated Feb. 13, 2012", 5 pgs.
"Canadian Application Serial No. 2,608,717, Office Action dated Apr. 4, 2013", 6 pgs.
"Canadian Application Serial No. 2,608,717, Response filed Sep. 8, 2010 to Office Action dated Mar. 8, 2010", 30 pgs.
"Canadian Application Serial No. 2,608,717, Response filed Oct. 4, 2013 to Office Action dated Apr. 4, 2013", 13 pgs.
"Soybean Accession No. PI 567543 C—Glycine max", USDA, ARS, National Genetic Resources Program. Germplasm Resources Information Network—(GRIN). [Online Database]. National Germplasm Resources Laboratory, Beltsville, MD. [retrieved on Sep. 19, 2013]. Retrieved from the Internet: <URL: http://www.ars-grin.gov/cgi-bin/npgs/acc/di,(2013), 2 pgs.
"Soybean Accession No. PI 567541 B—Glycine max", USDA, ARS, National Genetic Resources Program. Germplasm Resources Information Network—(GRIN). [Online Database]. National Germplasm Resources Laboratory, Beltsville, MD. [retrieved on Sep. 19, 2013]. Retrieved from the Internet: <URL: http://www.ars-grin.gov/cgi-bin/npgs/acc/display, (2013), 2 pgs.
"Soybean Accession No. PI 567597 C—Glycine max", USDA, ARS, National Genetic Resources Program. Germplasm Resources Information Network—(GRIN). [Online Database]. National Germplasm Resources Laboratory, Beltsville, MD. [retrieved on Sep. 19, 2013]. Retrieved from the Internet: <URL: http://www.ars-grin.gov/cgi-bin/npgs/acc/display, (2013), 2 pgs.
"Soybean Accession No. PI 567598 B—Glycine max", USDA, ARS, National Genetic Resources Program. Germplasm Resources Information Network—(GRIN). [Online Database]. National Germplasm Resources Laboratory, Beltsville, MD. [retrieved on Sep. 19, 2013]. Retrieved from the Internet: <URLhttp://www.ars-grin.gov/cgi-bin/npgs/acc/disp, (2013), 2 pgs.
"USDA, ARS, National Genetic Resources Program. Germplasm Resources Information Network—(GRIN). [Online Database]. National Germplasm Resources Laboratory, Beltsville, Maryland.", (Reference: Mian, M.A.R., Ronald B. Hannnond, and Steven K. St. Martin, 2008. New Plant Introductions with Resistance to the Soybean Aphid. Crop Sci. 48:, (May 28, 2009), 3 pgs.
Ballas, N., et al., "Efficient functioning of plant promoters and poly(A) sites in Xenopus oocytes.", Nucleic Acids Res., 17, (1989), 7891-7903.
Baute, T., "Soybean Aphid Factsheet and Soybean Webpage sponsored by the Ontario Ministry of Agriculture, Food and Rural Affairs (OMAFRA)", (2004), 12 pgs.
Beachy, R. N., et al., "Accumulation and assembly of soybean Beta-conglycinin in seeds of transformed petunia plants", The EMBO Journal, 4(12), (1985), 3047-3053.

Bevan, M., et al., "A chimaeric antibiotic resistance gene as a selectable marker for plant cell transformation", Nature, 304, (1983), 184-187.
Blochlinger, K., et al., "Hygromycin B Phosphotransferase as a Selectable Marker for DNA Transfer Experiments with Higher Eucaryotic Cells", Mol. Cell. Biol., 4(12), (1984), 2929-2931.
Bourouis, M., et al., "Vectors containing a prokaryotic dihydrofolate reductase gene transform Drosophila cells to methotrexate-resistance", The EMBO Journal, 2(7), (1983), 1099-1104.
Casas, A. M., et al., "Transgenic sorghum plants via microprojectile bombardment", Proc. Natl. Acad. Sci. USA. 90(23), (Dec. 1, 1993), 11212-11216.
Chao, W. S., et al. "Leucine Aminopeptidase RNAs, Proteins, and Activities Increase in Response to Water Deficit, Salinity, and the Wound Signals Systemin, Methyl Jasmonate, and Abscisic Acid.", Plant Physiol , 120, (1999), 979-992.
Christou, P., et al., "Production of Transgenic Rice (Oryza sativa L.) Plants from Agronomically Important Indica and Japonica Varieties via Electric Discharge Particle Acceleration of Exogenous DNA into Immature Zygotic Embryos", Bio/technology, 9, (Oct. 1991), 957-962.
Christou, P., et al., "Stable Transformation of Soybean Callus by DNA-Coated Gold Particles", Plant Physiol., 87(3), (Jul. 1988), 671-674.
Concibido, V. C., et al., "Genome Mapping of Soybean Cyst Nematode Resistance Genes in 'Peking', PI 90763, and PI 88788 Using DNA Markers", Crop Science, 37(1), (1997), 258-264.
Cornelious, B., et al., "Identification of QTLs underlying water-logging tolerance in soybean", Mol. Breed., 16, (2005), 103-112.
Cregan, P. B., "An Integrated Genetic Linkage Map of the Soybean Genome", Crop Science, 39, (1999), 1464-1490.
Crossway, A., et al., "Integration of Foreign DNA Following Microinjection of Tobacco Mesophyll Protoplasts", Mol. Gen. Genet., 202, (1986), 179-185.
Crossway, A., et al., "Micromanipulation Techniques in Plant Biotechnology.", BioTechniques, 4(4), (1986), 320-334.
Datta, S. K., et al., "Genetically Engineered Fertile Indica-Rice Recovered from Protoplasts", Bio/Technology, 8, (Aug. 1990), 736-740.
Davis, F. M., et al., "Entomological techniques and methodologies used in research programmes on plant resistance to insects.", Insect Sci. Appl., 6(3) (now International Journal of Tropical Insect Science), (1985), 391-400.
De Block, M., et al., "Expression of Foreign Genes in Regenerated Plants and Their Progeny", The EMBO Journal, 3(8), (1984), 1681-1689.
DiFonzo, C., et al., "Soybean aphid in Michigan: Update from 2001 season.", Michigan State University Extension Bulletin E-2746. Michigan State University East Lansing, MI., (2002), 4 pgs.
Fraley, R. T., et al., "Expression of bacterial genes in plant cells", Proc. Natl. Acad. Sci, USA, 80(15), (1983), 4803-4807.
Fraley, R. T., et al.. "Liposome-mediated delivery of tobacco mosaic virus RNA into tobacco protoplasts: A sensitive assay for monitoring lipolipo-some-protoplast interactions", Proc. Natl. Acad. Sci., USA. 79, (1982), 1859-1863.
Frisch, M., et al., "Comparison of Selection Strategies for Marker-Assisted Backcrossing of a Gene.", Crop Science, 39, (1999), 1295-1301.
Fromm, M. E., et al., "Expression of genes transferred into monocot and dicot plant cells by electroporation", Proc. Nat. Acad. Sci. USA, 82, (1985), 5824-5328.
Fromm, M. E., et al., "Inheritance and Expression of Chimeric Genes in the Progeny of Transgenic Maize Plants", Nature Biotechnology, 8, (1990), 833-839.
Garbarino, J. E., et al., "Isolation of a ubiquitin-ribosomal protein gene (ubi3) from potato and expression of its promoter in transgenic plants.", Plant Mol. Biol., 24(1), (1994), 119-127.
Glogoza, P., "Soybean Aphid, Aphis glycines, Management in North Dakota", North Dakota State University Extension Bulletin E-1232, (2002), 4 pgs.
Gordon-Kamm, W. J., et al., "Transformation of Maize Cells and Regeneration of Fertile Transgenic Plants", The Plant Cell, 2, (Jul. 1990), 603-618.

(56) References Cited

OTHER PUBLICATIONS

Graham, F. L., et al., "A New Technique for the Assay of Infectivity of Human Adenovirus 5 DNA", *Virology*, 52, (1973), 456-467.
Guerineau, F., et al., "Effect of deletions in the cauliflower mosaic virus polyadenylation sequence on the choice of the polyadenylation sites in tobacco protoplasts.", *Mol. Gen. Genet.*, 262(1-2), (1991), 141-144.
Hayashimoto, A., et al., "A Polyethylene Glycol-Mediated Protoplast Transformation System for Production of Fertile Transgenic Rice Plants.", *Plant Physiol.*, 93(3), (1990), 857-863.
Herman, J C, et al., "How a Soybean Plant Develops", Special Report No. 53. Cooperative Extension Service, Iowa State University of Science and Technology, Ames, Iowa, (1989), 1-20.
Herrera-Estrella, L., et al., "Expression of Chimaeric Genes Transferred Into Plant Cells Using a Ti-plasmid-derived Vector", *Nature*, 303, (1983), 209-213.
Hill, C. B., et al., "A single dominant gene for resistance to the soybean aphid in the soybean cultivar Dowling", *Crop Science*, 46, (2006), 1601-1605.
Hill, C. B., et al., "Resistance of *Glycine* Species and Various Cultivated Legumes to the Soybean aphid (Homoptera: Aphididae)", *J. of Econ. Entomol.*, 97, (2004), 1071-1077.
Hill, C. B., et al., "Resistance to the Soybean Aphid in Soybean Germplasm", *Crop Science*, 44, (2004), 98-106.
Hill, M., et al., "Biolistic introduction of a synthetic Bt gene into elite maize,", *Euphytica*, 85(1-3), (1995), 119-123.
Hinchee, M. A., et al., "Production of Transgenic Soybean Plants Using Agrobacterium-Mediated DNA Transfer", *Nature Biotechnology*, 6, (1988), 915-922.
Horsch, R. B., et al., "Inheritance of Functional Foreign Genes in Plants.", *Science*, 223, (1984), 496-498.
Ishida, Y., et al., "High efficiency transformation of maize (*Zea mays* L.) mediated by *Agrobacterium tumefaciens*", *Nature Biotechnology*, 14, (Jun. 1996), 745-750.
Jahne, A., et al., "Regeneration of Transgenic, Microspore-Derived, Fertile Barley", *Theor. Appl. Genet.*, 89, (1994), 525-533.
Joshi, C. P., "An inspection of the domain between putative TATA box and translation start site in 79 plant genes.", *Nucleic Acids Research*, 15(16), (1987), 6643-6653.
Joshi, C. P., et al., "Putative polyadenylation signals in nuclear genes of higher plants: a compilation and analysis", *Nucleic Acid Res.*, 15(23), (1987), 9627-9640.
Kalderon, D., et al., "A Short Amino Acid Sequence Able to Specify Nuclear Location", *Cell*, 39(3), (1984), 499-509.
Klein, T. M., et al., "Factors Influencing Gene Delivery into *Zea mays* Cells by High Velocity Microprojectiles", *Nature Biotechnology*, 6, (1988), 559-563.
Klein, T. M., et al., "Genetic Transformation of Maize Cells by Particle Bombardment", *Plant Physiology*, 91, (1989), 440-444.
Klein, T. M., et al., "Transfer of Foreign Genes into Intact Maize Cells with High-Velocity Microprojectiles", *Proc. Nat. Acad. Sci. USA*, 85, (1988), 4305-4309.
Knudsen, S., et al., "Transformation of the developing barley endosperm by particle bombardment.", *Planta*. 185, (1991), 330-336.
Kogan, M., et al., "Antixenosis—A New Term Proposed to Define Painter's "Nonpreference" Modality of Resistance.", *Bull. Entomol. Soc. Am*. 24, (1978), 175-176.
Koziel, M. G., et al., "Field Performance of Elite Transgenic Maize Plants Expressing as Insecticidal Protein Derived from *Bacillus thuringiensis*", *Nature Biotechnology*, 11, (1993), 194-200.
Krens, F. A., et al., "In vitro transformation of plant protoplasts with Ti-plasmid DNA.", *Nature*, 296, (1982), 72-74.
Lassner, M. W., et al., "Targeting of T7 RNA polymerase to tobacco nuclei mediated by an SV40 nuclear location signal", *Plant Molecular Biology*, 17(2), (1991), 229-234.
Li, Y., et al., "Effect of Three Resistant Soybean Genotypes on the Fecundity, Morality and Maturation of Soybean Aphid (Homoptera:Aphididae).", *J. Econ. Entomol.*, 97(3), (2004), 1106-1111.

Lin, C., et al., "Study on the control threshold of the soybean aphid in the field.", (w/ English Abstract), *Soybean Science*, 11(4), (1992), 318-321.
Luehrsen, K. R., et al., "Intron enhancement of gene expression and the splicing efficiency of introns in maize cells", *Mol. Gen. Genet.* 225(1), (1991), 81-93.
Maniatis, T., et al., "Regulation of Inducible and Tissue-Specific Gene Expression", *Science*, 236(4806), (1987), 1237-1245.
McCabe, D. E., et al., "Stable Transformation of Soybean (*Glycine max*) by Particle Acceleration", *Nature Biotechnology*, 6, (Aug. 1988), 923-926.
Mensah, C., et al., "Resistance to Soybean Aphid in Early Maturing Soybean Germplasm", *Crop Science*, 45, (2005), 2228-2233.
Messing, J., "A new pair of M13 vectors for selecting either DNA strand of double-digest restriction fragments", *Gene*,19(3), (1982), 269-276.
Mogen, B. D., et al., "Upstream sequences other than AAUAAA are required for efficient messenger RNA 3'-end formation in plants.", *The Plant Cell*, 2(12), (1990), 1261-1272.
Mueller, E., et al., "Evaluation of soybean germplasm for partial resistance to the soybean aphid", *The 2003 Entomological Society of America Annual Meeting and Exhibition*, Cincinnati, OH,, (Oct. 2003), 1 pg.
Munroe, D., et al., "Tales of poly( A): a review", *Gene*, 91(2), (1990), 151-158.
Narvel, J. M., et al., "A Retrospective DNA Marker Assessment of the Development of Insect Resistant Soybean", *Crop Science*, 41(6), (2001), 1931-1939.
Nehra, N. S., et al., "Self-fertile transgenic wheat plants regenerated from isolated scutellar tissues following microprojectile bombardment with two distinct gene constructs", *The Plant Journal*, 5(2), (1994), 285-297.
Odell, J., et al., "Identification of DNA Sequences Required for Activity of the Cauliflower Mosaic Virus 35S Promoter", *Nature*, 313, (1985), 810-812.
Ostlie, "Soybean Aphid", Pages published online by Just for Growers MN (University of Minnesota) Soybean Production, published online by the University of Minnesota, the University of Minnesota Extension Service, and the MN Soybean Research and Promotion Council, (Jul. 6, 2004), 5 pgs.
Painter, H., *Insect Resistance in Crop Plants*, Macmillan, New York, (1951), 3 pgs.
Paszkowski, J., et al., "Direct Gene Transfer to Plants", *The EMBO Journal*, 3(12), (1984), 2717-2722.
Proudfoot, N. J., "Poly(A) signals", *Cell*, 64, (1991), 671-674.
Ragsdale, D. W., et al., "Soybean Aphid Biology in North America.", *Ann. Entomol. Soc. Am.*, 97, (2004), 204-208.
Riggs, C. D., et al., "Stable transformation of tobacco by electroporation: evidence for plasmid concatenation", *Proc. Natl. Acad. Sci. USA*, 83(15), (1986), 5602-5606.
Rosenberg, A. H., et al., "Vectors for selective expression of cloned DNAs by T7 RNA Polymerase", *Gene*, 56(1), (1987), 125-135.
Sanfacon, H., et al., "A dissection of the cauliflower mosaic virus polyadenylation signal", *Genes Dev.*, 5, (1991), 141-149.
Sanford, J. C., et al., "Delivery of Substances into Cells and Tissues Using a Particle Bombardment Process", *Particulate Sci. Technol.*, 5, (1987), 27-37.
Saxena, R. C., et al., "Comparison Between Free-Choice and No-Choice Seedling Bulk Tests for Evaluating Resistance of Rice Cultivars to the Whitebacked Planthopper", *Crop Science*, 24(6), (1984), 1204-1206.
Shimamoto, K., et al., "Fertile transgenic rice plants regenerated from transformed protoplasts", *Nature*, 338, (1989), 274-276.
Smith, C. Michael, et al., *Plant Resistance to Insects: A Fundamental Approach*, Wiley, New York, NY, (1989), 2 pgs.
Smith, C. Michael, et al., *Techniques for Evaluating Insect Resistance in Crop Plants*, CRC Press, Inc., Boca Raton, FL, (1994), 4 pgs.
Somers, D. A., et al., "Fertile, Transgenic Oat Plants.", *Nature Biotechnology*, 10, (1992), 1589-1594.
Song, Q. J., et al., "A new integrated genetic linkage map of the soybean", *Theor. Appl. Genet.*, 109, (2004), 122-128.

(56) References Cited

OTHER PUBLICATIONS

Spencer, T. M., et al., "Bialaphos Selection of Stable Transformations from Maize Cell Culture", *Theor. Appl. Genet.*, 79, (May 1990), 625-631.

St. Schell, J., "Transgenic Plants as Tools to Study the Molecular Organization of Plant Genes.", *Science*, 237, (1987), 1176-1183.

Staub, J. M., et al., "Accumulation of D1 polypeptide in tobacco plastids is regulated via the untranslated region of the psbA mRNA.", *The EMBO Journal*,12(2), (1993), 601-606.

Staub, J. M., et al., "Long Regions of Homologous DNA are Incorporated into the Tobacco Plastid Genome by Transformation.", *The Plant Cell*, 4(1), (1992), 4-39.

Sun, Z., et al., "Study on the Utilization of Aphid Resistant Character in Wild Soybean. I. Aphid Resistant Performance of $F_2$ Generation From Crosses Between Cultivated and Wild Soybeans.", (w/ English Abstract), *Soybean Sci.* 10(2), (1919), 98-103.

Svab, Z., et al., "High-frequency plastid transformation in tobacco by selection for a chimeric aadA gene", *Proc. Nat!. Acad. Sci. USA*,. 90(3), (1993), 913-917.

Svab, Z., et al., "Stable transformation of plastids in higher plants", *Proc. Natl. Acad. Sci. USA*, 87, (1990), 8526-8530.

Tingey, W. M. "Techniques for Evaluating Plant Resistance to Insects", *In Insect-Plant Interactions*. Miller and Miller (Editors). Springer Series in Experimental Entomology 1986(Springer-Verlag,New York), (1986), 251-284.

Torbert, K. A., et al., "Use of paromomycin as a selective agent for oat transformation", *Plant Cell Reports*, 14, (1995), 635-640.

Umbeck, P., et al., "Genetically transformed cotton (*Gossypium hirsutum* L.) plants.", *Nature Biotechnology*, 5, (1987), 263-266.

Vasil, V., et al., "Rapid Production of Transgenic Wheat Plants by Direct Bombardment of Cultured immature Embryos", *Nature Biotechnology*, 11, (1993), 1553-1558.

Wan, Y., et al., "Generation of Large Numbers of Independently Transformed Fertile Barley Plants", *Plant Physiol.*, 104, (1994), 37-48.

Wang, D, et al., "A Low-Cost, High-Throughput Polyacrylamide Gel Electrophoresis System for Genotyping with Microsatellite DNA Markers.", *Crop Sci.*, 43, (2003), 1828-1832.

Wang, D., et al., "Resistance to Soybean Aphid in Early Maturing Soybean Germplasm", U.S. Appl. No. 60/682,583, filed May 18, 2005, 80 pgs.

Weeks, J. T., et al., "Rapid Production of Multiple Independent Lines of Fertile Transgenic Wheat (*Triticum aestivum*)", *Plant Physiol.*, 102, (1993), 1077-1084.

Weising, K., et al., "Foreign Genes in Plants: Transfer, Structure, Expression and Applications", *Ann. Rev. Genet.*, 22, (1988), 421-477.

Westman, A. L., et al., "The potential for cross-taxa simple-sequence repeat (SSR) amplication between *Arabidopsis thaliana* L. and crop brassicas",*Theor. Appl. Genet.*, 96, (1998), 272-281.

White, J., et al., "A cassette containing the bar gene of Streptomyces hygroscopicus: a selectable marker for plant transformation", *Nucleic Acids Research*, 18(4), (1990), 1062.

Wilcox, J. R., et al., "World Distribution and Trade of Soybean", In: *Soybeans: Improvement Production, and Uses*. Third Edition: Boerma and Specht (Eds ), Publisher American Society of Agronomy: Crop Science Society of America : Soil Science Society of America, Madison, Wisconsin, USA, 2004, Monograph Series 16; Rev.Ed., (2004), 1-14.

Wu, Xiaobing, et al., "Occurrence and Control of Soybean Aphid, Aphis glycines Matsumura", How Peasants Can Increase Wealth[Nongmin zhifu zhiyou], (6):20, (1999), 2 pgs.

Yi-Heng, Fan, "Screening for Soybean Varieties Resistant to Soybean Aphid", *Soybean Science*. 7(2):, (1988), 167-169.

Zhu, Y. L., et al., "Single-Nucleotide Polymorphisms in Soybean", Genetics Mar: 163(3), (2003), 1123-1134.

Zhuang, Binchang, "Biological studies of Chinese wild soybean", 1st ed., Science Publisher, Beijing, China, (1999), 6 pgs.

\* cited by examiner

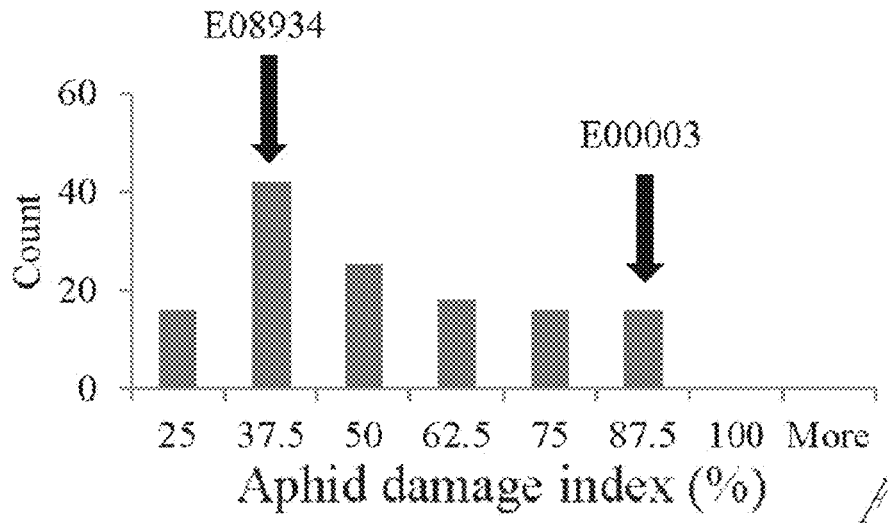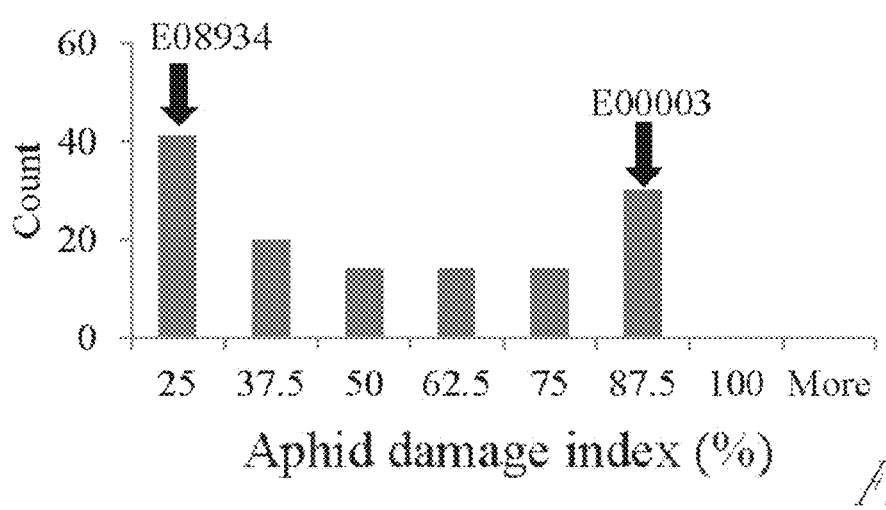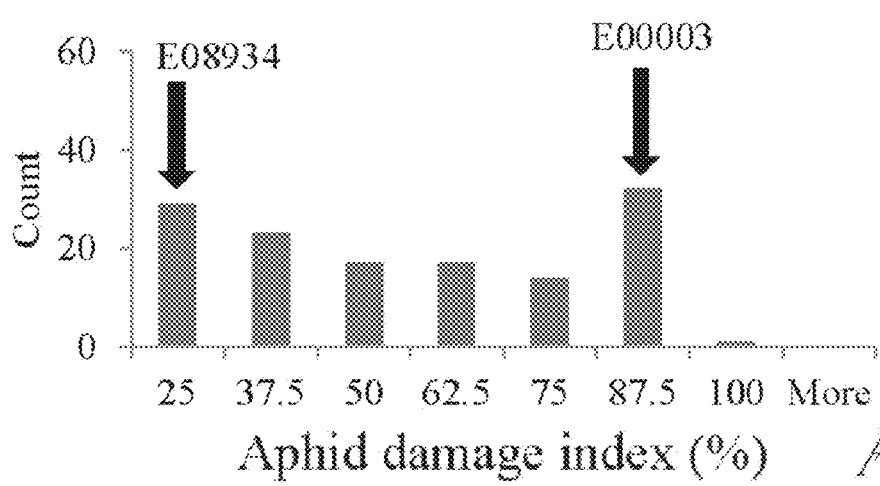

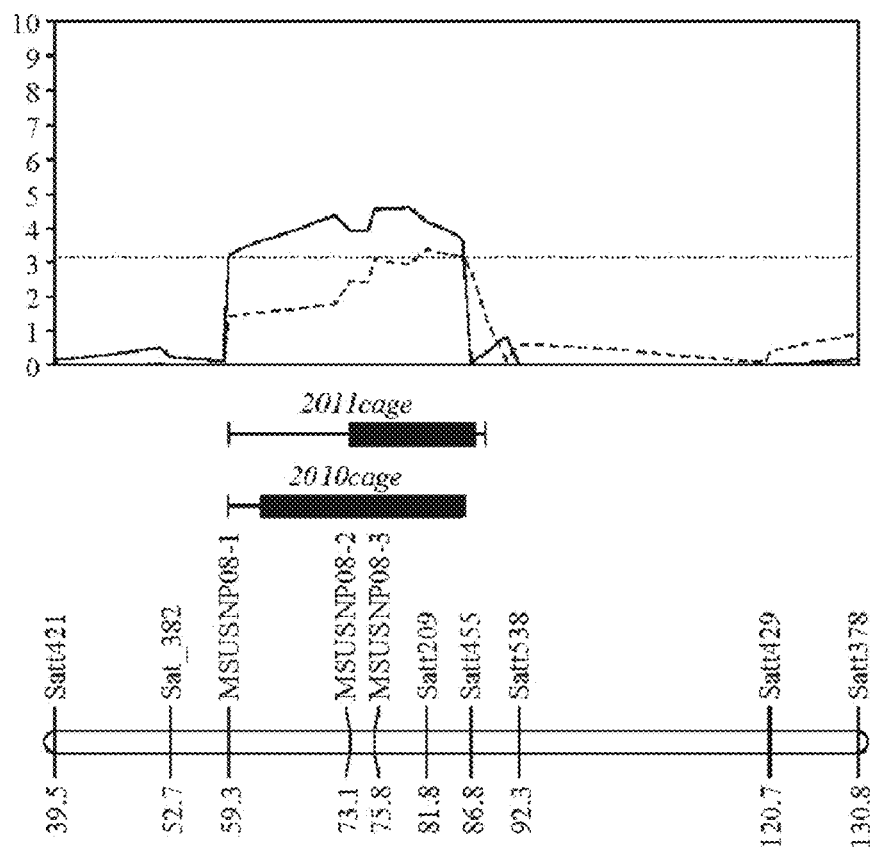

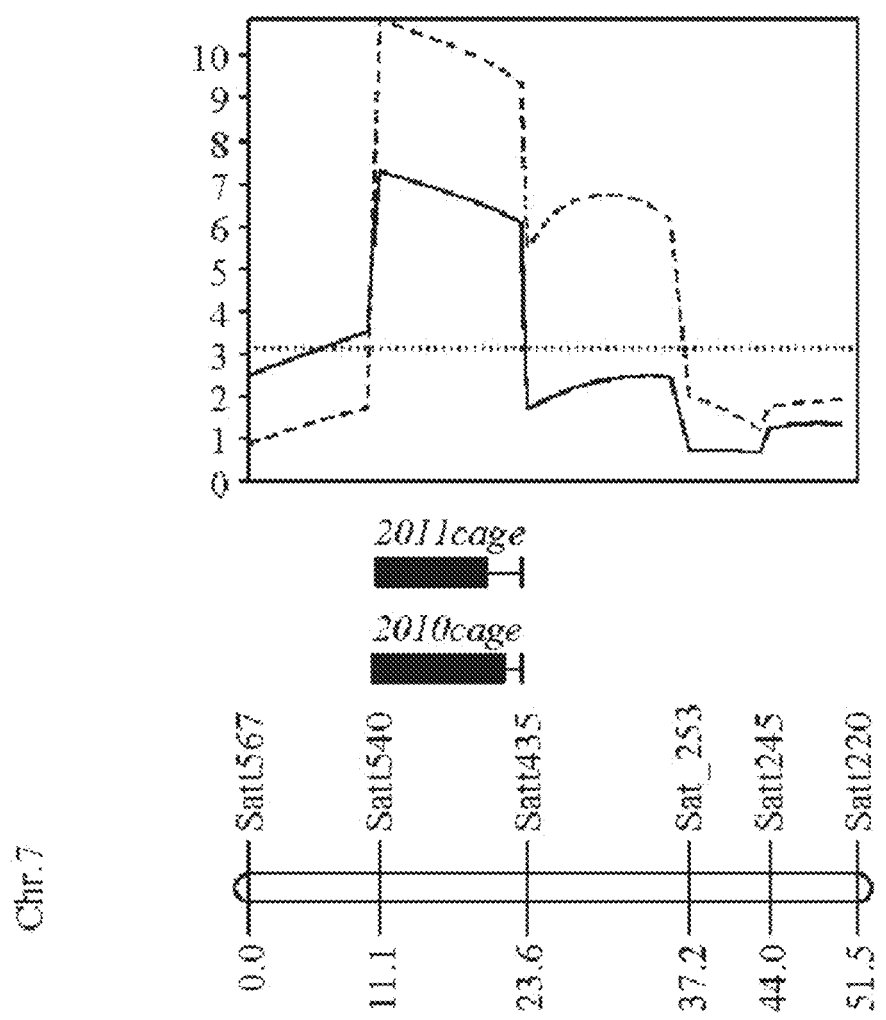

SEQUENCE LISTING

```
<160> NUMBER OF SEQ ID NOS: 16

<210> SEQ ID NO 1
<211> LENGTH: 26
<212> TYPE: DNA
<213> ORGANISM: Artificial Sequence
<220> FEATURE:
<223> OTHER INFORMATION: A synthetic primer

<400> SEQUENCE: 1
cggattgtgt cctttgttgt tattat                                    26

<210> SEQ ID NO 2
<211> LENGTH: 21
<212> TYPE: DNA
<213> ORGANISM: Artificial Sequence
<220> FEATURE:
<223> OTHER INFORMATION: A synthetic primer

<400> SEQUENCE: 2
acctcgcaca caatttgagt c                                         21
```

```
<210> SEQ ID NO 3
<211> LENGTH: 24
<212> TYPE: DNA
<213> ORGANISM: Artificial Sequence
<220> FEATURE:
<223> OTHER INFORMATION: A synthetic primer

<400> SEQUENCE: 3
gcgaaaggtc gagaaaatga aatg                                            24

<210> SEQ ID NO 4
<211> LENGTH: 23
<212> TYPE: DNA
<213> ORGANISM: Artificial Sequence
<220> FEATURE:
<223> OTHER INFORMATION: A synthetic primer

<400> SEQUENCE: 4
gcgtttgcct tgttggtgac ttg                                             23

<210> SEQ ID NO 5
<211> LENGTH: 25
<212> TYPE: DNA
<213> ORGANISM: Artificial Sequence
<220> FEATURE:
<223> OTHER INFORMATION: A synthetic primer

<400> SEQUENCE: 5
ttgtcaaatt tctgaagact tatcg                                           25

<210> SEQ ID NO 6
<211> LENGTH: 25
<212> TYPE: DNA
<213> ORGANISM: Artificial Sequence
<220> FEATURE:
<223> OTHER INFORMATION: A synthetic primer

<400> SEQUENCE: 6
tgttggagaa tattgttagc actca                                           25

<210> SEQ ID NO 7
<211> LENGTH: 121
<212> TYPE: DNA
<213> ORGANISM: Artificial Sequence
<220> FEATURE:
<223> OTHER INFORMATION: A synthetic oligonucleotide
<221> NAME/KEY: misc_feature
<222> LOCATION: 61
<223> OTHER INFORMATION: n = T or G

<400> SEQUENCE: 7
attgtaacta cattctgcaa tgcaacaatg atactatgca agtataaata tagatcaatt     60
nactgccaca gttttcctga gctgcaagta taaatagcaa aagaacagga aacaatctca    120
a                                                                    121

<210> SEQ ID NO 8
<211> LENGTH: 121
<212> TYPE: DNA
<213> ORGANISM: Artificial Sequence
<220> FEATURE:
<223> OTHER INFORMATION: A synthetic oligonucleotide
<221> NAME/KEY: misc_feature
<222> LOCATION: 61
<223> OTHER INFORMATION: n = A or G

<400> SEQUENCE: 8
```
gttgacttgt ccttgattgt gtttgccagt ctctacctca tttcctgtgt gtgtgcaccc    60
ncgcatactt gtgtgtgaac ttgcatgaat gtgtttatat acttctgtct tgacataccg   120
g                                                                   121

<210> SEQ ID NO 9
<211> LENGTH: 121
<212> TYPE: DNA
<213> ORGANISM: Artificial Sequence
<220> FEATURE:
<223> OTHER INFORMATION: A synthetic oligonucleotide
<221> NAME/KEY: misc_feature
<222> LOCATION: 61
<223> OTHER INFORMATION: n = A or C

<400> SEQUENCE: 9
cacagtccat aaatataaca tggcagcatc cagaatccaa ctacacataa aactcagtcc    60
nttccaaaaa agcactcggc tcgttgaacc cattacaaaa caaaatcgaa acatactaat   120
a                                                                   121

<210> SEQ ID NO 10
<211> LENGTH: 121
<212> TYPE: DNA
<213> ORGANISM: Artificial Sequence
<220> FEATURE:
<223> OTHER INFORMATION: A synthetic oligonucleotide
<221> NAME/KEY: misc_feature
<222> LOCATION: 61
<223> OTHER INFORMATION: n = T or C

<400> SEQUENCE: 10
tttttctttt ttttttgag tttttacaca ttcattcttc tactcacgta cagttcaatc    60
ncatccaatt tttttactca cagatcccaa atcgtcacct tcttcttta tttattttca   120 t                                                                   121

<210> SEQ ID NO 11
<211> LENGTH: 13
<212> TYPE: DNA
<213> ORGANISM: Artificial Sequence
<220> FEATURE:
<223> OTHER INFORMATION: A synthetic oligonucleotide

<400> SEQUENCE: 11
agaatgaggt tta                                                       13

<210> SEQ ID NO 12
<211> LENGTH: 207
<212> TYPE: DNA
<213> ORGANISM: Artificial Sequence
<220> FEATURE:
<223> OTHER INFORMATION: A synthetic oligonucleotide
<221> NAME/KEY: misc_feature
<222> LOCATION: 118
<223> OTHER INFORMATION: n =T or C
<221> NAME/KEY: misc_feature
<222> LOCATION: 144
<223> OTHER INFORMATION: n =A, T, G or C

<400> SEQUENCE: 12
gatttcattg ggccttggtt gggctatgtc caaaatagta tccccattag ttagtatccc    60
atgatgtcat gaggtgtaaa cttgttaaga catatcaaac ttagggttta agttaacnag   120
atccgaaaaa gctgccacta tagngccttc tctttgagta tgtggtaatt attgattgaa   180
ggcttgattg aaggatcatc ctcatag                                       207

<210> SEQ ID NO 13
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 13
gaggtgtaaa cttgttaaga c                                               21

<210> SEQ ID NO 14
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 14
atcaataatt accacatact caa                                             23

<210> SEQ ID NO 15
<211> LENGTH: 12
<212> TYPE: DNA
<213> ORGANISM: Artificial Sequence
<220> FEATURE:
<223> OTHER INFORMATION: A synthetic oligonucleotide

<400> SEQUENCE: 15
atctagttaa ct                                                         12

<210> SEQ ID NO 16
<211> LENGTH: 200
<212> TYPE: DNA
<213> ORGANISM: Artificial Sequence
<220> FEATURE:
<223> OTHER INFORMATION: A synthetic oligonucleotide

<400> SEQUENCE: 16
gttgggctat gtccaaaata gtatccccat tagttagtat cccatgatgt catgaggtgt      60
aaacttgtta agacatatca aacttagggt ttaagttaac cagatccgaa aaagctgcca     120
ctatagtgcc ttctctttga gtatgtggta attattgatt gaaggcttga ttgaaggatc     180
atcctcatag cttaggtttt                                                200

SOURCES OF APHID RESISTANCE IN SOYBEAN PLANTS

RELATED APPLICATION

This patent application claims the benefit of priority, under 35 U.S.C. § 119(e), to U.S. Provisional Patent Application Ser. No. 61/734,068, filed on Jan. 4, 2013, the contents of which application is specifically incorporated by reference herein in its entirety.

FIELD OF THE INVENTION

The present invention relates to compositions and methods for identifying and using new germplasm providing aphid resistant in soybean plants, particularly for use in breeding soybean plant lines and cultivars representing specific set(s) of germplasm. In particular, aphid resistant soybean plants comprising new sources of germplasm and stacked germplasm/genes conferring enhanced aphid resistance are provided. These enhanced aphid resistant plants find use in breeding soybean plant lines (cultivars) including lines having superior aphid resistance. Such enhanced plant cultivars are contemplated to find use for more effective resistance of aphids. Further, the inventions relate to providing new aphid resistant germplasm identified by markers associated with plants having decreased damage from aphid feeding, as well as plants having enhanced tolerance to aphid infestation. Even further, the invention relates to compositions and methods for using genetic markers in breeding methods for producing plants and plant cultivars having increased resistance to aphid damage and increased tolerance to aphids, while retaining and acquiring desired agronomic traits. In some embodiments, at least one region of aphid resistant germplasm from one aphid resistant plant line source may be combined with another region of aphid resistant germplasm from a different plant line source for providing a soybean plant cultivar having enhanced aphid resistance.

BACKGROUND OF THE INVENTION

Soybean is the leading oilseed crop produced and consumed worldwide (Wilcox World distribution and trade of soybean, 2004, Soybeans: Improvement, production, and Uses, 3rd ed., Agron. Monogr. 16, ASA, CSSA, and SSSA, Madison, Wis. p: 1-14; Hymowitz, 2004, Speciation and Cytogenetics, p. 97-136. In H. R. Boerma and J. E. Specht (ed) Soybeans: Improvement, production, and Uses, 3rd ed. Agron. Monogr. 16. ASA, CSSA, and SSSA, herein incorporated by reference in its entirety). In the past half century, the USA was the world's leading producer. In 2003, the USA produced 35% (65.8 million metric tons (MT)) of the world's total soybean (FAOSTAT, 2004, Production Crops). However, soybean plants have many insect pests, including the soybean aphid, limiting its production in other parts of the world around 2000 A.D., the soybean aphid (*Aphis glycines* Matsumura) a native to eastern Asia, became a major sucking pest of soybean [*Glycine max* (L.) Merr.] in North America. Since then, this insect pest has rapidly spread to the major soybean production areas in the USA and Canada (Plant Health Initiative, 2004, Soybean Aphids Research Update "Aphids discovered in Wisconsin" from the North Central Soybean Research Program (NCSRP) published online by the Plant Health Initiative Available at planthealth.info/soyaphid.htm (verified Oct. 5, 2004), herein incorporated by reference. Aphid outbreaks were severe in the northern part of the Midwestern USA and in Ontario, for example in years 2001 and 2003.

Several factors affect soybean aphid outbreaks, including environmental conditions, over-wintering success, cultural practices, natural enemies, and the synchronization of soybean and aphid development (Wu et al., 1999, How Peasants Can Increase Wealth [Nongmin zhifu zhiyou] 6:20, herein incorporated by reference). The soybean aphid develops large colonies on soybean plants. Plant damage occurs when large numbers of aphids remove significant amounts of water and nutrients as they feed (suck) on leaves and stems, causing leaves to wilt, curl, yellow, and even drop off. Other symptoms of direct feeding damage include plant stunting, poor pod fill, reduced pod and seed counts, smaller seed size, and nutrient deficiencies resulting in overall yield and quality reduction (DiFonzo and Hines, 2002, Michigan State University Extension Bulletin E-2746, herein incorporated by reference). Significant yield loss (8-25%) occurred when the aphid heavily infests the soybean plants during the early reproductive stage (DiFonzo and Hines, 2002, Michigan State University Extension Bulletin E-2746, herein incorporated by reference). Honeydew, a sticky substance excreted by soybean aphids onto the leaves, leads to the development of sooty mold, which affects photosynthesis and results in yield loss (Baute, 2004, (Soybean Aphid Factsheet and Soybean Webpage sponsored by the Ontario Ministry of Agriculture, Food and Rural Affairs (OMAFRA), published online). During the feeding process, soybean aphids are capable of transmitting viruses into host plants including alfalfa mosaic virus, soybean mosaic virus, and bean yellow mosaic virus. These viruses commonly occur together and form a disease complex that leads to plant stunting, leaf distortion, leaf and stem mottling, reduced pod numbers, and seed discoloration (Glogoza, 2002, North Dakota State University Extension Bulletin E-1232, herein incorporated by reference). Soybean aphids also feed on other crop plants such as beans and pumpkins while spreading viral diseases such as cucumber mosaic virus, zucchini yellow and watermelon mosaic between vegetable crops.

Aphids are particularly difficult to control because of their rapid reproduction rates and ability to disperse over wide areas. Populations build rapidly, for example, females give live birth to already pregnant young aphids that mature in 3-7 days, with a doubling time of 2-5 days under favorable conditions. Winged forms appear and disperse to other fields under high insect densities and when infested plants are stressed. Since aphids are relatively weak fliers, long-distance dispersal is often at the mercy of prevailing winds.

Aerial applicators of insecticides frequently report having to stop to clean their windshields from flying into clouds of these aphids above heavily infested fields. In 2001, the influx of winged soybean aphids into the open dome of the Toronto Blue Jays even caused an early end to a Toronto Blue Jays game. It's these flights that lead to rapid, progressive colonization of soybean fields, almost like a wave moving across the countryside. Under favorable conditions for aphid infestations, the settling of winged aphids into uninfested fields has been described as "aphid rain." (Ostlie, Soybean Aphid Pages published online by Just for Growers, MN (University of Minnesota) Soybean Production, published online by the University of Minnesota, the University of Minnesota Extension Service, and the MN Soybean Research and Promotion Council Jul. 6, 2004, herein incorporated by reference).

Insecticides are the primary available method of controlling soybean aphids in the United States. Although the use of insecticides can be a quick and easy way to control aphids, the ideal time to spray is not well defined and the insecticides may not have long term action. When applications of insecticides are poorly timed or applied incorrectly then aphid populations may resurge and further may develop resistance to the insecticide. The use of insecticides also has many adverse effects such as killing beneficial insects, environmental contamination, and increased production costs (Sun et al., 1991, Soybean Sci. 10(2): 98-103, herein incorporated by reference).

Another way of attempting to control soybean aphid infestations is by importing and releasing a natural enemy of the soybean aphid, such as *Binodozys communis*, a tiny stingless wasp. However these wasps may not over winter in large enough numbers to provide significant control in colder climates, such as the northern United States and Canada. Additionally, when a large number of flying aphids infest fields they would overcome smaller numbers of predator wasps. Testing is underway to determine whether these alien wasps will also attack beneficial insects.

Therefore there is a need for developing aphid resistant soybean plants having a higher resistance to aphids as a long-term solution to the aphid infestation of commercially grown soybean plants.

SUMMARY OF THE INVENTION

The present invention relates to compositions and methods for identifying and using new germplasm providing aphid resistant in soybean plants, particularly for use in breeding soybean plant lines and cultivars representing specific set(s) of germplasm. In particular, aphid resistant soybean plants comprising new sources of germplasm and stacked germplasm/genes conferring enhanced aphid resistance are provided. These enhanced aphid resistant plants find use in breeding soybean plant lines (cultivars) including lines having superior aphid resistance. Such enhanced plant cultivars are contemplated to find use for more effective resistance of aphids. Further, the inventions relate to providing new aphid resistant germplasm identified by markers associated with plants having decreased damage from aphid feeding, as well as plants having enhanced tolerance to aphid infestation. Even further, the invention relates to compositions and methods for using genetic markers in breeding methods for producing plants and plant cultivars having increased resistance to aphid damage and increased tolerance to aphids, while retaining and acquiring desired agronomic traits. In some embodiments, at least one region of aphid resistant germplasm from one aphid resistant plant line source may be combined with another region of aphid resistant germplasm from a different plant line source for providing a soybean plant cultivar having enhanced aphid resistance.

In one embodiment, the invention provides a *Glycine max* soybean cultivar comprising aphid resistant germplasm derived from soybean plant line E08934, or the soybean plant line E12902 whose seed was deposited under ATCC accession No. PTA-120715. Both of the E08934 and E12902 plant lines have the Rag3c and Rag6 aphid resistant genes.

In one embodiment, the invention provides an aphid resistant germplasm, derived from soybean plant line E08934, or the soybean plant line E12902 whose seed was deposited under ATCC accession No:PTA-120715, wherein said germplasm comprises an aphid resistant Rag6 region on chromosome 8 located between a marker pair selected from the group consisting of MSUSNP08-1;MSUSNP08-4, Sat_382;Satt455, Sat_382;Satt538, MSUSNP08-2;Satt209, MSUSNP08-2; MSUSNP08-3, MSUSNP08-1 (23293155_T_G);Satt538, and MSUSNP08-1 (23293155_T_G);Satt455 (see FIG. 2).

In one embodiment, the invention provides an aphid resistant germplasm, derived from soybean plant line E08934, or the soybean plant line E12902 whose seed was deposited under ATCC accession No: PTA-120715, wherein said germplasm comprises a Rag3c aphid resistant region on chromosome 16. The Rag3c aphid resistant region is located between a marker pair selected from the group consisting of Satt693;Sat_456, Satt693;Sat_370, Sat_370;Sat_456, Satt693;Satt465, MSUSNP16_10;Sat_370, MSUSNP16_10;Satt465, MSUSNP16_11;MSUSNP16_12, BARCSOYSSR_16_0383;Satt456, and BARCSOYSSR_16_0383; Sat_370.

In one embodiment, the invention provides an aphid resistant germplasm, derived from soybean plant line E12902 whose seed was deposited under ATCC accession No: PTA-120715, wherein said germplasm comprises a rag1c aphid resistant region on chromosome 7. The rag1c aphid resistant region is located between a marker pair selected from the group consisting of Satt567;Satt220, Satt567;Sat_253, Satt567:Satt435, Satt540;Sat_253; and Satt540;Satt435 (see FIG. 2).

In one embodiment, the invention provides an aphid resistant germplasm, derived from soybean plant line PI 567537, which is designated Rag3b and is a dominant gene that is located on chromosome 16.

In one embodiment, the invention provides an aphid resistant Rag3b germplasm, derived from soybean plant cultivar PI 567537, wherein said germplasm comprises an aphid resistant region on chromosome 16 located between a marker pair selected from the group consisting of Sat_339; Satt654, Sat_339;Sct_065 and Sct_065;Satt654. See FIG. 9.

In one embodiment, the invention provides aphid resistant germplasm, derived from soybean plant cultivar PI 567585A, wherein said germplasm comprises an aphid resistant region on chromosome 16 located between a marker pair selected from the group consisting of Satt622; Satt215, Satt674;Sct_065, Satt674;Satt622, Satt674; Satt654, and Sct_065;Satt622. See FIG. 11.

In one embodiment, the invention provides a method for producing an aphid resistant soybean plant, comprising: a) providing aphid resistant germplasm that comprises germplasm from one or more of soybean plants accession PI 567585A, accession PI 567537, and a progeny plant of line E08934 or E12902; and b) introducing said aphid resistant germplasm into a soybean plant so as to produce an aphid resistant soybean plant. Seed of the E12902 plant line was deposited with the American Type Culture Collection as ATCC accession No. PTA-120715 on Nov. 20, 2013. In one embodiment, said aphid resistant soybean plant has enhanced aphid resistance. In one embodiment, said plant having enhanced soybean aphid resistance is used for breeding a soybean plant line having an average aphid damage index of 0-9%. In one embodiment, said plant having enhanced soybean aphid resistance is used for breeding a soybean plant line having a resistance score of 0.5 to 2.0. In one embodiment, said enhanced soybean aphid resistance is resistance to an aphid isolate. In one embodiment, said method further comprises: providing, aphid resistant germplasm that comprises germplasm from one or more of soybean plants selected from the group consisting of accession PI567598B, accession PI567543C, accession PI567541B, accession PI567597C, line E06902 deposited under ATCC accession No: PTA-8794, and progeny thereof, and step c) introducing said aphid resistant germplasm into said aphid resistant soybean plant so as to produce a plant having enhanced soybean aphid resistance.

In one embodiment, the invention provides a method for producing an aphid resistant soybean plant, comprising:
  a) providing,
    i) an aphid resistant soybean plant, comprising aphid resistant germplasm derived from one or more of soybean plants accession PI 567585A, accession PI 567537, and/or a progeny plant of line E12902 whose seed was deposited under ATCC accession No. PTA-120715, and
    ii) an aphid susceptible soybean plant, and
  b) crossing said aphid resistant soybean plant with said aphid susceptible soybean plant so as to produce a F1 progeny soybean plant, and
  c) screening said F1 progeny soybean plants for selecting an F1 progeny aphid resistant soybean plant. In one embodiment, said method further comprises step d) backcrossing said aphid resistant F1 progeny soybean plant to said susceptible soybean plant so as to produce F2 progeny aphid resistant soybean plants. In one embodiment, said method further comprises step e) crossing said F2 progeny aphid resistant soybean plants so as to produce aphid resistant soybean plants having homozygosity of said aphid resistant germplasm.

In one embodiment, the invention provides a method of breeding, comprising,
  a) providing,
    i) a first soybean plant comprising aphid resistant germplasm, wherein said germplasm derives from soybean plant line E08934 or from soybean plant line E12902 whose seed was deposited under ATCC accession No. PTA-120715,
    ii) a second soybean plant comprising aphid resistant germplasm, wherein said germplasm derives from a soybean plant selected from the group consisting of accession PI567541B, line E06902 deposited under ATCC accession No: PTA-8794, line E00003, line IA 2070, Skylla, and progeny thereof, and
  b) crossing said first soybean plant to said second soybean plant for making a soybean plant having enhanced aphid resistance. In one embodiment, said enhanced aphid resistance is selected from the group consisting of a resistance score of 0.5-2.0, an average aphid damage index of 0-9% and resistance to an aphid isolate. In one embodiment, said crossing further comprises one or more of a backcrossing, an outcrossing, and a self-crossing. In one embodiment, said crossing creates a soybean seed. In one embodiment, said seed is germinated and grown into progeny soybean plants. In one embodiment, said progeny soybean plants have enhanced aphid resistance. In one embodiment, the invention provides a soybean seed of said aphid resistant plant.

In one embodiment, the invention provides a method of breeding, comprising,
  a) providing,
    i) a first soybean plant comprising aphid resistant germplasm, wherein said germplasm derived from soybean plant line E08934 or from soybean plant line E12902 whose progeny seed was deposited under ATCC accession No. PTA-120715,
    ii) a second soybean plant comprising aphid resistant germplasm, wherein said germplasm derives from a soybean plant selected from the group consisting of accession PI567598B, accession PI567543C, accession PI567541B, accession PI567597C, line E06902 deposited under ATCC accession No: PTA-8794, line E00003, line IA 2070, Skylla, and progeny thereof, and
  b) crossing said first soybean plant to said second soybean plant for making a soybean plant having enhanced aphid resistance.

In one embodiment, the invention provides a method of breeding, comprising,
  a) providing,
    i) a first soybean plant comprising aphid resistant germplasm, wherein said germplasm derived from soybean plant line E08934 or from soybean plant line E12902 whose progeny seed was deposited under ATCC accession No. PTA-120715,
    ii) a second soybean plant comprising aphid resistant germplasm, wherein said germplasm derives from soybean plant line E08929, and
  b) crossing said first soybean plant to said second soybean plant for making a progeny soybean plant having aphid resistance. In one embodiment, said aphid resistance includes decreased aphid damage on progeny plants relative to line E08929 soybean plants.

In one embodiment, said method further comprises a molecular marker selected from the group consisting of Satt540 (chromosome 7), Satt209 (chromosome 8), and BARCSOYSSR_16_0371 (chromosome 16) for identifying aphid resistance germplasm, and step c) using said molecular marker for identifying said aphid resistance in said progeny aphid resistant soybean plant. In one embodiment, said progeny aphid resistance soybean plant has at least a Rag6 region (e.g., on chromosome 8). In one embodiment, said aphid resistant soybean plant is used for breeding a soybean plant line having enhanced soybean aphid resistance.

In one embodiment, the invention provides a method of breeding, comprising,
  a) providing,
    i) a first soybean plant comprising aphid resistant germplasm is derived from soybean plant line E08934, or from soybean plant line E12902 whose seed was deposited under ATCC accession No: PTA-120715,
    ii) second soybean plant, and iii) a pair of molecular markers, and
  b) crossing said first soybean plant with said second soybean plant for providing a progeny soybean plant, using said set of molecular marker for identifying germplasm associated with enhanced aphid resistance in said progeny soybean plant. In one embodiment, said aphid resistant germplasm is located between said pair of molecular markers. In one embodiment, said pair is a marker pair selected from the group consisting of Sat_382;Satt455, Sat_382; Satt538, Satt455-Satt209, MSUSNP16_10;Satt465, and Satt693;Sat_370 (see FIG. 2).

In one embodiment, said second soybean plant is selected from the group consisting of an elite soybean plant, line E00003, line IA 2070, Skylla, accession PI567598B, accession PI567543C, accession PI567541B, accession PI567597C, PI 567537, PI 567585A, line E06902 deposited under ATCC accession No: PTA-8794, PI 200538, and progeny thereof. In one embodiment, said progeny soybean plant has enhanced aphid resistance. In one embodiment, said progeny soybean plant is used for breeding a plant line having enhanced aphid resistance. In one embodiment, the invention provides a plant line of said aphid resistant plant.

In one embodiment, the invention provides a method of identifying a marker for aphid resistance, comprising,
  a) providing,
    i) a first soybean plant germplasm, wherein said germplasm comprises nucleic acid sequences isolated from a soybean plant having a phenotype of aphid resistance selected from the group consisting of soybean plant line E08934, soybean plant line E12902 whose progeny seed was deposited under ATCC accession No. PTA-120715, accession PI 567585A, accession PI 567537, and progeny thereof, and ii) a second soybean plant germplasm, wherein said germplasm comprises nucleic acid sequences isolated from a soybean plant having less aphid resistance than the first soybean plant, and b) identifying a molecular marker on said first soybean plant germplasm that is not on said second soybean plant germplasm. In one embodiment, said molecular marker identifies an allele located at the Rag3 germplasm selected from the group consisting of Rag3c, Rag3b, and Rag3-1. For example, the germplasm can be from the Rag3c region or from the Rag3b region. The aphid resistant germplasm can be located between a pair of molecular markers, such as any of those described herein.

In one embodiment, the invention provides an aphid resistant soybean plant comprising aphid resistant germplasm derived from accession PI 567537 soybean plants. In one embodiment, the invention provides an aphid resistant soybean plant, wherein at least one ancestor of said soybean plant comprises aphid resistant germplasm of soybean plant accession PI 567537. In one embodiment, the invention provides an aphid resistant soybean plant, wherein at least one ancestor of said soybean plant comprises aphid resistant germplasm of soybean plant accession PI 567585A. In one embodiment, the invention provides an aphid resistant soybean plant comprising aphid resistant germplasm derived from accession PI 567537 soybean plants. In one embodiment, the invention provides an aphid resistant soybean plant, wherein at least one ancestor of said soybean plant comprises aphid resistant germplasm of soybean plant line E08934 or of soybean plant line E12902, whose seed was deposited under ATCC accession No: PTA-120715. In one embodiment, said soybean plant is a cultivar. In one embodiment, said soybean plant is a plant line. In one embodiment, said soybean plant comprises a trait selected from the group consisting of tolerance to an herbicide, resistance to an arthropod, resistance to a microorganism, resistance to a fungus, and an agronomic trait.

In one embodiment, said soybean plant further comprises introgressed germplasm for resistance to one or more of a Lepidopteran, Coleopteran, *Spodoptera*, Hemiptera, *Heliothis* sp., Soybean Cyst Nematode, Mexican Bean Beetle, and soybean leaf hopper.

In one embodiment, said soybean plant further comprises introgressed germplasm for resistance to microorganisms and diseases caused by microorganisms selected from the group consisting of leaf rot, brown leaf spot, frogeye leaf spot, stem rot, brown stem rot, stem canker, root rot, pod rot, powdery mildew, sudden death syndrome, bacterial pustule, reaction to bacterial pustule, bacterial blight, seedling blight, pod blight, stem blight, purple seed stain, mottling, stem mottling, pod mottling, leaf mottling, rust, soybean rust, Asian soybean rust fungus, a viral infection, a bacterial infection, and a fungal infection. In one embodiment, said agronomic trait is selected from the group consisting of a preferred oil content, protein content, seed protein content, seed fatty acid content, seed size, seed color, hilium color, seed coat thickness, seed sugar content, seed free amino acid content, seed germination rate, seed texture, seed fiber content, seed Vitamin E content, seed isoflavone content, seed phytate content, seed phytosterol content, seed isoflavone content, lecithin content, food-grade quality, hilium color, seed yield, plant type, plant height, lodging, shatter, herbicide resistance, disease resistance, insect resistance, nematode resistance, drought tolerance, drought resistance, water tolerance, water resistance, temperature tolerance, cold weather resistance, hot weather resistance, growth habit, maturity group, and field tolerance. In one embodiment, said soybean plant further comprises an introgressed heterologous gene. In one embodiment, said heterologous gene is selected from the group of genes encoding a modified phosphinothricin acetyltransferase (PAT) from the soil bacterium *Streptomyces viridochromogenes*, fatty acid desaturase (GmFad2-1) from soybean, a modified 5-enolpyruvylshikimate-3-phosphate synthase (EPSPS) from the soil bacterium *Agrobacterium tumefaciens*, one or more of a *Bacillus thuringiensis* (Bt) insecticidal crystal protein tIC851, Bt .DELTA.-endotoxin with insecticidal activity, mutant Bt .DELTA.-endotoxins with insecticidal activity, crystal protein (Cry) Bt toxins with insecticidal activity, for example, a cryIIIC toxin, cryET1 toxin, PS63B, PS176 toxin, NRRL B-18721 toxin, Bt protease resistant toxins such as BTS02618Aa or BTS02618Ab Bt nematode-active toxins, an enzyme for altering a fatty acid, .DELTA.-12 desaturase, plant acyl-ACP thioesterase, FAN1 protein for altering seed linolenic acid content, a palmitoyl-ACP thioesterase, an enzyme for reducing linolenic acid, an enzyme for reducing palmitic acid, an enzyme for increasing protein in a soybean seed, a protein for modifying an agronomic trait, and a protein for providing an agronomic trait. In some embodiments, the inventions provide a seed of said aphid resistant soybean plant.

In some embodiments, the aphid resistant germplasm in the form of seeds is deposited under the terms of the Budapest Treaty. In one embodiment, the seed has been deposited at the American Type Culture Collection (A.T.C.C./ATCC), 10801 University Boulevard, Manassas, Va., 20110-2209, United States of America. For example, seeds from soybean plant line E12902 were deposited with the ATCC under the terms of the Budapest Treaty on Nov. 20, 2013 and accorded ATCC accession No: PTA-120715.

DEFINITIONS

To facilitate an understanding of the present invention, a number of terms and phrases are defined below:

The use of the article "a" or "an" is intended to include one or more.

As used herein, the term "aphid" refers to any of various small plant-sucking insects with or without wings of the order Homoptera, further of the family Aphididae, wherein examples of Aphididae include but are not limited to a genius of *Aphis, Acyrthosiphum, Brevicoryne, Cavariella, Chaitophorus, Cinara, Diuraphis, Drepanosiphum, Elatobium, Macrosiphum, Megoura, Myzus, Phorodon, Rhopalosiphum, Sitobion, Toxoptera, Therioaphis, Tuberocephalus,* etc. while even further any one or more of the following genus-species of *Aphis*, for example, soybean aphid *Aphis glycines* Matsumura, Black Bean Aphid *Aphis faba*, Groundnut Aphid *Aphis craccivora* Cotton Aphid *Aphis gossypii* cotton/melon aphid, *Aphis gossypii, Acyrthosiphum*, for example, Pea Aphid *Acyrthosiphum pisum, Brevicoryne*, for example, Cabbage Aphid *Brevicoryne brassicae, Cavariella*, for example, Carrot Aphid *Cavariella aegopodii* Willow Aphid *Cavariella* spp. *Chaitophorus*, for example, Willow Leaf Aphids *Chaitophorus* spp., *Cinara*, for example, Black Pine Aphids *Cinara* spp., *Diuraphis*, for example, Russian wheat aphid *Diuraphis noxia, Drepanosiphum*, for example, Sycamore Aphid *Drepanosiphum platanoides, Elatobium*, for example, Spruce Aphids *Elatobium* spp., *Macrosiphum*, for example, English Grain Aphid *Macrosiphum avenae*, *Megoura*, for example, Vetch aphid *Megoura viciae*, *Myzus*, for example, Peach-Potato *Myzus persicae*, *Phorodon*, for example, Damson hop aphid *Phorodon humuli*, *Sitobion*, for example, Grain Aphid *Sitobion avenae*, *Rhopalosiphum* for example, Corn Leaf Aphid *Rhopalosiphum maidis*, the Oat Bird-Chemy Aphid *Rhopalosiphum padi Toxoptera*, for example, Black Citrus Aphid *Toxoptera auranti, Therioaphis*, for example, spotted alfalfa aphid *Therioaphis maculata, Tuberocephalus*, for example, peach aphid *Tuberocephalus momonis*, Giant Willow aphid *Tuberolachnus salignus* (aka *Lachnus salignus*) Gmellin and the like. For the purposes of the present invention, an aphid is a pest.

As used herein, the terms "soybean aphid" and "*Aphis glycines*" and "*Aphis glycines* Matsamura" refers to an aphid that feeds on soybean plants, for example, an aphid that derived from an eastern Asian soybean aphid, an aphid that typically feeds on another type of plant that also feeds upon a soybean plant, etc. For the compositions and methods of the present invention, any aphid that may be found on and thus potentially feeds upon a soybean plant, such as a cotton/melon aphid, *Aphis gossypii* Glover, is an aphid target for soybean aphid resistance germplasm and for aphid resistant plants.

As used herein, the terms "aphid resistant" and "aphid resistance" in reference to a plant refers to a capacity of a host plant to prevent and/or reduce the ability of an aphid to damage this host plant, such as reducing aphid feeding, reducing aphid growth, development or reproduction, and the like, including demonstrating antixenosis and/or antibiosis resistance when an aphid is in contact with an aphid resistant plant. Further, an aphid resistant host plant may have resistance related to tolerance (Painter 1951).

As used herein, the term "antibiosis" "antibiosis resistance" and "antibiosis resistance toxicity" in relation to aphid resistance refers to a trait having a negative effect on a pest when the pest is forced to interact with a plant having antibiosis defenses, such as shown in a no-choice study of the present invention. In some embodiments, aphid resistance in a plant line or plant cultivar was indicated as aphids had lower or loss of reproductively on the plants in a no-choice study as compared to a non-resistant plant line or plant cultivar. Examples of soybean plants of the present invention showing antibiosis resistance are soybean plants E08934 and E12902, and progeny plants comprising aphid resistant germplasm in addition to germplasm derived from other aphid resistant plants such as PI567541B and their aphid resistant progeny plants. Antibiosis further refers to adverse effects on an insect's life history after a resistant host plant has been used for its food (for example, in Painter, Insect Resistance in Crop Plants, Macmillan, New York (1951), herein incorporated by reference). Thus in some embodiments, antibiosis resistance of a plant comprises a toxin. In other embodiments, aphids feeding on plants having antibiosis resistance results in aphids having impaired development, such as lower weight, reduced fertility, and the like.

As used herein, the term "toxin" refers to any substance (usually a protein or conjugated protein) that is detrimental (i.e., poisonous) to cells and/or organisms, in particular, an insect organism, i.e. an insecticidal substance. In particularly preferred embodiments, the term refers to extracellular toxins and intracellular toxins produced by various plant species, including, but not limited to a contemplated soybean plant toxin that provides toxicity activity toward members of the genus *Glycine*. In one embodiment, a toxin results in a detrimental effect on an aphid. In one embodiment, a toxin results in the death of an aphid.

As used herein, the terms "antixenosis" and "antixenosis resistance" in relation to aphid resistance refers to a plant trait conferring nonpreference of insects for a host plant in a choice test (for example, Kogan and Ortman, (1978) Bull. Entomol. Soc. Am. 24:175-176, herein incorporated by reference), for example, "repellency to aphids" and "aphid repellent" in reference to soybean plant cultivars of the present invention demonstrating antixenosis resistance are PI 567537 and progeny comprising aphid resistant germplasm of PI 567537.

Seeds for the PI 567537 soybean cultivar are available from the USDA soybean germplasm collection and the Germplasm Resources Information Network (GRIN) (see the website on the worldwide web at ars-grin.gov/cgi-bin/npgs/acc/search.pl?accid=PI+567537).

Seeds for the PI 567585 A soybean cultivar are also available from the USDA soybean germplasm collection and the Germplasm Resources Information Network (GRIN) (see the website on the worldwide web at ars-grin.gov/cgi-bin/npgs/acc/display.pl?1500954).

Seeds for the PI 567598 B soybean cultivar are also available from the USDA soybean germplasm collection and the Germplasm Resources Information Network (GRIN) (see the website on the worldwide web at ars-grin.gov/cgi-bin/npgs/acc/display.pl?1500974).

Seeds for the PI 567543 C soybean cultivar are also available from the USDA soybean germplasm collection and the Germplasm Resources Information Network (GRIN) (see the website on the worldwide web at ars-grin.gov/cgi-bin/npgs/acc/display.pl?1500927).

Seeds for the PI 567541 B soybean cultivar are also available from the USDA soybean germplasm collection and the Germplasm Resources Information Network (GRIN) (see the website on the worldwide web at ars-grin.gov/cgi-bin/npgs/acc/display.pl?1500923).

Seeds for the PI 567597 C soybean cultivar are also available from the USDA soybean germplasm collection and the Germplasm Resources Information Network (GRIN) (see the website on the worldwide web at ars-grin.gov/cgi-bin/npgs/acc/display.pl?1500972).

As used herein, the term "tolerance" refers to a plant's ability to recover from or withstand insect damage, such as a tolerant aphid resistant plant sustaining aphid damage yet continuing to grow and reproduce in an agronomical acceptable manner.

As used herein, the term "repellent" such as an "insect repellent" and an "aphid repellent" refers to a substance, such as a substance produced by a plant, a protein, etc., that wards off and/or keeps away an insect, for example, an aphid, including "repel" as in "repelling an aphid." In one example, a plant may repel an aphid as demonstrated in a choice assay of the present inventions.

As used herein, the term "aphid resistant soybean plant" refers to a soybean plant individually or as a plant of a particular soybean plant line or of a particular soybean plant cultivar. In other words, lines and cultivars are populations of individual closely related plants demonstrating increased resistance to aphids (such as a lower damage index) relative to less resistant plants or susceptible plants.

An aphid resistant soybean plant having "enhanced aphid resistance" or "enhanced soybean aphid resistance" is a soybean plant, line or cultivar having at least one additional type of aphid resistance in addition to antibiosis and antixenosis, such as, broad aphid resistance, resistance to a specific aphid isolate, resistance to a specific aphid biotype, durable aphid resistance, superior aphid resistance and the like, produced by using aphid resistant germplasm of the present inventions derived from soybean plant lines and cultivars: E08934, E12902, PI 567537, PI 567585A (resistant sources of the present inventions) and genes derived from these resistance sources. In some embodiments, enhanced resistance is produced by stacking aphid resistant germplasm/genes, for example plants described herein having rag1c, Rag3c, and Rag6 stacked germplasm/genes.

As used herein, "superior aphid resistant germplasm," or "superior aphid resistance germplasm," refers to regions of germplasm capable of conferring superior aphid resistant to a soybean plant, for example, aphid resistance germplasm comprising a Rag6 germplasm (e.g., located on chromosome 8) and genes encoded within that germplasm, a combination of Rag6 germplasm/genes with a Rag3c germplasm/genes (e.g., located on chromosome 16), and a Rag6 germplasm/genes with a Rag3c germplasm/genes with a rag1c germplasm/genes (e.g., located on chromosome 7) of the present inventions, is considered superior aphid resistance germplasm when used in plants of the present inventions for providing superior aphid resistant plants. For another example, a new soybean plant, i.e. a *Glycine max* $F_4$ derived soybean plant line E08934 or E12902 was made as described herein, having superior aphid resistance germplasm comprising a Rag6 region and a Rag3c region.

An aphid resistant soybean plant having "superior aphid resistance" in reference to an aphid resistant soybean plant refers to a soybean plant or plant line or plant cultivar that demonstrated higher aphid resistance (such as a lower damage index (DI)) over other aphid resistant soybean plants. For some examples of superior in aphid resistance as measured by lower DI's, over PI 567598B aphid resistant soybean plants (see, FIG. 5) where plant line 131, comprising a superior aphid resistant germplasm/gene region, i.e. at least one copy of a Rag6 germplasm/gene region and plant line 19 with at least one each of a Rag6 region and a Rag3c region (see, FIG. 4) are shown.

An aphid resistant soybean plant having "stacked genes" in reference to an aphid resistant soybean plant refers to a soybean plant produced with aphid resistant germplasm from different plant sources combined within the same plant for providing aphid resistant plants. For example, a soybean plant of the present inventions having a rag1c germplasm/gene derived from PI 567541B aphid resistant germplasm was combined within a plant having at least one Rag3c germplasm/gene and Rag6 germplasm/gene derived from E08934 or E12902 soybean plants is an aphid resistant soybean plant having stacked aphid resistant germplasm/genes. In one embodiment, a soybean plant having stacked germplasm/genes has at least two aphid resistant genes, each from different plant sources of aphid resistant germplasm. In some embodiments, a soybean plant has at least three aphid resistant genes from at least two or more different plant sources. For exemplary sources of aphid resistant germplasm for use in stacking germplasm/genes, see nonlimiting examples in Table 5. Exemplary sources of aphid resistant germplasm for use in stacking are also described in U.S. patents including U.S. Pat. Nos. 7,781,648; 8,227,662; 8,237,02, and references cited in Table 10.

An aphid resistant soybean plant having "pyramided genes" in reference to an aphid resistant soybean plant refers to a soybean plant produced with aphid resistant germplasm from different plant sources within the same plant for combining aphid resistant genes at or near the same locus. As one example, a soybean plant has pyramided genes when two different regions of germplasm/genes at or near the rag 3 locus, such as when a soybean plant is produced having a Rag3c region of germplasm/genes and a Rag3 region of germplasm/genes. In some embodiments, a soybean plant having stacked genes may also be considered as having pyramided genes, and vice versus, when combining different sources of aphid resistant germplasm/genes at different further combined with two different regions of germplasm/genes at or near the same loci. For exemplary sources of aphid resistant germplasm for use in pyramiding aphid resistant genes, see nonlimiting examples in Table 5 for stacking different Rag3 regions. Exemplary sources of aphid resistant germplasm for use in stacking are also described in U.S. Patents including U.S. Pat. Nos. 7,781,648; 8,227,662; 8,237,02, and references cited in Table 10.

An aphid resistant soybean plant having "pyramided genes" in reference to an aphid resistant soybean plant refers to a soybean plant produced with aphid resistant germplasm from different plant sources within the same plant for combining aphid resistant genes at or near the same locus. As one example, a soybean plant has pyramided genes when two different regions of germplasm/genes at or near the rag 3 locus, such as when a soybean plant is produced having a Rag3c region of germplasm/genes and a Rag3 region of germplasm/genes. In some embodiments, a soybean plant having stacked genes may also be considered as having pyramided genes, and vice versus, when combining different sources of aphid resistant germplasm/genes at different further combined with two different regions of germplasm/genes at or near the same loci. For exemplary sources of aphid resistant germplasm for use in pyramiding aphid resistant genes, see nonlimiting examples in Table 5 for stacking different Rag3 regions. Exemplary sources of aphid resistant germplasm for use in stacking are also described in U.S. patents including U.S. Pat. Nos. 7,781,648; 8,227,662; 8,237,02, and references cited in Table 10.

An aphid resistant soybean plant having "pyramided genes" or pyramided germplasm" in reference to an aphid resistant soybean plant refers to a soybean plant produced with aphid resistant germplasm from different plant sources within the same plant for combining aphid resistant germplasm/genes at or near the same locus. As one example, a soybean plant has pyramided genes when two different genes at or near the rag 3 locus, such as when a soybean plant is produced having a Rag3c and a Rag3 gene. In some embodiments, a soybean plant having stacked genes may also be considered as having pyramided genes, such that a soybean plant having pyramided genes is also considered a soybean plant having stacked genes. For exemplary sources of aphid resistant germplasm for use in pyramiding aphid resistant genes, see nonlimiting examples in Table 5. Exemplary sources of aphid resistant germplasm for use in stacking are also described in U.S. patents including U.S. Pat. Nos. 7,781,648; 8,227,662; 8,237,02, and references cited in Table 10.

As used herein, "broad resistance" in reference to aphid resistance of a soybean plant refers to the capability of a soybean plant line or cultivar to provide resistance to more than one aphid biotype or aphid isolate.

As used herein, "durable resistance" in reference to aphid resistance of a soybean plant refers to the capability of a soybean plant line or cultivar to continue to provide resistance to new soybean aphid isolates or new biotypes which may infest aphid resistant soybean plants.

As used herein, the term "host plant" in reference to aphids refers to a target plant for any activity of aphids, including landing on the target plant, feeding on the target plant, reproducing on the target plant, etc.

As used herein, the terms "resistant" and "resistance" in reference to a plant, means a situation wherein insects and/or pathogens are prevented and/or inhibited from causing plant damage and/or diseases and the associated disease symptoms. Further, resistance to an insect or pathogen may refer to the capability of the plant to prevent or inhibit insect or pathogen reproduction. Alternatively, at least some of the disease symptoms caused by the insect or pathogen are minimized or lessened. This includes but is not limited to types of resistance such as aphid resistance, arthropod resistance, nematode resistance, such as resistance to a soybean cyst nematode pathogen resistance or disease resistance, such as resistance to Seed Mottling caused by viruses, such as Bean Pod Mottle Virus (BPMV) and Soybean Mosaic Virus (SMV), Sudden Death Syndrome (SDS) caused by a fungus *Fusarium solani*, bacterial pustule caused by *Xanthomonas campestris* pv. *Glycines*, etc., fungus resistance, such as soybean rust resistance, and the like.

In some embodiments, the amount of resistance of a plant or plant line to an insect or pathogen is relative to a similar plant or plant line without such resistance.

As used herein, the terms "resistant" and "resistance" in reference to insect resistance of plants refers to aphid resistance and arthropod resistance.

As used herein, the terms "resistant" and "resistance" in reference to pathogen resistance of plants refers to such pathogens including bacteria, virus and fungus.

As used herein, the term "increasing resistance" refers to increasing the ability of a host plant to repel an insect, such as an aphid, nematode, etc., pathogen, fungus, virus, disease, and the like, including by decreasing the physical impact on or damage to the plant of the particular insect, pathogen, disease, and/or nematode attack on a host plant, such as reducing the feeding activity of an aphid, reducing the feeding activity of an insect, reducing the feeding activity of an insect larvae, reducing the number of parasitic nematodes on a plant, reducing the number of parasitic nematodes on a plant, reducing egg laying activity of an insect, reducing the symptoms of infection such as stem rot, root rot, seed mottling, and the like. Increasing resistance also refers to increasing the ability of the host plant to diminished and/or entirely avoid infestation and damage by an aphid, an insect, a bacterium, a fungi, a virus, and a parasitic organism, for example, increasing soybean cyst nematode resistance in a soybean line see, U.S. Pat. No. 6,096,944, herein incorporated by reference, an infection, a disease, a fungus, and the like.

As used herein, the terms "Soybean Cyst Nematode" or "SCN" refer to small roundworms, such as *Heterodera glycines*, that cause root damage and subsequent aboveground disease symptoms to soybeans. At least sixteen physiological races of the SCN have been identified.

As used herein, the terms "arthropoda" and "arthropods" refer to a branch (phylum) of the animal kingdom whose members have jointed legs and are also made up of rings or segments, for example, Insecta, crustaceans, spiders, and the like. As used herein, some arthropod larvae (for example, grubs and maggots) are legless while spiders and ticks have four pairs of jointed legs.

As used herein, the terms "insect" and "Insecta" refer to a Class of Arthropoda whose members have a body with distinct head, thorax and abdomen;

the head bears one pair of antennae and paired mouthparts; the thorax bears three pairs of legs and one or two pairs of wings in winged insects (Pterygota) and none in primarily wingless insects (Apterygota); the abdomen bears no legs but other appendages might be present with three pairs of jointed legs and one pair of antennae, at least in the adult phase, for example, aphids, Lepidoptera, such as butterflies and moths, Coleoptera, such as Beetles, have this arrangement in the adult phase. As used herein, some insect larvae (for example, grubs) are legless.

As used herein, the terms "Nematoda" or "nemathelminths" refer to a branch (phylum) of the animal kingdom whose members include "nematode" and "roundworm" organisms that are bilaterally symmetrical and surrounded by a strong and flexible noncellular layer called a cuticle, such as a *Heterodera glycines* soybean cyst nematode.

As used herein, the terms "Sudden Death Syndrome" or "SDS" refer to a fungal disease of soybeans caused by a fungus, such as *Fusarium solani* fungus.

As used herein, the terms "Sclerotinia Stem Rot" or "SSR" or "white mold" in reference to a disease refers to a soil-borne disease caused by a fungus *Sclerotinia sclerotiorum*.

As used herein, the term "*Rhizoctonia* Root Rot" refers to a soil borne disease resulting in root rot and stunting of plant growth caused by a fungus *Rhizoctonia solani*.

As used herein, the terms "*Phytophthora* rot" in reference to a plant part, such as *Phytophthora* seed rot, *Phytophthora* stem rot or *Phytophthora* root rot, refers to a disease caused by a *Phytophthora* fungus.

As used herein, the term "damping-off" refers to a fungal disease in the soil causing seedlings to wilt and die, such as caused by *Pythium ultimum*.

As used herein, the terms "*Pythium* rot" in reference to a plant part, such as a *Pythium* seed rot, *Pythium* stem rot or *Pythium* root rot or *Pythium* seed decay, refers to a disease caused by a fungus *Pythium ultimum*.

As used herein, the terms "*Phomopsis* seed rot" refers to a disease caused by seed-borne fungi, *Phomopsis longicolla*, *Diaporthe phaseolorum* var. *sojae*, and *D. phaseolorum* var. *caulivora*.

As used herein, the term "powdery mildew" refers to fungal growth that appears as a white fuzzy coating on the upper leaves.

As used herein, the term "seedling blight" refers to a disease causing weakened or killed seedlings.

As used herein, the term "mottling" refers to a discoloration of a plant part, such as seed mottling, which is not fungal in origin. Mottling of soybean seed is caused by viruses such as Bean Pod Mottle Virus (BPMV) and Soybean Mosaic Virus (SMV).

As used herein, the term "Bean pod mottle virus" and "BPMV" refers to a virus with small isometric particles and a single-stranded RNA genome that is beetle-transmitted, such as Leaf-feeding beetles (Coleoptera) belonging to *Cerotoma trifurcata, Colaspis brunnea, C. lata, Diabrotica balteata, D. undecimpunctata howardi, Epicauta vittata*, and *Epilachna varivestis*, to soybean and causes a mottling of soybean leaves.

As used herein, the term "Soybean Mosaic Virus" and "SMV" refers to a flexuous rod consisting of positive-sense, single-stranded RNA infected cultivars are slightly stunted with fewer pods that are sometimes dwarfed and flattened, without hairs, and without seeds. At least 32 aphid species, belonging to at least 15 different genera, transmit SMV in a nonpersistent manner.

As used herein, the term "Tobacco ringspot virus" and "TRSV" refers to a bud blight causing nepovirus group of plant viruses with two single-stranded positive sense polyadenylated RNA molecules transmitted by nymphs of *Thrips tabaci*.

As used herein, the term "bacterial pustule" refers to an undesired physical condition, primarily of leaves and pods as the result of an infection, primarily a disease of leaves and pods of a plant [caused by *Xanthomonas campestris* pv. *Glycinea*.

As used herein, the term "bacterial blight" refers to a disease caused by bacteria, such as *Pseudomonas savastonoi* pv. *Glycinea*.

As used herein, the terms "rust" or "soybean rust" or "Leaf Rust" or "Asian soybean rust" refer to a fungal disease, such as that caused by fungi such as *Phakopsora pachyrhizi*.

As used herein, the terms "*Bacillus thuringiensis*" and "Bt" in reference to a toxin refers to insecticidal compounds, such as crystals and proteins, naturally produced by a *Bacillus thuringiensis* bacterium and modified by man for agricultural use.

As used herein, the term "host" refers to any organism (animal or plant) fed upon by a parasite or parasitoid. As used herein, when insects or nematodes feed upon plants they are considered parasites of those plants, and the plants are then referred to as "host plants."

As used herein, the term "plant" is used in it broadest sense. It includes, but is not limited to, any species of woody, ornamental or decorative, crop or cereal, fruit or vegetable, fruit plant or vegetable plant, flower or tree, macroalga or microalga, phytoplankton and photosynthetic algae (e.g., green algae *Chlamydomonas reinhardtii*). A plant also refers to a unicellular plant (e.g. microalga) and a plurality of plant cells that are largely differentiated into a colony (e.g. volvox) or a structure that is present at any stage of a plant's development. Such structures include, but are not limited to, a fruit, a seed, a shoot, a stem, a leaf, a flower petal, etc.

As used herein, the term "soybean plant" refers to a legume plant of the family Fabaceae, herein used in its broadest sense and includes but is not limited to any species of soybean, for example, a *Glycine* species. A soybean plant may be a *Glycine max*, such as a cultivated soybean plant, a *Glycine soja* [Sieb. & Zucc.], such as a wild form of soybean, and a *Glycine gracilis* Skvortz, such as a weedy form of soybean. The present invention is not meant to limit the type of soybean plant. Indeed numerous varieties of aphid resistant soybean plants are contemplated. In some embodiments, an aphid resistant soybean plant provides human food-grade soybeans, such as for soymilk, soynuts, whole soybeans, miso, tofu (such as soybean curd), tempeh, soy sauce (such as shoyu, tamari and teriyaki sauce), soybean oil, margarine, salad oil, and the like. In some embodiments, a human food-grade aphid resistant soybean provides pharmaceutical products, such as for cancer prevention, for example, providing genistein.

As used herein, the term "soybean" refers to a seed of a soybean plant, i.e. soybean seed.

As used herein, the term "seed" refers to a fertilized and ripened ovule of a plant, consisting of an embryo and a casing, such as a bean and a soybean, for example, a soybean is a seed. In reference to seed size, Seed size (i.e. weight per seed) is recorded in grams per 100 seeds based on a 100- or 200-seed sample. To convert to seeds per pound, divide this into 45,359.2.

As used herein, the term "pod" refers to a seed of a soybean plant.

As used herein, the term "hybrid" in reference to a seed or plant is produced as the result of controlled cross-pollination as opposed to a non-hybrid seed produced as the result of natural pollination, as in a "hybrid soybean seed" produced by breeding methods of the present invention.

The terms "leaf" and "leaves" refer to a usually flat, green structure attached to a stem or branch of a plant wherein photosynthesis and transpiration take place.

The term "stem" refers to a main ascending axis of a plant.

The term "node" refers to the joint of a stem and the region of attachment of leaves on a stem.

As used herein, the term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture.

As used herein, the term "plant part" as used herein refers to a plant structure or a plant tissue, for example, pollen, an ovule, a tissue, a pod, a seed, and a cell. In some embodiments of the present invention transgenic plants are crop plants.

As used herein, the terms "crop" and "crop plant" is used in its broadest sense. The term includes, but is not limited to, any species of plant or alga edible by humans or used as a feed for animals or fish or marine animals, or consumed by humans, or used by humans (natural pesticides), or viewed by humans (flowers) or any plant or alga used in industry or commerce or education.

As used herein, the term "agronomic trait" and "economically significant trait" refers to any selected trait that increases the commercial value of a plant part, for example, a preferred oil content, protein content, seed protein content, seed fatty acid content, seed size, seed color, hilium color, seed coat thickness, seed sugar content, seed free amino acid content, seed germination rate, seed texture, seed fiber content, seed Vitamin E content, seed isoflavone content, seed phytate content, seed phytosterol content, seed isoflavone content, lecithin content, food-grade quality, hilium color, seed yield, plant type, plant height, lodging, shatter, herbicide resistance, disease resistance, insect resistance, nematode resistance, drought tolerance, drought resistance, water tolerance, water resistance, temperature tolerance, such as cold weather resistance, hot weather resistance, and the like, growth habit, maturity group, field tolerance, and growth in a hardiness zone.

As used herein, the term "fatty acid" refers to a chemical unit occurring either as a single molecule or a molecule of at least 2 or more combined fatty acid units, wherein a fatty acid unit comprises any number of carbon (C), hydrogen (H), and oxygen (O) atoms arranged as a carbon chain skeleton with a carboxyl group (—COOH) at one end. A fatty acid may be a saturated fatty acid or an unsaturated fatty acid. Examples of fatty acids found in soybeans include but are not limited to palmitic, stearic, oleic, linoleic, and linolenic.

As used herein, the terms "saturated fatty acid," "SFAs," "hydrogenated fatty acid" refer to fatty acid molecules or chains of fatty acid molecules without double bonds between the carbon atoms for example, palmitic acid.

As used herein, the term "monounsaturated fatty acids" "MUFAs" refers to a fatty acid molecule with no more than one double bond, for example, oleic acid.

As used herein, the term "polyunsaturated fatty acids" "PUFAs" refers to a fatty acid molecule having more than one double bond, for example, linoleic acid, and linolenic acid found in soybean oil, wherein linolenic acid is an omega-3 polyunsaturated fatty acid that under certain conditions causes soybean oil to become rancid.

As used herein, the term "lecithin" refers to a naturally occurring emulsifier extracted from crude soybean oil.

As used herein, the terms "isoflavone" and "isoflavonoid" refer to a polyphenol molecule or phytoestrogen molecule or estrogen-like molecule found in soybeans, for example, genistein (genistin) a 4',5,7-trihydroxy-isoflavone or a 5,7-dihydroxy-3-(4-hydroxyphenyl)-4-benzopyrone of molecular formula $C15-H10-O5$ and CAS Registry Number 446-72-0; daidzein (daidzin) 4',7-dihydroxy- (8CI) Isoflavone or 4',7-dihydroxyisoflavone of molecular formula $C15-H10-O4$ and CAS Registry Number 486-66-8; glycinin of CAS Registry Number 9007-93-6; and glycitein a 7-hydroxy-3-(4-hydroxyphenyl)-6-methoxy-4H-1-benzopyran-4-one of molecular formula $C16-H12-O5$ and CAS Registry Number 40957-83-3.

As used herein, the term "shatter" in reference to shattering refers to a percentage of open pods determined at the time of harvest.

As used herein, the term "lodging" refers to measurement of soybean plants leaning or having fallen or laying on the ground at harvest.

As used herein, the term "growth habit" refers to indeterminate growth habit or determinate growth habit of a soybean plant, in particular, to a growth habit of a variety of soybean plant. For example, indeterminate soybean plant varieties are adapted to maturity group IV and earlier (northern U.S.) have overlapping vegetative and reproductive growth periods. On the other hand, determinate soybean plant varieties with a determinate growth habit are adapted to maturity group V and later (southern U.S.) having distinct vegetative and reproductive development periods.

As used herein, the term "plant type" refers to a physical characteristic of a plant ranging from highly branching types to thin-line types that produce a single main stem.

As used herein, the term "Glycine" refers to a genus containing soybean plants, while "subgenus" in reference to a soybean plant refers to one or more of a "soja" and a "soia," and a "max", wherein a soja and a soia refer to a wild-type soybean plant while max refers to a cultivated plant.

As used herein, the term "soybean maturity group" refers to an industry division of groups of varieties based on the zones in which the varieties are adapted. Soybean maturity groups range from 000-X, wherein 000 represents the earliest and X the latest. Plants adapted to northern day-lengths are classified as early-maturing; those adapted to the southern regions are classified as late-maturing. Maturity groups may include very long day length varieties (000, 00, 0) and extend to very short day length varieties (VII, VII, IX, X). For example, maturity group I soybean plant cultivars are typically grown in southern Minnesota, whereas maturity group IV soybean plant cultivars are typically grown in southern Illinois.

As used herein, the term "early maturing" or "early maturity group" in reference to a variety, line or cultivar of a soybean plant refers to soybean plants assigned to a maturity group ranging from 000 to III.

As used herein, the term "early season" or early season variety" in reference to a U.S. variety refers to a variety, line or cultivar of a soybean plant assigned to a maturity group ranging from 000 to IV.

As used herein, the term "relative maturity" when used in reference to a soybean plant maturity group subdivides a maturity group into tenths and provides a more precise maturity assignment, for example, a relative maturity of 3.3 is assigned to a later maturing early maturity group III soybean cultivar than a 3.0 soybean cultivar. The number following the decimal point refers to the relative earliness or lateness within each maturity group, for example, a 3.0 is an early group III variety, while a 3.9 is a late group III variety.

As used herein, the term "line" refers to a nursery term to describe a group of individuals from similar parentage with similar traits; for example, $F_3$-recombinant inbred lines were produced by crossing aphid resistant soybean plant line E08934 or E12902 with aphid susceptible soybean plant line E00003 that produced at least 140 progeny soybean plant lines having a range of aphid resistance, such that at least eight lines demonstrated aphid resistance while at least eight lines were aphid susceptible. In other examples of plant lines the plants have more uniform characteristics, such as when a plant line is "pure", such that plants in the pure line retain the trait or traits characteristic of that line, such as aphid resistance. For example, a pure line of plants is produced by "self-pollination" or "selfed", as one example, line E08934 was produced as a pure line when plant E08934 was self-pollinated. Similarly, line E12902 has been produced as a pure line when plant E12902 was self-pollinated.

As used herein, the term "cultivar" refers to a plant or grouping of plants selected for one or more desirable characteristics, such as aphid resistance, that are maintained, i.e. propagated, by man. In some embodiments, propagation by man includes but is not limited to using asexual reproduction, vegetative propagation, inbreeding, cross pollinating, plants grown "true from seed" and the like. Cultivars may also be produced by genetically engineering plants for introducing a new or modified characteristic or for removing a characteristic. Seed-raised cultivars may be produced or propagated by uncontrolled pollination when characters that are distinct, uniform and stable are passed from parents to progeny. Some cultivars are "lines" that are produced by repeated self-fertilization or inbreeding or "multilines" that are made up of several closely related lines. Sometimes a cultivar may be a F1 hybrid which was the result of a deliberate repeatable single cross between two pure lines. Other selected generations may be used to produce a cultivar, when a repeatable cross is used to produce the cultivar. Characteristics of a cultivar, including a cultivar bred for commercial use, includes but is not limited to a plant variety whose plants have uniform and stable characteristics, such as similar heights, leaf shape, seed shape, or other agronomic trait. In reference to aphid resistance, an aphid resistant cultivar would have genetically stable aphid resistance characteristics, whereas succeeding generations would have similar aphid resistant qualities when tested on the same aphid biotype. In other words, the aphid resistant germplasm/genes would be "fixed" in the plant cultivar. In some embodiments, a cultivar is distinct, uniform and stable. To be distinct, the plants must have characteristics that easily distinguish them from any other known plant cultivar. To be uniform and stable, the plants must retain these characteristics under repeated propagation. One example of a cultivar is the soybean plant cultivar 'Skylla'

As used herein, the term "true from seed" refers to plants retaining their distinguishing characteristic when grown from seed, as in aphid resistant plants of the present inventions.

As used herein, the term "germinate" or "geminated" refers to when the embryo in a seed begins to grow.

As used herein, the term "soybean cultivar" or "soybean plant cultivar" is used in its broadest sense and includes but is not limited to any group of soybean plants that is cultivated by man. As such, as soybean cultivar may also be a soybean line.

As used herein, the term "cultivated" in reference to a plant includes any plant or plant part grown and maintained by man for use in food compositions or in nonfood compositions.

As used herein, the term "group" in reference to a plant refers to an artificial category between species and cultivar used to designate a collection of cultivars with similar parentage.

As used herein, the terms "variety" and "varietas" and "var" refer to a rank of taxa below subspecies but above form a, for example, a plant which retains most of the characteristics of the species, but differs in some way such as seed oil content, seed color, seed size, insect resistance, soybean aphid resistance, and the like.

As used herein, the terms "F-generation" and "filial generation" refers to any of the consecutive generations (progeny) of cells, tissues or organisms. In reference to plants and seeds of the present inventions, an additional F-generation seed and plant results after from the fertilization of an ovule with a sperm (pollen grain), i.e. mating or breeding, etc. The generation resulting from a mating of the founder or source plants (i.e. parents) is the first filial generation (designated as "F1" or "$F_1$") in reference to a seed and it's plant, while the generation resulting from crossing of F1 individuals is the second filial generation (designated as "F2" or "$F_2$") in reference to a seed and it's plant. As one example, an F4 seed and a resulting F4 plant may be produced by self-pollination of F3, while later F generations may be produced from cross pollination of the immediate prior generation.

As used herein, the terms "plant introductions" and "PI" refers to a plant accession number that can be assigned by the USDA Plant Introduction Office, for example, PI 567537, PI 567585A, etc.

As used herein, the term "germplasm" refers to any genetic material of plants, animals or other organisms containing functional units of heredity. In one embodiment, germplasm may be manipulated by the hand of man to become incorporated into the genome of a progeny plant that without manipulation would not have this germplasm. In other embodiments, germplasm may be isolated and manipulated by the hand of man. In other words germplasm comprises nucleic acid sequences or nucleic acid sequences molecules, such as genomic DNA in a plant or isolated and replicated DNA, including fragments of genomic DNA, contigs, BACs, genes, cDNA, mRNA, etc. In some embodiments the germplasm is a cDNA, or a nucleic acid segment that includes a cDNA.

As used herein, the term "germplasm" in reference to "aphid resistant germplasm" and "aphid resistance germplasm" refers to and encompasses hereditary material in a region of a soybean chromosome that provides resistance to aphids, in particular resistance to soybean aphids. Such hereditary material can include one or more nucleic acid segments, for example, one or more cDNAs encoding one or more aphid resistance proteins or RNA molecules.

As used herein, the term "elite germplasm" in reference to a soybean cultivar or line refers to soybean plant hereditary material of proven genetic superiority, for example, a commercial cultivar of a soybean plant, such as a "ROUND-UP READY™" soybean plant, a soybean plant having a desired agronomic trait, such as lodging, oil content, nematode resistance, et cetera, and for the purposes of the present inventions, elite germplasm includes aphid resistant germplasm of the present inventions.

As used herein, the term "polymorphic locus" refers to a genetic locus present in a population, such as within a population of non-aphid resistant soybean plants, that shows variation between members of the population (i.e., the most common allele has a frequency of less than 0.95). Thus, "polymorphism" refers to the existence of a character, such as a short DNA sequence or single nucleotide found in two or more variant forms within a population, for example, between Williams82 and IA 2070.

As used herein, the terms "single nucleotide polymorphism" and "SNP" and "single polynucleotide polymorphism" refers a genetic locus having a single nucleotide base that may be occupied by one of at least two different nucleotides, for example, SNP loci or SNP sites within aphid resistant germplasm/genes show nucleotide differences from the same or similar regions of reference germplasm from non-aphid resistant soybean plants. In contrast, a "monomorphic locus" refers to a genetic locus at which little or no variations are seen between members of the population (generally taken to be a locus at which the most common allele exceeds a frequency of 0.95 in the gene pool of the population). In other words, the terms "single nucleotide polymorphism" and "SNP" refer to a single nucleotide difference at the same or equivalent positions between two highly similar (high identity) DNA sequences, for example, between reference germplasm from non-aphid resistant plants and isolated aphid resistant germplasm.

SNP analysis can be combined with whole-genome genotyping (WGG) assays based on a two-color, single-base extension (SBE). For example, a variety of immobilized probes can be employed for hybridization capture of WGA product(s), and single base extensions can be performed with detection by two-color antibody-based staining (and signal amplification if needed). For example, biotin and dinitrophenol (DNP) can be used as detectable haptens in the assay, so that the two colors can be visualized on an array. Three different genotype states are readily discernable (e.g., using differently colored lebels): red (homozygous AA), yellow (heterozygous AB) and green (homozygous BB) beads. Red and green signal intensities for nonpolymorphic controls can be included. Genotyping plots, genotyping clustering plots, and haplotype maps can be generated. For example, the data can be plotted as R values (¼ log-based normalized intensity) versus θ values ($\theta=(2/\pi) \times arctan(B/A)$) to visualize clusters of genotypes. For example, the number of data points (samples) in each cluster can be shown above an x axis of cluster separation scores (CSS). Histograms of CSS scores across numerous SNP assays can also be generated to facilitate identification of a successful assay. See, Steemers et al., Nature Methods 3:31-33 (2006).

As used herein, the terms "marker" and "DNA marker" and "molecular marker" in reference to a "selectable marker" refers to a physiological or morphological trait which may be determined as a marker for its own selection or for selection of other traits closely linked to that marker, for example, a gene or germplasm or trait that associates with aphid resistance, such as a DNA marker including but not limited to simple sequence repeat (SSR), single nucleotide polymorphism (SNP) analysis, for example, MSUSNP markers, random amplified polymorphic DNA analysis (RAPID), amplified fragment length polymorphism analysis (AFLP), and the like that will link phenotype information, such as aphid resistance to a quantitative trait locus (QTL), to provide a genomic map, for example a fingerprint map, and chromosome location and/or map.

As used herein, the terms "simple sequence repeat" and "SSR" refer to short, tandem repeat nucleotide sequences that are useful as genetic markers, for example, microsatellite DNA is a highly polymorphic DNA marker comprised of mononucleotides, dinucleotides, trinucleotides or tetranucleotides that are repeated in tandem arrays and distributed throughout the genome, for examples, CA (alternatively GT) dinucleotide repeats. Examples of SSR markers include but are not limited to "Satt" markers, such as markers named Sct.

As used herein, "Satt" and "Sat" refer to a SSR marker comprising "att" and "at" repeats. Satt and Sat markers refer to a genomic fragment amplified using PCR primers, typically a forward and a reverse PCR primer, for amplifying the genomic fragment thus identifying a "linkage group" or location (region) on a soybean chromosome. SSR markers with a name starting with "Satt" means the allele differences of the markers are based on the differences of the number of "att" nucleotide tandem repeats between the forward and reverse SSR primers, e.g. one allele may have 50 tandem "att" repeat while the other allele may have 60 tandem "att" tandem repeats (thus the amplified fragment size difference and distance between the two alleles is 10×3=30 bp). Similarly, SSR markers starting with "Sat" means the allele differences are based on the differences of the number of "at" tandem repeats occurring between the forward and reverse SSR primer pairs in the amplified fragment. For the purposes of the present inventions, a reference to a particular Satt or Sat marker, such as Satt455, refers to the region of a chromosome amplified by specific primers (as published in Cregan et al. 1999, and by Soybase and the Soybean Breeder's Toolbox, website at soybase.org/search/index.php, such that for Satt 455 primer 1 is CGGATTGTGTC-CTTTGTTGTTATTAT (SEQ ID NO:1) and primer 2 is ACCTCGCACACAATTTGAGTC (SEQ ID NO:2). For another example, Sat_382 represents regions amplified by

```
primer 1:
                                 (SEQ ID NO: 3)
GCGAAAGGTCGAGAAAATGAAATG
and primer 2:
                                 (SEQ ID NO: 4)
GCGTTTGCCTTGTTGGTGACTTG.
```

Sat and Satt markers by also be identified by BARC-SOYSSR names, for example, Sat_382 may also be represented by a BARCSOYSSR_08_1246 marker name.

As used herein, the term "linkage group" or "LG" refers to a group of two or more genetically or physically mapped loci with observed linkage to a trait, for example, one or more of a SSR, SNP, AFLP, and RAPD marker of the present invention that may map to aphid resistant germplasm. Examples of soybean linkages groups associated with aphid resistant germplasm comprise, for example, A2 and J, as discovered and shown herein.

As used herein, the terms "random amplified polymorphic DNA" and "RAPD" refer to a common technique for amplifying anonymous stretches of DNA using PCR with arbitrary primers, for example, using random PCR primers used to amplify genomic DNA to provide a pattern of bands, such that one pattern of bands may be different between individuals in a population, such as between aphid resistant and aphid susceptible plants or show germplasm differences between closely related plants.

As used herein, the term "derives from" or "derived from" generally refers to relatedness of the items that were derived. For example, when "germplasm derives from" or "germplasm derived from" a plant line, then the germplasm was isolated from that plant line. As another example, when a plant line is derived from another plant line, then at least some of the hereditary material is similar between the plant lines, in other words the plants may be genetically related. Furthermore, the hereditary material may specifically include aphid resistant germplasm, such as when a soybean plant or plant line, comprising aphid resistant germplasm was derived from or was progeny of another plant line shown to have aphid resistant germplasm of the present inventions. As yet another example, when the term "germplasm derived from" is used in reference to germplasm it refers to hereditary material, such as genomic DNA, genes, etc. The term "derived from" may also refer to "inherited from", as in a soybean plant line may inherit aphid resistant germplasm from another soybean plant line.

As used herein, the term "hybrid" refers to a seed and a plant produced as the result of controlled pollination as opposed to a seed and a plant produced as the result of natural pollination.

As used herein, the term "trait" refers to an observable and/or measurable characteristics of an organism, such as a trait of a plant, for example, resistance to a soybean aphid, tolerance to an herbicide, an agronomic trait, insect, and microbe.

As used herein, the term "breeding" or "crossing" refers to artificially or naturally contacting a pollen granule with an egg of a soybean plant for sexually producing a soybean seed, i.e. wherein genes from each parent are randomly passed onto progeny grown from the seed. Breeding may be inbreeding, self-crossing, back-crossing, out-crossing, etc. When breeding parents that are homozygous for a particular allele then progeny plants will be homozygous for that allele. When at least one parent is heterozygous at a particular allele then the progeny plants may or may not inherit that allele.

As used herein, the term "single seed descent" refers to a method of breeding the next generation involving collecting and using one seed per plant (i.e. descending) for growing the next generation of plants. The use of single seed descent for producing the next generation of plants allows growing multiple generations per year for advancing a population to a genetically stable generation for a desired characteristic, such as aphid resistance, a desired agronomic trait, etc., in a much shorter time period than when using conventional plant breeding methods that generally produce one generation per year.

As used herein, the term "introducing" or "conferring" or "deriving" or "introgressing" in reference to aphid resistant germplasm or an aphid resistant gene refers to genetic inheritance of aphid resistant germplasm from a source plant or parent plant.

As used herein, the term "introgress" and "introgressing" refers to incorporating, as in inheriting, a genetic substance, such as germplasm, loci, allele, gene, DNA, and the like for deliberately introducing a trait into an organism, such as a plant, a soybean cultivar and the like, for example, incorporating aphid resistant germplasm into a previously aphid susceptible plant variety or into another soybean plant for mapping or validation studies or for enhancing the aphid resistance of a soybean plant. Introgression may refer to a breeding method for a incorporating a genetic trait, such as aphid resistance, including compositions and methods for using QTL, DNA markers including but not limited to simple sequence repeat (SSR), single nucleotide polymorphism analysis (SNP), random amplified polymorphic DNA (RAPD), amplified fragment length polymorphism analysis (AFLP), DNA fingerprinting, and the like for incorporating aphid resistant germplasm into a formerly aphid-susceptible plant variety.

As used herein, the terms "quantitative trait locus" and "QTL" refer to a genomic region including germplasm and gene(s) underlying a trait on which many genes act, in other words a genetic locus that affects a quantitative trait, for example, a QTL is associated with soybean cyst nematode resistance as shown herein and in U.S. Pat. No. 6,538,175, herein incorporated by reference.

As used herein, the term "QTL" (quantitative trait locus) in relation to a linkage, such as "QTL J aphid resistant germplasm and the like" refers to a polymorphic location of a banding pattern of a marker unique to the soybean plants showing a specific phenotypic trait, such as an aphid resistant phenotype, and other phenotypes as described herein.

As used herein, the terms "associated region gene" or "ARG" in reference to a mapped QTL refers to the actual germplasm, including one or more genes controlling or influencing a phenotype, in other words a "true QTL"

As used herein, the terms "restriction fragment length polymorphism" and "RFLP" refer to genetic variation between individuals such that DNA fragment sizes resulting from a difference in DNA sequence that affects the recognition sequence for restriction enzymes when cut by specific restriction enzymes. When a particular enzyme digests DNA the fragment sizes will differ depending on the presence or absence of the proper recognition sequence for the enzyme. Polymorphic sequences that result in RFLPs are used as markers on both physical maps and genetic linkage maps. RFLPs can be caused by a change in at least one nucleotide at a cutting site.

As used herein, the term "BARCSOYSSR" in reference to a molecular marker refers to a SSR marker, i.e. a DNA sequence resulting from PCR amplification using a 5' and a 3' primer pair (also called an upper or lower primer) for a specific BARCSOYSSR marker is found in The BARCSOYSSR Potential SSR Database as identified by Qijian Song and Perry Cregan (Crop Sci 2010, 50:1950-1960)//soybase.org/BARCSOYSSR/index.php, all of which are herein incorporated by reference. As one example, primer sequences for PCR amplification of a specific BARCSOYSSR marker, such as BARCSOYSSR_16_0371 where a SSR_start_position/SNP containing fragment_start_position is 6129244 and the SSR_end_position/SNP containing fragment_end_position is 6129297, the PCR product size is 348 nucleotides starting from the Upper_primer_sequence TTGTCAAATTTCTGAAGACTTATCG (SEQ ID NO:5) and Lower primer sequence TGTTGGAGAATATTGTTAGCACTCA (SEQ ID NO:6).

As used herein, the terms "amplified fragment length polymorphism" and "AFLP" refer to a highly sensitive method for detecting polymorphisms in DNA. Following restriction enzyme digestion of DNA, a subset of DNA fragments is selected for PCR amplification and visualization.

As used herein, the term "DNA fingerprinting" refers to techniques for uniquely identifying an individual among a population based on one's DNA. This type of method of isolating and visualizing sequences of DNA may show a unique pattern of DNA fragments revealed by Southern hybridization or by a polymerase chain reaction (PCR) analysis.

As used herein, the term "polymerase chain reaction" and "PCR" refer to the method of K. B. Mullis (U.S. Pat. Nos. 4,683,195 4,683,202, and 4,965,188, hereby incorporated by reference), which describe a method for increasing the concentration of a segment of a target sequence in a mixture of genomic DNA without cloning or purification. This process for amplifying the target sequence consists of introducing an excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term plant cell "compartments or organelles" is used in its broadest sense. As used herein, the term includes but is not limited to, the endoplasmic reticulum, Golgi apparatus, trans Golgi network, plastids, sarcoplasmic reticulum, glyoxysomes, mitochondrial, chloroplast, thylakoid membranes and nuclear membranes, and the like.

As used herein, the term "gene" refers to a nucleic acid (e.g., DNA or RNA) sequence that comprises coding sequences necessary for the production of RNA, or a polypeptide or its precursor (e.g., proinsulin). A functional polypeptide can be encoded by a full-length coding sequence or by any portion of the coding sequence as long as the desired activity or functional properties (e.g., enzymatic activity, ligand binding, signal transduction, etc.) of the polypeptide are retained.

As used herein, the term "gene" encompasses the coding regions of a structural gene and includes sequences located adjacent to the coding regions on both the 5' and 3' ends for a distance of about 1 kb on either end such that the gene includes the length of the full-length mRNA.

As used herein, the terms "allele" and "alleles" refer to each version of germplasm or a gene for a same locus that has more than one sequence. For example, an allele of a gene, i.e. two closely related sequences located in the same or similar position in a genome may have at least one nucleotide difference resulting in a different function.

As used herein, the term "portion" when used in reference to a germplasm or gene refers to a fragment of that germplasm or gene. The fragments may range in size from a few nucleotides to the entire germplasm or gene sequence minus one nucleotide.

As used herein, the terms "recessive," "recessive gene," and "recessive phenotype" refers to an allele that has a phenotype when two alleles for a certain locus are the same as in "homozygous" or as in "homozygote" and then partially or fully loses that phenotype when paired with a more dominant allele as when two alleles for a certain locus are different as in "heterozygous" or in "heterozygote."

As used herein, the terms "dominant," "dominant," and "dominant phenotype" refers to an allele that has an effect to suppress the expression of the other allele in a heterozygous (having one dominant and one recessive allele) condition. A dominate germplasm/gene may also show partial dominance or co-dominance, such that variations of the affect, such as aphid resistance, may be observed.

As used herein, the term "heterologous" when used in reference to a germplasm or genes or nucleic acid sequence refers to genetic material that has been manipulated in some way. For example, a heterologous genetic material or gene from one species is introduced into another species. For one example, a "heterologous gene" or "heterologous germplasm" in a plant may also include germplasm/genes native to one plant that has been altered in some way in another plant (e.g., mutated, added in multiple copies, linked to a non-native promoter or enhancer sequence, etc.). Examples of a heterologous germplasm/genes includes a germplasm/gene encoding an insecticidal protein, an herbicide resistant protein, or for providing an agronomic trait. Heterologous genes may comprise plant germplasm/gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

As used herein, the term "nucleic acid sequence," "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "structural" when used in reference to a gene or germplasm or to a nucleotide sequence refers to genetic material whose ultimate expression product is a protein (such as an enzyme or a structural protein), an rRNA, an snRNA, a tRNA, etc.

As used herein, the term "cDNA" refers to a nucleotide copy of the "messenger RNA" or "mRNA" for a gene. In some embodiments, cDNA is derived from (i.e. copied using deoxyribonucleotides) the mRNA. In some embodiments, cDNA is derived from genomic DNA sequences.

As used herein, the term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

As used herein, the term "polynucleotide" refers to refers to a molecule comprised of several deoxyribonucleotides or ribonucleotides, and is used interchangeably with oligonucleotide. Typically, oligonucleotide refers to shorter lengths, and polynucleotide refers to longer lengths, of nucleic acid sequences.

As used herein, the term "an oligonucleotide having a nucleotide sequence encoding a gene" or "a nucleic acid sequence encoding" a specified polypeptide refers to a nucleic acid sequence comprising the coding region of a gene or in other words the nucleic acid sequence that encodes a gene product. The coding region may be present either in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers, exogenous promoters, splice junctions, intervening sequences, polyadenylation signals, etc. or a combination of both endogenous and exogenous control elements.

As used herein, the term "exogenous promoter" refers to a promoter in operable combination with a coding region wherein the promoter is not the promoter naturally associated with the coding region in the genome of an organism. The promoter which is naturally associated or linked to a coding region in the genome is referred to as the "endogenous promoter" for that coding region.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular germplasm and gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the terms "in operable combination" and "in operable order" and "operably linked" refer to the linkage of nucleic acid sequences in such a manner that a nucleic acid molecule capable of directing the transcription of a given gene and/or the synthesis of a desired protein molecule is produced. As used herein, the term also refers to the linkage of amino acid sequences in such a manner so that a functional protein is produced.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, (1987), herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Maniatis, et al., supra (1987), herein incorporated by reference).

As used herein, the terms "promoter element," "promoter," or "promoter sequence" refer to a DNA sequence that is located at the 5' end (i.e. proceeds) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

As used herein, the term "regulatory region" refers to a gene's 5' transcribed but untranslated regions, located immediately downstream from the promoter and ending just prior to the translational start of the gene.

As used herein, the term "promoter region" refers to the region immediately upstream of the coding region of a DNA polymer, and is typically between about 500 by and 4 kb in length, and is preferably about 1 to 1.5 kb in length.

Promoters may be "constitutive" or "inducible." As used herein, the term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098, herein incorporated by reference), and ubi3 promoters (see e.g., Garbarino and Belknap, Plant Mol. Biol. 24:119-127 (1994), herein incorporated by reference). Such promoters have been used successfully to direct the expression of heterologous nucleic acid sequences in transformed plant tissue.

In contrast, an "inducible" promoter is one that is capable of directing a level of transcription of an operably linked nucleic acid sequence in the presence of a stimulus (e.g., heat shock, chemicals, light, etc.) that is different from the level of transcription of the operably linked nucleic acid sequence in the absence of the stimulus.

As used herein, the term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, et cetera.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species or from different species).

As used herein, the term "naturally linked" or "naturally located" when used in reference to the relative positions of nucleic acid sequences means that the nucleic acid sequences exist in nature in the relative positions.

As used herein, the term "vector" refers to nucleic acid molecules that transfer DNA segment(s). Transfer can be into a cell, cell-to-cell, etc.

As used herein, the term "vehicle" is sometimes used interchangeably with "vector."

As used herein, the term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment), *Agrobacterium* infection, and the like.

As used herein, the term "stable transfection" or "stably transfected" refers to the introduction and integration of foreign DNA into the genome of the transfected cell. As used herein, the term "stable transfectant" refers to a cell that has stably integrated foreign DNA into the genomic DNA.

As used herein, the term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes.

As used herein, the term "transient transfectant" refers to cells that have taken up foreign DNA but have failed to integrate this DNA.

As used herein, the term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973), herein incorporated by reference) has been modified by several groups to optimize conditions for particular types of cells. The art is well aware of these numerous modifications.

As used herein, the terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, herein incorporated by reference), and are commercially available (e.g., the helium gas-driven microprojectile accelerator (PDS-1000/He, BioRad).

As used herein, the term "transgene" refers to a foreign gene that is placed into an organism by the process of transfection.

As used herein, the term "foreign gene" refers to any nucleic acid (e.g., gene sequence) that is introduced into the genome of an organism by experimental manipulations and may include gene sequences found in that organism so long as the introduced gene does not reside in the same location as does the naturally-occurring gene, i.e. a heterologous gene.

As used herein, the terms "transformants" or "transformed cells" include the primary transformed cell and cultures derived from that cell without regard to the number of transfers. Resulting progeny may not be precisely identical in DNA content, due to deliberate or inadvertent mutations. Mutant progeny that have the same functionality as screened for in the originally transformed cell are included in the definition of transformants.

As used herein, the term "wild-type" when made in reference to germplasm and/or a gene refers to genetic material common throughout a population of non-aphid resistant soybean plants, such as aphid susceptible E00003 soybean plants. As used herein, the term "wild-type" when made in reference to a germplasm/gene product refers to a germplasm/gene product common throughout an outbred population of non-aphid resistant soybean plants. A wild-type germplasm/gene is that which is most frequently observed in a non-aphid resistant soybean plant population and is thus arbitrarily designated the "normal" or "wild-type" form of the gene.

As used herein, the terms "modified" or "mutant" when made in reference to a gene or germplasm or to a product of the genetic material refers to a product which displays modifications in sequence and/or functional properties (i.e., altered characteristics) when compared to the wild-type product. Thus, the terms "variant" and "mutant" when used in reference to a nucleotide sequence refer to an nucleic acid sequence that differs by at least one or more nucleotides from another, usually related nucleotide acid sequence. A "variation" is a difference between two different nucleotide sequences; typically, one sequence is a reference sequence, such as Williams82 soybean genetic sequences as used herein.

As used herein, the terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) *Molecular Cloning: A Laboratory Manual*, Cold Spring Harbor Press, NY, pp 9.31-9.58, herein incorporated by reference).

As used herein, the term "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al. supra, pp 7.39-7.52, (1989), herein incorporated by reference).

As used herein, the terms "protein," "polypeptide," "peptide," "encoded product," "amino acid sequence," are used interchangeably to refer to compounds comprising amino acids joined via peptide bonds and. A "protein" encoded by a gene is not limited to the amino acid sequence encoded by the gene, but includes post-translational modifications of the protein. Where the term "amino acid sequence" is recited herein to refer to an amino acid sequence of a protein molecule, the term "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include but not limited to glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence.

As used herein, the term "isolated" when used in relation to a nucleic acid such as an isolated DNA molecule or polypeptide, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

As used herein, an "isolated soybean cultivar" refers to a soybean cultivar or plant of the present invention removed from a Soybean Germplasm Collection, as isolated or separated by a distinguishing trait not found in other cultivars (or accessions), is at least one selected cultivar of 10 other cultivars, is at least one selected cultivar of 100 other cultivars, is at least one selected cultivar of 1000 other cultivars in a collection.

As used herein, an "isolated soybean plant" refers to choosing one plant from a population of plants, for example, the choice of an F4 plant E08934 from a population of F4 plants, or choosing one plant from an F3 population of E12902 plants.

As used herein, an "Asian soybean cultivar" refers to a cultivar originating from G. soya plants, for example, having vinineess and small seeds.

As used herein, the term "portion" when used in reference to a protein (as in "a portion of a given protein") refers to fragments of that protein. The fragments may range in size from four amino acid residues to the entire amino acid sequence minus one amino acid.

As used herein, the term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, the term "positional cloning" refers to an identification of a germplasm regions and genes based on its physical location in the genome.

As used herein, the term "elite plant," "elite soybean plant," "elite soybean plant line," or "elite soybean plant cultivar" refers to any plant, plant line or plant cultivar, respectively, that has resulted from breeding and selection for superior agronomic performance. For example, an elite soybean plant may be aphid resistant plants described herein, in addition to E00003 plants having desired agricultural traits. Elite soybean plants also include transgenic plants comprising transgenes for conferring a desired trait. Therefore, an "elite soybean germplasm" refers to genetic material for providing the desired traits of the elite plants. Examples of elite soybean plants for use in breeding aphid resistant plants having agriculturally desired traits includes but is not limited to soybean plant cultivars comprising a transgene that provides an agriculturally desired trait such as resistance to herbicides, nematodes, fungi, or an agronomic traits, including but not limited to soybean plants such as PI257345 and its progeny 51346, PI71506, Hutcheson, Resnik, Lincoln, Richland, Patoka, PI 81041, Illini, PI 54610, PI 88788, Mukden, Palmetto, Haberlandt No. 171, PI 257345, PI 71506, Lincoln, Mandarin (Ottawa), PI 90763, CNS, PI 209332, Richland, Tokyo, S-100, Minsoy, Ogden, Noir 1, A.K. (Harrow), Archer, Dunfield, Evans, Mukden, Clark, Jackson, Harosoy, Illini, Essex, Roanoke, PI 88788, Peking, Asgrow AG4201, Asgrow AG3703, Croplan Genetics RC4432, FFR RT446, HARTZ™ variety H4994, HARTZ™ variety H5218, HARTZ™ variety H5350, HARTZ™ variety H5545, HARTZ™ variety H5050, HARTZ™ variety H5454, HARTZ™ variety H5233, HARTZ™ variety H5488, HARTZ™ variety HLA572, HARTZ™ variety H6200, HARTZ™ variety H6104, HARTZ™ variety H6255, HARTZ™ variety H6586, HARTZ™ variety H6191, HARTZ™ variety H7440, HARTZ™ variety H4452 ROUNDUP READY™, HARTZ™ variety H4994 ROUNDUP READY™, HARTZ™ variety H4988 ROUNDUP READY™, HARTZ™ variety H5000 ROUNDUP READY™, HARTZ™ variety H5147 ROUNDUP READY™, HARTZ™ variety H5247 ROUNDUP READY™, HARTZ™ variety H5350 ROUNDUP READY™, HARTZ™ variety H5545 ROUNDUP READY™, HARTZ™ variety H5855 ROUNDUP READY™, HARTZ™ variety H5088 ROUNDUP READY™, HARTZ™ variety H5164 ROUNDUP READY™, HARTZ™ variety H5361 ROUNDUP READY™, HARTZ™ variety H5566 ROUNDUP READY™, HARTZ™ variety H5181 ROUNDUP READY™, HARTZ™ variety H5889 ROUNDUP READY™, HARTZ™ variety H5999 ROUNDUP READY™, HARTZ™ variety H6013 ROUNDUP READY™, HARTZ™ variety H6255 ROUNDUP READY™, HARTZ™ variety H6454 ROUNDUP READY™, HARTZ™ variety H6686 ROUNDUP READY™, HARTZ™ variety H7152 ROUNDUP READY™, HARTZ™ variety H7550 ROUNDUP READY™, HARTZ™ variety H8001 ROUNDUP READY™ (HARTZ™ SEED, Stuttgart, Ark., USA); A0868, AG0901, A1553, A1900, AG1901, A1923, A2069, AG2101, AG2201, A2247, AG2301, A2304, A2396, A2401, AG2501, A2506, A2553, AG2701, AG2702, AG2703, A2704, A2833, A2869, AG2901, AG2902, AG2905, AG3001, AG3002, AG3204, A3237, A3244, AG3301, AG3302, A3404, A3469, AG3502, AG3503, A3559, AG3601, AG3701, AG3704, AG3750, A3834, AG3901, A3904, A4045 AG4301, A4341, AG4401, AG4501, AG4601, AG4602, A4604, AG4702, AG4901, A4922, AG5401, A5547, AG5602, A5704, AG5801, AG5901, A5944, A5959, AG6101, AJW2600CCOR, FPG26932, QR4459 and QP4544 (Asgrow Seeds, Des Moines, Iowa, USA); DKB26-52, DKB28-51, DKB32-52, DKB35-51 and DeKalb variety CX445 (DeKalb, Ill., USA); 91B91, 92B24, 92B37, 92B63, 92B71, 92B74, 92B75, 92B91, 93B01, 93B11, 93B26, 93B34, 93B35, 93B41, 93B45, 93B51, 93B53, 93B66, 93B81, 93B82, 93B84, 94B01, 94B32, 94B53, 95B71, 95B95, 9306, 9294, and 9344 (Pioneer Hi-bred International, Johnstonville, Iowa, USA), A2704-12, A2704-21, A5547-35 (Aventis CropScience), A5547-127, GU262, W62, W98, (Bayer CropScience (Aventis CropScience (AgrEvo))), G94-1, G94-19, G168 (DuPont Canada Agricultural Products), GTS 40-3-2 (Monsanto Company), OT96-15 (Agriculture & Agri-Food Canada), Maple Glen, PI361088B, Ohio FG1, Agracola Farms AF271, Burtch Seed BBF44, H.A.P.I. Ohio GL2930, LG Seed EX230FG, Wellman WFG268, Line Trelay 230 (comprising *Phytophthora* resistance germplasm), Trelay 271 (comprising *Phytophthora* resistance germplasm), and the like. For the purposes of the present inventions, an elite soybean plant also refers to plants related to line E08934, line E12902, accession PI 567537 and accession PI 567585A comprising aphid resistant germplasm of the present inventions.

BRIEF DESCRIPTION OF THE DRAWINGS

FIGS. 1A-1F shows exemplary phenotypic distributions of soybean aphid damage indices for a mapping population of 140 $F_3$-derived lines from an E00003×E08934 cross (FIGS. 1A-1D), and of a validation population of 252 $F_2$-derived lines from an E08929×E08934 cross (FIGS. 1E-1F). Parents are indicated by arrows. FIG. 1A shows results of greenhouse trial during year 2. FIGS. 1B-1D shows results of three successive years of caged field trials (trails 1-3). FIGS. 1E-1F shows results for a validation population from the last two years of field trials for comparison.

FIGS. 2A-2H shows chromosomal locations of soybean aphid-resistant loci detected in the mapping population E00003×E08934 and the validation population E08929×E08934 with the composite interval mapping method with 1000 permutations. 1-LOD and 2-LOD intervals of each locus are indicated by thick and thin bars. Threshold line was drawn with P=0.01 from 1000 permutations. FIG. 2A shows a map of linkage group A2 (Chromosome 8) with the aphid resistance locus on the right from four trials in the mapping population, with LOD score plot on the right. FIG. 2B shows a soybean consensus map of linkage group A2 (Chromosome 8) (Song et al., 2004). FIG. 2C shows a map of linkage group A2 (Chromosome 8) with the aphid resistance locus on the right from two field trials in the validation population, with LOD score plot on the right. FIG. 2D shows a map of linkage group J (Chromosome 16) with the aphid resistance locus on the right from four trials in the mapping population, with LOD score plot on the right. FIG. 2E shows a soybean consensus map of linkage group J (Chromosome 16) (Song et al., 2004). FIG. 2F shows a map of linkage group J (Chromosome 16) with the aphid resistance locus on the right from two field trials in the validation population, with LOD score plot on the right. FIG. 2G shows a map of linkage group M (Chromosome 7) (i.e. rag1c region) with the aphid resistance locus on the right from two field trials in the validation population, with LOD score plot on the right. FIG. 2H shows a soybean consensus map of linkage group M (Chromosome 7) (Song et al., 2004).

FIG. 3A shows the average damage indices (DI) of genotypic group AA, AB and BB of marker Satt540 (close to rag1c), three bars on the left are from field trial 2, and bars on the right are from field trial 3. FIG. 3B shows the average damage indices (DI) of genotypic group AA, AB and BB of marker Satt209 (close to Rag6), three bars on the left are from the field trial 2, and bars on the right are from field trial 3. FIG. 3C shows the average damage indices (DI) of genotypic group AA, AB and BB of marker BARC-SOYSSR_16_0371 (close to Rag3c), three bars on the left are from the first field trial, and bars on the right are from field trial 3.

FIG. 6A shows a histogram of single-base extension y values generated from resequencing the base adjacent to homozygous SNPs (defined as SNPs with y of 0.2 or y as 0.8 as observed in FIGS. 6B and 6C; total of 65,518 loci). SNP loci containing a cytosine or guanine adjacent to the SNP site are shown in green, and loci with an adenine or thymine are shown in red. SBE y values can be calculated as follows: 2/πC×arctan (Agreen/Ared) or 2/πC×arctan (Bgreen/Bred)) depending on homozygosity state (A/A or B/B) of SNP. FIGS. 6B and 6C show histograms of ASPE y values (2/πC×arctan (Bgreen/Agreen) or 2/πC×arctan (Bred/Ared)) generated from the green channel (48,768 loci; FIG. 6B) or red channel (52,803 loci; FIG. 6C) using the two-color SBE reaction. The green or red channel was used to analyze the SNP depending on the adjacent base. Data in these three histograms are from a single representative array experiment.

FIG. 8A shows the number of lines with various aphid resistance scores for the mapping population (PI 567537×E00003) rated in a greenhouse trial. FIG. 8B shows the number of lines with various aphid resistance scores for the mapping population (PI 567537×E00003) rated the field trial. FIG. 8C shows the number of lines with various aphid resistance scores for the validation population (PI 567537× Skylla) with rating in a field trial.

FIG. 9A shows a map of chromosome 16 (linkage group J) for data from the mapping population PI 567537×E00003 with the aphid resistance locus on the left. FIG. 9B shows a map of chromosome 16 (linkage group J) on the consensus map (Song et al. 2004). FIG. 9C shows a map of chromosome 16 (linkage group J) for data from the validation population PI 567537×Skylla with the aphid resistance locus on the right.

FIG. 10A shows DI scores for 070082 F4:5 recombinant inbred lines (RILs) in the validation population in relation to PI 567585A and Skylla. FIG. 10B shows 070016 PI 567598B $F_{3:4}$ RILs mapping population in relation to PI 567585A and IA 2070.

FIG. 11A shows an aphid resistance germplasm/gene position in the mapping population for greenhouse and field trials. FIG. 11B shows a relevant segment of the soybean LG according to the integrated soybean map of Song et al., (2004). FIG. 11C shows the aphid resistance germplasm/gene position in the validation population.

DETAILED DESCRIPTION OF THE INVENTION

Figure 1D:
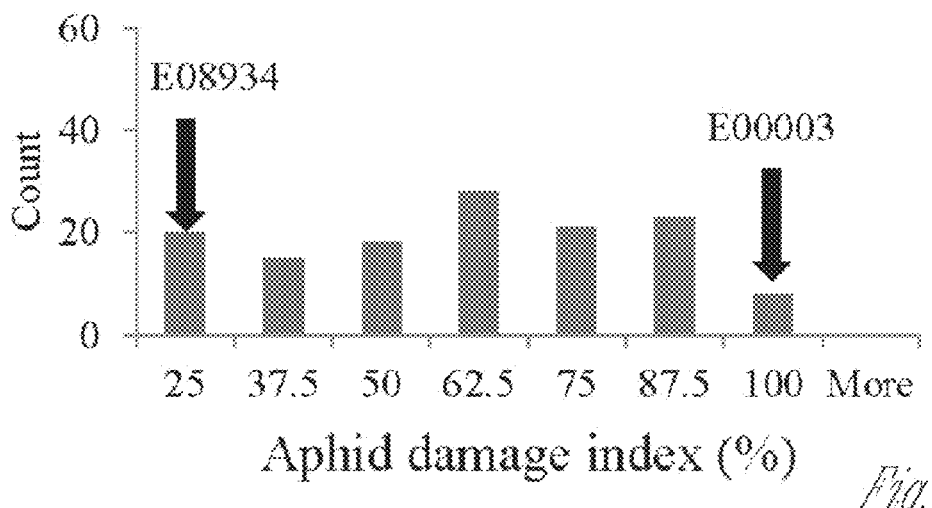

The present invention relates to compositions and methods for identifying and using new germplasm providing aphid resistant in soybean plants, particularly for use in breeding soybean plant lines and cultivars representing specific set(s) of germplasm. In particular, aphid resistant soybean plants comprising new sources of germplasm and stacked germplasm/genes conferring enhanced aphid resistance are provided. These enhanced aphid resistant plants find use in breeding soybean plant lines (cultivars) including lines having superior aphid resistance. Such enhanced plant cultivars are contemplated to find use for more effective resistance of aphids. Further, the inventions relate to providing new aphid resistant germplasm identified by markers associated with plants having decreased damage from aphid feeding, as well as plants having enhanced tolerance to aphid infestation. Even further, the invention relates to compositions and methods for using genetic markers in breeding methods for producing plants and plant cultivars having increased resistance to aphid damage and increased tolerance to aphids, while retaining and acquiring desired agronomic traits. In some embodiments, at least one region of aphid resistant germplasm from one aphid resistant plant line source may be combined with another region of aphid resistant germplasm from a different plant line source for providing a soybean plant cultivar having enhanced aphid resistance.

Specifically, this invention discloses novel soybean lines and cultivars including transgenic, hybrid, outcrossed, backcrossed, inbred and self-fertilized progeny comprising soybean aphid resistant soybean germplasm, specifically founder soybean plants of line E08934 *Glycine max* (L.) Merr. max, PI 567537 and PI 567585A and their progeny are disclosed. More specifically, the E12902 line is disclosed herein comprising soybean aphid resistant soybean germplasm that is stably transmitted to its progeny. The invention relates to the seeds and plants of novel aphid resistant lines and cultivars, to the groups of plants comprising aphid resistant lines and cultivars and to methods, such as cultivar E08934 or cultivar E12902, for producing an aphid resistant soybean plant obtained by crossing founder aphid resistant soybean plants (i.e. line E08934, line E12902, accession cultivar PI 567537 and accession cultivar PI 567585A) and plants derived from these lines and accessions (i.e. progeny pants, hybrid plants, etc.) comprising aphid resistant germplasm, with another soybean variety having desirable agronomic traits, and in some embodiments, including other types of aphid resistant soybean plants such as plants of accessions PI 567543C, PI 567597C, PI 567541B, PI 567598B, and plants having aphid resistant germplasm derived from these plants), including backcrosses with the founder cultivars, backcrosses with the original soybean variety, and further, crosses within and between a filial generation (F), for example, one or more of an F1-F7, or more generations, including but not limited to inbreeding using self-pollination, crossbreeding of inbred plants, outbreeding, etc. The present invention further relates to the generation of a commercially viable aphid resistant early maturing soybean seed and plant produced by the compositions and methods of the present invention. Additionally, the present invention relates to the generation of molecular markers, including SSR and other DNA markers for identifying linkage groups comprising aphid resistant germplasm, for example, sequences for PCR primers used to amplify SSR loci in Soybean, Zhu et al. Genetics 2003 163(3):1123-34, for genes relating to aphid resistance and using molecular marker analysis for identifying and using genes relating to aphid resistance.

In the year 2000, the soybean aphid (*Aphis glycines* Matsumura) was reported found in the Midwest United States, since then it has spread to most soybean-growing states and became a major destructive insect pest in the USA (Jun et al., 2012; Kim et al., 2008; Mian et al., 2008a; Ragsdale et al., 2004; Zhang et al., 2010, herein incorporated by reference). The soybean aphid sucks plant sap and causes plant damage. Symptoms like curling, witling, yellowing, or puckered leaves often occur on heavily infested plants stunting plant growth and causing plant death in heavy infestations (Jun et al., 2012; Zhang et al., 2010, herein incorporated by reference). Also sooty mold, a charcoal-colored residue, often appears after plants are heavily infested.

A soybean aphid infestation reduces the oil content and greatly affects the seed quality (Beckendorf et al. 2008, herein incorporated by reference). Aphid infestation caused considerable yield loss on soybean seed yield where yield losses reported due to soybean aphid infestations in Minnesota were more than 50% (Ostlie, 2002, herein incorporated by reference) and 58% in soybean-growing provinces of China (Wang et al., 1996, herein incorporated by reference). Beckendorf et al. (2008, herein incorporated by reference) estimated the potential yield loss due to the soybean aphid would reach up to 88%. Moreover, the various soybean aphid transmitted viruses are also a major concern for soybean producers (Clark and Perry 2002; Davis et al. 2005, all of which are herein incorporated by reference). Other severe effects on seed quality losses and virus-transmission were reported due to soybean aphid infestation (Clark and Perry, 2002; Hartman et al., 2001; Hill et al., 2001; Iwaki et al., 1980; Jun et al., 2012; Mueller and Grau, 2007, all of which are herein incorporated by reference). Soybean aphid as a phloem feeder transmitted plant virus, such as soybean mosaic virus, Tobacco ring-spot virus to soybean, and Potato virus Y to healthy potato (Clark and Perry, 2002; Davis et al., 2005; Pedersen et al., 2007, all of which are herein incorporated by reference). The most common means to control aphids is chemical control that is expensive, causes environmental pollution and kills beneficial insects. Insecticide application among the 12 north-central soybean growing states in the United States increased from 4 to 14 M ha year-1 due to the rapid outbreak of soybean aphids (O'Neal and Johnson, 2010, herein incorporated by reference). However effectiveness is highly variable and often ineffective with high costs of numerous insecticide applications. Since chemical insecticides add more cost and may harm beneficial insects and the environment, breeding host resistance soybean plants is contemplated as part of effective integrated pest management (IPM) against soybean aphids (O'Neal and Johnson, 2010). Further contemplated is enhancing plant resistance in order to eliminate the use of chemical insecticides.

Thus, compared with the use of insecticide control alone, the inventors contemplate that by enhancing host-resistance of plants, the use of these aphid resistant plants would be more effective, economical, i.e. cost-effective, and environmentally sound, i.e. friendly, for soybean aphid control compared with the chemical control. Thus the use of these plants having enhanced aphid resistance should reduce the amount of insecticides used, thus reducing environmental pollution and loss of beneficial (bystander/nontarget insects). Further, an integrated pest management strategy is contemplated for use combining insecticide usage with plants having aphid resistance in order to control the soybean aphids, i.e. lessen and prevent aphid damage to plants and/or crop yield.

However, commercial varieties having desired agronomic traits, such as having optimal growth characteristics for a particular growing region, desirable phenotypic qualities, resistance to other types of pests, high seed yield, high oil seed yield, etc. with a need for enhanced soybean aphid resistance in aphid resistant soybean plants. Aphid resistance was considered a quantitative trait with continuous phenotype distribution of damage index (Mensah et al., 2005, herein incorporated by reference). There are two types of host resistance to insects: antibiosis and antixenosis (Painter 1951, herein incorporated by reference). Antibiosis affects insect biology and reduces the amount of insects. Antixenosis affects insect behavior and is expressed as non-preference for the insects. Research groups in the United States discovered several aphid-resistant germplasm accessions (Hill et al., 2004; Mensah et al., 2005; Diaz-Montano et al., 2006; Hesler et al., 2007; Hesler and Dashiell 2008; Mian et al., 2008a, all of which are herein incorporated by reference). Genetic studies showed that aphid resistance in later maturing groups of soybean plants was mostly controlled by a single dominant gene (Hill et al., 2006a, b, 2009; Kang et al., 2008), i.e. Rag1. The antibiosis gene Rag1 in 'Dowling' and another antibiosis gene (Rag) in 'Jackson' were both mapped with molecular markers to the same genomic region on chromosome 7 [linkage group (LG) M] (Li et al., 2007, herein incorporated by reference). The antibiosis gene Rag2 in PI 243540 was located on chromosome 13 (LG F) (Mian et al., 2008b, herein incorporated by reference). However, in field trials soybean plants having these genes did not provide broad aphid resistance (such as resistance to more than one aphid biotype) and failed to provide aphid resistance to aphid isolates.

In contrast, the antibiosis resistance in other soybean plant lines, such as PI 567541B and PI 567598B were each controlled by two recessive genes (Mensah et al., 2008, herein incorporated by reference). Two genes in PI 567541B were located on chromosomes 7 and 13 (LG M and F) (Zhang et al., 2009, herein incorporated by reference). The germplasm/genes on chromosome 7 (LG M) that mapped to the same genomic region as Rag1 and was designated rag1_provisional, i.e. rag1c. The germplasm/gene on chromosome 13 (LG F) was designated rag4 (Zhang et al., 2009, herein incorporated by reference). An antixenosis gene in PI 567543C, Rag3, was mapped on chromosome 16 (LG J) (Zhang et al. 2010, herein incorporated by reference). Additionally, significant germplasm/gene interaction for increased aphid resistance in soybean plants was found between those two genes identified in PI 567541B (Zhang et al., 2009). Soybean plants having these genes frequently showed broad aphid resistance to more than one aphid biotype or isolate, including aphid resistance to certain aphid biotypes.

Collectively, at least five genetic loci, together with at least seven alleles, Rag1, rag1, Rag2, Rag3, rag3, rag4 and Rag5 were reported for aphid resistance with either antixenosis or antibiosis resistance in soybean plants (collectively, Hill et al., 2006a; Hill et al., 2006b; Jun et al., 2012; Kang et al., 2008; Li et al., 2007; Mian et al., 2008; Zhang et al., 2009; Zhang et al., 2010, all of which are herein incorporated by reference). However, because of the capability of soybean aphids to have or develop populations that become insensitive, i.e. overcome or break plant aphid resistance, there is a continued need to develop aphid resistant soybean plants having more effective genetic resistance and/or design soybean plants to have specific aphid resistant genes for providing resistance to specific aphid biotypes. Further, soybean plants bred to have specifically stacked and/or pyramided soybean aphid resistant genes for enhanced aphid resistance are contemplated for use in breeding commercial varieties adapted for specific growing regions. Even further, soybean plants bred to have specifically stacked and/or pyramided soybean aphid resistant genes for resisting aphid biotypes are contemplated.

Moreover stacking specific aphid resistant genes or alleles are contemplated for use in providing soybean plants having enhanced aphid resistance, including broad aphid resistance and resistance to specific aphid biotype) or durable aphid resistance (aphid resistance lasting for numerous generations, i.e. plantings in the same area). Thus plants, germplasm and genes of the present inventions can be used to develop soybean varieties with resistance to soybean aphids in order to deter aphid infestations and destruction of soybean plants for increasing soybean plant growth and reproduction, including seed yield, wherever soybean aphids are present.

Therefore, the inventors screened soybean plants from the Soybean Collection stored and maintained by the National Plant Germplasm System as part of the United States Department of Agriculture Agricultural Research Service. After extensive screening using the method as described by Mensah et al. (2005, herein incorporated by reference), *Glycine soja* accessions 85-32, PI 567537 and PI 567585A plants were discovered as having aphid resistance. Therefore, three new sources of aphid resistance with resistance genes originated from wild or domesticated soybean pants were identified. The resistance genes from these sources were mapped and contemplated as either new genes or alleles at specific loci. In addition at least one germplasm/ genes from the wild soybean mapped to a new locus that is different from known aphid resistance genes.

Thus a new aphid resistance germplasm/gene locus provisionally called Rag6, conferred antibiosis aphid resistance that was superior to previously tested aphid resistant germplasm. When a soybean plant line 19 having both Rag6 and Rag3c was compared to a soybean plant line 131 containing Rag6 alone or soybean plant line 24 containing Rag3c alone, the plants having both Rag6 and Rag3c containing germplasm showed enhanced aphid resistance in cage tests during field trials when compared to plants having one of these genes, see, FIG. 5. In no-choice tests plants having Rag6 alone showed superior aphid resistance when compared to plants from PI 567598B and plants having Rag3c alone. Furthermore, when Rag6 was genetically stacked with at least one other aphid resistance gene, i.e. Rag3b from plant line E08934 (or line E12902), the resulting plants showed enhanced aphid resistance when compared to plants having one of these genes. Therefore, stacking and pyramiding multiple resistance genes in the same plant is contemplated in one embodiment, as a strategy to make aphid resistance in soybean plants more durable and/or broader, for example, broadening the resistance of the soybean plants to resist more than one type of aphid population (biotype). Therefore, the aphid resistant germplasm described herein is contemplated for use in commercial soybean plant variety development. See, Tables 5 and 11 for exemplary aphid resistant sources which are contemplated to find use in embodiments of aphid resistant plants of the present inventions.

Specifically, new soybean plants discovered to have aphid resistant germplasm are cultivars: line E08934, line E12902, developed at Michigan State University, accessions PI 567537, and PI 567585A. The resistance genes from these sources were mapped using SSR and SNP genotyping. One of the new genes, i.e. Rag6 was discovered in soybean cultivar E08934 and progeny line E12902. Rag6 was unique from other aphid resistance genes when it was mapped to a different map location than known aphid resistance genes. Data obtained during the development of the present inventions showed that Rag6 aphid resistance is a partially dominant trait, i.e. co-dominant.

The following describes these new plants and genes for use in making aphid resistant soybean plants of the present inventions.

I. Aphid Resistant Soybean Plants of the Present Inventions.

The following resistance sources are described for use in providing aphid resistant germplasm, including genes and alleles. In particular, resistant sources are provided as seeds and plants, including *Glycine max* line E08934, line E12902, PI 567537 and PI567585A soybean plants.

A. Soybean Plant Line Cultivar E08934 *Glycine max* was Derived from a *Glycine soja* Plant Source.

Aphid resistant soybean plant line cultivar E08934 and aphid resistant soybean plant line cultivar E12902, comprising aphid resistant germplasm from *Glycine (G.) soja* soybean plants were developed by the inventors as described herein. An accession of wild type soybean, *Glycine soja* line 85-32, was found resistant to aphids along with *G. soja* accessions 85-39 and 85-1, Yang et al. (2004), herein incorporated by reference. However, *G. soja* soybean plants are not used for commercial agriculture due to undesirable agronomic characteristics, such as vining, small seed sizes, etc. compared to commercial *G. max* varieties having desirable agronomic traits such as a lack of vining, large seed sizes, etc. Therefore in order to move (and adapt) the aphid resistant germplasm into a *G. max* genetic background, 85-32 soybean plants were crossed with elite Jiyu 71 soybean plants. Jiyu 71 is an aphid susceptible soybean (*Glycine max*) variety having acceptable agronomic traits. In addition to screening progeny plants for aphid resistance an additional selection criteria was based upon observation of plants that retained a high percentage of elite genome. As an example, a progeny plant that demonstrated aphid resistance was visually examined for elite genome as demonstrated by having desirable agronomic traits more like the *G. max* elite parent, such as absence of vining After the first (initial) parental cross (Jiyu 71×85-32), $F_1$ progeny plants were backcrossed with Jiyu 71 plants for providing a $F_2$ generation (F1 of backcross 1, i.e. BC1F1), where Jiyu 71 was used as the female parent and an 85-32 plant was used as the male parent. These $F_2$ plants were screened for aphid resistance using the inventors' established screening method (Mensah et al., 2005, herein incorporated by reference). An $F_2$ plant that demonstrated aphid resistance (and desired agronomic characteristics) was used as a male parent to backcross to Jiyu 71 (the female parent) which produced F3 seed and F3 plants (BC2F1). A $F_1$ plant from this second backcross (BC2F1) with a female Jiyu 71 parent was selfed (i.e. made to self-pollinate) such that pollen from the same plant as the ovules was used to produce $F_2$ seeds. These $F_2$ seeds were planted to produce $F_2$ plants (BC2F2). These $F_2$ plants were screened for aphid resistance using the inventors' established screening method (Mensah et al., 2005, herein incorporated by reference). After section of aphid resistant F2 plants demonstrating desired elite germplasm, each plant was selfed for producing F3 seed (BC2F3). A single $F_3$ seed from each F2 plant having aphid resistance was planted to produce $F_3$ plants (BC2F3). $F_3$ plants were then evaluated for aphid resistance using the same method used for selection of the $F_2$ plants for use further breeding methods. After section of aphid resistant F3 plants that demonstrated expression of desired elite germplasm, each plant was selfed for producing F4 seed (BC2F4).

One seed from each F4 plant was used for growing F4 plants (BC2F4). $F_4$ plants were then evaluated for aphid resistance and desired elite agronomic traits as described above. One of the aphid resistant $F_4$ plants having desired elite soybean plant agronomic traits was selected and designated as plant E08934. This plant E08934 was selfed for production of seed that was harvested then used to grow the first generation of line E08934 ($F_{4:1}$), an F4 derived line. Line E08934 was maintained by planting a sub-sample (less than the total harvested number of seeds) of the F4 derived seeds whose plants were cross-pollinated for producing the next generation of F4 derived seeds and F4 derived plants (e.g. $F_{4:2}$, $F_{4:3}$, $F_{4:4}$, $F_{4:5}$, $F_{4:6}$, $F_{4:7}$, etc.) and re-evaluated for aphid resistance for demonstrating that progeny plants maintained aphid resistance along with desired *G. max* elite agronomic traits.

Therefore, soybean plant line E08934 was derived (produced) from a single $F_4$ plant selection (i.e. plant number E08934) that is resistant to soybean aphids. In other words, E08934, a single plant selection derived from the backcross of Jiyu 71×(Jiyu 71×85-32) was the result of adapting (moving) the aphid resistance genes from *G. soja* to a new soybean plant variety having a cultivated background, i.e. to a *Glycine max* background.

The aphid resistance germplasm in E08934 was additionally conferred to progeny plants (such that progeny plants were derived from E08943 plants including the E12902 line) or providing a mapping population that consisted of 140

F$_3$-recombinant inbred lines developed by crossing the F4 derived E08934 plants with aphid susceptible line E00003 (*Glycine max*). Aphid resistance phenotyping was conducted one season in greenhouse and three seasons in field cage. The broad-sense heritability from field trials was 0.84. From the result of genotyping eight resistant and eight susceptible lines on 6K soybean SNP Beadchip, three genomic regions, 38.8 to 43.9 mega base (MB) on Chromosome (Chr.) 8 (linkage group (LG) A2), 4.8 to 11.3 MB and 24.6 to 28.5 MB on Chr. 16 (LG J), were detected with clusters of polymorphic SNPs consistent with aphid damage index.

After genotyping the population using polymorphic SSRs from these three regions, integrated with SNPs from Tag-Man® allele specific, two major QTLs were detected in intervals of 13.5 cM between Sat_382 and Satt455 on Chr. 8, and 3.5 cM between Satt693 and Sat_370 on Chr. 16, respectively. The locus on Chr. 8 explained 40.8% of the phenotypic variance in the greenhouse trial, and 46.4, 19.5 and 39.1% in field trials. The locus on Chr. 16 explained 12.5 to 22.9% of the phenotypic variance.

Further, these two loci were both confirmed as present in a validation population that consisted of 252 F$_2$-derived lines from crossing line E08934 with line E08929, an accession from PI 567541B. Non-choice test indicated both loci are antibiotic resistant to aphids. The novel locus between Sat_382 and Satt455 on Chr. 8 (LG A2) was denoted as Rag6, since it showed significant dominant effect in the validation population (P<0.05). An allelism test showed the locus within Satt693 and Sat_370 on Chr. 16 (LG J) (i.e. Rag3c) was close to Rag3 from PI 567543C, with 2.2% of the progeny having intermediate-resistant to aphids.

When moving desired germplasm from one species to another there is a potential for retention of undesirable genes in the progeny plants, i.e. sometimes referred to as linkage drag. Linkage drag should be reduced by the use of marker assisted selection (Narvel et al., (2001) Crop Science 41:1931-1939, herein incorporated by reference). For one example, when moving aphid resistant genes from a *G. soja* species to a *G. max* species as described herein, there is a possibility of moving undesirable agronomic traits along with the desired aphid resistant germplasm. With the discovery that SNPs identified herein were closely linked to resistance loci the inventors' contemplated that by using breeding methods described herein further comprising marker assisted selection, for example, using a marker identified herein for identifying the presence of aphid resistant germplasm, there would be further reduced linkage drag when breeding soybean plant varsities (i.e. *G. max*) for aphid resistance using germplasm from exotic wild type soybean (*G. soja*) as compared to backcrossing and selection of plants without using such markers. Thus in one embodiment, marker assisted selection is contemplated for use in breeding new aphid resistant *G. max* soybean commercial plant varieties having agronomic traits of the elite soybean parent using aphid resistant germplasm derived from *G. soja* plants varieties having desired agronomic traits. In further embodiments, the elite variety soybean parent having desired agronomic traits for the new soybean plant line is selected from but not limited to the varieties listed herein. In some embodiments, the source of *G. soja* aphid resistant germplasm is a *G. max* line comprising *G. soja* germplasm. In other embodiments, the source of *G. soja* aphid resistant germplasm is a *G. soja* plant. In yet other embodiments, the source of *G. soja* germplasm is a hybrid soybean plant having characteristics of both wild *G. soja* and *G. max* agronomic traits.

Thus, a novel aphid resistance Rag6 germplasm/gene(s) from a wild species of soybean *Glycine soja* was mapped in an interval between marker Sat_382 and Satt455 or between marker Sat_382 and Satt538 on Chromosome 8 in the F$_3$-derived mapping population. The interval between marker Sat_382 and Satt455 is equivalent to 13.5 cM on the soybean consensus map (Song et al., 2004). The location was further confirmed in a validation population when the germplasm/gene(s) mapped to the same interval. One aphid resistance gene, Rag5, was mapped to Chr. 8 and located between Satt437 and Satt327 (Jun et al., 2012, herein incorporated by reference). In contrast, the location of Rag6 was different from that of Rag5, because the marker Satt209 closest to the peak of LOD score was 18.6 cM distance away from Satt327, based on the soybean consensus map (Song et al., 2004, herein incorporated by reference). When comparing the Rag6 location to other genes in the area, Meng et al. (2011), herein incorporated by reference, reported one QTL qRa_1 located near marker Satt470 on Chr. 8, conferring aphid resistance in a high isoflavone content variety "Zhongdou27". Compared to the consensus map (Song et al., 2004) Rag6 was about 6.2 cM away from marker Satt470. Therefore, the inventors provisionally named this germplasm/genes Rag6 for presenting to the Soybean Genetics Committee.

In the validation population, distribution of phenotypic traits and the aphid damage index were skewed to the resistant side, because both parents F4 derived E08934 plants and E08929 plants possessed resistance loci. Furthermore, based on the results in FIG. 4, a progeny plant is contemplated to have a lower DI when comprising at least one of the three resistance genes. Then as soybean plants are bred to have more resistance genes, then the progeny becomes more resistant, i.e. a higher DI, etc. For example, soybean plant line cultivar E12902 carries all three aphid resistance genes on Chr. 7, Chr. 8, and Chr. 16 (i.e. genes rag1c, Rag6, and Rag3c, respectively).

Therefore, the validation population skewed to the resistant side. E08929 as an accession from PI 567541B, was expected to have both rag1c and rag4 genes (Zhang et al., 2009, herein incorporated by reference). Surprisingly, rag4 was not detected in the validation population. According to SNP genotypic data from the SNP Beadchip, plants of line E08929 have heterozygousity in the rag4 region based on rag4 fine mapping results however with at least Rag6, Rag3c and rag1c genes present, the contemplated effect of the rag4 allele from heterozygous parent E08929 was as a masked germplasm/gene(s) in the validation population. Alternatively, the majority of line E08929 plants did not inherit a rag4 resistant germplasm/gene(s) from the original plant introduction. Regardless, line E08929 plants used herein are not considered to have an effective rag4 resistance gene.

From these results obtained during the development of the present inventions, novel aphid resistance alleles that demonstrated enhanced and superior aphid resistance, along with loci identified with molecular markers as described herein were discovered. Thus, soybean plant breeders have new genes and markers for effectively introgressing the resistance genes from *G. soja* into aphid susceptible *G. max* elite soybean plant cultivars.

B. Genetics of Soybean PI 567537 Plants.

PI 567537 is an aphid resistance germplasm source (Chen et al. 2007, herein incorporated by reference). Little was known about the genetic basis of aphid resistance in PI 567537, which hindered its utilization as an aphid resistance germplasm/gene source. Quantitative trait locus (QTL) analysis is a powerful tool to elucidate the genetic composition since it identified loci associated with quantitative traits in addition to their effects. Thus objectives of this study were to identify the aphid resistance loci in PI 567537 with molecular markers and further validate them in a different genetic background. Therefore, a mapping population of 86 $F_4$ lines was made from a cross between PI 567537 and a susceptible parent E00003 then investigated for the aphid resistance in both greenhouse and field trials. A genomic region associated with the aphid resistance in PI 567537 was revealed on chromosome 16 (linkage group J) with molecular markers. This locus was coincidentally located in the same region as Rag3 and explained most of the phenotypic variation ranging from 87.4% in the greenhouse trial to 78.9% in the field trial. This resistant germplasm was further confirmed in an $F_2$ population derived from (i.e. were progeny of) a cross of PI 567537×Skylla soybean plants. The segregation of the $F_2$ population indicated that aphid resistance in PI 567537 was controlled by a single dominant germplasm was mapped in the $F_4$ derived population (from the resistant parent PI 567537) as described herein. This germplasm was designated Rag3b since it was located at or near the Rag3 region. Rag3 was contemplated to be related to a disease resistance (R) gene, which encoded proteins contain a nucleotide binding site (NBS) and C-terminal leucine rich repeat (LRR) (Zhang et al. 2010). The mapping of the aphid resistance germplasm in PI 567537 and identification of associated markers is contemplated for use in marker assisted selection when using PI 567537 as an aphid resistance source for producing aphid resistant soybean plants.

Figure 2A:
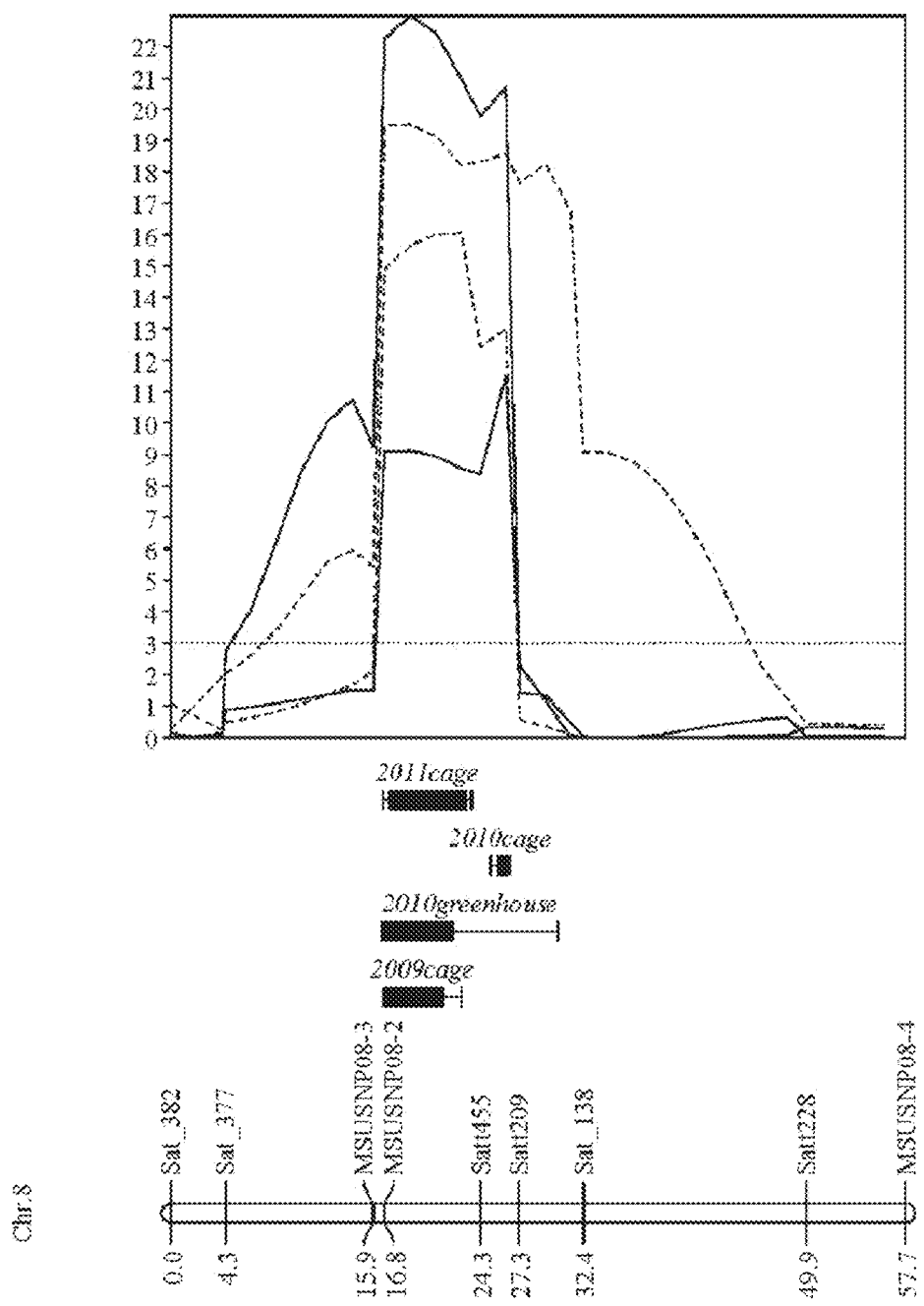

The results from this study were used to genetically map a major germplasm controlling the aphid resistance in PI 567537 and were validated it in another population. When maps generated during the development of the present inventions were compared with the consensus map (Song et al. 2004), maps generated herein were discovered to be inflated. The inflations presented in this study were very similar as in the study of Zhang et al. (2010, herein incorporated by reference), where they made a linkage group map for chromosome 16 with a different population. The similar inflation was also observed for LG F in the study of Mian et al. (2008b). These inflations explain differences in marker positions, for example, Sct_065 in this study was closely linked with Satt654 (FIG. 2C), which is different from its position in the consensus map (where Sct_065 is located almost in the middle between Sat_339 and Satt654) (Song et al. 2004) (FIG. 9B). However, the map position of Sct_065 in this study was in agreement with the soybean transcript map by Choi et al. (2007), where Sct_065 was 0.5 cM above Satt654, but far away (12 cM) from Sat_339. Williams et al. (1995) proposed that the varied map distances and positions among populations were related to a number of chromosome factors such as deletions, insertions, and translocations or other chromosome modifications in one or both parents.

The Rag3b germplasm discovered in these PI 567537 soybean plants as well as in soybean plants derived from PI 567537 plants, explained the majority of the phenotypic variation for both populations, i.e. as genetically mapped as a major germplasm controlling aphid resistance as validated for another population. The phenotypic data observed in both mapping and validation populations also suggested the dominance nature of this gene's mode of action. Hence, the aphid resistance in PI 567537 is controlled by a single dominant gene. Many studies have reported other single dominant genes controlling aphid resistance in soybean (Hill et al. 2006a, b; Kang et al. 2008; Hill et al. 2009, all of which are herein incorporated by reference), wheat (*Triticum aestivum* L.) (Liu et al. 2005), and peach (*Prunus persicae* L.) (Pascal et al. 2002, herein incorporated by reference).

The germplasm discovered during the development of the present inventions was coincidentally located in a same genomic region as Rag3 on chromosome 16 (LG J) (Zhang et al. 2010, herein incorporated by reference), indicating that the germplasm found in PI 567537 might be the same as Rag3 or a closely linked different gene. Aphid resistance genes from different germplasm sources were mapped at or near similar genomic regions, for example, soybean aphid resistance germplasm rag1c in PI 567541B was located at a same interval on chromosome 7 as Rag1 (Zhang et al. 2009, herein incorporated by reference) while the aphid resistance germplasm in PI 200538 was also positioned at a same location on chromosome 13 as Rag2 (Hill et al. 2009, herein incorporated by reference). Moreover, at least nine aphid resistance genes in wheat were mapped at or near similar regions on chromosome 7DS (Liu et al. 2005, herein incorporated by reference).

Surprisingly, PI 567537 (Rag3b) plants provided antibiosis resistance instead of the antixenosis resistance of PI 567543C (Rag3) plants. Rag3b appeared codominant in a population with a same susceptible parent E00003 as the mapping population in this study. Therefore, these two Rag3 germplasm regions are contemplated as different alleles of the same germplasm/genes or completely different germplasm/genes. Similar types of genetics for other genes, for example, soybean rust resistant genes, were reported by Garcia et al. (2008, herein incorporated by reference), where genes for soybean rust (*Phakopsora pachyrhizi*) resistance showing distinct types of gene action (dominance, incomplete dominance, and recessive) were mapped to a same genomic interval. Hence, the germplasm found during the development of the present inventions was named Rag3b according to the conventions of Soybean Genetics Committee.

It was contemplated that Rag3 was related to the disease resistance (R) gene, which encoded proteins containing the nucleotide binding site (NBS) and C-terminal leucine rich repeat (LRR) (Zhang et al. 2010, herein incorporated by reference). The NBS-LRR loci were often found as a gene cluster due to the tandem gene duplications (Leister 2004, herein incorporated by reference). Hence, it is contemplated that Rag3b and Rag3 are tightly linked different genes. Thus in one embodiment, Rag3 and Rag3b are contemplated to find use as stacked genes (i.e. plants having both genes) to provide broad resistance to soybean aphids. It is contemplated that Rag3b and Rag3 are tightly linked genes or alleles of the same gene. Therefore the resistance locus discovered in this aphid resistant germplasm source provided new genetic material contemplated for use in methods for soybean breeding programs for providing aphid resistant soybean plants to meet new and/or emerging resistance of aphids to existing plants.

The molecular markers linked to Rag3b are contemplated for use in transferring this locus to adapted elite soybean plant cultivars in additions to methods of stacking and/or pyramiding this locus with other resistance loci.

C. Soybean Aphid Resistance Germplasm in PI567585A Soybean Plants.

Genetic linkage mapping of aphid resistance genes in PI 567585A soybean plants is described. Plants of accession PI 567585A were surprisingly shown herein to possess soybean aphid resistance controlled by a single co-dominant germplasm/gene with antibiosis activity. This result was surprising because previous genes showing dominant activity that mapped near or at a rag3 location in soybean plants showed antixenosis activity. The following describes how the genetic basis of PI 567585A soybean plants was determined.

A mapping population of 158 $F_{4:5}$ (i.e. the fifth generation from F4 derived plants) were produced as described herein with the use of PI 567585A plants as the aphid resistant plants. Recombinant inbred lines (RILs) were derived from a cross between PI 567585A (resistant to soybean aphid) and 'Skylla' (cultivar susceptible to soybean aphid) as validation lines. These mapping and validation lines were evaluated for aphid resistance in both the greenhouse and caged field trials.

Broad-sense heritability estimate of aphid resistance in a representative field trial was 95.5%. The single aphid resistance germplasm region was mapped in an interval between Satt674 and Sct_065, simple sequence repeat (SSR) markers on chromosome 16 (linkage group J) using the composite interval mapping method. The locus explained 93.1% of the phenotypic variation in the field trial, and was located in the same genomic region as Rag3. This single aphid resistance germplasm region in PI 567585A was confirmed in another $F_{3:4}$ RIL population derived from a cross between PI 567585A and a susceptible parent IA2070. The SSR markers linked to aphid resistance in PI 567585A discovered in this study, for one example, Satt674 and Sct_065, are contemplated for use in isolating aphid resistant germplasm in PI 567585A plants and derived from PI 567585A plants. Mapping also shows that the aphid resistance in PI 567585A is on chromosome 16 between markers Satt674 and Satt654.

Increased genetic distance was found in two mapping populations when compared to the consensus map for LG J. This distance was contemplated due to at least three possible reasons: 1) the parents used for the SSR map, as prepared herein, were more distantly related and expected to have a lower recombination rate that used for other mapping populations; 2) the average distance was larger among the markers which were closely linked to the resistance gene; 3) the Join-Map method utilized two-point detection unlike the MapMaker, method that used three-point detection approach for the other maps. MapMaker cannot be set to accept data from $F_4$-derived families. The aphid resistance in PI 567585A was controlled by a single co-dominant germplasm region with additive effect, that mapped between Satt674 and Sct_065 on Chromosome 16 (LG J).

The germplasm region discovered in PI 567585A plants as described herein was located in the same general region as the aphid resistance germplasm Rag3 in PI 567543C (Zhang et al., 2009b, herein incorporated by reference). In a previous study, the resistance germplasm in PI 567543C plants was found as a single co-dominant trait that possessed additive effects along with antixenosis activity. Thus, unlike the previous Rag3 gene, the Rag3-1 discovered herein has antibiosis activity. Therefore data obtained herein indicated that the resistance germplasm region (named Rag3-1 and Rag3_1) in PI 567585A is a new resistance genetic source in addition to Rag3 of PI 567543C.

Genetic allelism discovered herein for the rag3 loci exists in aphid resistant loci in other soybean aphid resistant accessions. For example, Rag1 in 'Dowling' and Rag in 'Jackson' were mapped to the same position on LG M (Li et al., 2007, herein incorporated by reference). The resistance germplasm region in PI 200538 was mapped to the same region as the aphid resistance germplasm region Rag2 in PI 234550 on soybean LG F (Mian et al., 2008; Hill et al., 2009, all of which are herein incorporated by reference). As an example in relation to other aphid resistant genes, the recessive rag1c germplasm in PI 567541B plants mapped at or near the dominant Rag1 locus.

Moreover, a QTL conferring resistance to brown stem (caused by *Phialophora gregata*) was mapped to the same region in five different PIs, which originated from central China (Klos et al., 2005, herein incorporated by reference). The mapping of soybean aphid resistance to LG J is surprising because several resistance genes, such as powdery mildew resistance locus (Rmd), corn earworm (CEW) resistance genes (CEW6-2 and CEW 7-4), brown stem rot (BSR) resistance gene, *Phytophthora* resistance Rps2, soybean cyst nematode (SCN) race-2 and race-3 resistance genes, sudden death syndrome resistance genes (SDS), and soybean rust resistance genes (Rpp2) (Grant et al., 2009, herein incorporated by reference), were localized to this LG. In addition, five classes of disease resistance gene analogs (RGAs) were extensively clustered on chromosome 16 (LG J), including RGA1, RGA2, RGA3, RGA5, and RGA6 (Kanazin et al., 1996, herein incorporated by reference). Previous studies showed the presence of genes in the same region conferring resistance to several diseases, which may explain the correlation between a variety of disease resistance traits. For example, the similar gene location for BSR and powdery mildew resistance (Rmd) was suggested to explain the positive association between these resistance traits (Lewers et al., 1999, herein incorporated by reference).

Among these resistance loci, the Rag3-1 region overlapped with the two CEW resistance QTLs and SDS resistance locus (Sanitchon et al., 2004, herein incorporated by reference). Thus, Rag3 or Rag3-1 regions and the CEW QTLs may not occupy the same locus on chromosome 16. Studies on CEW and aphid resistance showed that the two traits were inherited separately.

Therefore, in one embodiment, alleles and genes located at or near the rag3 locus is contemplated for use in to pyramid (i.e. stack) multiple genes into a soybean cultivar for producing enhanced resistance, such as more durable aphid resistance. In other embodiments, a Rag 3 germplasm region or allele of the present inventions is contemplated for use in stacking along with other independent aphid resistance genes from diverse germplasm for providing soybean plants having enhanced aphid resistance.

II. Plant Breeding Methods of the Present Inventions for Making Aphid Resistant Soybean Plants of the Present Inventions.

The discovery and isolation of an early maturing aphid resistant soybean cultivar is disclosed herein. Specifically, soybean plant cultivars corresponding to line E08934, accessions PI 567537 and PI 567585A were disclosed. The invention also relates to a seed of one or more of a soybean line E08934, PI 567537 and PI 567585A, to the plants, i.e. comprising aphid resistant germplasm, of one or more of a soybean line E08934, PI 567537 and PI 567585A, and to methods for producing a soybean seed and plant produced by crossing any one of a cultivar of line E08934, PI 567537 and PI 567585A, with itself or another soybean variety, and further to provide offspring comprising the aphid resistant germplasm of the present invention. The invention further relates to an aphid resistant soybean plant and seed from that plant comprising germplasm of any one of a soybean cultivar line E08934, PI 567537 and PI 567585A. Examples of offspring comprising the aphid resistant germplasm of the present invention include the soybean lines E070020-19, E12902, E12905, E12909, etc. Lines E12902, E12905, E12909, comprise aphid resistant germplasm from the following soybean plants: line E12902 comprises aphid resistant germplasm derived from lines E08934 and PI 567541B; line E12905 comprises aphid resistant germplasm derived from line PI 567585A and line E12909 comprises aphid resistant germplasm derived from line PI 567537.

The methods of the present invention are not limited to the use of any particular soybean plant as an elite plant for use in breeding an aphid resistant soybean plant line for commercial use, such as for use by farmers, breeders, etc. Thus in some embodiments, aphid resistant germplasm is introgressed into a food-grade soybean plant that includes but is not limited to Ohio FG1, Agracola Farms AF271, Burtch Seed BBF44, H.A.P.I. Ohio GL2930, LG Seed EX230FG, Wellman WFG268, and the like. In some embodiments an aphid resistant a food-grade soybean plant is a specialty soybean plant, for example, provides Edamame soybeans, and the like. In some embodiments, aphid resistant germplasm is introgressed into a soybean plant that provides food for livestock, such as poultry, cattle, swine, etc., for example, a conventional soybean plant that includes but is not limited to Asgrow AG2905, Pioneer 93B01, and Public Sandusky. In some embodiments a soybean plant provides a non-food product, for example, a fuel additive, such as a diesel fuel additive, soy biodiesel, soybean ink, soy crayons, soybean based wood adhesive, soybean based lubricants, and the like.

Evaluation of progeny plants for aphid resistance was as described by Mensah et al. (2005, herein incorporated by reference) as choice and non-choice tests for aphid resistance under greenhouse and field conditions. Evaluation of progeny plants for their genome compositions using SSR DNA markers was described by Wang et al (2003, herein incorporated by reference). In brief, the PCR amplification was carried out in a PTC-0220 DNA Engine Dyad Peltier Thermal Cycler manufactured by MJ Research (Waltham, Mass. 02451, USA). The reaction volume was 20 µl and the reaction mixture contained 45 ng of template DNA, 2 µM primer, 30 mM MgCl, 3 mM each of dNTP, 2.5 units of Taq polymerase, and 1×PCR buffer that was provided by the Taq polymerase manufacturer. The PCR was run with an initial denaturation at 95° C. for 2 min, followed by 38 cycles of 25 sec denaturation at 94° C., 25 sec of annealing at annealing temperature specified for each primer pair, and 45 sec extension at 70° C. The final cycle was followed by a min extension at 72° C. The PCR product was held at 4° C. prior to analysis using the electrophoresis system described by Wang et al (2003, herein incorporated by reference).

Figure 7:
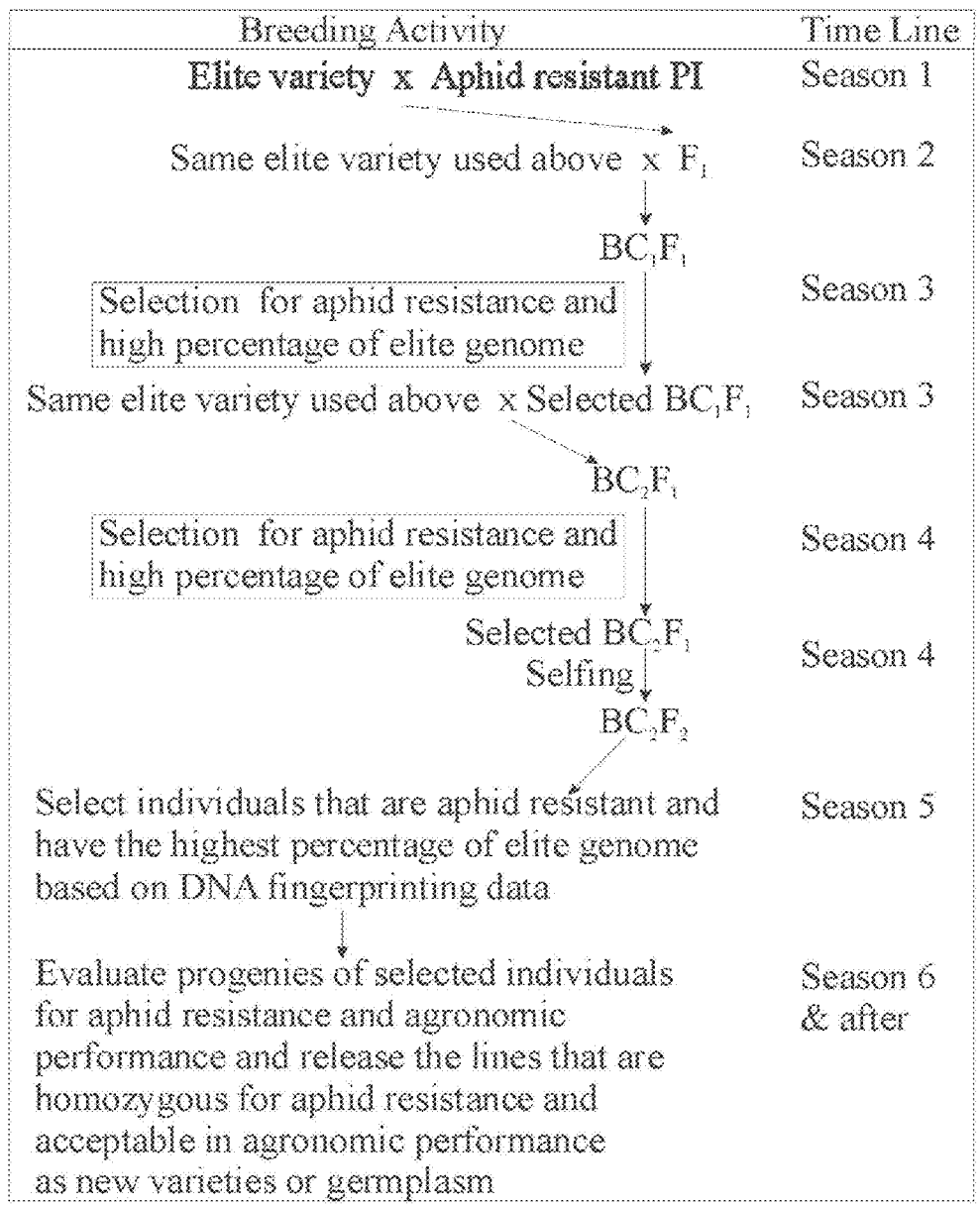
FIG. 7 shows exemplary general plant breeding methods to transfer the aphid resistance from the aphid resistant germplasm to elite soybean germplasm.
Figure 8A:
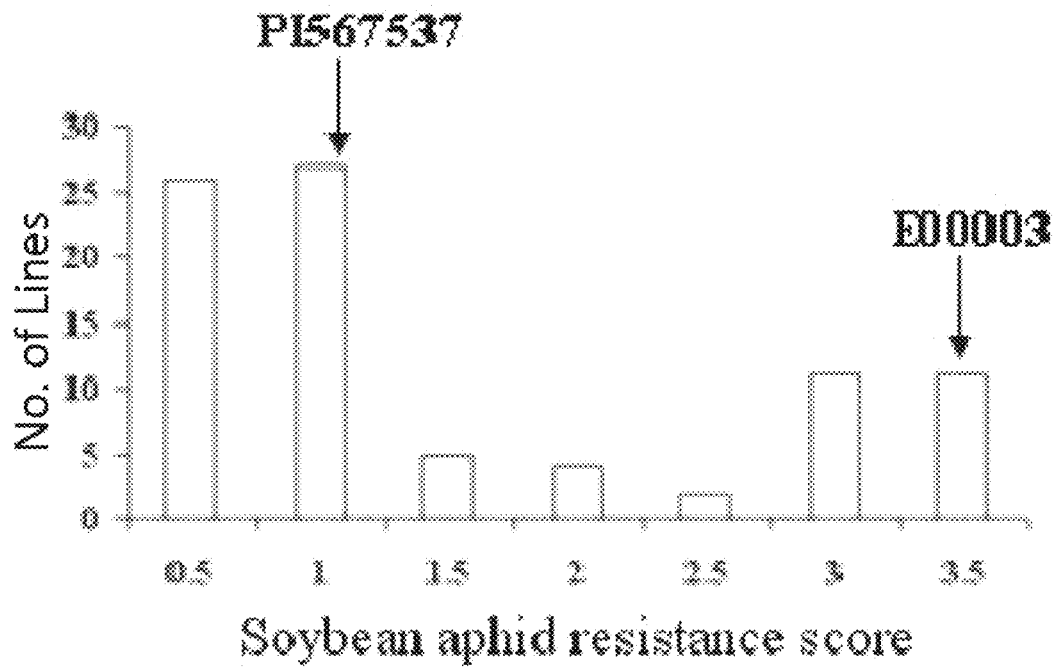
FIGS. 8A-8C shows exemplary frequency distribution of soybean aphid resistance score for 86 lines derived from the cross of parents shown by arrows. Parents are shown by arrows.
Figure 8B:
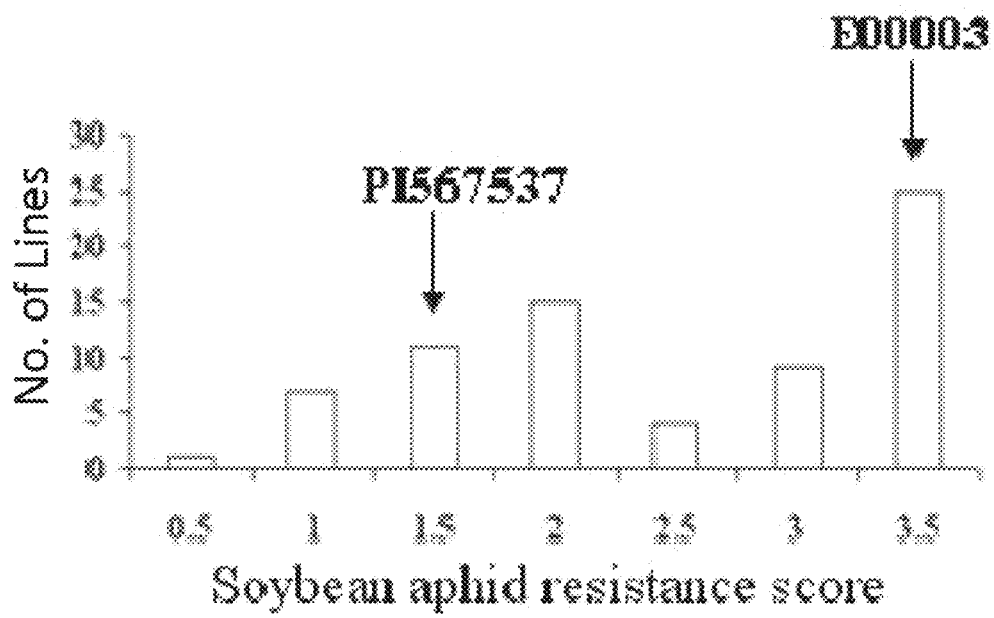
Figure 8C:
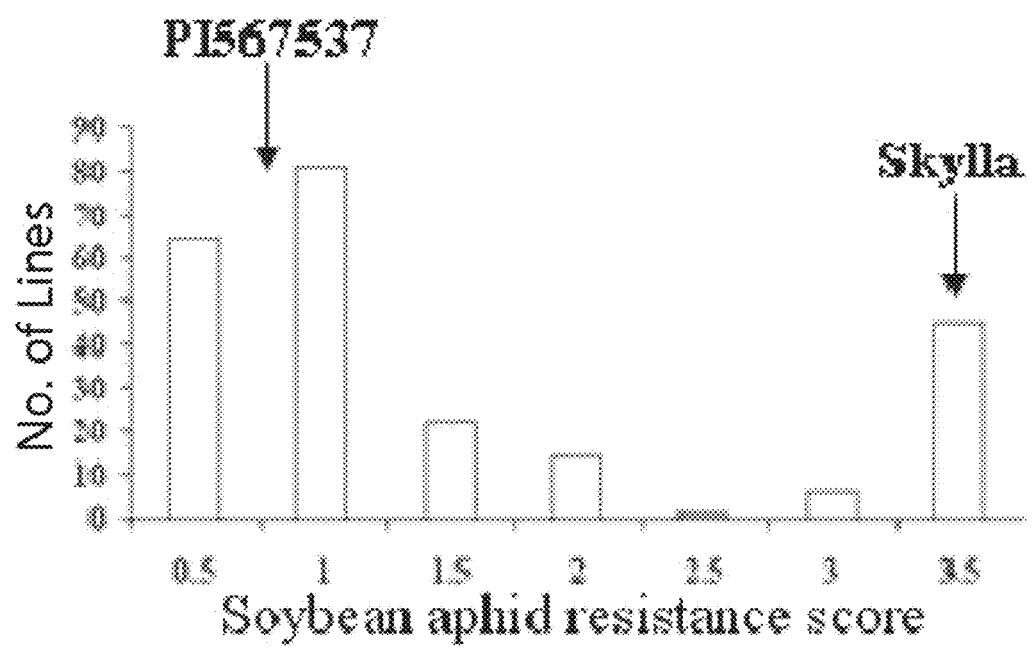

In particular, the invention is contemplated for use in soybean variety development by transferring aphid resistance germplasm from the aphid resistant germplasm to elite soybean germplasm for making commercial superior aphid resistant soybean plant lines. A backcross breeding method, such as the example shown in FIG. 7 is contemplated as an efficient method to transfer the resistant gene(s) from the aphid resistant germplasm to elite soybean germplasm. The elite variety is contemplated as any soybean variety including plants contributing aphid resistant germplasm, including the germplasm from E08934, E12902, PI 567537, and PI 567585A, and progeny (hybrid) soybean plants made by methods of the present inventions.

In order to shorten the total time needed between plant generations for transferring genetic material from parents to progeny plants, greenhouses or winter nurseries are contemplated for use to shorten the reproductive cycle of plants in place of any outdoor growing season shown in FIG. 7. Up to three seasons per year are contemplated instead of one season per year. To minimize the transfer of undesirable genes from the parental aphid resistant soybean plants to germplasm of progeny elite soybean plants, DNA markers are contemplated for use to select progeny plants with a minimum proportion of the genome comprising the aphid resistance germplasm. For example, forty to eighty simple sequence repeat (SSR) DNA markers evenly spaced on the soybean linkage map in addition to markers developed during the development of the present inventions are contemplated for use to assist the selection. Computer simulation showed that 93% of the genome of the recurrent parent was recovered in two cycles of backcrosses when DNA markers are used to assist the selection (Frisch et al., 1999, herein incorporated by reference).

Variations of the method described above: The method outlined in FIG. 7 can be modified. The following are examples of modifications:

Modification 1: In season 3, self-pollinate the selected BC1F1 to obtain BC1F2. In season 4, select BC individuals that are aphid resistant and have the highest percentage of elite genome based on DNA fingerprinting data. In season 5 and after, evaluate progenies of selected individuals for aphid resistance and agronomic performance and release the lines that are homozygous for aphid resistance and acceptable in agronomic performance as new varieties or germplasm.

Modification 2: In season 2, self-pollinate the F1 to obtain F2. In season 3, select F2 individuals that are aphid resistant and have the highest percentage of elite genome based on DNA fingerprinting data. In season 4 and after, evaluate progenies of selected individuals for aphid resistance and agronomic performance and release the lines that are homozygous for aphid resistance and acceptable in agronomic performance as new varieties or germplasm.

Modification 3: Use the method outlined in FIG. 7 or the modifications 1 and 2 described above without fingerprinting with SSR DNA markers and/or without selection based on DNA fingerprinting data.

There remains a challenge of evolving aphid biotypes that may overcome the effects of existing aphid resistance genes thus reducing aphid resistant effectiveness in the field and in tests for aphid resistance. Therefore new sources of germplasm/gene(s) and derived plants, such as those described herein, are contemplated for use in methods of stacking certain combinations of aphid resistant genes for designing specific types of aphid resistance in soybean plants. In part by choosing which aphid resistant genes are expressed in specific plant lines, soybean plant breeders would be able to stay ahead of resistance that might develop in new aphid biotypes. In other words, rotation of a range of types of aphid resistant soybean plant varieties, on a seasonal, bi-seasonal, tri-seasonal, etc. basis, would reduce the possibility that local aphid populations would develop resistance to continued plantings of one aphid resistant soybean variety.

In preferred embodiments, soybean plants, lines and cultivars having enhanced aphid resistance are *Glycine max.*

III. Methods of Making Aphid Resistant Soybean Plants of the Present Inventions Using Established Transgenic Plants.

The present invention contemplates providing commercial lines of transgenic aphid resistant soybean plants by introgressing the aphid resistance germplasm of the present invention into commercially established transgenic soybean lines. In addition, introgressing the germplasm comprising a preferred transgene into aphid resistant soybean plants for developing commercial lines of aphid resistant transgenic soybean plants is contemplated.

Numerous cultivars and lines of transgenic soybean plants were and are being developed as commercial varieties for use by growers and breeders for providing preferred agronomic traits including such traits as a preferred herbicide resistance, a preferred insect resistance, a preferred nematode resistance, a preferred microorganism, such as fungi or bacterial resistance, a preferred soybean seed oil content and the like.

Therefore, one contemplated aspect of the present invention is for providing an aphid resistant transgenic plant by introgressing aphid resistant germplasm of the present invention into a transgenic variety. In one embodiment, the germplasm of a transgenic plant comprising an integrated transgene is used for introgressing said transgene into an aphid resistant soybean plant, for example, transgenic plants comprising a transgenes providing one or more of herbicide resistance, insect resistance, nematode resistance, fungal resistance, bacterial resistance, an agronomic trait and the like. Examples of transgenic plants for providing herbicide resistance transgenes include but are not limited to transgenic soybean lines such as lines A2704-12 (U.S. Pat. No. 4,940,835, herein incorporated by reference), A2704-21, A5547-35 (Aventis CropScience) developed tolerate the use of glufosinate ammonium, the active ingredient in phosphinothricin herbicides (BASTA®, IGNITE®, RELY®, LIBERTY®, HARVEST®, and FINALE®) as a weed control option and lines A5547-127 (Bayer Crop Science (Aventis Crop Science(AgrEvo) developed for tolerating the use of glufosinate ammonium, the active ingredient in phosphinothricin herbicides (BASTA®, IGNITE®, RELY®, LIBERTY®, HARVEST®, and FINALE®) as a weed control option, GU262, genetically engineered to express tolerance to glufosinate ammonium, the active ingredient in phosphinothricin herbicides (BASTA®, RELY®, FINALE®, and LIBERTY®) (website at worldwideweb.agbios.com/dbase.php?action=ShowProd&data=W62%2C+W98 (Bayer Crop Science (Aventis Crop Science (AgrEvo)) W62, W98 (Bayer Crop Science (Aventis Crop Science (AgrEvo)) genetically engineered to express tolerance to glufosinate ammonium, the active ingredient in phosphinothricin herbicides (BASTA®, RELY®, FINALE®, and LIBERTY®; GTS 40-3-2 (Monsanto Company) developed for tolerating glyphosate, the active ingredient in the herbicide ROUNDUP®, as a weed control option by inserting a modified 5-enolpyruvylshikimate-3-phosphate synthase (EPSPS) encoding gene from the soil bacterium Agrobacterium tumefaciens, all of which are herein incorporated by reference. Other glyphosate-resistant plants are provided by U.S. Pat. No. 4,940,835, herein incorporated by reference.

As used herein, the terms "ROUNDUP READY" and "RR" refer to a registered trademark of Monsanto Chemical Company. The present invention contemplates the use of experimental and commercial ROUNDUP READY tolerant transgenic soybean lines in compositions and methods of the present invention for providing herbicide tolerance to ROUNDUP, glyphosate-isopropylammonium, MON-0573 in aphid resistant plants. In addition, the present invention provides methods for introgressing aphid resistant germplasm into ROUNDUP READY soybean plants for providing aphid resistant ROUNDUP tolerant soybean plants for experimental use and commercial development. Numerous varieties of ROUNDUP READY soybean plants are contemplated for use in the present invention, including, but not limited to, ROUNDUP READY (RR) soybeans for early maturity varieties of soybeans in maturity group I, Mars 618RR, and High Cycle ROUNDUP READY soybeans in Maturity/Group 0-1.7, 2111RR, 2133RR, 2143RR, 2154RR, 2162RR, 2163RR, 2174RR, 2175RR; GROUP II, Munsee IVRR, Mohegan 624RR, Apache 626RR, Sioux IIRR, Shawnee 527RR, and Shawnee 527RR, High Cycle ROUNDUP READY soybeans in maturity/group 1.8-2.4 2183RR, 2184RR, 2194RR, 2202RR, 2213RR, 2222RR, 2223RR, 2224RR, 2232RR, 2245RR; GROUP III Jefferson 630RR, Grant IIIRR, Truman 636RR, Kennedy 538RR, Washington IXRR, AG 3702, AG 3902, DPX 3919RR, DPX 3761RR, DPX 3940RR, Asgrow 3906, Delta King 3968, DPL 3861, Progeny 3900, Dyna-Gro 31139, Mor Soy 3883N; High Cycle ROUNDUP READY soybeans, maturity/group 2.5-3 Line High Cycle 2274 (further comprising germplasm conferring white mold tolerances, *Phytophthora* tolerance and Brown stem Rot (BSR) resistance), Line High Cycle 2274 (further comprising germplasm conferring excellent *Phytophthora* field tolerance), Line High Cycle 2293 (further comprising germplasm conferring excellent *Phytophthora* tolerance, Soybean Cyst Nematode (SCN) resistant (Race 3, MR14), all of which are herein incorporated by reference. Examples of early season roundup resistant soybean lines for use in the present invention in maturity group III include, but are not limited to, AG 3901, HTS 3600RR, 3902-4 8390 RR, HTS 3600RR, CX 383RR, H 3090RR and maturity group IV Manokin DP, 4344RR, AP 4602RR, DP 4750RR, CX 444cRR, H 4252RR, 8411 RR, 4001-4, CX 414cRR, CX 433RR, AP 4888RR, and AP 4980RR lines.

In some embodiments, aphid resistant germplasm is contemplated for use for introgressing into ROUNDUP READY soybean plant lines. Alternatively, in some embodiments, germplasm comprising the ROUNDUP READY transgene is contemplated for use introgressing into aphid resistant plants. In some embodiments, the ROUNDUP READY transgene is contemplated for use inserting directly (i.e. by transformation) into an aphid resistant soybean plant genome so as to provide ROUNDUP herbicide tolerant aphid resistant soybean seeds and plants. The present invention contemplates the use of transgenic plants comprising heterologous transgenes for providing insect resistance, including but not limited to, Bt derived transgenes (e.g., a gene encoding a Coleopteran inhibitory insecticidal crystal protein tIC851 as described in U.S. Patent Application. Nos. 20020103362, 20030229919 and U.S. Pat. No. 6,541,448); genes and their encoded crystal proteins that exhibit insecticidal activity against lepidopteran insects (see, e.g., U.S. Patent Application. No. 20030237111); genes encoding novel crystal Δ-endotoxin proteins which exhibit insecticidal activity against lepidopteran insects (see, e.g., U.S. Pat. No. 6,593,293); genes encoding Δ-endotoxins, mutant endotoxins and endotoxin derived proteins having pesticidal activity against pests of the order Coleoptera as described in U.S. Patent Application. Nos. 20020151709 and 20030177528; genes encoding Δ-endotoxins such as for Cry9 and derived proteins for having pesticidal activity against insect pests, including but not limited to Lepidoptera (see, e.g., U.S. Patent Application. No. 20050138685); Bt genes encoding Δ-endotoxins having pesticidal activity against insect pests (see, e.g., U.S. Patent Application. No. 20040091505, 20050261188, and 20050261483; genes encoding proteins with toxicity to Coleopteran insects (see, e.g., U.S. Pat. No. 5,763,241); genes encoding synthetic insecticidal crystal protein gene derived from Bt (see, e.g., U.S. Pat. Nos. 5,380,831 5,567,862); Bt genes encoding protease resistant toxins BTS02618Aa or BTS02618Ab (see, e.g., U.S. Pat. Nos. 5,861,543 and 6,143,550) (all references are herein incorporated by reference).

The present invention contemplates the use of transgenic plants comprising a heterologous transgene for providing nematode resistance and pest resistance, in particular Soybean cyst nematode, as described in International patent application nos. 20020144310, 20030005491, 20060095987, WO96/30517, and WO93/19181, and U.S.

Pat. Nos. 6,538,175, and 6,096,944, all of which are herein incorporated by reference in their entireties. In some embodiments, the present invention provides plants comprising transgenes that provide resistance for a variety of diseases and pathogens. The present invention is not limited to any particular resistance gene. Those known and later discovered resistance genes will find use in the present invention (see, e.g., U.S. Patent Application Nos. 20060059580 and 20060041954; each of which are incorporated by reference in their entireties).

Examples of transgenic plants used for providing germplasm providing an agronomic trait, such as a preferred oil content, include but are not limited to lines G94-1, G94-19, G168 (DuPont Canada Agricultural Products). The present invention further contemplates the use of methods and compositions for identifying soybean plants that are tolerant, have improved tolerance or are susceptible to iron deficient growth conditions (see, e.g., U.S. Patent Application Nos. 20060041951 and 20060005276). Providing experimental transgenic aphid resistant soybean plants for identifying any loss of desirable traits by inserting a particular transgene into an aphid resistant soybean plant is also contemplated.

Another aspect of the present invention is to provide aphid resistant transgenic plants by introgressing the aphid resistant germplasm into transgenic soybean plants comprising a transgene (e.g., a transgene providing for preferred agronomic traits and preferred economic traits, preferred herbicide resistance, preferred insect resistance, preferred nematode resistance, preferred microorganism, such as fungi or bacterial resistance).

IV. Quantitative Trait Loci for Identifying Desired Agricultural Traits for Use in Producing Plant Lines and Cultivars of the Present Inventions.

Quantitative trait loci (QTL) region identification and use is contemplated for use in breeding methods and developing commercial cultivars of aphid resistant soybean plants of the present inventions. In some embodiments, the inventors identify QTLs comprising aphid resistant germplasm of the present inventions. In some embodiments, QTLs, such as examples shown in Tables A-G, are contemplated for use in producing plants of the present inventions with specific characteristics. In general, QTL mapping shows QTLs underlying a trait of interest on a genetic linkage map, where the genetic linkage map is a linear map showing the relative positions of genetic markers. Therefore, genetic markers and linkage maps are essential for any QTL mapping study. Several types of genetic markers are available in soybean which are contemplated for use in the present inventions, including classical markers, isozyme markers, restriction fragment length polymorphism (RFLP) markers, random amplified polymorphic DNA (RAPD) markers, amplification fragment length polymorphism (AFLP) markers, simple sequence repeat (SSR) markers, and single nucleotide polymorphism (SNP) markers. Some of the most abundant markers developed for soybean are RFLP markers (Apuya et al. 1988; Keim et al. 1989, all of which are herein incorporated by reference), SSR markers (Akkaya et al. 1995, herein incorporated by reference), AFLP markers (Keim et al. 1997, herein incorporated by reference), and SNP markers (Choi et al. 2007, herein incorporated by reference). The first soybean molecular linkage map was published in 1990 by Keim et al. (1990a, herein incorporated by reference). This map contained 150 RFLP markers and three classical markers. The map was further expanded to include 355 RFLP markers and 16 other types of markers by 1993 (Shoemaker and Olson 1993, herein incorporated by reference). By 1999, the map was expanded to have 501 RFLPs markers, 486 SSRs, and 27 markers of other types (Cregan et al. 1999, herein incorporated by reference). This map was integrated with two maps developed with two additional mapping populations (Cregan et al. 1999). The integrated map had 689 RFLPs, 606 SSRs, 79 RAPDs, and 47 markers of other types. Using the three mapping populations and two additional mapping populations, a new version of the integrated map was constructed in 2004 (Song et al. 2004). The new integrated map contained 1015 SSRs, 709 RFLPs, 73 RAPDs, and 52 markers of other types, with a total map length of 2523.6 cM (Song et al. 2004, herein incorporated by reference). The most recent version of the integrated map was published in 2007 (Choi et al. 2007, herein incorporated by reference). This map contains 2,989 markers, including 1141 SNPs, 1014 SSRs, 709 RFLPs, and 125 other types of markers. The map consists of 20 linkage groups with a total map length of 2550.3 cM (Choi et al. 2007). The molecular markers, especially the SSR markers, from the integrated maps have been widely used in QTL mapping studies in soybean (Diers et al. 1992; Keim et al. 1990a; Neto et al. 2007; Wang et al. 2004a; Zhu et al. 2006, all of which are herein incorporated by reference).

In addition to the integrated linkage maps, several other molecular linkage maps were developed for soybean. A map with over 600 RFLP markers was developed by the DuPont Corporation (Rafalski and Tingey 1993, herein incorporated by reference). A map with 132 RFLP markers and 8 other types of markers was developed by Lark et al. (Lark et al. 1993, herein incorporated by reference). A map with 650 AFLPs, 165 RFLPs, and 25 RAPDs was developed by Keim et al. (1997, herein incorporated by reference). Liu et al. (2000) developed a map containing 100 RFLPs, 62 RAPDs, 42 AFLPs, 33 SSRs, and three other types of markers. Matthews et al. (2001, herein incorporated by reference) developed a map with 105 AFLPs, 39 RFLPs, 25 SSRs, 17 RAPDs, and four classical markers. Yamanaka et al. (2001, herein incorporated by reference) developed a map with 401 RFLPs, 96 SSRs, and six other types of markers. Wu et al. (2001, herein incorporated by reference) constructed a map with 486 AFLPs, 196 RFLPs, 87 SSRs, 18 RAPDs, and five other types of markers. This map and the mapping population have been used in several QTL mapping studies in China (Fu et al. 2007; Wang et al. 2004b, 2004c; Wang et al. 2004d, all of which are herein incorporated by reference).

A. Regions Controlling Agronomic Traits in QTL Mapping Studies in Soybean Plants.

Based on the data collected in the SoyBase database (Grant et al. 2008, herein incorporated by reference), at least 85 traits within over 1,100 QTLs were identified. These agronomic traits were mapped to at least one QTL controlling region for each trait including abnormal seedling, acidic protein fraction, alpha prime conglycinin protein fraction, aluminum tolerance, arabinose, arabinose-galactose basic protein fraction, beginning maturity, beginning pod, beta conglycinin protein fraction, brown stem rot resistance, canopy height, canopy width, carbon isotope discrimination, cell wall polysaccharide, chlorimuron ethyl sensitivity, common cutworm resistance, conglycinin protein fraction, corn earworm resistance, daidzein content, first flower, flooding tolerance, flowering time, fructose content, galactose content glycinin protein fraction, glycitein content, height/lodging, hypocotyl length, iron efficiency, javanese root-knot nematode resistance, leaf area, leaf ash, leaf chlorosis leaf length, leaf phosphorus content, leaf width, leaflet area, leaflet shape, linoleic acid content, linolenic acid content, lodging, nitrogen accumulation at growth stage R5, oil content, oil/protein ratio, oleic acid concentration, palmitic acid concentration, peanut root-knot nematode resistance, pectin concentration, *phomopsis* seed decay, photoperiod insensitivity, *phytophthora sojae* partial resistance, plant height, pod dehiscence, pod maturity date, protein concentration, reproductive period, *rhizoctonia* rot and hypocotyl rot, root necrosis, salt tolerance, *sclerotinia* stem rot, seed abortion, seed coat hardness, seed filling period, seed number, seed set, seed weight, southern root-knot nematode resistance, soybean cyst nematode resistance, soybean looper resistance (229-M), specific leaf weight, sprout yield, stearic acid concentration, stem diameter, stem length, sucrose concentration, sudden death syndrome resistance, tobacco budworm resistance (229-M), tobacco ringspot virus resistance, trigonelline concentration (dry weight), trigonelline concentration (fresh weight), water use efficiency, and yield, such as Yield/Height, Yield/Seed weight, SoyBase (Grant et al. 2008, herein incorporated by reference).

Some of the QTLs listed as separate QTLs in SoyBase appear to be the same QTL identified in the same population (e.g. SCN 29-1, SCN 29-4, and SCN 29-8 on linkage group G) while some other QTLs might be the same QTL identified in different populations (see the "consensus QTL regions" section below). The amount of phenotypic variation accounted for by a single QTL varied from 1% to 97%. The majority of the QTLs listed in SoyBase were not confirmed by separate studies. However, independent mapping studies with populations developed from different parents frequently identified QTLs for the same trait in a similar region on the integrated linkage map. The consistence of the QTL locations found in independent studies with different mapping populations indicates the existence of a real QTL in the region. For example, see, SCN resistance, Table D.

1. Maturity Group Markers.

QTLs encoding germplasm related to time of maturity (i.e. maturity group) were found in eight consensus regions on six LGs: C1, C2, D I a, I, L, and M (For example, Table A). The regions 53-66 cM on LG C1, 37-49 cM on LG D1a, 31-36 cM on LG 1, 54-68 cM on LG L, and near 18-20 cM on LG M were each found containing QTLs for maturity in two different mapping populations with three or four mapping parents (Table A). The 111-125 cM region on LG C2 was found with five different mapping populations developed from eight mapping parents. The region 88-96 cM on LG L and the region 32-40 cM on LG M were each found with three mapping populations developed from five or six mapping parents (Table A).

2. Identifying Maturity Groups for Use in Determining the Maturity Group in Plants of the Present Inventions.

The inventors' contemplate establishing the maturity group for lines and cultivars developed during the development of the present inventions. The following is an exemplary method for determining the maturity group of a soybean line or cultivar. Uniform Test areas were planted in multiple-row plots with three or four replications, and the center rows are harvested for yield and seed quality determinations. Preliminary Tests are multiple-row plots with two replications. Usually 15 to 20 feet of each row was planted and 12 to 16 feet harvested, to eliminate end-of-row effects. Coefficients of variability are included with replicated test data. Discretion was used in including data with high CVs in the regional means. If the CV was greater than 15, the reason should be recorded, such as a disease or environmental conditions. Lines may be heterogeneous for morphological traits the first year in the Uniform Tests but must be pure lines the second year of testing. It is the responsibility of the breeder to purify heterogeneous lines. "Generation Composited" is the generation after the final single-plant selection, when seeds from plants or rows are composited. Previous Testing is the number of previous years in the same Uniform Test or, in the case of new entries, a reference to the previous year's test, abbreviated to PT HA for Preliminary Test HA, for example. Yield was measured after the seeds have been dried to uniform moisture content and is recorded in bushels (60 pounds) per acre. To convert to kilograms/hectare multiply by 67.25. Maturity is the date when 95% of the pods have ripened, as indicated by their mature pod color. Delayed leaf drop and green stems are not considered in assigning maturity. Maturity is expressed as days earlier (−) of later (+) than the average date of the reference variety. To aid in maturity group classification, one earlier (E) and one later (L) check variety are given in the maturity column for each test, or a maturity check from an earlier or later maturity group is included. Current reference and check varieties and the maturity group limits relative to the reference varieties are:

TABLE A

Consensus Regions for Maturity Groups.

| Trait/QTL | LG[a] | Start position[b] | End position[b] | Mapping parent 1 | Mapping parent 2 | Reference (herein incorporated by reference) |
|---|---|---|---|---|---|---|
| Maturity | | | | | | |
| Pod mat 1-1 | C1 | 53 | 55 | A81356022 | PI 468916 | Keim et al. (1990a) |
| Pod mat 8-5 | C1 | 64 | 66 | Archer | Minsoy | Orf et al. (1999b) |
| Pod mat 8-1 | C2 | 111 | 113 | Archer | Minsoy | Orf et al. (1999b) |
| Pod mat 13-4 | C2 | 111 | 113 | Minsoy | Noir 1 | Specht et al. (2001) |
| Pod mat 14-3 | C2 | 112 | 114 | IA2008 | PI 468916 | Wang et al. (2004a) |
| Pod mat 4-1 | C2 | 117 | 119 | PI 27890 | PI 290136 | Mansur et al. (1996) |
| Pod mat 1-5 | C2 | 123 | 125 | A81356022 | PI 468916 | Keim et al. (1990a) |
| Pod mat 1-2 | D1a | 37 | 39 | A81356022 | PI 468916 | Keim et al. (1990a) |
| Pod mat 13-2 | D1a | 47 | 49 | Minsoy | Noir 1 | Specht et al. (2001) |
| Pod mat 12-1 | I | 31 | 33 | Parker | PI 468916 | Yuan et al. (2002) |
| Pod mat 11-1 | I | 34 | 36 | A81356022 | PI 468916 | Yuan et al. (2002) |
| Pod mat 14-1 | L | 54 | 56 | IA2008 | PI 468916 | Wang et al. (2004a) |
| Pod mat 8-4 | L | 66 | 68 | Archer | Minsoy | Orf et al. (1999b) |
| Pod mat 13-6 | L | 88 | 90 | Minsoy | Noir 1 | Specht et al. (2001) |
| Pod mat 4-3 | L | 91 | 93 | PI 27890 | PI 290136 | Mansur et al. (1996) |
| Pod mat 9-2 | L | 94 | 96 | Archer | Noir 1 | Orf et al. (1999b) |
| Pod mat 8-2 | M | 18 | 20 | Archer | Minsoy | Orf et al. (1999b) |
| Pod mat 13-7 | M | 18 | 20 | Minsoy | Noir 1 | Specht et al. (2001) |
| Pod mat 14-4 | M | 32 | 34 | IA2008 | PI 468916 | Wang et al. (2004a) |
| Pod mat 10-2 | M | 33 | 35 | Minsoy | Noir 1 | Orf et al. (1999b) |
| Pod mat 7-1 | M | 38 | 40 | PI 27890 | PI 290136 | Lark et al. (1994) |

| Group | Reference | Range | Early check | Late check |
|---|---|---|---|---|
| 00 | MN0071 | −7 to +5 | Jim | Trail (L) |
| 0 | Lambert | −6 to +2 | Traill (E) | Parker (L) |
| I | MN1410 | −4 to +4 | Lambert (0) | IA1008 (SCN) |
| II | IA2068 | −3 to +5 | IA1021 (I) | IA3024 (L) |
| III | IA3023 | −6 to +2 | IA3024 | Macon (L) |
| IV | LD00-3309 | −4 to +7 | Macon (III) | |
| 00RR | RG700RR | | | AG0202 |
| 0RR | RG200RR | | RG200RR | SD1111RR (L) |
| IRR | SD1611RR | | SD1111RR (E) | AG2002 |
| IIRR | AG2403 | | AG2002 | NEX2905A0R (L) |
| IIIRR | AG3505 | | NEX2905A0R (E) | DKB3852 |
| IVRR | AG4103 | | DKB38-52 | AG4403 |

These maturity group ranges are based on long-term means over many locations. When using data from other environments, the interval between reference varieties may vary, and the division between maturity groups should be estimated in proportion to the above figures. Additional check varieties may be included in specific tests such as IA 1022 (SCN) for resistance to the soybean cyst nematode in UT I, or IA3024 as a 1% linolenic check in PTII, and PTIII.

3. Lodging.

The use of lodging germplasm in making plants of the present inventions having agronomical acceptable lodging characteristics. Lodging is rated at maturity according to the following scores: 1. The majority of plants erect; 2 The majority of plants leaning slightly or a few plants down; 3 around 100% of plants leaning moderately (45 degrees), or 25% to 50% of the plants down. 4; The majority of plants leaning considerably, or 50% to 80% of the plants down. 5; The majority of plants down.

QTLs for lodging were found in three consensus regions on two LGs: C2 and L (Table B). Three regions, 107-116 cM on LG C2, 3-11 cM on LG L, and 68-101 cM on LG L were each found in three mapping populations developed from five or six mapping parents (Table B).

TABLE B

Consensus Regions for Lodging.

| Trait/QTL | LG[a] | Start position[b] | End position[b] | Mapping parent 1 | Mapping parent 2 | Reference (herein incorporated by reference) |
|---|---|---|---|---|---|---|
| Lodging | | | | | | |
| Ldge 6-1 | C2 | 107 | 109 | Archer | Minsoy | Orf et al. (1999b) |
| Ldge 9-1 | C2 | 111 | 113 | Minsoy | Noir 1 | Specht et al. (2001) |
| Ldge 3-2 | C2 | 114 | 116 | PI 27890 | PI 290136 | Orf et al. (1999b) |
| Ldge 5-11 | L | 3 | 5 | PI 416937 | Young | Lee et al. (1996a) |
| Ldge 3-3 | L | 8 | 10 | PI 27890 | PI 290136 | Mansur et al. (1996) |
| Ldge 9-3 | L | 9 | 11 | Minsoy | Noir 1 | Specht et al. (2001) |
| Ldge 1-1 | L | 68 | 87 | PI 27890 | PI 290136 | Mansur et al. (1996) |
| Ldge 8-4 | L | 88 | 90 | Minsoy | Noir 1 | Orf et al. (1999b) |
| Ldge 4-2 | L | 88 | 90 | Coker237 | PI 97100 | Lee et al. (1996c) |
| Ldge 9-5 | L | 88 | 90 | Minsoy | Noir 1 | Specht et al. (2001) |
| Ldge 4-3 | L | 89 | 101 | Coker237 | PI 97100 | Lee et al. (1996c) |
| Ldge 3-1 | L | 91 | 93 | PI 27890 | PI 290136 | Mansur et al. (1996) |

4. Height.

Height refers to the average length in inches of mature plants from the ground to the tip of the main stem. To convert to centimeters, multiply by 2.54.

QTLs for plant height were found in 10 consensus regions on eight LGs: C2, D1b, F, I, J, K, L, and M (Table C). The 107-118 cM region on LG C2 was found in five mapping populations developed from nine mapping parents (Table C). The regions 120-133 cM on LG D1b, 66-69 cM on LG F, 34-38 cM on LG 1, 36-48 cM on LG K, 8-15 cM on LG L, and 34-44 cM on LG L were each found in two mapping populations developed from four mapping parents. The regions 11-29 cM on LG J and 32-40 cM on LG M were each found in three mapping populations developed from six mapping parent. The 68-114 cM region on LG L was found in six mapping populations developed from nine mapping parents (Table C).

TABLE C

Consensus regions for Plant height.

| Trait/QTL | LG[a] | Start position[b] | End position[b] | Mapping parent 1 | Mapping parent 2 | Reference (herein incorporated by reference) |
|---|---|---|---|---|---|---|
| Plant height | | | | | | |
| Pl ht 8-1 | C2 | 107 | 109 | Archer | Minsoy | Orf et al. (1999b) |
| Pl ht 18-4 | C2 | 112 | 114 | IA2008 | PI 468916 | Wang et al. (2004a) |

TABLE C-continued

Consensus regions for Plant height.

| Trait/QTL | LG[a] | Start position[b] | End position[b] | Mapping parent 1 | Mapping parent 2 | Reference (herein incorporated by reference) |
|---|---|---|---|---|---|---|
| Pl ht 13-2 | C2 | 112 | 114 | Minsoy | Noir 1 | Specht et al. (2001) |
| Pl ht 11-1 | C2 | 116 | 118 | S100 | Tokyo | Mian et al. (1998) |
| Pl ht 6-3 | C2 | 116 | 118 | PI 27890 | PI 290136 | Lark et al. (1995) |
| Pl ht 6-12 | D1b | 120 | 122 | PI 27890 | PI 290136 | Lark et al. (1995) |
| Pl ht 5-5 | D1b | 131 | 133 | PI 416937 | Young | Lee et al. (1996a) |
| Pl ht 5-8 | F | 66 | 68 | PI 416937 | Young | Lee et al. (1996a) |
| Pl ht 11-3 | F | 67 | 69 | S100 | Tokyo | Mian et al. (1998) |
| Pl ht 12-1 | I | 34 | 36 | A81356022 | PI 468916 | Yuan et al. (2002) |
| Pl ht 16-1 | I | 36 | 38 | Essex | Williams | Chapman et al. (2003) |
| Pl ht 13-5 | J | 11 | 13 | Minsoy | Noir 1 | Specht et al. (2001) |
| Pl ht 6-6 | J | 20 | 22 | PI 27890 | PI 290136 | Lark et al. (1995) |
| Pl ht 5-9 | J | 27 | 29 | PI 416937 | Young | Lee et al. (1996a) |
| Pl ht 18-3 | K | 36 | 38 | IA2008 | PI 468916 | Wang et al. (2004a) |
| Pl ht 15-1 | K | 46 | 48 | Flyer | Hartwig | Yuan et al. (2002) |
| Pl ht 6-7 | L | 8 | 10 | PI 27890 | PI 290136 | Lark et al. (1995) |
| Pl ht 13-7 | L | 13 | 15 | Minsoy | Noir 1 | Specht et al. (2001) |
| Pl ht 5-12 | L | 34 | 36 | PI 416937 | Young | Lee et al. (1996a) |
| Pl ht 6-4 | L | 42 | 44 | PI 27890 | PI 290136 | Lark et al. (1995) |
| Pl ht 8-4 | L | 66 | 68 | Archer | Minsoy | Orf et al. (1999b) |
| Pl ht 1-1 | L | 68 | 87 | PI 27890 | PI 290136 | Mansur et al. (1993) |
| Pl ht 8-3 | L | 69 | 71 | Archer | Minsoy | Orf et al. (1999b) |
| Pl ht 6-1 | L | 86 | 88 | PI 27890 | PI 290136 | Lark et al. (1995) |
| Pl ht 4-2 | L | 88 | 90 | Coker237 | PI 97100 | Lee et al. (1996c) |
| Pl ht 13-8 | L | 88 | 90 | Minsoy | Noir 1 | Specht et al. (2001) |
| Pl ht 4-4 | L | 89 | 101 | Coker237 | PI 97100 | Lee et al. (1996c) |
| Pl ht 3-1 | L | 91 | 93 | PI 27890 | PI 290136 | Mansur et al. (1996) |
| Pl ht 5-10 | L | 100 | 102 | PI 416937 | Young | Lee et al. (1996a) |
| Pl ht 9-2 | L | 106 | 108 | Archer | Noir 1 | Orf et al. (1999b) |
| Pl ht 6-2 | L | 112 | 114 | PI 27890 | PI 290136 | Lark et al. (1995) |
| Pl ht 18-6 | M | 32 | 34 | IA2008 | PI 468916 | Wang et al. (2004a) |
| Pl ht 13-9 | M | 33 | 35 | Minsoy | Noir 1 | Specht et al. (2001) |
| Pl ht 6-5 | M | 38 | 40 | PI 27890 | PI 290136 | Lark et al. (1995) |

5. QTLs for Soybean Cyst Nematode Resistance.

Soybean cyst nematode (SCN) resistance was mapped to QTLs. SCN QTLs also contained other types of genes. As an example, a QTL for SCN resistance was identified in the 0-37 cM region on linkage group G in 14 mapping populations. The major SCN resistance gene rhg1 was also found in this region (Concibido et al. 2004, herein incorporated by reference). For SCN resistance, at least 99 QTLs were identified (see, Table D for examples).

TABLE D

Consensus regions for QTLs for soybean cyst nematode resistance listed in SoyBase by Grant et al. (2008).

| QTL | $R^2$ (%)[a] | LOD score | P-value | LG[b] | Start position[c] | End position[c] | Peak marker/interval | Mapping parent 1 | Mapping parent 2 | Reference (herein incorporated by reference) |
|---|---|---|---|---|---|---|---|---|---|---|
| SCN 2-3 | 1.0 | | 0.0008 | A1 | 7.8 | 9.8 | A487_1 | Hartwig | Williams 82 | Vierling et al. (1996) |
| SCN 18-1 | 7.4 | 2.78 | 0.0010 | A1 | 30.9 | 53.4 | A262_1, Satt300 | PI 438489B | Hamilton | Yue et al. (2001a) |
| SCN 1-1 | | | 0.0015 | A2 | 31.2 | 33.2 | A085_1 | M85-1430 | M83-15 | Concibido et al. (1994) |
| SCN 19-1 | 19.1 | 7.00 | 0.0010 | A2 | 45.6 | 53.1 | K400_2, T155_2 | PI 438489B | Hamilton | Yue et al. (2001a) |
| SCN 27-2 | 26.2 | 5.20 | | A2 | 47.6 | 49.6 | E(CCG)M(AAC)405 | Essex | Forrest | Meksem et al. (2001) |
| SCN 9-2 | 25.0 | | | A2 | 47.8 | 49.8 | I | Peking | Essex | Mahalingam et al. (1995) |
| SCN 3-1 | 9.0 | 5.80 | | A2 | 47.8 | 49.8 | I | PI 437654 | BSR101 | Webb et al. (1995) |
| SCN 29-5 | 17.7 | 14.50 | | A2 | 49.4 | 60.6 | Sat_400, Satt424 | Hamilton | PI 90763 | Guo et al. (2006) |
| SCN 8-5 | 23.2 | 5.10 | | A2 | 53.2 | 55.2 | BLT065_1 | Essex | Forrest | Chang et al. (1997) |
| SCN 13-2 | 40.0 | | 0.6400 | A2 | 53.2 | 55.2 | BLT065_1 | Flyer | Hartwig | Prabhu et al. (1999) |
| SCN 9-3 | 8.0 | | | A2 | 56.9 | 58.9 | S07a | Peking | Essex | Mahalingam et al. (1995) |
| SCN 30-3 | 29.0 | | 0.0005 | A2 | 59.6 | 61.6 | Satt424 | PI 437654 | Bell | Brucker et al. (2005) |

TABLE D-continued

Consensus regions for QTLs for soybean cyst nematode resistance listed in SoyBase by Grant et al. (2008).

| QTL | R² (%)[a] | LOD score | P-value | LG[b] | Start position[c] | End position[c] | Peak marker/interval | Mapping parent 1 | Mapping parent 2 | Reference (herein incorporated by reference) |
|---|---|---|---|---|---|---|---|---|---|---|
| SCN 8-4 | 15.1 | 2.80 | | A2 | 65.8 | 67.8 | OW15_400 | Essex | Forrest | Chang et al. (1997) |
| SCN 9-1 | 12.5 | | | A2 | 70.4 | 72.4 | A136_1 | Peking | Essex | Mahalingam et al. (1995) |
| SCN 26-1 | 9.5 | 3.71 | 0.0011 | B1 | 58.9 | 64.8 | A118_1, A006_1 | PI 89772 | Hamilton | Yue et al. (2001) |
| SCN 2-1 | 91.0 | | 0.0001 | B1 | 63.8 | 65.8 | A006_1 | Hartwig | Williams82 | Vierling et al. (1996) |
| SCN 23-1 | 16.6 | 6.83 | 0.0001 | B1 | 64.8 | 84.2 | A006_1, Satt583 | PI 89772 | Hamilton | Yue et al. (2001b) |
| SCN 24-1 | 6.8 | 2.78 | 0.0035 | B1 | 64.8 | 84.2 | A006_1, Satt583 | PI 89772 | Hamilton | Yue et al. (2001b) |
| SCN 17-1 | 12.7 | 4.20 | 0.0010 | B1 | 84.2 | 101.0 | Satt583, Sat_123 | PI 438489B | Hamilton | Yue et al. (2001a) |
| SCN 18-2 | 7.4 | 2.79 | 0.0010 | B1 | 84.2 | 101.0 | Satt583, Sat_123 | PI 438489B | Hamilton | Yue et al. (2001a) |
| SCN 20-1 | 11.0 | 2.70 | 0.0010 | B1 | 84.2 | 101.0 | Satt583, Sat_123 | PI 438489B | Hamilton | Yue et al. (2001a) |
| SCN 29-10 | 11.2 | 6.00 | | B1 | 102.6 | 124.0 | Satt359, Satt453 | Hamilton | PI 90763 | Guoetal (2006) |
| SCN 2-2 | 1.0 | | 0.0001 | B1 | 125.0 | 127.0 | A567_1 | Hartwig | Williams 82 | Vierling et al. (1996) |
| SCN 17-2 | 11.7 | 2.75 | 0.0010 | B2 | 55.2 | 62.7 | A329_1, Satt168 | PI 438489B | Hamilton | Yue et al. (2001a) |
| SCN 19-2 | 8.1 | 2.56 | 0.0010 | B2 | 55.2 | 62.7 | A329_1, Satt168 | PI 438489B | Hamilton | Yue et al. (2001a) |
| SCN 10-1 | 21.0 | | | B2 | 97.5 | 99.5 | A593_1 | Peking | Essex | Qiu et al. (1999) |
| SCN 10-3 | 15.0 | | | B2 | 117.7 | 119.7 | T005_1 | Peking | Essex | Qiu et al. (1999) |
| SCN 11-3 | 9.0 | | | B2 | 117.7 | 119.7 | T005_1 | Peking | Essex | Qiu et al. (1999) |
| SCN 21-1 | 11.1 | 3.61 | 0.0010 | C1 | 18.6 | 21.0 | A059_1, A463_1 | PI 438489B | Hamilton | Yue et al. (2001a) |
| SCN 18-3 | 10.2 | 2.56 | 0.0010 | C1 | 21.0 | 24.1 | A463_1, Satt396 | PI 438489B | Hamilton | Yue et al. (2001a) |
| SCN 22-1 | 5.0 | 4.40 | | C2 | 1.0 | 1.0 | A121_1 | PI 468916 | A81356022 | Wang et al. (2001) |
| SCN 9-6 | 8.0 | | | C2 | 94.6 | 96.6 | A635_1 | Peking | Essex | Mahalingam et al. (1995) |
| SCN 17-3 | 7.1 | 6.80 | 0.0010 | C2 | 126.2 | 145.5 | Satt202, Satt371 | PI 438489B | Hamilton | Yue et al. (2001a) |
| SCN 20-2 | 8.3 | 3.05 | 0.0010 | C2 | 126.2 | 145.5 | Satt202, Satt371 | PI 438489B | Hamilton | Yue et al. (2001a) |
| SCN 19-3 | 10.7 | 5.47 | 0.0010 | D1a | 6.4 | 34.9 | A398_1, K478_1 | PI 438489B | Hamilton | Yue et al. (2001a) |
| SCN 20-3 | 9.4 | 4.17 | 0.0010 | D1a | 6.4 | 34.9 | A398_1, K478_1 | PI 438489B | Hamilton | Yue et al. (2001a) |
| SCN 21-2 | 7.4 | 4.14 | 0.0010 | D1a | 6.4 | 34.9 | A398_1, K478_1 | PI 438489B | Hamilton | Yue et al. (2001a) |
| SCN 26-2 | 7.8 | 3.30 | 0.0015 | D1a | 43.8 | 48.1 | Satt342, Satt368 | PI 89772 | Hamilton | Yue et al. (2001b) |
| SCN 23-2 | 9.7 | 4.59 | 0.0014 | D2 | 15.0 | 39.4 | B132_4, Satt372 | PI 89772 | Hamilton | Yue et al. (2001b) |
| SCN 16-1 | 41.0 | | 0.0010 | D2 | 86.3 | 88.3 | Satt082 | Hartwig | BR92-31983 | Schuster et al. (2001) |
| SCN 12-2 | 9.0 | | | E | 16.1 | 18.1 | A963_1 | Peking | Essex | Qiu et al. (1999) |
| SCN 22-3 | 23.0 | 3.50 | | E | 33.2 | 35.2 | Satt598 | PI 468916 | A81356022 | Wang et al. (2001) |
| SCN 29-9 | 12.5 | 7.20 | | E | 35.8 | 43.1 | Satt573, Satt204 | Hamilton | PI 90763 | Guoetal. (2006) |
| SCN 18-4 | 8.0 | 2.57 | 0.0010 | E | 37.3 | 45.1 | A656_1, Satt452 | PI 438489B | Hamilton | Yue et al. (2001a) |
| SCN 21-3 | 18.7 | 5.01 | 0.0010 | E | 37.3 | 45.1 | A656_1, Satt452 | PI 438489B | Hamilton | Yue et al. (2001a) |
| SCN 25-1 | 15.7 | 3.56 | 0.0053 | E | 51.0 | 70.2 | A135_3, Satt231 | PI 89772 | Hamilton | Yue et al. (2001b) |
| SCN 29-1 | 14.7 | 7.90 | | G | 0.0 | 12.5 | Satt163, Satt688 | Hamilton | PI 90763 | Guo et al. (2006) |
| SCN 29-4 | 28.1 | 22.10 | | G | 0.0 | 12.5 | Satt163, Satt688 | Hamilton | PI 90763 | Guo et al. (2006) |
| SCN 29-8 | 13.0 | 7.10 | | G | 0.0 | 12.5 | Satt163, Satt688 | Hamilton | PI 90763 | Guo et al. (2006) |

TABLE D-continued

Consensus regions for QTLs for soybean cyst nematode resistance listed in SoyBase by Grant et al. (2008).

| QTL | $R^2$ (%)[a] | LOD score | P-value | LG[b] | Start position[c] | End position[c] | Peak marker/interval | Mapping parent 1 | Mapping parent 2 | Reference (herein incorporated by reference) |
|---|---|---|---|---|---|---|---|---|---|---|
| SCN 4-1 | 26.2 | | 0.0001 | G | 0.8 | 2.8 | C006_1 | Evans | Peking | Concibido et al. (1997) |
| SCN 5-1 | 44.8 | | 0.0001 | G | 0.8 | 2.8 | C006_1 | Evans | PI 90763 | Concibido et al. (1997) |
| SCN 6-1 | 36.3 | | 0.0001 | G | 0.8 | 2.8 | C006_1 | Evans | PI 88788 | Concibido et al. (1997) |
| SCN 13-1 | 6.4 | | 0.0760 | G | 0.8 | 2.8 | Satt038 | Flyer | Hartwig | Prabhu et al. (1999) |
| SCN 8-3 | 12.9 | 2.70 | | G | 1.0 | 3.0 | 0I03_450 | Essex | Forrest | Chang et al. (1997) |
| SCN 4.4 | 28.1 | | | G | 1.8 | 8.6 | C006_1, Bng122_1 | Evans | Peking | Concibido et al. (1996) |
| SCN 5-3 | 52.7 | | | G | 1.8 | 8.6 | C006_1, Bng122_1 | Evans | PI 90763 | Concibido et al. (1996) |
| SCN 6-2 | 40.0 | | | G | 1.8 | 8.6 | C006_1, Bng122_1 | Evans | PI 88788 | Concibido et al. (1996) |
| SCN 7-1 | 51.4 | | | G | 1.8 | 8.6 | C006_1, Bng122_1 | Evans | PI 209332 | Concibido et al. (1996) |
| SCN 30-1 | 14.0 | | 0.0400 | G | 3.5 | 5.5 | Satt309 | PI 437654 | Bell | Brucker et al. (2005) |
| SCN 30-2 | 32.0 | | 0.0001 | G | 3.5 | 5.5 | Satt309 | PI 437654 | Bell | Brucker et al. (2005) |
| SCN 14-2 | 97.0 | | 0.0001 | G | 3.5 | 5.5 | Satt309 | Essex | Forrest | Meksem et al. (1999) |
| SCN 23-3 | 26.6 | 13.67 | 0.0001 | G | 4.5 | 5.8 | B053_1, Satt309 | PI 89772 | Hamilton | Yue et al. (2001b) |
| SCN 24-2 | 4.6 | 2.53 | 0.0095 | G | 4.5 | 5.8 | B053_1, Satt309 | PI 89772 | Hamilton | Yue et al. (2001b) |
| SCN 25-2 | 23.0 | 12.65 | 0.0001 | G | 4.5 | 5.8 | B053_1, Satt309 | PI 89772 | Hamilton | Yue et al. (2001b) |
| SCN 26-3 | 10.0 | 5.02 | 0.0001 | G | 4.5 | 5.8 | B053_1, Satt309 | PI 89772 | Hamilton | Yue et al. (2001b) |
| SCN 28-1 | 87.0 | 40.60 | | G | 4.5 | 8.6 | Satt309, Bng122 | Bell | Colfax | Glover et al. (2004) |
| SCN 28-3 | 64.0 | 17.70 | | G | 4.5 | 8.6 | Satt309, Bng122 | Bell | Colfax | Glover et al. (2004) |
| SCN 27-1 | 24.1 | 5.10 | | G | 4.8 | 6.8 | E(ATG)M(CGA)87 | Essex | Forrest | Meksem et al. (2001) |
| SCN 15-1 | | | | G | 5.8 | 35.5 | B053_1, A112_1 | PI 88287 | PI 89008 | Vaghchhipawala et al. (2001) |
| SCN 8-2 | 11.3 | 2.50 | | G | 7.6 | 9.6 | Bng122_1 | Essex | Forrest | Chang et al. (1997) |
| SCN 14-1 | 19.0 | | 0.0730 | G | 7.6 | 9.6 | Bng122_1 | Essex | Forrest | Meksem et al. (1999) |
| SCN 8-1 | 4.2 | 1.20 | | G | 10.6 | 12.6 | QG13_490 | Essex | Forrest | Chang et al. (1997) |
| SCN 3-2 | 22.0 | 15.40 | | G | 11.0 | 13.0 | PHP05354a, PHP05219a | PI 437654 | BSR101 | Webb et al. (1995) |
| SCN 1-3 | 36.0 | | 0.0001 | G | 23.1 | 25.1 | K069_1 | M85-1430 | M83-15 | Concibido et al. (1994) |
| SCN 17-4 | 15.8 | 9.08 | 0.0010 | G | 23.1 | 54.7 | A096_3, Satt130 | PI 438489B | Hamilton | Yue et al. (2001a) |
| SCN 18-5 | 12.8 | 7.52 | 0.0010 | G | 23.1 | 54.7 | A096_3, Satt130 | PI 438489B | Hamilton | Yue et al. (2001a) |
| SCN 19-4 | 13.6 | 4.46 | 0.0010 | G | 23.1 | 66.6 | Satt012, Satt130 | PI 438489B | Hamilton | Yue et al. (2001a) |
| SCN 2-4 | 1.0 | | 0.0018 | G | 34.5 | 36.5 | A112_1 | Hartwig | Williams 82 | Vierling et al. (1996) |
| SCN 20-4 | 5.8 | 2.03 | 0.0010 | G | 62.2 | 66.6 | Satt012, Satt199 | PI 438489B | Hamilton | Yue et al. (2001a) |
| SCN 22-2 | 27.0 | 4.80 | | G | 89.0 | 91.0 | A245_2 | PI 468916 | A81356022 | Wang et al. (2001) |
| SCN 29-3 | 6.7 | 3.00 | | G | 102.6 | 124.0 | Satt453, Satt359 | Hamilton | PI 90763 | Guo et al. (2006) |
| SCN 4-2 | 17.6 | | 0.0002 | G | 108.5 | 110.5 | A378_1 | Evans | Peking | Concibido et al. (1997) |
| SCN 10-5 | 12.0 | | | H | 120.3 | 122.3 | K014_1 | Peking | Essex | Qiu et al. (1999) |
| SCN 11-2 | 9.0 | | | H | 120.3 | 122.3 | K014_1 | Peking | Essex | Qiu et al. (1999) |
| SCN 10-4 | 13.0 | | | H | 123.1 | 125.1 | B072_1 | Peking | Essex | Qiu et al. (1999) |
| SCN 11-1 | 13.0 | | | H | 123.1 | 125.1 | B072_1 | Peking | Essex | Qiu et al. (1999) |

TABLE D-continued

Consensus regions for QTLs for soybean cyst nematode resistance listed in SoyBase by Grant et al. (2008).

| QTL | $R^2$ (%)[a] | LOD score | P-value | LG[b] | Start position[c] | End position[c] | Peak marker/interval | Mapping parent 1 | Mapping parent 2 | Reference (herein incorporated by reference) |
|---|---|---|---|---|---|---|---|---|---|---|
| SCN 12-1 | 11.0 | | | I | 37.1 | 39.1 | K011_1 | Peking | Essex | Qiu et al. (1999) |
| SCN 28-2 | 2.0 | 2.50 | | J | 65.0 | 67.8 | Satt244, Satt547 | Bell | Colfax | Glover et al. (2004) |
| SCN 28-4 | 7.0 | 3.40 | | J | 65.0 | 78.6 | Satt244, Satt431 | Bell | Colfax | Glover et al. (2004) |
| SCN 29-2 | 7.8 | 4.60 | | J | 67.8 | 75.1 | Satt547, Sat_224 | Hamilton | PI 90763 | Guo et al. (2006) |
| SCN 29-6 | 4.2 | 13.90 | | J | 67.8 | 75.1 | Satt547, Sat_224 | Hamilton | PI 90763 | Guo et al. (2006) |
| SCN 1-2 | | | 0.0001 | J | 73.0 | 75.0 | B032_1 | M85-1430 | M83-15 | Concibido et al. (1994) |
| SCN 5-2 | 18.8 | | 0.0001 | J | 73.0 | 75.0 | B032_1 | Evans | PI 90763 | Concibido et al. (1997) |
| SCN 29-7 | 4.0 | 3.00 | | L | 87.4 | 93.9 | Sat_286, Satt229 | Hamilton | PI 90763 | Guo et al. (2006) |
| SCN 3-3 | 7.0 | 4.80 | | M | 74.0 | 76.0 | PHP02275a, PHP02301a | PI 437654 | BSR101 | Webb et al. (1995) |
| SCN 4-3 | 14.3 | | 0.001 | N | 33.9 | 35.9 | A280_1 | Evans | Peking | Concibido et al. (1997) |
| SCN 10-2 | 16.0 | | | | | | A018_3 | Peking | Essex | Qiu et al. (1999) |
| SCN 9-4 | 6.0 | | | | | | E01c | Peking | Essex | Mahalingam et al. (1995) |
| SCN 9-5 | 6.0 | | | | | | G15d | Peking | Essex | Mahalingam et al. (1995) |

[a]$R^2$ = Phenotypic variation explained by a QTL
[b]LG = linkage group. The linkage group names are from the integrated map by Song et al. (2004).
[c]The start positions and end positions are from the integrated map by Song et al. (2004).

When a single marker that was associated with a QTL in a published study could be placed on the consensus map, an arbitrary 2 cM interval with 1 cM on either side of the marker was defined as the QTL region in SoyBase.

TABLE E

Consensus regions for QTLs for Soybean Cyst Nematode Resistance and Earworm Resistance.

| QTL | LG[b] | Start position[c] | End position[c] | Mapping parent 1 | Mapping parent 2 | Reference (herein incorporated by reference) |
|---|---|---|---|---|---|---|
| Soybean cyst nematode resistance | | | | | | |
| SCN 19-1 | A2 | 46 | 53 | Hamilton | PI 438489B | Yue et al. (2001) |
| SCN 3-1 | A2 | 48 | 50 | BSR101 | PI 437654 | Webb et al. (1995) |
| SCN 9-2 | A2 | 48 | 50 | Essex | Peking | Mahalingam et al. (1995) |
| SCN 29-4 | A2 | 49 | 61 | Hamilton | PI 90763 | Guo et al. (2006) |
| SCN 8-5 | A2 | 53 | 55 | Essex | Forrest | Chang et al. (1997) |
| SCN 13-2 | A2 | 53 | 55 | Flyer | Hartwig | Prabhu et al. (1999) |
| SCN 30-3 | A2 | 60 | 62 | Bell | PI 437654 | Brucker et al. (2005) |
| SCN 2-1 | B1 | 64 | 66 | Hartwig | Williams82 | Vierling et al. (1996) |
| SCN 24-1 | B1 | 65 | 84 | Hamilton | PI 89772 | Yue et al. (2001) |
| SCN 20-1 | B1 | 84 | 101 | Hamilton | PI 438489B | Yue et al. (2001) |
| SCN 29-7 | B1 | 103 | 124 | Hamilton | PI 90763 | Guo et al. (2006) |
| SCN 22-3 | E | 33 | 35 | A81356022 | PI 468916 | Wang et al. (2001) |
| SCN 29-6 | E | 36 | 43 | Hamilton | PI 90763 | Guo et al. (2006) |

TABLE E-continued

Consensus regions for QTLs for Soybean Cyst Nematode Resistance and Earworm Resistance.

| QTL | LG[b] | Start position[c] | End position[c] | Mapping parent 1 | Mapping parent 2 | Reference (herein incorporated by reference) |
|---|---|---|---|---|---|---|
| SCN 21-3 | E | 37 | 45 | Hamilton | PI 438489B | Yue et al. (2001) |
| SCN 25-1 | E | 51 | 70 | Hamilton | PI 89772 | Yue et al. (2001) |
| SCN 29-5 | G | 0 | 13 | Hamilton | PI 90763 | Guo et al. (2006) |
| SCN 4-1 | G | 1 | 3 | Evans | Peking | Concibido et al. (1997) |
| SCN 5-1 | G | 1 | 3 | Evans | PI 90763 | Concibido et al. (1997) |
| SCN 6-1 | G | 1 | 3 | Evans | PI 88788 | Concibido et al. (1997) |
| SCN 13-1 | G | 1 | 3 | Flyer | Hartwig | Prabhu et al. (1999) |
| SCN 8-3 | G | 1 | 3 | Essex | Forrest | Chang et al. (1997) |
| SCN 7-1 | G | 2 | 9 | Evans | PI 209332 | Concibido et al. (1996) |
| SCN 30-2 | G | 4 | 6 | Bell | PI 437654 | Brucker et al. (2005) |
| SCN 23-3 | G | 5 | 6 | Hamilton | PI 89772 | Yue et al. (2001) |
| SCN 15-1 | G | 6 | 36 | PI 88287 | PI 89008 | Vaghchhipawala et al. (2001) |
| SCN 3-2 | G | 11 | 13 | BSR101 | PI 437654 | Webb et al. (1995) |
| SCN 19-4 | G | 23 | 67 | Hamilton | PI 438489B | Yue et al. (2001) |
| SCN 1-3 | G | 23 | 25 | M83-15 | M85-1430 | Concibido et al. (1994) |
| SCN 2-4 | G | 35 | 37 | Hartwig | Williams 82 | Vierling et al. (1996) |
| SCN 28-4 | J | 65 | 79 | Bell | Colfax | Glover et al. (2004) |
| SCN 29-2 | J | 68 | 75 | Hamilton | PI 90763 | Guo et al. (2006) |
| SCN 5-2 | J | 73 | 75 | Evans | PI 90763 | Concibido et al. (1997) |
| SCN 1-2 | J | 73 | 75 | M83-15 | M85-1430 | Concibido et al. (1994) |
| *Corn earworm resistance* | | | | | | |
| CEW 3-1 | C2 | 90 | 102 | Cobb | PI 227687 | Rector et al. (1999) |
| CEW 8-3 | C2 | 111 | 113 | Archer | Minsoy | Terry et al. (2000) |
| CEW 8-1 | E | 2 | 4 | Archer | Minsoy | Terry et al. (2000) |
| CEW 7-1 | E | 8 | 10 | Minsoy | Noir 1 | Terry et al. (2000) |
| CEW 2-2 | H | 49 | 62 | Cobb | PI 171451 | Rector et al. (1999) |
| CEW 3-2 | H | 49 | 62 | Cobb | PI 227687 | Rector et al. (1999) |
| CEW 9-3 | H | 53 | 61 | Cobb | PI 229358 | Narvel et al. (2001) |
| CEW 6-2 | J | 15 | 17 | Cobb | PI 229358 | Rector et al. (2000) |
| CEW 7-4 | J | 20 | 22 | Minsoy | Noir 1 | Terry et al. (2000) |
| CEW 6-3 | M | 59 | 71 | Cobb | PI 229358 | Rector et al. (2000) |
| CEW 4-1 | M | 59 | 71 | Cobb | PI 171451 | Rector et al. (2000) |

TABLE F

Consensus Regions for Qtls For Disease Resistance.

| QTL | LG | Start position | End position | Mapping parent 1 | Mapping parent 2 | Reference (herein incorporated by reference) |
|---|---|---|---|---|---|---|
| *Phytophthora resistance* | | | | | | |
| Phyto 1-1a | F | 16 | 18 | Conrad | Sloan | Burnham et al. (2003) |
| Phyto 1-1b | F | 16 | 18 | Conrad | Williams | Burnham et al. (2003) |
| Phyto 1-1c | F | 16 | 21 | Conrad | Harosoy | Burnham et al. (2003) |

TABLE F-continued

Consensus Regions for Qtls For Disease Resistance.

| QTL | LG | Start position | End position | Mapping parent 1 | Mapping parent 2 | Reference (herein incorporated by reference) |
|---|---|---|---|---|---|---|
| Sudden death syndrome resistance | | | | | | |
| SDS 8-2 | C2 | 120 | 122 | Douglas | Pyramid | Njiti et al. (2002) |
| SDS 2-6 | C2 | 131 | 133 | Essex | Forrest | Chang et al. (1996) |
| SDS 8-1 | G | 0 | 1 | Douglas | Pyramid | Njiti et al. (2002) |
| SDS 3-2 | G | 1 | 3 | Essex | Forrest | Chang et al. (1996) |
| Brown stem rot resistance | | | | | | |
| BSR 1-1 | J | 67 | 69 | BSR101 | PI 437654 | Lewers et al. (1999) |
| BSR 4-1 | J | 78 | 80 | Century | PI 437833 | Bachman et al. (2001) |
| BSR 3-1 | J | 78 | 80 | Century84 | L78-4094 | Bachman et al (2001) |
| *Sclerotinia* stem rot resistance | | | | | | |
| Sclero 5-1 | A2 | 60 | 62 | S19-90 | Williams82 | Arahana et al. (2001) |
| Sclero 6-2 | A2 | 60 | 62 | Vinton81 | Williams82 | Arahana et al. (2001) |
| Sclero 2-2 | A2 | 60 | 62 | Corsoy79 | Williams82 | Arahana et al. (2001) |
| Sclero 4-1 | D1a | 109 | 110 | DSR173 | Williams82 | Arahana et al. (2001) |
| Sclero 5-3 | D1a | 109 | 110 | S19-90 | Williams82 | Arahana et al. (2001) |
| Sclero 3-5 | D1b | 118 | 120 | Dassel | Williams82 | Arahana et al. (2001) |
| Sclero 2-7 | D1b | 118 | 120 | Corsoy79 | Williams82 | Arahana et al. (2001) |
| Sclero 2-12 | F | 63 | 65 | Corsoy79 | Williams82 | Arahana et al. (2001) |
| Sclero 5-6 | F | 63 | 65 | S19-90 | Williams82 | Arahana et al. (2001) |
| Sclero 5-9 | G | 85 | 97 | S19-90 | Williams82 | Arahana et al. (2001) |
| Sclero 6-7 | G | 96 | 98 | Vinton81 | Williams82 | Arahana et al. (2001) |
| Sclero 2-20 | L | 54 | 56 | Corsoy79 | Williams82 | Arahana et al. (2001) |
| Sclero 3-14 | L | 54 | 56 | Dassel | Williams82 | Arahana et al. (2001) |
| Sclero 6-13 | O | 120 | 129 | Vinton81 | Williams82 | Arahana et al. (2001) |
| Sclero 3-19 | O | 120 | 129 | Dassel | Williams82 | Arahana et al. (2001) |
| Sclero 4-11 | O | 127 | 129 | DSR173 | Williams82 | Arahana et al. (2001) |

B. Consensus QTL Regions Containing QTLs for Multiple Traits.

In QTL mapping studies, it is common to find QTLs for different traits mapped to a common genomic region. In many cases, the traits affected by the co-localized QTLs are correlated, while in other cases, the trait correlation may not be obvious. While it remains to be resolved whether the co-localized QTLs are tightly linked QTLs or the same QTL with pleiotropic effects, it is useful to document the genomic regions containing QTLs for multiple traits. Five genomic regions, 88-96 cM on LG A1, near 9-11 cM on LG C1, 26-36 cM on LG E, 31-40 cM on LG I, and 35-40 cM on LG M contain QTLs for both seed protein and seed oil contents. Soybean protein content and oil content are highly negatively correlated with a correlation coefficient as high as −0.98 (P<0.001) (Mansur et al. 1996, herein incorporated by reference). It is, therefore, expected to have some QTLs for two traits mapped to common genomic regions. Four genomic regions, near 34-36 cM on LG 1, 15-22 cM on LG J, 36-42 cM on LG K, and 35-40 cM on LG M, contain QTLs for both yield and plant height. Yield was correlated (r=0.59, P<0.001) with plant height in the study by Mansur et al. (1996). Yield was also correlated (r=0.48, P<0.001) with maturity (Mansur et al. 1996). Three genomic regions, near 34-36 cM on LG I, near 18-20 cM on LG M, and 35-40 cM on LG M, contain QTLs for both yield and maturity. Yield was negatively correlated (r=−0.58, P<0.001) with protein content and positively correlated (r=0.60, P<0.001) with oil content (Mansur et al. 1996). Two genomic regions, near 34-36 cM on LG 1 and 35-40 cM on LG M, contain QTLs for yield, protein content, and oil content. Another region, 36-42 cM on LG K, contains QTLs for yield and protein content. Lodging was highly correlated with plant height (r=0.84, P<0.001) (Mansur et al. 1996). Three genomic regions, 107-113 cM on LG C2, 8-11 cM on LG L, and 68-101 cM on LG L, contain QTLs for these two traits.

QTLs for *Sclerotinia* stem rot resistance were co-localized with QTLs for plant height near 120 cM on LG D1b and near 65 cM on LG F, for maturity near 54-56 cM on LG L, for SCN resistance near 60-62 cM on LG A2, and for protein content in 89-98 cM on LG G. *Sclerotinia* stem rot disease severity index was correlated with plant height (r=0.54, P<0.001) and maturity (r=0.67, P<0.001) in the study by Kim and Diers (2000, herein incorporated by reference). Shorter plant and earlier maturity were associated with greater resistance to *Sclerotinia* stem rot, which was considered an escape mechanism (Kim and Diers 2000).

However, the QTLs co-localized with plant height on LG D1b and LG F and with maturity on LG L were for physiological resistance to *Sclerotinia* stem rot (Arahana et al. 2001, herein incorporated by reference). Therefore, the resistance associated with shorter plant and earlier maturity may also involve physiological resistance. A significant correlation (r=0.40, P<0.05) between *Sclerotinia* stem rot disease severity index and protein content was reported by Hoffman et al. (1998), herein incorporated by reference. There is no report of a correlation between *Sclerotinia* stem rot resistance and SCN resistance.

QTLs for SCN resistance were co-localized with QTLs for sudden death syndrome (SDS) near 4-6 cM on LG G, for brown stem rot resistance in 67-79 cM on LG J, for oil content in 33-36 cM on LG E, and for *Sclerotinia* stem rot resistance as described above. Coinheritance of SDS resistance with SCN resistance was reported by Chang et al. (1997), herein incorporated by reference, and the locus underlying the coinheritance was assigned to the region on LG G where the major SCN resistance was located (Chang et al. 1997). The region on LG J is known to contain multiple resistance genes to different pathogens (Bachman et al. 2001, herein incorporated by reference). Correlation of SCN resistance with oil content was not reported in the literature. Qiu et al. (1999, herein incorporated by reference) carried out a QTL mapping study in a population that was segregating for both SCN resistance and oil content. A marker on LG H was found to be associated with both SCN resistance and oil content.

QTLs for corn earworm resistance were co-localized with QTLs for plant height in 107-113 cM on LG C2 and in 15-22 cM on LG J. There is no observation of a correlation between corn earworm resistance and plant height in soybean.

C. Consensus QTL Regions for Seed Protein and Oil Contents.

Using the integrated linkage map developed by Song et al. (Theor Appl Genet. 109(1):122-8, 2004) as a reference map, when QTLs identified in different mapping populations for the same trait were less than 10 cM from one another, the region containing these QTLs were considered a consensus QTL region for the trait. These consensus QTL regions are used to determine the true location of the QTL. Table G summarizes the consensus QTL regions for each trait, i.e. seed yield, protein content, and oil content, based on the QTL data collected in SoyBase. The chromosome length in cm (centimorgan) generally covered by a single marker associated with a QTL on the consensus map, is contemplated as an arbitrary 2 cM interval with 1 cM on either side of the marker defined as the QTL region, for example, as shown for QTL mapping in SoyBase. Thus the true QTL position (i.e. the actual gene (DNA sequence) controlling the mapped trait) may be outside the arbitrary 2 cM region. For use in the present inventions the arbitrary 2 cM region was used for each marker, such that the actual region identified by the markers of the present inventions may extend at least 1 cM before and after the most distant areas identified preferably 10 cM before and after the most distant areas identified herein. In addition to providing markers for use in breeding plants of the present inventions, consensus regions are examples for establishing consensus regions for identifying QTLs containing aphid resistant germplasm of the present inventions.

QTLs for protein content were found in 13 consensus regions on 11 LGs: A1, A2, B1, B2, C1, C2, E, G, I, K, and M (Table G). The regions 93-96 cM on LG A1, 145-151 cM on LG A2, 28-37 cM on LG B1, 28-46 cM on LG B2, 9-34 cM on LG C1, 90-98 cM on LG C1, 123-128 cM on LG C1, 117-123 cM on LG C2, 89-98 cM on LG G, and 31-42 cM on LG K were each found in two mapping populations developed from four mapping parents (Table G). The 26-32 cM region on LG E and the 33-40 cM region on LG M were each found in three mapping populations developed from five or six mapping parents (Table G). The 31-40 cM region on LG I was found in four mapping populations developed from seven mapping parents.

QTLs for oil content were found in nine consensus regions on eight LGs Table G: A1, C1, E, H, I, K, L, and M). The 88-96 cM region on LG A1 was found in four mapping populations developed from seven mapping parents. The regions near 9-11 cM on LG C1, 23-36 cM on LG E, 86-91 cM on LG H, 98-106 cM on LG K, 34-38 cM on LG L, and 35-40 cM on LG M were each found in two mapping populations developed from three or four mapping parents. The 22-40 cM region on LG I was found in five mapping populations developed from nine mapping parents. The 91-96 cM region on LG L was found in three mapping populations developed from six mapping parents.

TABLE G

Consensus regions for Soybean QTLs relating to yield, protein content and oil content that were less than 10 cM apart but were identified in different populations for the same trait.

| Trait/QTL | LG[a] | Start position[b] | End position[b] | Mapping parent 1 | Mapping parent 2 | Reference |
|---|---|---|---|---|---|---|
| Yield | | | | | | |
| Sd yld 11-1 | C2 | 39 | 41 | Minsoy | Noir 1 | Specht et al. (2001) |
| Yld/SW 2-2 | C2 | 45 | 47 | Archer | Noir 1 | Orf et al. (1999b) |
| Sd yld 15-1 | C2 | 97 | 99 | BSR 101 | LG82-8379 | Kabelka et al. (2004) |
| Sd yld 5-1 | C2 | 107 | 109 | Archer | Noir 1 | Orf et al. (1999b) |
| Yld/Ht 2-1 | C2 | 107 | 109 | Archer | Minsoy | Orf et al. (1999b) |
| Sd yld 16-3 | C2 | 112 | 114 | IA2008 | PI 468916 | Wang et al. (2004a) |

TABLE G-continued

Consensus regions for Soybean QTLs relating to yield, protein content and oil content that were less than 10 cM apart but were identified in different populations for the same trait.

| Trait/QTL | LG[a] | Start position[b] | End position[b] | Mapping parent 1 | Mapping parent 2 | Reference |
|---|---|---|---|---|---|---|
| Sd yld 3-2 | C2 | 117 | 119 | PI 27890 | PI 290136 | Mansur et al. (1996) |
| Yld/Ht 4-2 | C2 | 117 | 119 | Minsoy | Noir 1 | Orf et al. (1999b) |
| Sd yld 5-2 | D2 | 47 | 49 | Archer | Noir 1 | Orf et al. (1999b) |
| Yld/Ht 2-4 | D2 | 53 | 55 | Archer | Minsoy | Orf et al. (1999b) |
| Sd yld 10-1 | I | 31 | 33 | Parker | PI 468916 | Yuan et al. (2002) |
| Sd yld 9-1 | I | 34 | 36 | A81356022 | PI 468916 | Yuan et al. (2002) |
| Sd yld 14-1 | I | 36 | 37 | A3733 | PI 437088A | Chung et al. (2003) |
| Yld/Ht 4-1 | J | 11 | 13 | Minsoy | Noir 1 | Orf et al. (1999b) |
| Yld/Ht 1-3 | J | 20 | 22 | PI 27890 | PI 290136 | Mansur et al. (1996) |
| Sd yld 16-1 | K | 36 | 38 | IA2008 | PI 468916 | Wang et al. (2004a) |
| Sd yld 12-1 | K | 46 | 47 | Essex | Forrest | Yuan et al. (2002) |
| Sd yld 13-1 | K | 47 | 50 | Flyer | Hartwig | Yuan et al. (2002) |
| Sd yld 8-1 | L | 70 | 72 | Archer | Minsoy | Orf et al. (1999a) |
| Sd yld 11-6 | L | 88 | 90 | Minsoy | Noir 1 | Specht et al. (2001) |
| Yld/Ht 1-1 | L | 91 | 93 | PI 27890 | PI 290136 | Mansur et al. (1996) |
| Yld/Ht 3-1 | L | 94 | 96 | Archer | Noir 1 | Orf et al. (1999b) |
| Sd yld 6-1 | M | 18 | 20 | Minsoy | Noir 1 | Orf et al. (1999b) |
| Yld/Ht 2-2 | M | 18 | 20 | Archer | Minsoy | Orf et al. (1999b) |
| Yld/SW 1-1 | M | 35 | 37 | Archer | Minsoy | Orf et al. (1999b) |
| Sd yld 3-1 | M | 38 | 40 | PI 27890 | PI 290136 | Mansur et al. (1996) |
| Protein content | | | | | | |
| Prot 2-1 | A1 | 93 | 95 | PI 27890 | PI 290136 | Mansur et al. (1996) |
| Prot 12-1 | A1 | 94 | 96 | Minsoy | Noir 1 | Specht et al. (2001) |
| Prot 21-1 | A2 | 145 | 147 | BSR 101 | LG82-8379 | Kabelka et al. (2004) |
| Prot 14-1 | A2 | 149 | 151 | M91-212006 | SZG9652 | Vollmann et al. (2002) |
| Prot 3-2 | B1 | 28 | 30 | A87296011 | C1763 | Brummer et al. (1997) |
| Prot 16-1 | B1 | 35 | 37 | Essex | Williams | Chapman et al. (2003) |
| Prot 4-11 | B2 | 28 | 30 | PI 416937 | Young | Lee et al. (1996b) |
| Prot 1-6 | B2 | 32 | 34 | A81356022 | PI 468916 | Diers et al. (1992) |
| Prot 4-10 | B2 | 43 | 46 | PI 416937 | Young | Lee et al. (1996b) |
| Prot 9-2 | C1 | 9 | 11 | Minsoy | Noir 1 | Orf et al. (1999b) |
| Prot 4-4 | C1 | 20 | 22 | PI 416937 | Young | Lee et al. (1996b) |
| Prot 12-2 | C1 | 32 | 34 | Minsoy | Noir 1 | Specht et al. (2001) |
| Prot 3-3 | C1 | 90 | 92 | A87296011 | C1763 | Brummer et al. (1997) |
| Prot 4-3 | C1 | 96 | 98 | PI 416937 | Young | Lee et al. (1996b) |
| Prot 21-2 | C1 | 123 | 125 | BSR 101 | LG82-8379 | Kabelka et al. (2004) |
| Prot 4-2 | C1 | 126 | 128 | PI 416937 | Young | Lee et al. (1996b) |
| Prot 17-1 | C2 | 117 | 119 | Essex | Williams | Hyten et al. (2004) |
| Prot 13-2 | C2 | 121 | 123 | Ma.Belle | Proto | Csanadi et al. (2001) |
| Prot 4-6 | E | 26 | 28 | PI 416937 | Young | Lee et al. (1996b) |
| Prot 3-6 | E | 30 | 32 | A87296011 | C1763 | Brummer et al. (1997) |
| Prot 18-1 | E | 30 | 32 | Coker 237 | PI 97100 | Fasoula et al. (2004) |
| Prot 1-8 | G | 89 | 91 | A81356022 | PI 468916 | Diers et al. (1992) |
| Prot 3-10 | G | 96 | 98 | A87296011 | C1763 | Brummer et al. (1997) |
| Prot 11-1 | I | 31 | 33 | Parker | PI 468916 | Yuan et al. (2002) |
| Prot 1-3 | I | 31 | 33 | A81356022 | PI 468916 | Diers et al. (1992) |
| Prot 3-12 | I | 31 | 33 | A87296011 | C1763 | Brummer et al. (1997) |
| Prot 10-1 | I | 34 | 36 | A81356022 | PI 468916 | Yuan et al. (2002) |
| Prot 15-1 | I | 36 | 37 | A3733 | PI 437088A | Chung et al. (2003) |
| Prot 1-2 | I | 38 | 40 | A81356022 | PI 468916 | Lark et al. (1994) |
| Prot 5-4 | K | 31 | 33 | Coker237 | PI 97100 | Lee et al. (1996b) |
| Prot 12-3 | K | 40 | 42 | Minsoy | Noir 1 | Specht et al. (2001) |
| Prot 12-4 | M | 33 | 35 | Minsoy | Noir 1 | Specht et al. (2001) |
| Prot 13-3 | M | 33 | 35 | Ma.Belle | Proto | Csanadi et al. (2001) |
| Prot 7-1 | M | 38 | 40 | Archer | Minsoy | Orf et al. (1999b) |
| Oil content | | | | | | |
| Oil 8-1 | A1 | 88 | 90 | Archer | Minsoy | Orf et al. (1999b) |
| Oil 4-3 | A1 | 91 | 93 | A87296011 | C1763 | Brummer et al. (1997) |
| Oil 3-2 | A1 | 93 | 95 | PI 27890 | PI 290136 | Mansur et al. (1996) |
| Oil 13-1 | A1 | 94 | 96 | Minsoy | Noir 1 | Specht et al. (2001) |
| Oil 9-1 | C1 | 9 | 11 | Archer | Noir 1 | Orf et al. (1999b) |
| Oil 8-2 | C1 | 9 | 11 | Archer | Minsoy | Orf et al. (1999b) |
| Oil 5-1 | E | 23 | 25 | PI 416937 | Young | Lee et al. (1996b) |
| Oil 2-9 | E | 34 | 36 | A81356022 | PI 468916 | Diers et al. (1992) |
| Oil 17-2 | H | 86 | 88 | Coker 237 | PI 97100 | Fasoula et al. (2004) |
| Oil 19-2 | H | 89 | 91 | N87-984-16 | TN93-99 | Panthee et al. (2005) |
| Oil 14-3 | I | 22 | 24 | Ma.Belle | Proto | Csanadi et al. (2001) |
| Oil 12-1 | I | 31 | 33 | Parker | PI 468916 | Yuan et al. (2002) |
| Oil 11-1 | I | 31 | 33 | A81356022 | PI 468916 | Yuan et al. (2002) |
| Oil 13-4 | I | 34 | 36 | Minsoy | Noir 1 | Specht et al. (2001) |

TABLE G-continued

Consensus regions for Soybean QTLs relating to yield, protein
content and oil content that were less than 10 cM apart but were identified
in different populations for the same trait.

| Trait/QTL | LG[a] | Start position[b] | End position[b] | Mapping parent 1 | Mapping parent 2 | Reference |
|---|---|---|---|---|---|---|
| Oil 15-1 | I | 36 | 37 | A3733 | PI 437088A | Chung et al. (2003) |
| Oil 2-2 | I | 38 | 40 | A81356022 | PI 468916 | Diers et al. (1992) |
| Oil 4-11 | K | 98 | 100 | A87296011 | C1763 | Brummer et al. (1997) |
| Oil 14-2 | K | 104 | 106 | Ma.Belle | Proto | Csanadi et al. (2001) |
| Oil 18-2 | L | 34 | 36 | PI 416937 | Young | Fasoula et al. (2004) |
| Oil 2-7 | L | 36 | 38 | A81356022 | PI 468916 | Diers et al. (1992) |
| Oil 5-3 | L | 36 | 38 | PI 416937 | Young | Lee et al. (1996b) |
| Oil 3-1 | L | 91 | 93 | PI 27890 | PI 290136 | Mansur et al. (1996) |
| Oil 16-1 | L | 93 | 95 | Essex | Williams | Hyten et al. (2004) |
| Oil 9-3 | L | 94 | 96 | Archer | Noir 1 | Orf et al. (1999b) |
| Oil 16-2 | M | 35 | 37 | Essex | Williams | Hyten et al. (2004) |
| Oil/Prot 1-2 | M | 38 | 40 | PI 27890 | PI 290136 | Lark et al. (1994) |

[a]LG = linkage group. The linkage group names are from the integrated map by Song et al. (2004).
[b]The start positions and end positions are from the integrated map by Song et al. (2004). When a single marker that was associated with a QTL in a published study was placed on the consensus map, an arbitrary 2 cM interval with 1 cM on either side of the marker was defined as the QTL region in SoyBase.

D. QTL Discovery in Soybean Germplasm.

Over a thousand SNP markers were added to the integrated soybean linkage map (Choi et al. 2007, herein incorporated by reference). High-throughput SNP genotyping systems were developed and are commercially available. For example, the Illumina BeadStation 500 (Shen et al. 2005, herein incorporated by reference) analyzes 1536 SNP loci in parallel in 192 DNA samples with at least three days. The addition of thousands of SNP markers to the integrated linkage map and the availability of high-throughput SNP genotyping systems will significantly reduce the time needed to genotype mapping populations and accelerate QTL discovery in soybean.

The first draft sequence of the whole soybean genome was released in 2008 (JGI 2008, herein incorporated by reference). The availability of a whole genome sequence allows scientists to fine-map QTLs and pinpoint the specific mutations that cause the phenotypic variations under investigation.

The development of new statistical approaches and computer software allows joint analysis of multiple populations and increased the ability to identify existing QTLs, especially QTLs with small effects. Bink et al. (2008, herein incorporated by reference) developed a pedigree-based approach that jointly analyzes the data from multiple populations that are related through their common ancestors in the pedigree. This approach is currently implemented in the computer software FlexQTL™. Jourjon et al. (2005, herein incorporated by reference) developed a computer software package named MCQTL that can perform QTL mapping in multi-cross designs.

The major limitation to QTL discovery in soybean is the difficulty in obtaining accurate measurement of the traits with low heritability. For certain traits such as field resistance to Sclerotinia stem rot, reliable measurement was difficult to obtain even with efforts to provide the optimum conditions to induce the disease. Large experiments with multiple locations in multiple years are often required to obtain the phenotypic data. Thus the inventors contemplate identifying specific genes contributing to aphid resistance within the QTLs identified during the development of the present inventions.

V. Exemplary Methods for Making Transgenic Plants of the Present Inventions.

In some embodiments, a transgenic plant having enhanced aphid resistance is made by methods of the present inventions for expressing specific aphid resistant germplasm.

A. Plants.

The discovery and isolation of an early maturing aphid resistant soybean cultivar is disclosed herein. Specifically, soybean plant cultivars corresponding to line E08934, PI 567537 and PI 567585A are disclosed. The invention relates to a seed of one or more of a soybean line E08934, PI 567537 and PI 567585A, to the plants, i.e. comprising aphid resistant germplasm, derived from one or more of a soybean line E08934, PI 567537 and PI 567585A, and to methods for producing a soybean seed and plant produced by crossing any one of a cultivar of line E08934, PI 567537 and PI 567585A, with itself or another soybean variety, and further to provide offspring comprising the aphid resistant germplasm of the present invention. The invention further relates to an aphid resistant soybean plant and seed from that plant comprising germplasm of any one of a soybean cultivar line E08934, PI 567537 and PI 567585A. Examples of offspring comprising the aphid resistant germplasm of the present invention include the soybean lines E070020-19, E12902, E12905, E12909, etc.

The methods of the present invention are not limited to the use of any particular plant. Indeed, a variety of plants are contemplated for introducing aphid resistance, including but not limited to soybean, beans, tomato, pepper, cotton, barley, sorghum, sunflowers, rice, corn, wheat, Brassica, and flowers.

In some embodiments, aphid resistant germplasm is introgressed into a food-grade soybean plant that includes but is not limited to Ohio FG1, Agracola Farms AF271, Burtch Seed BBF44, H.A.P.I. Ohio GL2930, LG Seed EX230FG, Wellman WFG268, and the like. In some embodiments an aphid resistant a food-grade soybean plant is a specialty soybean plant, for example, provides Edamame soybeans, and the like. In some embodiments, aphid resistant germplasm is introgressed into a soybean plant that provides food for livestock, poultry, cattle and swine, for example, a conventional soybean plant that includes but is not limited to Asgrow AG2905, Pioneer 93B01, and Public Sandusky. In some embodiments a soybean plant provides a non-food product, for example, a fuel additive, such as a diesel fuel additive, soy biodiesel, soybean ink, soy crayons, soybean based wood adhesive, soybean based lubricants, and the like.

B. Vectors.

The methods of the present invention contemplate the use of a heterologous gene such as a gene encoding an insect resistant protein, an herbicide resistant protein, a gene for providing a selected agronomic trait, or more than one gene, such as a linkage group for providing a selected agronomic trait (such as aphid resistant germplasm or germplasm comprising an integrated transgene).

Heterologous genes intended for expression in plants are first assembled in expression cassettes comprising a promoter. Methods which are well known to or developed by those skilled in the art may be used to construct expression vectors containing a heterologous gene and appropriate transcriptional and translational control elements. These methods include in vitro recombinant DNA techniques, synthetic techniques, and in vivo genetic recombination. Exemplary techniques are widely described in the art (See e.g., Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y., herein incorporated by reference).

In general, these vectors comprise a nucleic acid sequence encoding a heterologous gene, or encoding a sequence designed to decrease endogenous gene expression, (as described above) operably linked to a promoter and other regulatory sequences (e.g., enhancers, polyadenylation signals, etc.) required for expression in a plant.

Promoters include but are not limited to constitutive promoters, tissue-specific, organ-specific, and developmentally-specific promoters, and inducible promoters. Examples of promoters include but are not limited to: constitutive promoter 35S of cauliflower mosaic virus; a wound-inducible promoter from tomato, leucine amino peptidase ("LAP," Chao et al., Plant Physiol 120:979-992 (1999), herein incorporated by reference); a chemically-inducible promoter from tobacco, Pathogenesis-Related 1 (PRO (induced by salicylic acid and BTH (benzothiadiazole-7-carbothioic acid S-methyl ester)); a heat shock promoter (U.S. Pat. No. 5,187,267, herein incorporated by reference); a tetracycline-inducible promoter (U.S. Pat. No. 5,057,422, herein incorporated by reference); and seed-specific promoters, such as those for seed storage proteins (e.g., phaseolin, napin, oleosin, and a promoter for soybean beta conglycin (Beachy et al., (1985) EMBO J. 4:3047-3053, herein incorporated by reference). All references cited herein are incorporated in their entirety.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters such as those disclosed herein. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (See e.g., Odell et al., Nature 313:810 (1985); Rosenberg et al., Gene, 56:125 (1987); Guerineau et al., Mol. Gen. Genet. 262:141 (1991); Proudfoot, Cell, 64:671 (1991); Sanfacon et al., Genes Dev., 5:141; Mogen et al., Plant Cell, 2:1261 (1990); Munroe et al., Gene, 91:151 (1990); Ballas et al., Nucleic Acids Res. 17:7891 (1989); Joshi et al., Nucleic Acid Res., 15:9627 (1987), all of which are incorporated herein by reference).

In addition, in some embodiments, constructs for expression of the heterologous gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. Intron sequences have been routinely incorporated into plant transformation vectors, typically within the non-translated leader.

In some embodiments of the present invention, a construct for expression of the heterologous nucleic acid sequence of interest also includes a regulator such as a nuclear localization signal (Kalderon et al., Cell 39:499 (1984); Lassner et al., Plant Molecular Biology 17:229 (1991)), a plant translational consensus sequence (Joshi, Nucleic Acids Research 15:6643 (1987)), an intron (Luehrsen and Walbot, Mol. Gen. Genet. 225:81 (1991)), and the like, operably linked to the nucleic acid sequence encoding an heterologous gene.

In preparing the construct comprising the nucleic acid sequence encoding an heterologous gene, or encoding a sequence designed to decrease heterologous gene expression, various DNA fragments can be manipulated, so as to provide for the DNA sequences in the desired orientation (e.g., sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra, Gene 19: 259 (1982); Bevan et al., Nature 304:184 (1983), all of which are incorporated herein by reference), the bar gene which confers resistance to the herbicide phosphinothricin (White et al., Nucl Acids Res. 18:1062 (1990); Spencer et al., Theor. Appl. Genet. 79:625 (1990), all of which are incorporated herein by reference), the hph gene which confers resistance to the antibiotic hygromycin (Blochlinger and Diggelmann, Mol. Cell. Biol. 4:2929 (1984), incorporated herein by reference)), and the dhfr gene, which confers resistance to methotrexate (Bourouis et al., EMBO J., 2:1099 (1983), incorporated herein by reference).

In some preferred embodiments, the Ti (T-DNA) plasmid vector is adapted for use in an *Agrobacterium* mediated transfection process (See e.g., U.S. Pat. Nos. 5,981,839; 6,051,757; 5,981,840; 5,824,877; and 4,940,838; all of which are herein incorporated by reference). Construction of recombinant Ti and Ri plasmids in general follows methods typically used with the more common vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The use of T-DNA as a flanking region in a construct for integration into a Ti- or R1-plasmid has been described in EPO No. 116,718 and PCT Application Nos. WO 84/02913, 02919 and 02920 all of which are herein incorporated by reference). See also Herrera-Estrella, Nature 303:209-213 (1983); Fraley et al., Proc. Natl. Acad. Sci, USA 80:4803-4807 (1983); Horsch et al., Science 223:496-498 (1984); and DeBlock et al., EMBO J. 3:1681-1689 (1984), all of which are herein incorporated by reference).

The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available. In other embodiments of the invention, the nucleic acid sequence of interest is targeted to a particular locus on the plant genome. Site-directed integration of the nucleic acid sequence of interest into the plant cell genome may be achieved by, for example, homologous recombination using Agrobacterium-derived sequences. Generally, plant cells are incubated with a strain of Agrobacterium which contains a targeting vector in which sequences that are homologous to a DNA sequence inside the target locus are flanked by Agrobacterium transfer-DNA (T-DNA) sequences, as previously described (U.S. Pat. No. 5,501,967 herein incorporated by reference). One of skill in the art knows that homologous recombination may be achieved using targeting vectors that contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known. Agrobacterium tumefaciens is a common soil bacterium that causes crown gall disease by transferring some of its DNA to the plant host. The transferred DNA (T-DNA) is stably integrated into the plant genome, where its expression leads to the synthesis of plant hormones and thus to the tumorous growth of the cells. A putative macromolecular complex forms in the process of T-DNA transfer out of the bacterial cell into the plant cell.

In yet other embodiments, the nucleic acids such as those disclosed herein is utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted heterologous polynucleotide can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

In some embodiments of the present invention, where a heterologous nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the E. coli GUS gene and the CaMV 35S transcriptional terminator (WO 93/07278, herein incorporated by reference).

C. Transformation Techniques.

Once a nucleic acid sequence encoding an heterologous gene is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See e.g., U.S. Pat. Nos. 5,451,513; 5,545,817; 5,545,818; PCT application WO 95/16783 all of which are incorporated herein by reference). The basic technique for chloroplast transformation involves introducing regions of cloned plastid DNA flanking a selectable marker together with the nucleic acid encoding the RNA sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al., PNAS, 87:8526 (1990); Staub and Maliga, Plant Cell, 4:39 (1992), all of which are incorporated herein by reference). The presence of cloning sites between these markers allowed creation of a plastid targeting vector introduction of foreign DNA molecules (Staub and Maliga, EMBO J., 12:601 (1993), herein incorporated by reference). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, PNAS, 90:913 (1993), herein incorporated by reference). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway, Mol. Gen. Genet, 202:179 (1985), herein incorporated by reference). In still other embodiments, the vector is transferred into the plant cell by using polyethylene glycol (Krens et al., Nature, 296:72 (1982); Crossway et al., BioTechniques, 4:320 (1986), all of which are herein incorporated by reference); fusion of protoplasts with other entities, either minicells, cells, lysosomes or other fusible lipid-surfaced bodies (Fraley et al., Proc. Natl. Acad. Sci., USA, 79:1859 (1982), herein incorporated by reference); protoplast transformation (EP 0 292 435); direct gene transfer (Paszkowski et al., EMBO J., 3:2717 (1984); Hayashimoto et al., Plant Physiol. 93:857 (1990), all of which are herein incorporated by reference).

In still further embodiments, the vector may also be introduced into the plant cells by electroporation. (Fromm, et al., Proc. Natl. Acad. Sci. USA 82:5824 (1985); Riggs et al., Proc. Natl. Acad. Sci. USA 83:5602 (1986), all of which are herein incorporated by reference). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (e.g., available from Agracetus, Inc., Madison, Wis. and Dupont, Inc., Wilmington, Del.), see e.g., U.S. Pat. No. 4,945,050; and McCabe et al., Biotechnology 6:923 (1988), all of which are incorporated herein by reference). Examples of methods for transforming crop plants are provided for soybean plants in U.S. Pat. No. 5,015,580, herein incorporated by reference, Christou et al., Plant Physiol., 87:671 (1988) (soybean); McCabe et al., Bio/Technology 6:923 (1988) (soybean); and other plants such as Weissinger et al., Annual Rev. Genet. 22:421 (1988); Sanford et al., Particulate Science and Technology, 5:27 (1987) (onion); Svab et al., Proc. Natl. Acad. Sci. USA, 87:8526 (1990) (tobacco chloroplast); Klein et al., Proc. Natl. Acad. Sci. USA, 85:4305 (1988) (maize); Klein et al., Bio/Technology, 6:559 (1988) (maize); Klein et al., Plant Physiol., 91:4404 (1988) (maize); Fromm et al., Bio/Technology, 8:833 (1990); and Gordon-Kamm et al., Plant Cell, 2:603 (1990) (maize); Koziel et al., Biotechnology, 11:194 (1993) (maize); Hill et al., Euphytica, 85:119 (1995) and Koziel et al., Annals of the New York Academy of Sciences 792:164 (1996); Shimamoto et al., Nature 338: 274 (1989) (rice); Christou et al., Biotechnology, 9:957 (1991) (rice); Datta et al., Bio/Technology 8:736 (1990) (rice); European Application EP 0 332 581 (orchardgrass and other Poaceae); Vasil et al., Biotechnology, 11: 1553 (1993) (wheat); Weeks et al., Plant Physiol., 102: 1077 (1993) (wheat); Wan et al., Plant Physiol. 104: 37 (1994) (barley); Jahne et al., Theor. Appl. Genet. 89:525 (1994) (barley); Knudsen and Muller, Planta, 185:330 (1991) (barley); Umbeck et al., Bio/Technology 5: 263 (1987) (cotton); Casas et al., Proc. Natl. Acad. Sci. USA 90:11212 (1993) (*sorghum*); Somers et al., Bio/Technology 10:1589 (1992) (oat); Torbert et al., Plant Cell Reports, 14:635 (1995) (oat); Weeks et al., Plant Physiol., 102:1077 (1993) (wheat); Chang et al., WO 94/13822 (wheat) and Nehra et al., The Plant Journal, 5:285 (1994) (wheat), all of which are herein incorporated by reference.

In addition to direct transformation, in some embodiments, the vectors comprising a nucleic acid sequence encoding a heterologous gene are transferred using *Agrobacterium*-mediated transformation (Hinchee et al., Biotechnology, 6:915 (1988); Ishida et al., Nature Biotechnology 14:745 (1996), all of which are herein incorporated by reference). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention) can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell, (1987) Science, 237:1176). Species which are susceptible infection by *Agrobacterium* may be transformed in vitro. Transformation methods for producing transgenic soybean plants using *Agrobacterium*-mediated transformation are provided in U.S. Patent Appln. No. 20020157139, U.S. Pat. Nos. 6,384,301, 5,416,011, 5,569,834, and 5,824,877, all of which are herein incorporated by reference D. Regeneration.

After selecting for transformed plant material that can express a heterologous gene encoding a heterologous gene or variant thereof, whole plants are regenerated, for example methods for regenerating transformed soybean plants are provided in U.S. Pat. No. 5,015,580, herein incorporated by reference. Plant regeneration from cultured protoplasts is described in Evans et al., Handbook of Plant Cell Cultures, Vol. 1: (MacMillan Publishing Co. New York, (1983); and Vasil I. R. (ed.), Cell Culture and Somatic Cell Genetics of Plants, Acad. Press, Orlando, Vol. I, (1984) and Vol. III, (1986), herein incorporated by reference. Many types of plants are regenerated from cultured cells or tissues, including but not limited to major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

E. Generation of Transgenic Aphid Resistant Soybean Lines.

Transgenic lines are established from transgenic plants by tissue culture propagation. The presence of nucleic acid sequences encoding a heterologous gene or mutants or variants thereof in a transgenic plant line may be introgressed into aphid resistant plants for providing transgenic aphid resistant plants using traditional plant breeding techniques. Transgenic lines of aphid resistant soybean cultivars may be utilized for evaluation of aphid resistant activity, insect resistance ratios, phenotype, pathogen resistance and other agronomic traits, such as agronomic shown for transgenic soybean plants in European Patent No. 301,749, herein incorporated by reference, in the presence of an introgressed transgene.

VI. Soybean Plant Resistance to Certain Aphid Populations.

Aphid resistant germplasm showed differential results when infested with different aphid populations. As one example, aphid resistant soybean plants having Rag1 provided resistant to an aphid biotype 1 isolated from a natural aphid population found in Illinois. In contrast, these Rag1 plants showed susceptibility to aphids in a natural (i.e. wild) population in Ohio in addition to susceptibility to an aphid population (biotype 2) isolated from this natural Ohio population. Aphid resistant soybean plants having Rag2 genes (i.e. PI 200538) showed resistance to aphid biotypes 1 and 2. In other words, soybean plants having Rag1 genes were susceptible to aphid biotype 2 while soybean plants having Rag2 genes were resistant. However, a third aphid biotype, i.e. biotype 3, was isolated in Indiana which overcame resistance for plants having Rag1 or Rag2, demonstrating that aphid resistant germplasm is needed for providing resistance to different populations of aphids.

Therefore, in some embodiments, aphid resistant soybean plants comprising genes (aphid resistant germplasm) derived from aphid resistant germplasm sources of the present inventions are contemplated for use in producing aphid resistant soybean plants having enhanced aphid resistance to at least one, two, three or more aphid isolates. In other embodiments, production of aphid resistant soybean plants having enhanced resistance to at least one, two, or more aphid biotypes are contemplated by stacking at least one Rag germplasm region of the present inventions with other Rag genes. In some embodiments, molecular markers specifically linked to and/or identifying aphid resistant germplasm of the present inventions will be useful for developing aphid-resistant soybean plant cultivars having enhanced aphid resistance to aphid biotypes.

A. Aphids Isolated from Natural Populations.

Individual aphid biotypes were isolated and used in methods for testing aphid resistance of soybean plants as described in Hill et al., 2010. Aphid isotypes were first identified when an aphid resistant soybean plant line derived from Rag1 plants, resistant to an aphid isolate derived from a natural aphid population found in Illinois, was overcome by a natural aphid population in Ohio. For specific testing, an Ohio isolate was made from aphids collected from this natural population. This isolate showed the same results as the natural population and was maintained for use in further testing of aphid resistant plant lines. Therefore, isolates of natural aphid populations were made from field trial areas and maintained in the laboratory, for exemplary isolation and maintenance methods, see, Hill, et al., "A New Soybean Aphid (Hemiptera: Aphididae) Biotype Identified." J. Econ. Entomol. 103(2): 509-515 (2010). The following is one example of how aphids were cultured and maintained. Soybean aphid isolates included an Illinois isolate originally collected in 2000, tested in several previous studies (Hill et al. 2004a,b, 2006a,b, 2009; Li et al. 2004, 2007; Kim et al. 2008b) and referred to as biotype 1; an Ohio isolate collected in 2005, distinguished from the Illinois isolate by its ability to colonize plants with Rag1 (Kim et al. 2008b) and referred to as biotype 2; and biotype 3, an isolate collected from *F. alnus* in Springfeld Fen, Ind., during spring 2007. Biotype 4 was isolated from Wisconsin that can readily colonize Rag1 and Rag2 genotypes and soybean lines with the stack of both Rag1/Rag2 genes (Alt and Ryan-Mahmutagic 2013). Biotype 1 was maintained on a continuous supply of Williams 82 plants in growth chambers as described previously (Hill et al. 2004b). Biotype 2 was maintained on the soybean breeding line LD05-16611 that possesses Rag1. SF-55 was initially maintained on Williams 82 plants until preliminary tests indicated that it readily colonized PI 200538, after which was maintained on that accession to prevent contamination with biotypes 1 and 2, which did not colonize PI 200538. Soybean aphid isolates were periodically cloned from isolated nymphs and were maintained in different plant growth chambers to avoid mixing.

Isolates of natural populations were assigned individual numbers when an aphid isolate (i.e. population) demonstrated differential responses to the same aphid resistant germplasm derived from a specific resistance source. In other words, when soybean plants derived from one resistance source showed aphid resistance to one isolate (significantly lower DI) that did not show aphid resistance to another aphid isolate (i.e. instead had DI levels similar to known non-aphid resistant plants) then the aphid isolate was numbered as in Hill et al., 2010.

At least one aphid population was isolated from a natural population found in Michigan, i.e. Michigan isolate, and maintained in the greenhouse for use in choice and non-choice testing of the plants of the present inventions. Specifically, a Michigan aphid isolate was used to infest plants for trials described herein was collected from a naturally infested field on the Agronomy Farm of MSU the year before the trials began and maintained in the greenhouse on soybean plants.

B. Characterization of Aphid Isolates in Relation to Sources of Aphid Resistant Germplasm.

Different aphid biotypes or isolates showed a differential reaction when tested on soybean plants in comparative experiments between different soybean plant aphid resistance sources. At least three aphid biotypes, i.e. 1, 2 and 3, isolates of natural aphid populations found in Ohio, Illinois and Indiana, respectively, (Kim et al. 2008; Hill et al., 2010, all of which are herein incorporated by reference) in addition to at least one aphid population isolated from Michigan aphids (Michigan isolate) were maintained in separate greenhouses/laboratories. These biotypes were identified by their differential ability to overcome a particular aphid resistant germplasm region or particular aphid resistant loci derived from a resistance source of germplasm.

For one example of aphid biotype identification, a soybean plant derived from Dowling soybean plants having the Rag1 aphid resistance germplasm without introduction of any additional aphid resistant germplasm, demonstrated resistant to aphid isolates designated Biotype 1 and 3 but not when exposed to an aphid population isolate designated Biotype 2. As another example, soybean plants having a Rag2 aphid resistance germplasm derived from PI 200538 soybean plants without introduction of any additional aphid resistant germplasm, showed resistant to Biotypes 1 and 2 but not to 3. Thus one possible solution for providing durable or broad aphid resistance to at least 3 aphid biotypes is to stack Rag1 and Rag2. However, Hill et al., 2010 that "stacking Rag1 and Rag2 together may not provide long-term (or durable) resistance to the soybean aphid." Page 514. Further, soybean plants having the aphid resistance genes Rag1 (Dowling) or Rag2 did not provide resistance in plants that were infested with a Michigan aphid isolate. In contrast to Hill et al., 2010, results from stacking aphid resistant germplasm of the present inventions showed exemplary enhanced aphid resistance when tested with Michigan isolates.

C. Soybean Plants having Stacked Genes Show Enhanced Resistance to a Michigan Aphid Isolate.

Specifically, aphid resistant soybean plants of the present inventions showed enhanced resistance, i.e. lower average DI, in comparative tests using a Michigan aphid isolate as described herein. For one example, soybean plants of line 131 (having Rag6 germplasm) and line 19 (having both a Rag3c and a Rag6 germplasm (Rag3cRag6) derived from resistance source E08934 of the present inventions showed enhanced aphid resistance, i.e. superior aphid resistance over plants from resistance source PI 567598B, when tested with at least one Michigan aphid isolate as described herein, see, FIG. 5. E12902 plants also have Rag3c and Rag6 germplasm and exhibit superior aphid resistance.

Furthermore, soybean plants provided herein having stacked aphid resistant germplasm (genes) showed superior resistance, i.e. lower average DI, over soybean plants in comparative tests when tested with a Michigan aphid isolate. Specifically, soybean plant lines having stacked genes from different resistant sources were produced using line E08934 and PI 567541B plants. Some examples of plants having stacked genes showing enhanced resistance over plant lines having each one of these genes alone were soybean plant lines having the following sets of stacked genes: Rag3cRag6; Rag6rag1c; Rag3cRag6Rag1c; see, FIG. 4. For example, plants with E12902 germplasm have all the three aphid resistance genes on Chr. 7, Chr. 8, and Chr. 16 (i.e. genes rag1c, Rag6, and Rag3c, respectively) and was selected based on the marker genotypes at these three loci.

Additionally at least one germplasm region in or derived from PI 567585A soybean plants provided a Rag3-1 germplasm that provided resistance to Michigan aphid isolates in two caged field trials.

Therefore, contemplated embodiments include pyramiding and/or stacking aphid resistant alleles of the present inventions for providing enhanced aphid resistant soybean plants. In some embodiments, enhanced aphid resistant soybean plants provide superior resistance to aphids, including lower DI for characteristics comprising antibiosis, antixenosis and tolerance. In some embodiments, these plants may find use for resistance of new aphid biotypes or aphid isolates. In some embodiments, such enhanced aphid resistant plants may find use in methods of crop rotation.

Specifically, in one embodiment, a pyramided loci for genes or alleles at or near the Rag3 loci, including but not limited to exemplary combinations such as Rag3b/Rag3b; Rag3b/Rag3c, Rag3b/Rag3; Rag3b/rag3; Rag3b/Rag3-1; Rag3c/Rag3c; Rag3c/Rag3-1; Rag3-1//Rag3-1; etc. In one embodiment, a pyramided loci for genes or allele at or near the Rag3 loci is in combination with stacking genes or alleles at other resistant loci, including but not limited to exemplary combinations such as Rag1/Rag2/rag4; rag1c/Rag2/rag4; rag1c/Rag2/Rag6; etc., in a single cultivar, where dominant or co-dominate genes may be heterozygous or homozygous, where recessive genes may be heterozygous or homozygous depending upon the intended effect. In preferred embodiments, recessive genes are homozygous unless pyramided with other genes. In preferred embodiments, such pyramided and/or stacked genes are provided in a single aphid resistant soybean cultivar in order to provide durable and/or broad aphid resistance in plants.

The following references are specifically incorporated herein by reference in their entireties:

Alt J, Ryan-Mahmutagic M (2013) Soybean Aphid Biotype 4 Identified. Crop Science 53:1491. doi: 10.2135/cropsci2012.11.0672

Beckendorf, et al. (2008) Soybean aphid feeding injury and soybean yield, yield components, and seed composition. Agron J 100:237-246

Chen, et al. (2007) SSR marker diversity of soybean aphid resistance sources in North America. Genome 50:1104-1111

Choi, et al. (2007) A soybean transcript map: gene distribution, haplotype and single-nucleotide polymorphism analysis. Genetics 176:685-696

Churchill, et al. (1994) Empirical threshold values for quantitative trait mapping. Genetics 138:963-971

Clark, et al. (2002) Transmissibility of field isolates of soybean viruses by *Aphis glycines*. Plant Dis 86:1219-1222

Cregan, et al. (1997) Simple sequence repeat DNA marker analysis. In Caetano-Anolles Gresshoff PM (eds) DNA markers: Protocols, applications and overviews. John Wiley & Sons, New York, pp. 173-185

Davis, et al. (2005) Soybean aphid, *Aphis glycines* Matsumura, a new vector of potato virus Y in potato. Amer J Potato Res 82:197-201

Diaz-Montano, et al. (2006) Characterization of antibiosis and antixenosis to the soybean aphid in several soybean genotypes. J Econ Entomol 999:1884-1889

DiFonzo, C. D., and R. Hines. 2002. Soybean aphid in Michigan: Update from the 2001 season. Michigan State Univ. Ext. Bull. E-2748. Michigan State Univ., East Lansing.

Fehr, et al. (1977) Stages of soybean development. Special Report, Agriculture and Home Economics Experiment Station, Iowa State University. 1977 No. 80 pp1 1

Fletcher, et al. (2000) The soybean aphid, *Aphis glycines*, present in Australia. worldwideweb.agric.nsw.gov.au/hort/ascu/insects/aglycin.htm, Accessed 18 Feb. 2010

Frisch, et al. 1999. Comparison of selection strategies for marker-assisted backcrossing of a gene. Crop Science 39:1295-1301.

Garcia, et al. (2008) Molecular mapping of soybean rust (*Phakopsora pachyrhizi*) resistance genes: Discovery of a novel locus and alleles. Theor Appl Genet. 117:545-553

Grant, et al. (2009) SoyBase, The USDA-ARS soybean genome database. Website at soybase.agron.iastate.edu, Accessed on 18 Feb. 2010.

Hartman, et al. (2001) Occurrence and distribution of *Aphis glycines* on soybeans in Illinois in 2000 and its potential control. Plant Health Progress. [Online] Available at: worldwideweb.plantmanagementnetwork.org/sub/php/brief/aphisglycines/ worldwideweb.plantmanagementnetwork.org/pub/php/brief/aphisglycines, Accessed on 18 Feb. 2010.

Hesler, et al. (2008) Identification and characterization of new sources of resistance to *Aphis glycines* Matsumura (Hemiptera: Aphididae) in soybean lines. Appl Entomol Zool.

Hesler, et al. (2007) Characterization of resistance to *Aphis glycines* in soybean accessions. Euphytica 154:91-94.

Hill, et al. (2004) Resistance to the soybean aphid in soybean germplasm. Crop Sci 44:98-106

Hill, et al. 2005. Evaluation of the USDA Soybean Germplasm Collection: Maturity Groups 000-IV(PI 507670-PI 574486), United States Department of Agriculture, Agricultural Research Service Technical Bulletin Number 1914.

Hill, et al. (2006a) A single dominant gene for resistance to the soybean aphid in the soybean cultivar Dowling. Crop Sci 46:1601-1605.

Hill, et al. (2006b) Soybean aphid resistance in soybean Jackson is controlled by a single dominant gene. Crop Sci 46:1606-1608.

Hill, et al. (2009) Inheritance of resistance to the soybean aphid in soybean PI 200538. Crop Sci 49:1193-1200.

Jeong, et al. 2001. Diversity and evolution of a non-TIR-NBS sequence family that clusters to a chromosomal hotspot for disease resistance genes in soybean. Theor. Appl. Genet. 103:406-414.

Kanazin, et al. 1996. Resistance gene analogs are conserved and clustered in soybean. Proc Natl Acad Sci 93:11746-11750.

Kang, et al. (2008) Soybean aphid resistance in PI 243540 is controlled by a single dominant Gene. Crop Sci 48:1744-1748.

Kim, et al. (2008) Discovery of soybean aphid biotypes. Crop Sci 48:923-928

Kisha, et al. (1997) Relationship between genetic distance among parents and genetic variance in populations of soybean. Crop Sci 37:1317-1325.

Klos, et al. 2000. Molecular Markers Useful for Detecting Resistance to Brown Stem Rot in Soybean. Crop Sci. 40:1445-1452.

Leister, (2004) Tandem and segmental gene duplication and recombination in the evolution of plant disease resistance gene. Trends Genet. 20:116-122.

Lewers, et al. 1999. Detection of linked QTL for soybean brown stem rot resistance in 'BSR 101' as expressed in a growth chamber environment. Molecular Breeding 5:33-42, 1999.

Li, et al. (2007) Soybean aphid resistance genes in the soybean cultivars Dowling and Jackson map to linkage group M. Mol Breed 19:25-34

Liu, et al. (2001) Microsatellite markers linked to six Russian wheat aphid resistance genes in wheat. Theor Appl Genet. 102:504-510

Mensah, et al. (2005) Resistance to soybean aphid in early maturing soybean germplasm. Crop Sci 45:2228-2233

Mensah, et al. (2008) Inheritance of soybean aphid resistance in PI 567541B and PI 567598B. Crop Sci 48:1759-1763

Mian, et al. (2008a) New plant introductions with resistance to the soybean aphid. Crop Sci 48:1055-1061

Mian, et al. B (2008b) Genetic linkage mapping of the soybean aphid resistance gene in PI 243540. Theor Appl Genet. 117:955-962

Michelmore, et al. (1991) Identification of markers linked to disease resistance genes by bulked segregant analysis: a rapid method to detect markers in specific genomic regions by using segregating populations. Proc Natl Acad Sci 88:9828-9832

OMAFRA (2002) Soybeans: soybean aphid. Agronomy guide for field crops-Publication 811. http://worldwideweb.omafra.gov.on.ca/english/crops/pub81 1/4aphid.htm, Accessed on 2 Jan. 2009.

Ostlie, (2002) Managing soybean aphid, University of Minnesota Extension Service, St Paul. worldwideweb.soybeans.umn.edu/crop/insects/aphid/aphid_publication_managingsba.htm, Accessed on 18 Feb. 2010.

Painter, (1951) Insect resistance in crop plants. Macmillan Publishing Co, New York Pascal, et al. (2002) Inheritance of green peach aphid resistance in the peach cultivar 'Rubira'. Plant Breed 121:459-461

Sanitchon, et al. 2004. Identification of Simple Sequence Repeat Markers Linked to Sudden Death Syndrome Resistance in Soybean. Science Asia 30: 205-209.

SAS Institute (1999) SAS/SAT Users Guide, version 8.0. SAS Institute, Cary, N.C.

Song, et al. (2004) A new integrated genetic linkage map of the soybean. Theor Appl Genet. 109:122-128

Van Ooijen, et al. (2001) JoinMap 3.0, Software for the calculation of genetic linkage maps in experimental populations. Kyazma, BV, Wageningen Voegtlin, (2008) United States soybean aphid commentary, website at sba.ipmpipe.org/cgibin/sbr/public.cgi?host=A11%20Legumes/Kudzu&pest=soybean aphid, Accessed on 18 Feb. 2010.

Voorrips, (2002) MapChart: Software for the graphical presentation of linkage maps and QTLs. J Heredity 93:77-78

Wang, et al. (2003) A low-cost and high-throughput system for high-resolution genotyping with microsatellite DNA markers. Crop Sci 43:1828-1832

Wang, et al. (2006) Registration of 'Skylla' soybean. Crop Sci 46:974-975

Wang, et al. (2008) Windows QTL Cartographer 2.5. Dept of Stat, North Carolina State Univ, Raleigh. Website at statgen.ncsu.edu/qtlcart/WQTLCart.htm, Accessed on 18 Feb. 2010.

Williams, et al. (1995) Comparative recombination distances among Zea mays L. inbreds, wide crosses and interspecific hybrids. Genetics 141:1573-1581

Wu, et al. (2004) The soybean aphid in China: a historical review. Ann Entomol Soc Amer 97:209-218

Zeng, 1994. Precision mapping of quantitative trait loci. Genetics 136:1457-1468.

Zhang, et al. 2009a. Molecular mapping of soybean aphid resistance genes in PI 567541B. Theor. Appl. Genet. 118:473-482.

Zhang, et al. 2009b. Detection and verification of an aphid resistance locus in Soybean PI 567543C. In 2009 annual meeting abstracts [CD-ROM]. ASA, CSSA, and SSSA, Pittsburg, Pa.

Zhang, et al. (2010) A novel locus for soybean aphid resistance. Theor Appl Genet.

EXPERIMENTAL

The following examples are provided in order to demonstrate and further Illustrate certain preferred embodiments and aspects of the present invention and are not to be construed as limiting the scope thereof.

In the experimental disclosure which follows, the following abbreviations apply: M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml (milliliters); µl (microliters); cm (centimeters); mm (millimeters); µm (micrometers); nm (nanometers); ° C. (degrees Centigrade/Celsius).

Example I

This example describes the discovery of Rag6 and Rag3c in aphid resistant germplasm obtained from soybean line E08934.

Figure 1E:
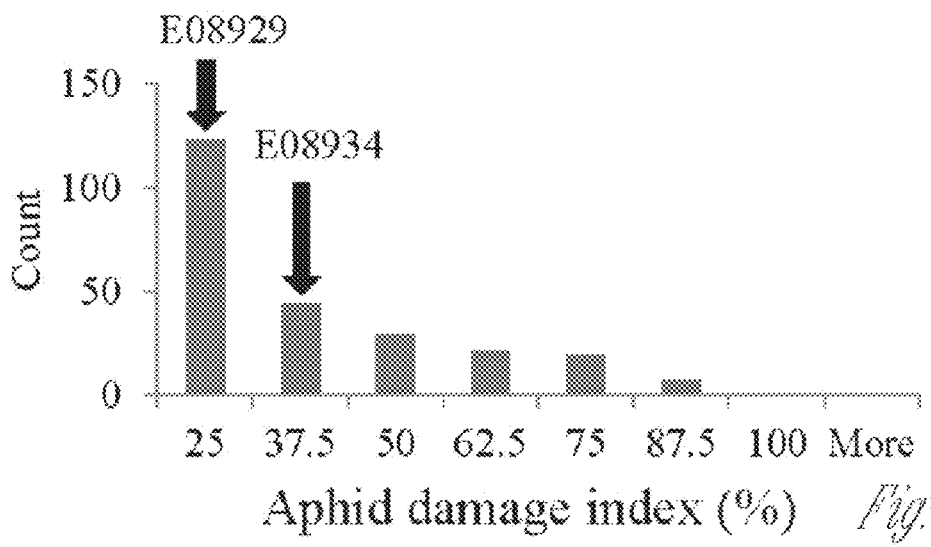
Figure 1F:
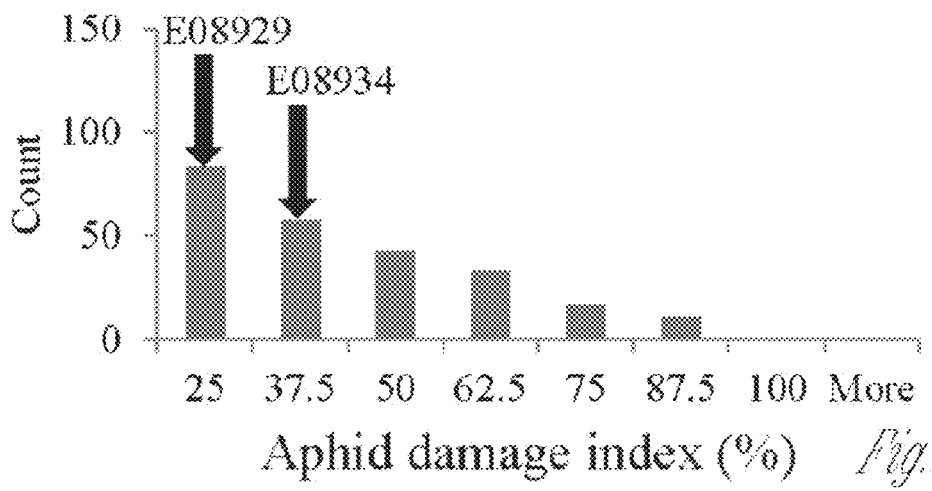

Phenotype distribution of the mapping population. The aphid damage index (DI) of the two parents, from lines E08934 and E00003, together with the 140 $F_3$-derived lines from the mapping population is summarized in Table 1. After four trials, resistant parent E08934, derived from *G. soja* accession had significantly lower DI than susceptible parent E00003 ($P<0.001$). DI of the $F_3$-derived lines from the mapping population varied significantly ($P<0.001$) from 6.3 to 100.0 with standard errors of 19.6 to 27.4. The correlations between the three field trials are 0.71, 0.65 and 0.63 ($P<0.05$). The broad-sense heritability for DI of the field trials was estimated as 0.84 ($P<0.001$). The distribution of DI from the mapping population in the greenhouse trial and the three-year field trial is shown in FIGS. 1A-1D. The two field trials show similar patterns that are bimodal with a ratio of 1:1. However, no pattern was observed between one greenhouse trial during the first year and one caged field trial in the third year (FIG. 1).

Aphid resistance locus mapping. Overall, 95.0% SNPs from the 52K SNP Beadchip identified the genotype successfully for the two parents and the two segregating bulks from the mapping population, with 37.6% polymorphic between the two parents and 26.4% between the two bulks. Polymorphic SNPs with genotypes consistent with sample phenotypes were distributed throughout all linkage groups. Interestingly, polymorphic SNPs from LG A2 and J clustered more intensively than other groups.

From the genotypic data of 6K SNP Beadchip with eight resistant and eight susceptible lines selected from the two bulks, three regions were detected that were clustered with SNPs that significantly correlated with aphid resistance for all four trials (P<0.001). They are 38.8 to 43.9 mega base (MB) on LG A2, 4.8 to 11.3 MB and 24.6 to 28.5 MB on LG J. Among the 104 SSRs covering LG A2 and J on the consensus map (Song et al., 2004), Satt209 and Satt455 on LG A2, Satt693 and Sat_370 on LG J genotyped highly consistent with the aphid resistance for the two parents and bulks, and further approved correlations with the entire mapping population. Therefore, to cover ±20 cM region nearby, a total of six SSRs from LG A2, eight SSRs from LG J, were genotyped with the remaining lines of the entire mapping population. At least eight TaqMan® SNP allele-specific genotyping markers were developed during the development of the present inventions, including MSUSNP08-1 (23293155_T_G), MSUSNP08-2 (40320904_A_G), MSUSNP08-3 (41114696_A_C) and MSUSNP08-4 (45189358_TS) derived (isolated and copied) from 38.8 to 45.2 MB of LG A2 (see, FIG. 2C), MSUSNP16-10 (6262227_C_T), MSUSNP16-11 (6413214_A_G), MSUSNP16-12 (6423098_G_A) and MSUSNP16-15 (8051585_T_C) derived (isolated and copied) from 4.8 to 11.3 MB region of LG J (see, FIG. 2D). Within the parentheses are the physical positions of each SNP marker and its SNP type.

Figure 2B:
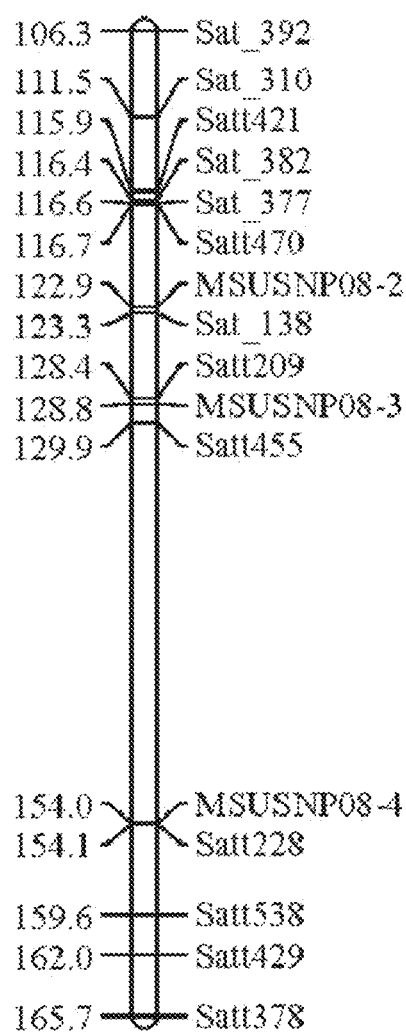
Figure 2D:
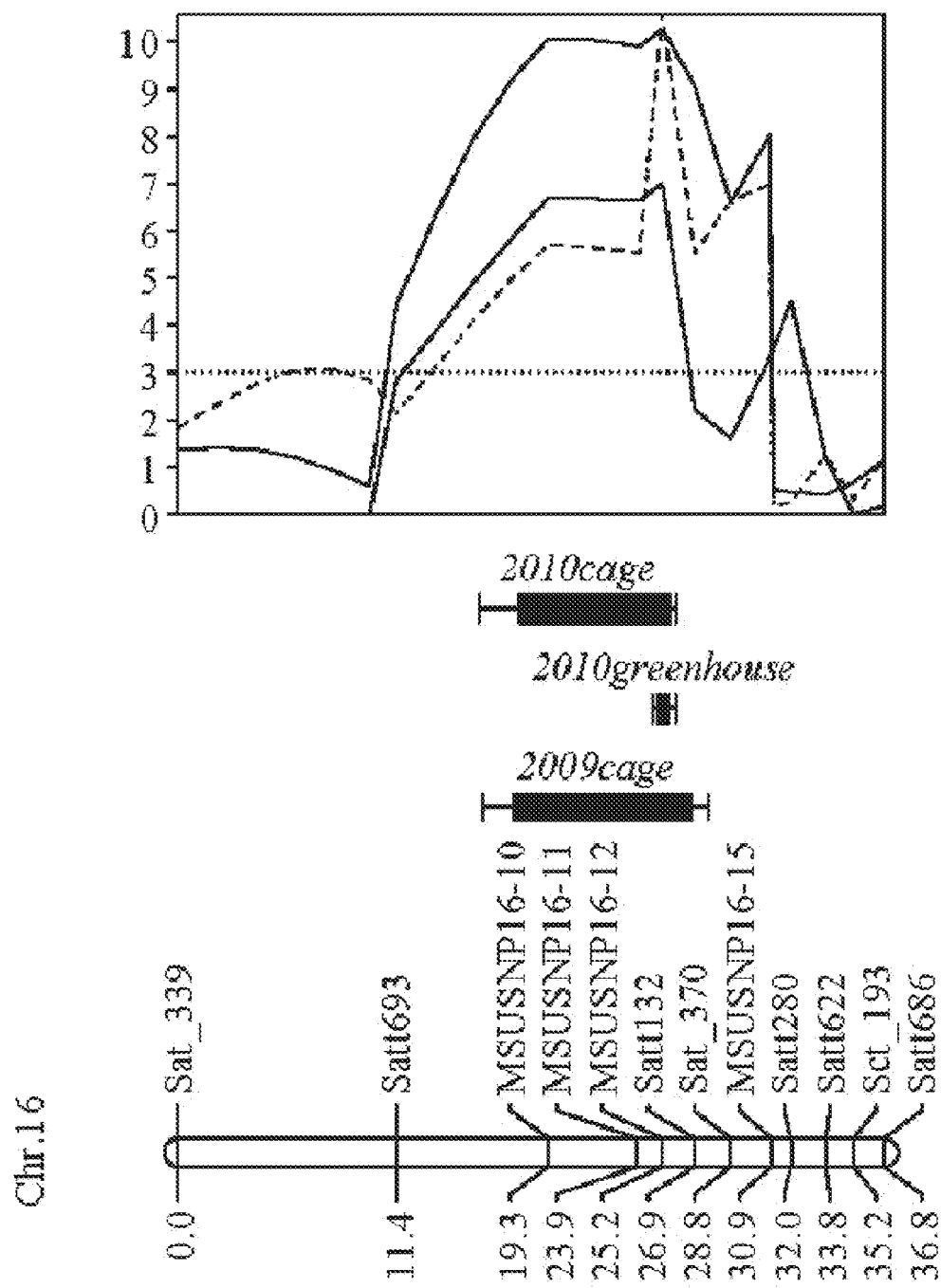
Figure 2E:
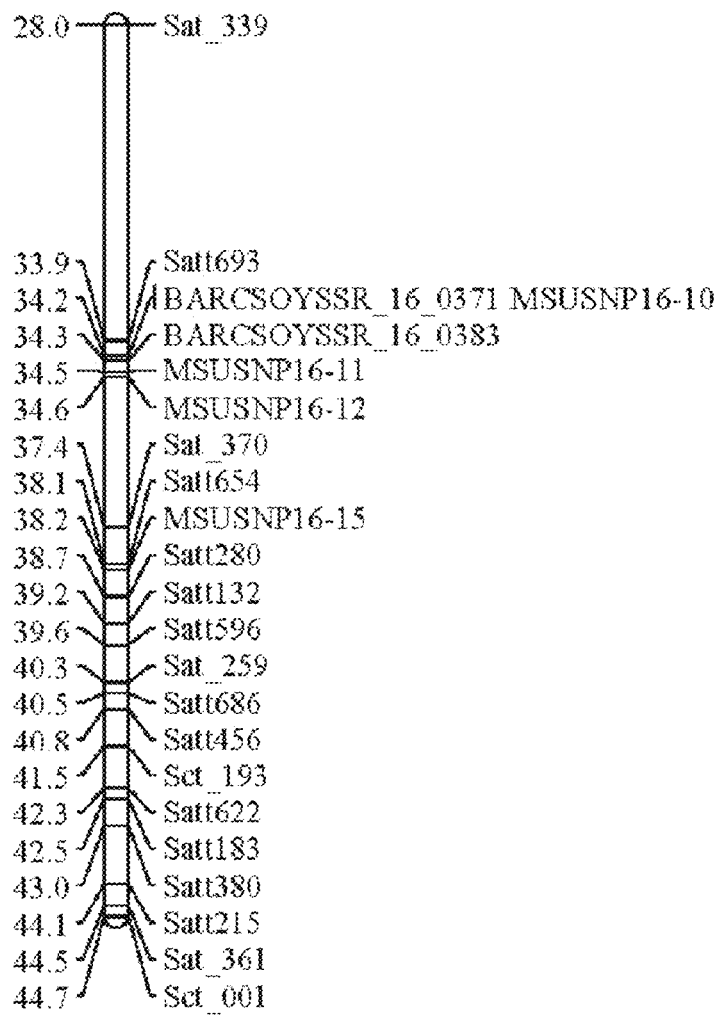

With the genotypic data of SSRs and SNPs, nine markers formed one linkage group, denoted as Chr. 8/LG A2 with 57.7 cM (FIG. 2A) and 12 markers formed another linkage group Chr. 16/LG J with 36.8 cM (FIG. 2D), that were highly comparable with the consensus map (Song et al., 2004) (FIGS. 2B and 2E). The linkage maps were used with composite interval mapping (CIM) method in QTL analysis. On LG A2 (Chr. 8), one QTL was consistently detected between SNP MSUSNP08-2 (40320904_A_G) and Satt209 in at least four trials (Table 2 and FIG. 2A), explaining 19.5 to 46.4% of the phenotypic variance. On LG J (Chr. 16), a QTL located within the interval between Satt693 and Sat_370 was identified for a greenhouse trial, and 2 field trials, explaining 12.5 to 22.9% of the phenotypic variance. As expected, the resistance allele comes from E08934. However, no significant interaction was detected between these two loci with multiple-interval mapping method in QTL Cartographer.

Aphid resistance loci validation. The validation population contained 252 $F_2$-derived lines from the cross of E08929 plants×F4 derived E08934 plants, as described herein. The aphid damage index of the population distributed continuously, but skewed to the resistant side in two field trials in adjacent years. The correlation between the two trials was estimated 69.7% (P<0.05). After the entire validation population was genotyped, seven SSRs with three SNPs from LG A2 (Chr. 8) (Song et al., 2010) formed one linkage group (FIG. 2C). Ten SSRs having two BARCSOYSSR markers formed LG J (Chr. 16) and six SSRs formed LG M (Chr. 7) in FIGS. 2F-G. The marker order was highly comparable with consensus map but with inflation (FIGS. 2B-2H). Marker data with phenotypic traits were analyzed with QTL Cartographer in CIM method. On Chr. 8, one QTL was detected between MSUSNP08-1 (23293155_T_G) and Satt455 for both trials (FIG. 2C). That interval was equivalent to 13.5 cM onto the consensus map between marker Sat_382 and Satt455 (FIG. 2B). This confirmed the location of the resistance locus identified on Chr. 8 in the mapping population. This locus was denoted as Rag6 for convenience.

For LG J (Chr. 16), one QTL was detected within the same interval as in the mapping population between Satt693 and Sat_370 in the second year of field trials. The interval detected by the first field trial was between Satt693 and Satt456 was larger, but covering the region identified in the mapping population (FIG. 2F). This confirmed the finding of the locus on LG J in the mapping population.

Figure 2H:
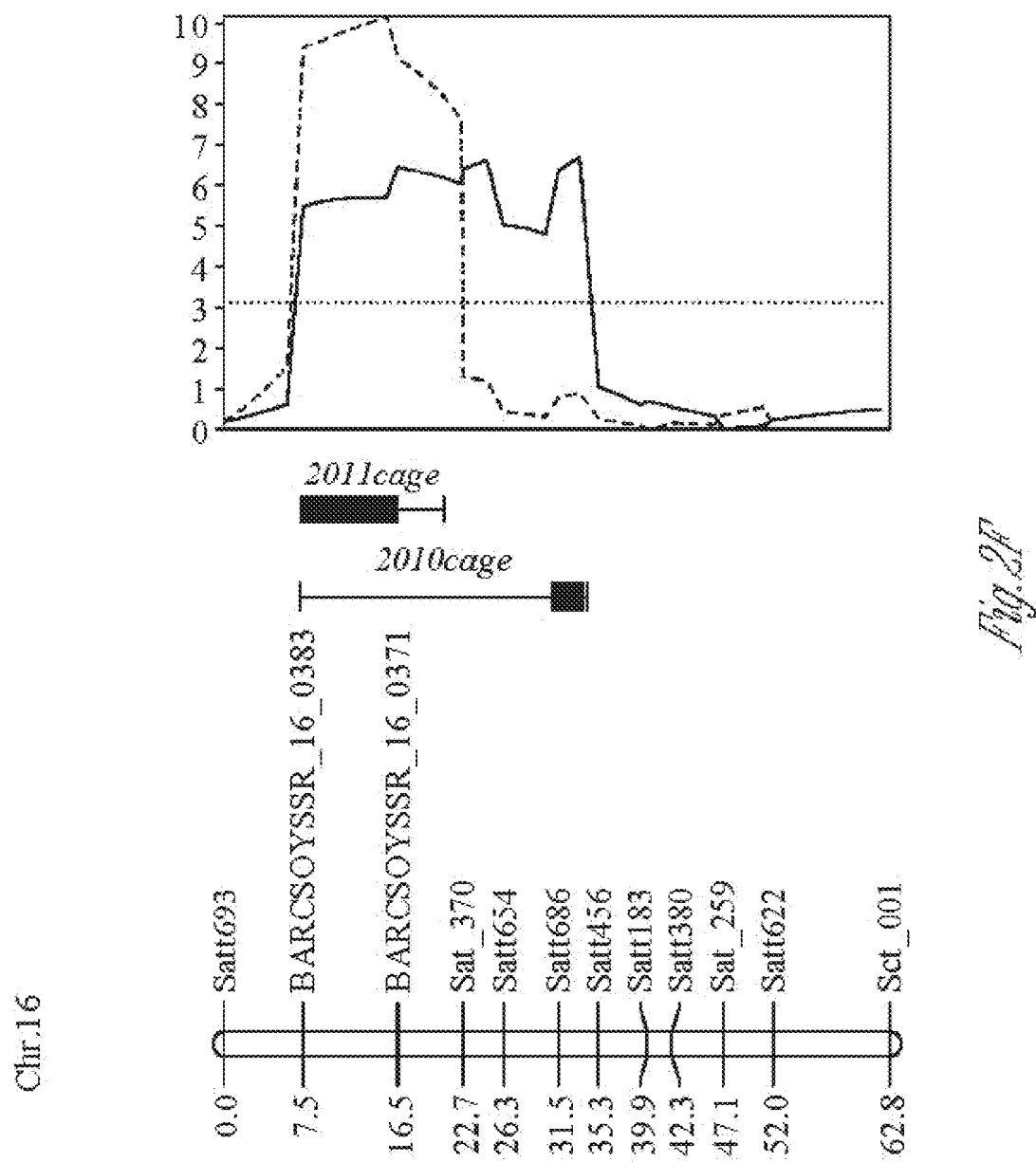
Figure 2H:
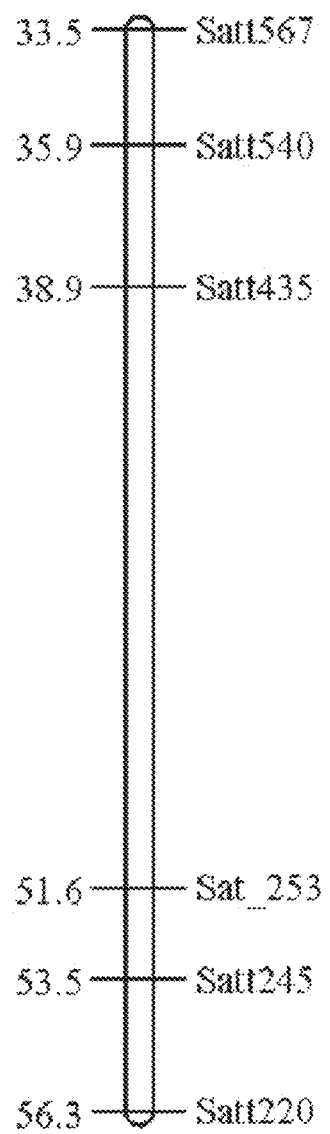

One of the parents of the validation population, E08929 was an accession from PI 567541B, therefore, it was contemplated to have both aphid resistance loci rag1c and rag4. The QTL detected from LG M (Chr. 7) in both field trials confirmed the location of rag1c between markers Satt540 and marker Satt435 (FIG. 2G-H). Recessive allele rag4 was not detected in the validation population. Therefore the three loci detected in the validation population explained 4.1 to 13.9% of the phenotypic variance individually (Table 2). Though they explained small proportion of the phenotypic variance, three loci detected from two years of field trials were significant by 1000 permutations (P<0.01). The resistance allele of the locus on Chr. 7 derives from parent E08929, and the other two resistance alleles on Chr. 8 and Chr. 16 respectively came from (derived from, i.e. were genetically inherited from parent E08934. One progeny from this cross, E12902, that carries all the three aphid resistance genes on Chr. 7, Chr. 8, and Chr. 16 (i.e. genes rag1c, Rag6, and Rag3c, respectively) was selected based on the marker genotypes at the three loci.

Figure 3A:
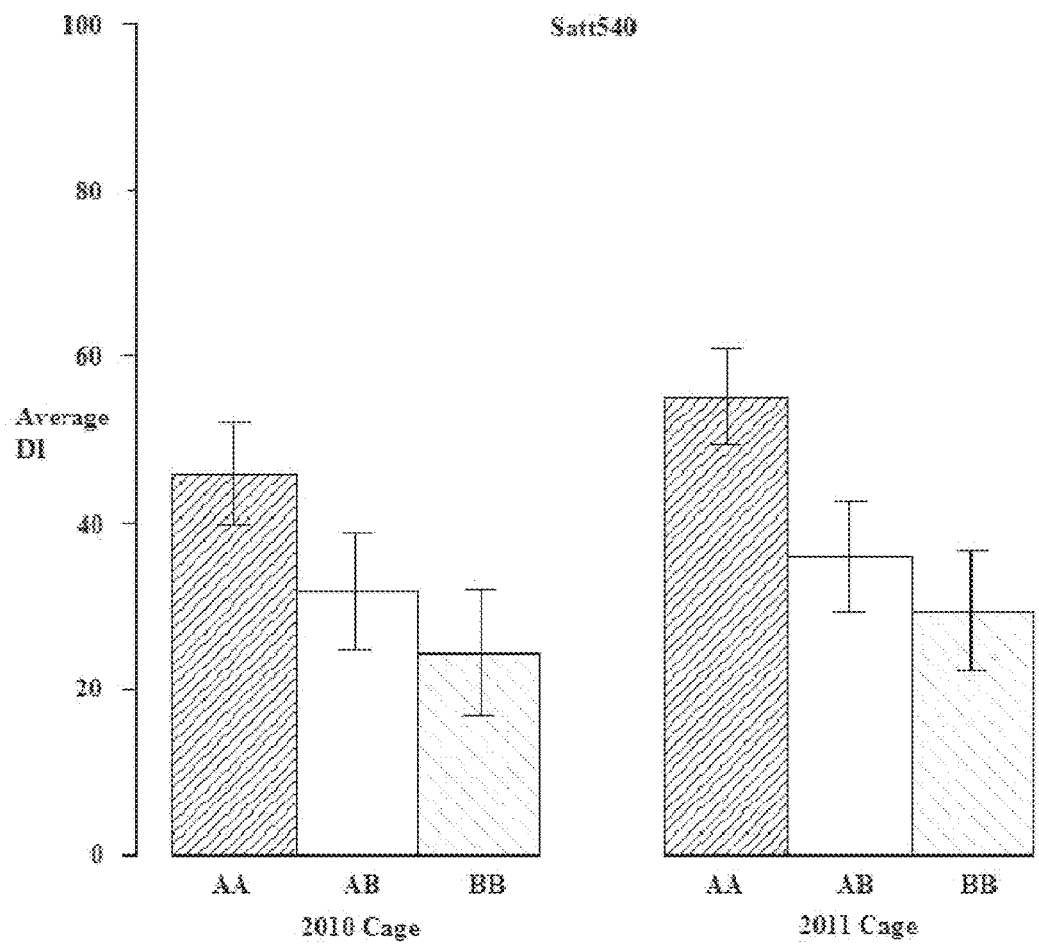
FIG. 3A-3C show exemplary average aphid damage indeces of progeny in three genotypic groups for each marker close to the aphid resistance locus detected in the validation population E08929×E08934, in cage field trials 2 and 3. The homozygous group with allele from parent E08934 was denoted as AA. The homozygous group with allele from parent E08929 was denoted as BB. The heterozygous group with both alleles was denoted as AB. One-way Analysis of Variance was conducted at a significance level of 0.05. Error bars indicate 95% confidence interval of average DI.
Figure 3B:
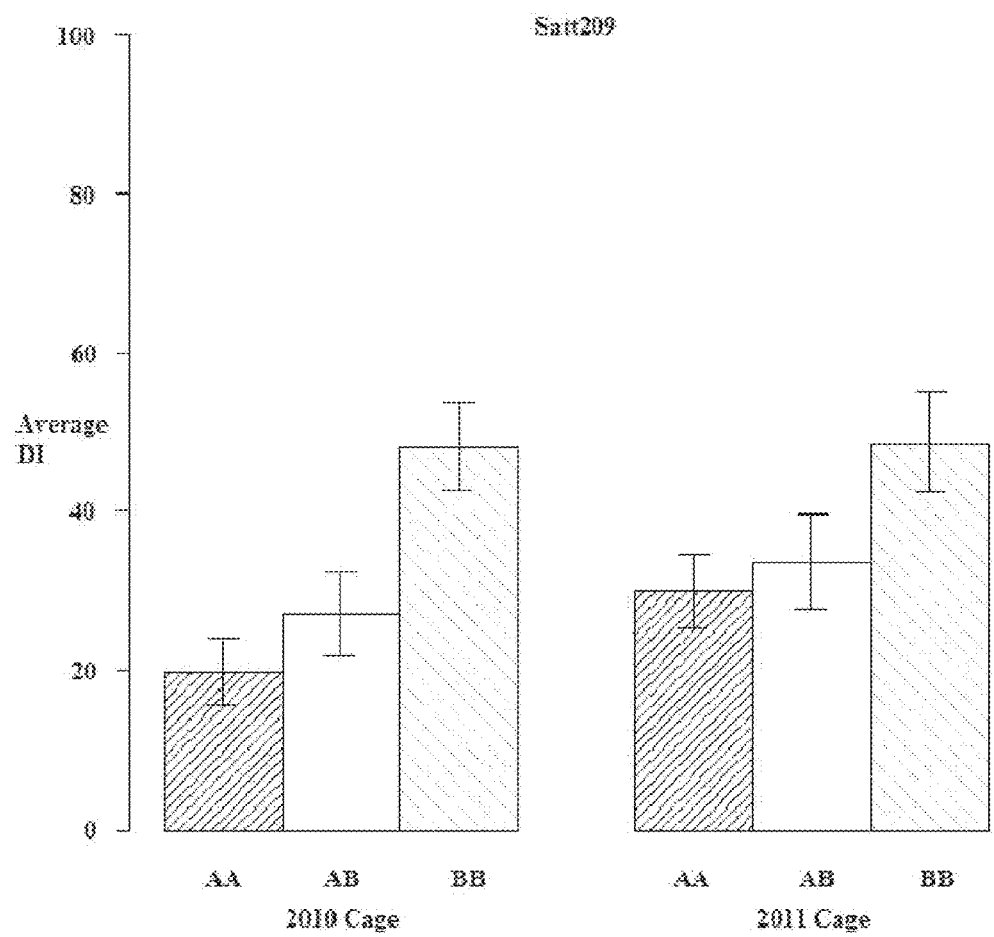
Figure 3C:
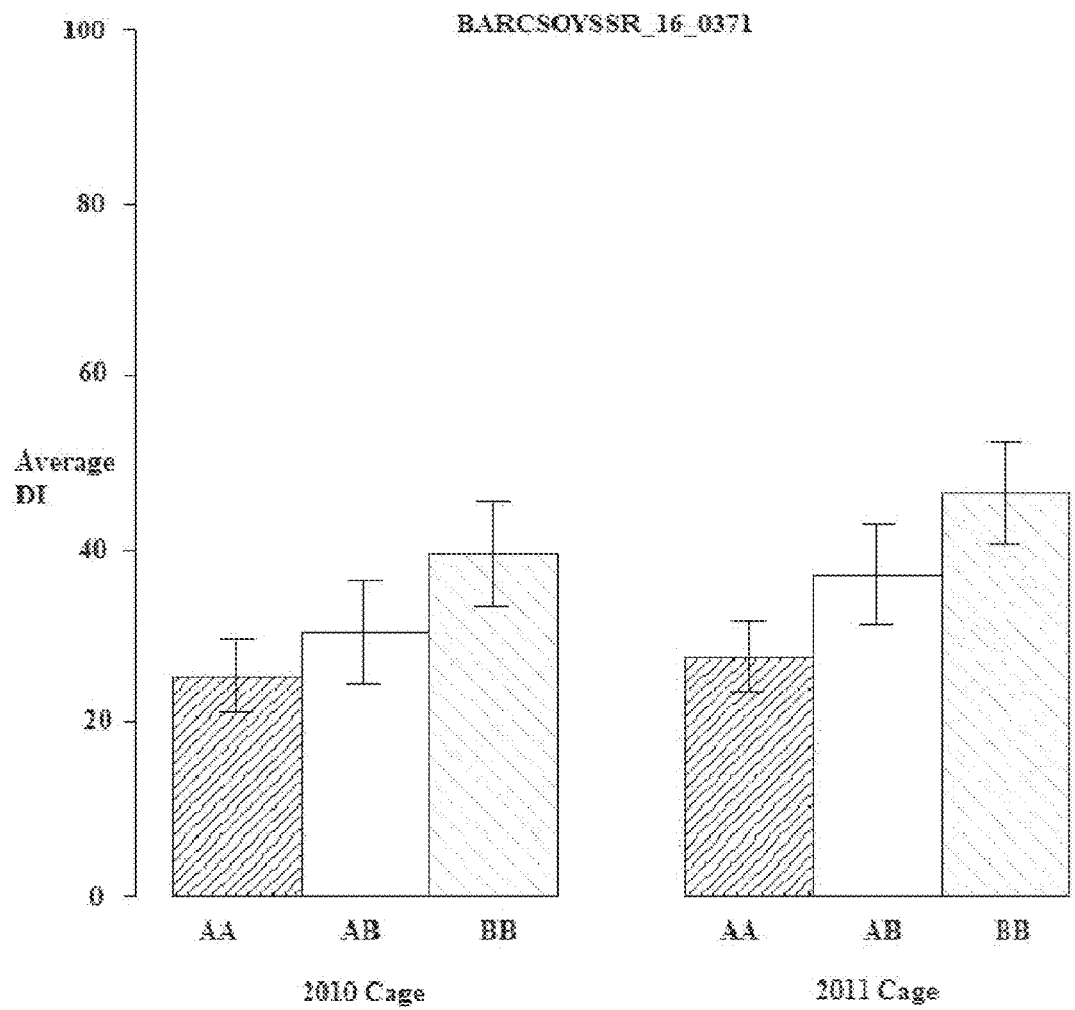

Gene action in a validation population. To determine the action of the loci in the validation population, the 252 $F_2$-derived lines were divided into three genotypic groups for the markers that are closest to the peak LOD score, Satt540 for rag1c, Satt209 for the locus on LG A2 for Rag6, and BARCSOYSSR_16_0371 for Rag3c (FIG. 3). Average DI for each genotypic group was calculated and compared in Table 3. The average DI was measured in order to discover if it significantly differed among three genotypic groups for each marker by One-way Analysis of Variance (ANOVA). The results surprising showed the association was significant even after adjusting the multiple testing (Bonferroni correction) (P<0.0001, Table 3). The pairwise differences among three groups for each marker was then investigated for determining germplasm/gene actions. For marker Satt540, the closest marker to rag1c, the average DI of the heterozygous group was significantly (P<0.05) lower than that of the homozygous group of allele from E08934, but not significantly different from that of the homozygous group of allele from E08929 in data from two field trials (FIG. 3A). This result showed that rag1c from parent E08929 has a partially dominant effect instead of a recessive effect in these plants. For marker Satt209, the closest marker to the locus on LG A2, the average DI of the heterozygous group was significantly (P<0.05) lower than that of the homozygous group of allele from E08929, but not significantly different from that of the homozygous group of allele from E08934 in two years of tests (FIG. 3B), indicating a partially dominant effect of this locus. The location of this novel locus from *G. soja* was different from that of the locus identified by Jun et al. (2012)

on LG A2. Therefore, the loci on chromosome 8 was called Rag6 for the conventions of the Soybean Genetics Committee.

For marker BARCSOYSSR_16_0371 on LG J (Chr. 16), located within the interval of Rag3c, the average DI of the heterozygous group was neither significantly different from that of the homozygous group of plants having this resistance allele from E08929, or from that of the homozygous rag1c group of plants having the resistance allele from E08934 in both years (FIG. 3C) at significance size of 0.05. Therefore, Rag3c is contemplated to be effective as both a heterozygous and homozygous allele. However, the average DI of the homozygous group of plants having the allele rag1c from E08929 was significantly different from that of the homozygous group of Rag3c allele from E08934 (P<0.05). Therefore, further research was done to determine the germplasm/gene action of Rag3c located on LG J from *G. soja* in relation to aphid resistance, see, below, and FIG. 4 and FIG. 5.

Figure 4:
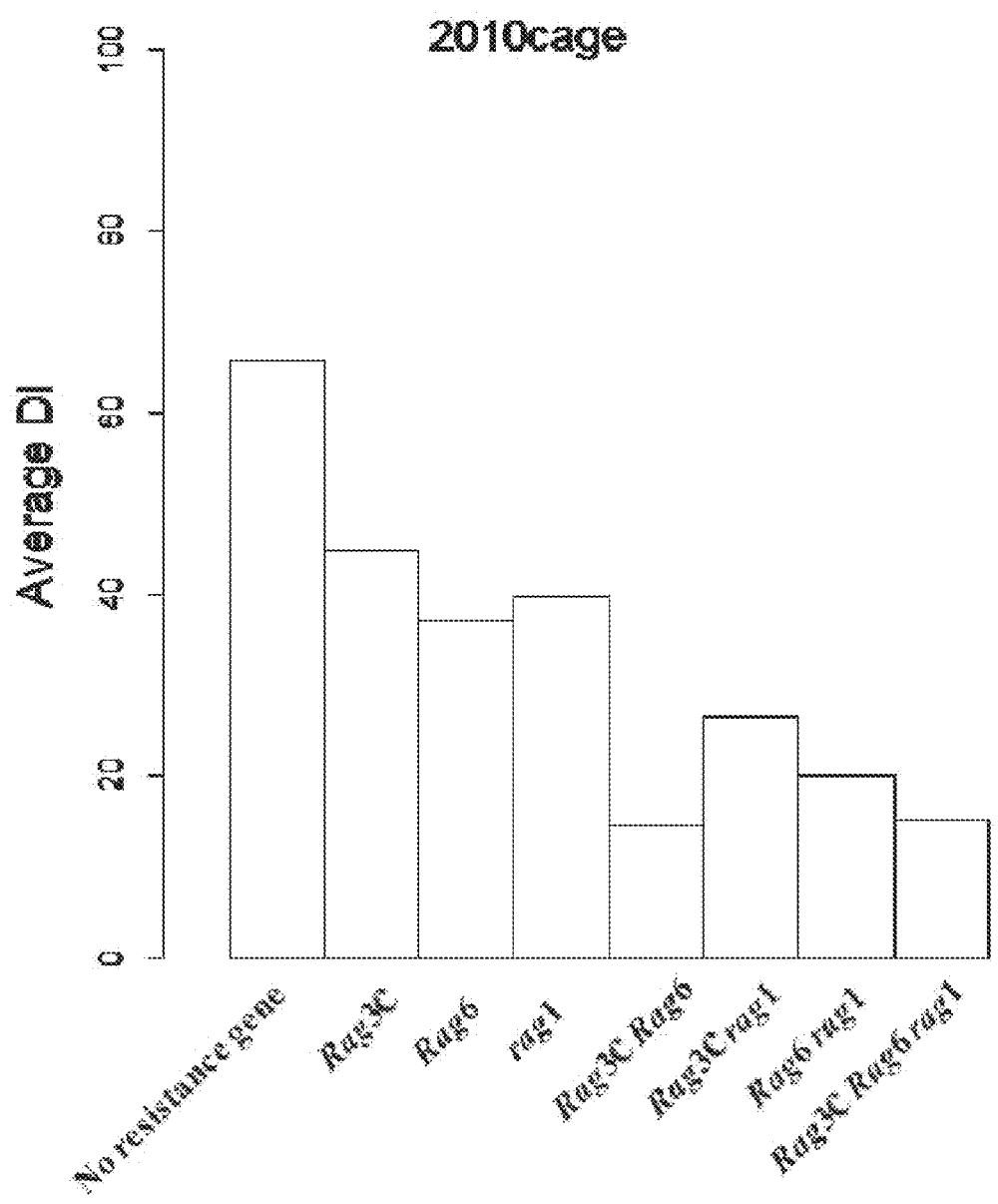
FIG. 4 shows exemplary average aphid damage indices for progeny that have no resistance genes, one locus, two loci and three loci from the validation population E08929× E08934 in cage field trial 2.

Progeny that possessed different aphid resistance genes or without any resistance germplasm was sorted out from the validation population. The average DI of different combination of Rag3c, Rag6 and rag1c from one field trial was estimated and plotted in FIG. 4. Average DI was calculated for progeny that have no resistance germplasm, one resistance germplasm region, two resistance germplasm regions combined and three germplasm regions combinations of Rag3c, Rag6 and rag1c (FIG. 4). A clear trend of decreasing DI can be observed as more resistance genes are combined. However, the difference of average DI observed was not significant due to the small number of individuals in each combination. E12902 carries all the three aphid resistant genes Rag3c, Rag6 and rag1c and consistently showed strong resistance to soybean aphids in the field trial.

Figure 5:
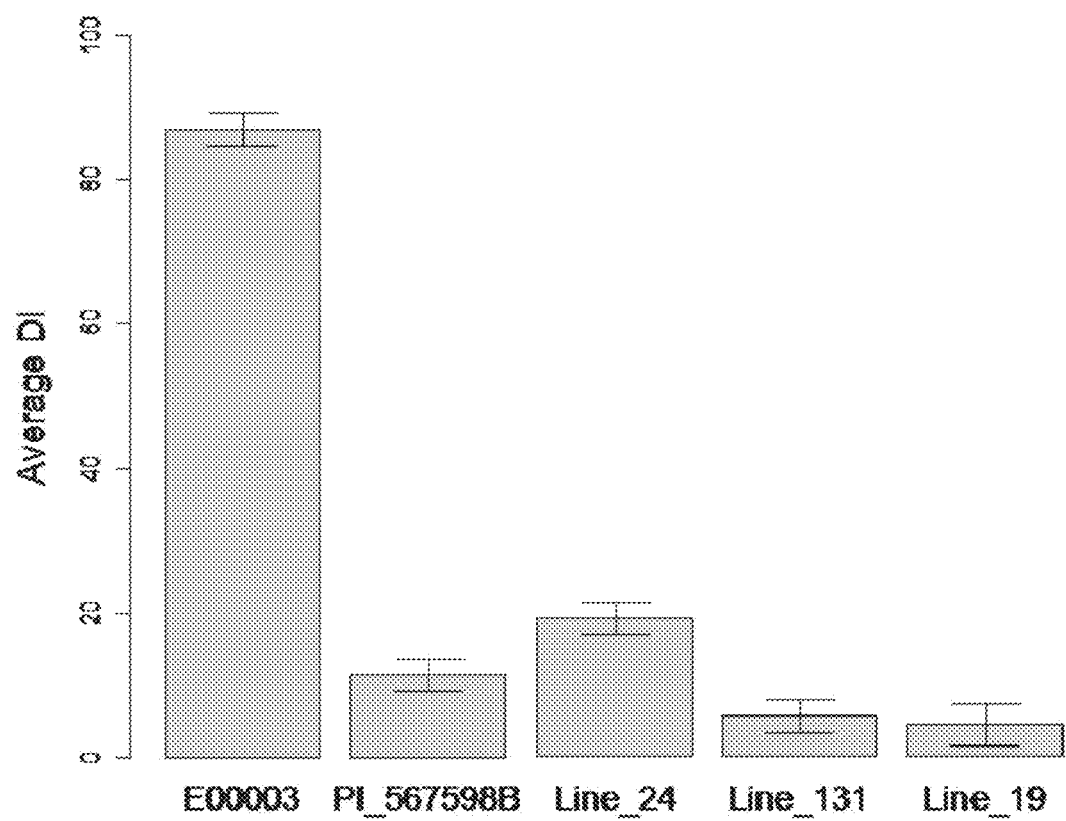
FIG. 5 shows exemplary average damage indices from aphid non-choice test of selected lines from the mapping population E00003×E08934, line 24 with Rag3c, line 131 with Rag6 and line 19 with both loci. E00003 was used as susceptible check, and PI 567598B was antibiosis resistance check. One-way Analysis of Variance was conducted at a significance level of 0.05. Error bars indicate 95% confidence interval of average damage index. NOTE: rag1=rag1c.
Figure 6A:
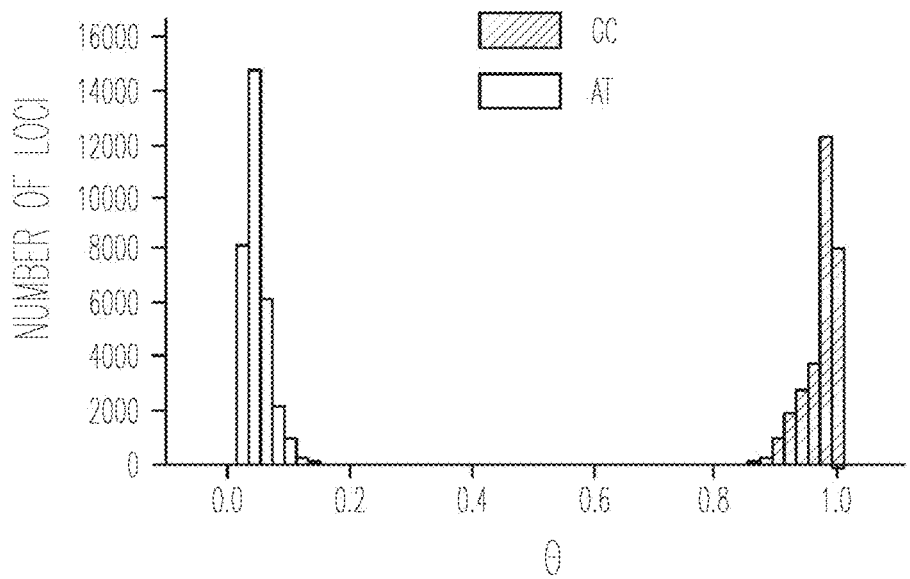
FIGS. 6A-6C illustrate exemplary combined single-base extension resequencing and allele-specific primer extension (ASPE) genotyping on the Sentrix Human-1 Genotyping BeadChip (100k exon-centric).
Figure 6B:
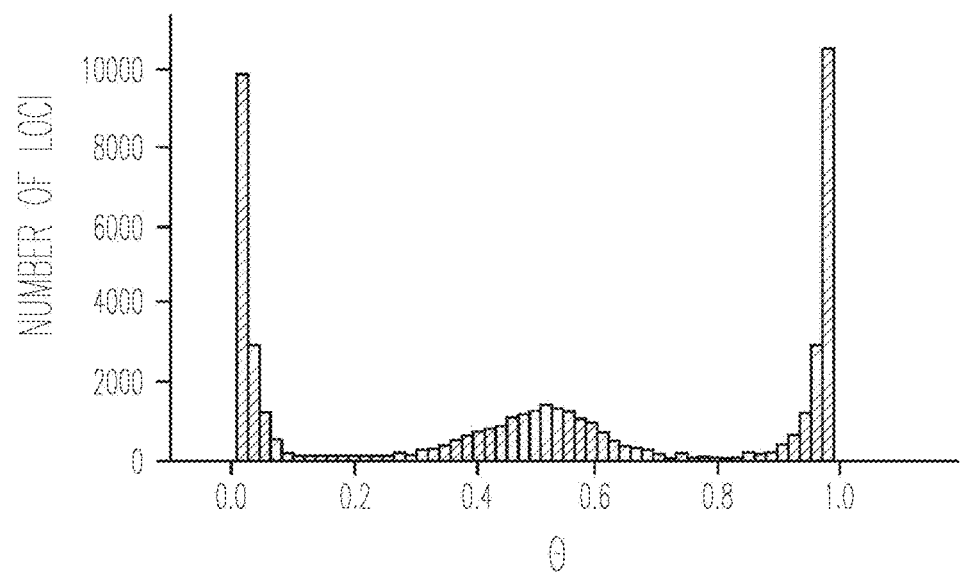
Figure 6C:
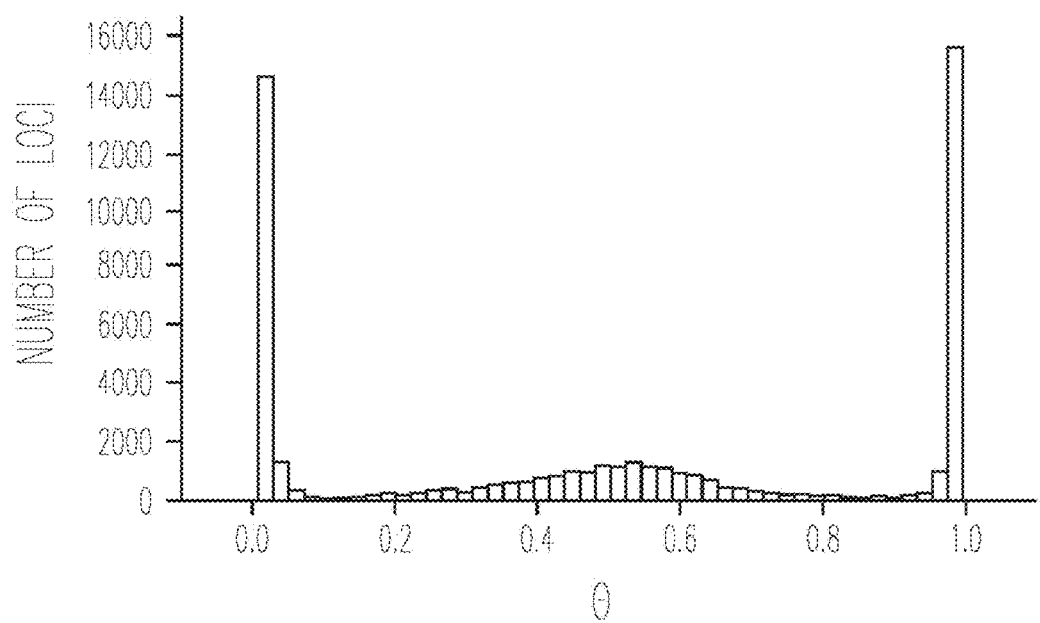

Non-choice test in the mapping population. The DI for plants E00003, PI 567598B, line 24 (Rag3c), line 131 (Rag6), and line 19 (Rag3c and Rag6) from the mapping population were analyzed and summarized in Table 4. FIG. 5 shows the bar graph of the DI with 95% confidence interval derived from One-way Analysis of Variance conducted at a significance level 0.05. Though the average DI of PI 5767598B was significantly lower than that of line 24 (Rag3c), higher than that of line 131(Rag6), and line 19 (Rag3c and Rag6), average DI of these lines were significantly lower than that of susceptible check E00003. The aphid resistance loci in PI 567898B was shown as antibiosis (Mensah et al., 2005). Therefore the new Rag3c and the new locus Rag6, and associated genes, both possessed antibiosis aphid resistance.

TABLE 1

Aphid damage index (DI, %) for the two parents of the mapping population, E08934 and E00003, and 140 $F_3$-derived lines, in the greenhouse and field trials.

| Trials | Parents | | $F_3$-derived lines | | |
|---|---|---|---|---|---|
| | E08934 | E00003 | Mean | Range | SE[††] |
| Greenhouse Year 2. | | | | | |
| | 26.6[a†] | 84.4[b] | 47.3 | 14.1-85.9 | 27.4 |
| Field cage | | | | | |
| Year 1 | 12.5[a] | 87.5[b] | 46.4 | 12.5-87.5 | 19.6 |
| Year 2 | 12.5[a] | 87.5[b] | 52.3 | 12.5-93.8 | 26.1 |
| Year 3 | 20.8[a] | 100.0[b] | 57.7 | 6.3-100.0 | 23.1 |

DI = Σ (scale value × no. of plants in the category)/(4 × total no. of plants) × 100, ranged from 0 being no infestation and 100 being the heaviest infestation (Mensah et al., 2005).
[†]Means followed by different letters in the parent column within the same row are significantly different at P < 0.0001.
[††]SE = standard error.

TABLE 2

Aphid resistance loci identified in the mapping population E00003 × E08934 and validation population E08929 × E08934 with composite interval mapping method with 1000 permutations. MSUSNP08-1 (23293155_T_G), and MSUSNP08-2 (40320904_A_G) are derived from 6K SNP chip; MSUSNP16-11 (6413214_A_G) and MSUSNP16-12 (6423098_G_A) are derived from 52K SNP chip.

| Population | Trials | Chr/LG[a] | Peak Pos.[b] | Flanking markers | LOD | $R^{2c}$ | $a^d$ |
|---|---|---|---|---|---|---|---|
| E00003 × E08934 | Greenhouse | | | | | | |
| | Year 2 | 8/A2 | 18.8 | MSUSNP08-2-Satt455 | 19.5 | 40.8 | 12.7 |
| | | 16/J | 25.2 | MSUSNP16-11-MSUSNP16-12 | 10.6 | 22.9 | 9.7 |
| | Field cage | | | | | | |
| | Year 1 | 8/A2 | 18.8 | MSUSNP08-2-Satt455 | 22.9 | 46.4 | 19.0 |
| | | 16/J | 25.2 | Satt693-Sat_370 | 10.3 | 16.7 | 11.9 |
| | Year 2 | 8/A2 | 18.8 | Satt455-Satt209 | 9.1 | 19.5 | 11.7 |
| | | 16/J | 25.2 | Satt693-Sat_370 | 7.0 | 12.5 | 10.6 |
| | Year 3 | 8/A2 | 20.8 | MSUSNP08-2-Satt455 | 16.0 | 39.1 | 14.7 |
| E08929 × E08934 | Field cage | | | | | | |
| | Year 2 | 7/M | 11.1 | Satt540-Satt435 | 7.3 | 8.4 | 8.5 |
| | | 8/A2 | 79.8 | MSUSNP08-1-Satt455 | 4.6 | 6.4 | −7.1 |
| | | 16/J | 16.5 | BARCSOYSSR_16_0383-Satt456 | 6.4 | 6.9 | −6.1 |

TABLE 2-continued

Aphid resistance loci identified in the mapping population
E00003 × E08934 and validation population E08929 × E08934
with composite interval mapping method with 1000 permutations.
MSUSNP08-1 (23293155_T_G), and MSUSNP08-2 (40320904_A_G) are
derived from 6K SNP chip; MSUSNP16-11 (6413214_A_G) and
MSUSNP16-12 (6423098_G_A) are derived from 52K SNP chip.

| Population | Trials | Chr/LG[a] | Peak Pos.[b] | Flanking markers | LOD | R[2c] | a[d] |
|---|---|---|---|---|---|---|---|
| | Year 3 | 7/M | 11.1 | Satt540-Satt435 | 10.8 | 13.9 | 10.7 |
| | | 8/A2 | 81.8 | MSUSNP08-1-Satt455 | 3.4 | 4.1 | −4.9 |
| | | 16/J | 15.5 | BARCSOYSSR_16_0383-Sat_370 | 10.2 | 12.5 | −7.8 |

[a]Chromosome/linkage group. The chromosome number and linkage group name are according to the SoyBase (Grant et al., 2010).
[b]Peak position is presented in centiMorgan (cM).
[c]$R^2$, percentage of phenotypic variation that can be explained by the locus.
[d]Additive effect.

TABLE 3

Summary of average damage index for genotypic groups of markers
near LOD peak from validation population E08929 × E08934.

| Trials | E08934 type | Heterozygous type | E08929 type | P values (F-test) |
|---|---|---|---|---|
| Satt540-Chr 7 (LG. M) | | | | |
| Year 2 field | 45.8a[†] | 31.8b | 24.4b | 8.598E−07 |
| Year 3 field | 55.0a | 36.0b | 29.4b | 2.226E−10 |
| Satt209-Chr. 8 (LG. A2) | | | | |
| Year 2 field | 19.8a | 27.0a | 48.3b | 2.2E−16 |
| Year 3 field | 29.8a | 33.6a | 48.8b | 5.191E−09 |
| BARCSOYSSR_16_0371-Chr. 16 (LG. J) | | | | |
| Year 2 field | 25.2ab | 30.4abc | 39.5bc | 0.00002309 |
| Year 3 field | 27.5ab | 37.2abc | 46.6bc | 3.209E−09 |

[†]Means followed by different letters within the same row are significantly different at P < 0.001.

Thus, plants identified with Satt540 that were heterozygous for the aphid resistance rag1c germplasm showed less aphid resistance than plants homozygous for rag1c. Further, plants identified with BARCSOYSSR_16_0371 that were heterozygous for the aphid resistance Rag3c germplasm showed intermediate aphid resistance compared to plants homozygous for Rag3c and homozygous for a non-aphid resistance germplasm at that locus. Unlike for plants identified by Satt209 as heterozygous and homozygous plants for the Rag6 germplasm showed superior aphid resistance over plants having alleles not associated with aphid resistance at this locus in this comparative test.

TABLE 4

Exemplary superior aphid resistance in Line 131 and Line
19 over Line 24, cultivar PI567598B plants and an elite
aphid susceptible plant line E00003. Summary of aphid damage
index from a non-choice test with selected F3-derived lines
with resistance genes from a mapping population.

| Test lines | Average DI (%) | SE[†] |
|---|---|---|
| E00003 | 86.98 | 1.17 |
| PI 567598B | 11.46 | 1.17 |
| Line 24 (Rag3c) | 19.27 | 1.17 |
| Line 131 (Rag6) | 5.73 | 1.17 |
| Line 19 (Rag3c, Rag6) | 4.46 | 1.53 |

[†]= SE standard error

Exemplary materials and methods for linkage-based QTL mapping was employed with bi-parental populations to locate and validate aphid resistance loci. A mapping population consist of 140 $F_3$-derived lines was used for initial mapping, and a confirmation population of 240 $F_2$-derived lines was used to validate the aphid resistance loci.

B. Aphid Resistance Loci Mapping.

Population development and phenotype evaluation. The mapping population was developed by crossing the aphid-resistant line E08934, derived from a *G. soja* accession, with an aphid-susceptible, advanced breeding line E00003, and followed with single seed descent. The population was evaluated in choice-test for aphid resistance in the greenhouse during the second growing year, and in 3 field cage trails over three successive seasons. Parents were replicated three times in each trial, rather than the entire mapping population, because aphid resistance was considered as a high heritability trait (about 0.90) according to previous knowledge (Zhang et al., 2009, herein incorporated by reference). In the spring of the second field trial, one greenhouse trial was conducted in the Plant Science Greenhouse at Michigan State University (MSU) in East Lansing, Mich. Over three summers, field trials were performed independently on the Agronomy Farm of MSU in East Lansing. The greenhouse maintenance, planting strategy in the field cage, aphid infestation, evaluation scale (Mensah et al., 2008; Mensah et al., 2005, herein incorporated by reference) were adopted as described by Zhang et al. (2010), herein incorporated by reference. The phenotypic data was scored when the susceptible parent E00003 reached the maximum of the rating scale, with more than 800 aphids per plant. An aphid damage index (DI) defined as DI=Σ(scale value×no. of plants in the category)/(4×total no. of plants)× 100, ranging from 0 being no infestation to 100 being the most severe damage (Mensah et al., 2008; Mensah et al., 2005, herein incorporated by reference) was used as phenotypic indicator in quantitative trait analysis.

DNA preparation and marker genotyping. Plant tissues of the mapping population and the two parents were collected during the field cage trial in the first season. CTAB (hexadecyltrimethyl ammonium bromide) DNA extraction protocol was adopted from Zhang et al. (2010). Two segregating bulks were formed with 15 most resistant lines and 15 most susceptible lines for the purpose of a bulk segregant analysis (BSA), proposed by Michelmore et al. (1991), herein incorporated by reference. First, these two bulks, together with the two parents, were genotyped on 52K soybean SNP Beadchip, covering the entire soybean genome with more than 52,000 SNPs (Song et al., 2011). Then, eight lines selected from the resistant pool and eight lines from the susceptible pool were individually genotyped on newly developed 6K soybean SNP Beadchip, covering the most gene-abundant genomic regions throughout the soybean genome.

After the selective genotyping above, simple sequence repeat (SSR) markers from candidate genomic regions were used to genotype the two segregating pools and the two parents. In association analysis, SSRs correlated with traits were used to genotype the remaining lines of the entire mapping population.

To achieve better resolution, SNP markers for TaqMan® SNP allele-specific genotyping assays were designed with the information from SNPs located within candidate region on 52K and 6K chips. These SNPs were further genotyped with the entire mapping population. Taqman® probe-based PCR protocol using LightCycler® 480 was performed as described herein.

Statistical analysis and mapping analysis. The statistical correlation analysis with aphid damage index data from the four trials was carried out in R. The broad-sense heritability of DI from the three-year field trial was estimated according to Fehr (1987) as follows: $Y_{ij}=\mu+Genotype_i+\varepsilon$. i=1,2, . . . 140; j=3 seasons of trials. Linkage maps were constructed with JoinMap 4.0 using Kosambi's and LOD of 3.0 in regression method (Van Ooijen, 2006, herein incorporated by reference). Composite interval mapping (CIM) in QTL Cartographer Version 2.5 (Wang et al., 2008, herein incorporated by reference) with 1000 permutations described by Zhang et al. (Zhang et al., 2010) was conducted to determine the locations of the aphid resistance loci from *G. soja*. The maps with locus positions were visualized by MapChart (Voorrips, 2002, herein incorporated by reference). Non-choice test data were also analyzed with One-way Analysis of Variance in R, at significance level of 0.05.

Validation of aphid resistance loci. To confirm the location and determine the genetic action (i.e. function) of the aphid resistance loci identified from E08934, a validation population was developed by crossing E08934 with E08292, an aphid-resistant accession from PI 456741B with recessive allelic germplasm for rag1 and rag4 (Zhang et al., 2009). Over two consecutive summers, the second and third of the three, the entire validation population together with the two parents were evaluated for aphid resistance in field-cage trials similar to the mapping population. DNA extraction was performed using the CTAB method. Polymorphic and associated SSRs and SNPs from the regions identified in the mapping population, along with markers in region rag1 and rag4 were genotyped in the validation population. Linkage and mapping analysis were conducted in the same manner as above in the mapping population. Data of germplasm action and germplasm combination in the validation population were analyzed in One-way Analysis of Variance with Bonferroni correction in R, at a significance level of 0.05.

Combination of Aphid Resistance Loci in Validation Population: Non-choice Test.

Plant lines were produced for testing the effects of specific aphid resistant genes. Then in the spring after the three field trials, three replications of aphid non-choice test were performed with E00003 (susceptible control), PI 567598B (antibiosis resistant control), line 24 (possessing Rag3c on Chr. 16), line 131 (possessing Rag6 on Chr. 8), and line 19 (possessing both Rag3c and Rag6) from the mapping population, in the Plant Science Greenhouse at MSU. In each replication, eight seeds from each line were planted in a 105-mm-diameter and 125-mm-deep plastic pot, maintained at 26/15° C. day/night temperature with sodium vapor lights as supplement. Each plant was infested with two healthy wingless aphids at the VI stage (Fehr and Cavinese, 1977) and immediately covered with a mesh-cage from bottom to top (Mensah et al., 2008). Aphid resistance was rated, and the aphid damage index was calculated, as mentioned in the mapping population phenotype evaluation, when the susceptible control E00003 reached the maximum of the rating scale, the most severe damage stage. Data of average damage index were analyzed using One-way Analysis of Variance in R.

Example II

This example describes MSU Soybean whole genome sequence data preparation and analysis as exemplary SNP site identification in Rag6 and Rag3c in aphid resistant germplasm obtained from soybean line E08934. In general, methods are described in Steemers, et al., Whole-genome genotyping with the single-base extension assay, Nature Methods, 3(1): 2006.

A. Plant Materials.

Table 5 shows sources of germplasm for use in producing (making) aphid resistant soybean plants of the present inventions. As one example, Line 19 was made from the cross E00003×E08934 which is new line E070020-19. E08934 was the male parent of E070020-19 and the female parent is E00003.

TABLE 5

Parental lines for use in whole genome sequencing, and their breeding purposes.

| ACCESSION | PURPOSE |
| --- | --- |
| PI 567597C | Aphid resistance (antixenosis) |
| PI 567598B | Aphid resistance (two recessive genes: rag3, rag1b) (antibiosis) |
| PI 567543C | Aphid resistance (Rag3) (antixenosis) |
| PI 567541B | Aphid resistance (two recessive genes: rag4, rag1c) (antibiosis) |
| PI 567537 | Aphid resistance (antixenosis) |
| PI 567585A | Aphid resistance (antibiosis) |
| E00003 | High yield, *P. sojae* resistance, aphid susceptible |
| Skylla | High yield, aphid susceptible |
| E06902 | Breeding line, aphid resistance (rag3, rag1b) |
| E07051 | High yield, SCN and *P. sojae* resistance |
| E08934 | Aphid resistance (Rag6 and Rag3c) |
| E070020-19 | Aphid resistance (Rag6 and Rag3c) |
| E07906-2 | Breeding line, aphid resistance (rag4, rag1c) |

B. Whole Genome Sequencing Preparation.

Leaf tissue samples were collected from young soybean seedlings at VC stage grown in the greenhouse (27° C./24° C. day/night and 16 h/8 h light/dark). DNA extraction was performed using Promega's Wizard® Genomic DNA Purification Kit and quantified using Quanti-IT™ Picogreen® dsDNA Quantitation reagent. A total of 5 ug of DNA per sample was submitted for pooling and library preparation at the Research Technology Support Facility at Michigan State University (East Lansing, Mich.). Accessions were indexed during library preparation using Illumina TruSeq DNA Sample Prep kit. With that, four accessions were pooled into one lane of the Illumina HiSeq 2000 flow cell.

C. Next Generation Sequence (NGS) Workflow and Parameters.

NGS data quality assessment. FastQC (worldwideweb.bioinformatics.babraham.ac.uk/projects/fastqc/) was used for quality control check to visually examine sequence quality. FASTX-Toolkit (hannonlab.cshl.edu/fastx_toolkit/) was used to remove Illumina adapter sequences (fastx_clipper program) and requiring a minimum sequence length of 20 bp after trimming Read mapping to the reference genome. Bowtie version 0.12.7 was used to map the cleaned short reads into the reference genome, Williams 82 (Gmax_109 assembly data obtained from worldwideweb.phytozome.com/soybean). The parameters used include using the paired-end mode for paired end reads and -v mode for single end reads. Two mismatches were allowed for a read to map to the reference sequence. Reads that map once (unique alignments) were processed for SNP calling.

Calling SNPs. Alignments for reads that mapped uniquely to the chromosomes were processed using the sort, index, and pileup programs within SAMtools version 0.1.12a to generate unfiltered pileup files that are then filtered for quality using the varFilter option. The SAMTools varFilter parameters considered for high quality SNPs are: a) should at least have at least 3 read depth coverage (minimum), b) should have up to 20 read depth coverage (maximum), c) Per base SNP quality should be greater than 20 phred score (at least 1/100 error rate).

TABLE 6

Exemplary SSR marker locations and location in aphid resistance germplasm.
Rag6 was on Chromosome 8 while Rag3 loci were located on Chromosome 16.

| Gene/Marker name | cM* | Genomic position Start | End | URL/Source |
|---|---|---|---|---|
| Rag6 | | | | |
| Sat_382 | 116.41 | 23678134 | 23678181 | soybeanbreederstoolbox.org/search/search_results.php?search_term=Sat_382&category=LocusName |
| Satt455 | 129.86 | 41986016 | 41986075 | soybeanbreederstoolbox.org/search/search_results.php?search_term=Satt455&category=LocusName |
| Rag3c | | | | |
| Satt693 | 33.91 | 6273738 | 6273797 | ** |
| Sat_370 | 37.26 | 7054224 | 7054297 | ** |
| Satt456 | 41.87 | 18741972 | 18742261 | * |
| Rag3b (PI 567537) | | | | |
| Sat_339 | 27.98 | 6177215 | 6177246 | ** |
| Sct_065 | 32.09 | 10498970 | 10499035 | soybeanbreederstoolbox.org/search/search_results.php?search_term=Sct_065&category=LocusName |
| Satt654 | 38.09 | 7799231 | 7799265 | soybeanbreederstoolbox.org/search/search_results.php?search_term=Satt654&category=LocusName |
| Rag3_1 (PI567585A) | | | | |
| Satt674 | 15.97 | 1543264 | 1543314 | soybeanbreederstoolbox.org/search/search_results.php?search_term=Satt674&category=LocusName |
| Sct_065 | 32.06 | 10498970 | 10499035 | soybeanbreederstoolbox.org/search/search_results.php?search_term=Sct_065&category=LocusName |
| Satt622 | 42.35 | 27633674 | 27633754 | soybeanbreederstoolbox.org/search/search_results.php?search_term=Satt622&category=LocusName |
| Satt215 | 44.81 | 28589359 | 28589391 | soybeanbreederstoolbox.org/search/search_results.php?search_term=Satt215&category=LocusName |

* cM is based upon a consensus genomic location shown in a published genetic map of cross-over locations within a population, such that a higher cM value represents a greater number of cross-overs or recombination frequency.
* Song Q J, Marek L F, Shoemaker R C, et al. (2004) A new integrated genetic linkage map of the soybean. TAG Theoretical and Applied Genetics 109: 122-128. doi: 10.1007/s00122-004-1602-3.
** Song Q, Jia G, Zhu Y, et al. (2010) Abundance of SSR Motifs and Development of Candidate Polymorphic SSR Markers (BARCSOYSSR_1.0) in Soybean. Crop Science 50: 1950. doi: 10.2135/cropsci2009.10.0607.

D. Validation of High Quality Filtered SNPs.

Custom KASP-by-design (worldwideweb.kbiosciences.co.uk) SNP assays were obtained by submitting 100-bp upstream and downstream sequences of the identified SNPs from the NGS data described herein. Exemplary target sequences used for primer and probe design include:

MSU SNP08-1 at genomic position 23,293,155:
(SEQ ID NO: 7)
5'-ATTGTAACTACATTCTGCAATGCAACAATGATACTATGCAAGTAT

AAATATAGATCAATT[T/G]ACTGCCACAGTTTTCCTGAGCTGCAAGTA

TAAATAGCAAAAGAACAGGAAACAATCTCAA-3'.

Where in the bracketed nucleotides, the first nucleotide, T, was found in the reference allele and the second nucleotide, G, was found in the aphid resistant germplasm.

MSUSNP08-2 at genomic position 40,320,904:
(SEQ ID NO: 8)
5'-GTTGACTTGTCCTTGATTGTGTTTGCCAGTCTCTACCTCATTTCCT

GTGTGTGTGCACCC[A/G]CGCATACTTGTGTGTGAACTTGCATGAATG

TGTTTATATACTTCTGTCTTGACATACCGG-3'.

MSUSNP08-3 at genomic position 41,114,696:
(SEQ ID NO: 9)
5'-CACAGTCCATAAATATAACATGGCAGCATCCAGAATCCAACTACA

CATAAAACTCAGTCC[A/C]TTCCAAAAAAGCACTCGGCTCGTTGAACC

CATTACAAAACAAAATCGAAACATACTAATA-3'.

MSUSNP08-4, 45,189,358,
(SEQ ID NO: 10)
5'-TTTTTCTTTTTTTTTTGAGTTTTTACACATTCATTCTTCTACTCACG

TACAGTTCAATC[T/C]CATCCAATTTTTTTACTCACAGATCCCAAATCG

TCACCTTCTTCTTTTATTTATTTTCAT-3'.

The genomic position is relative to the reference genome Williams82 (Glyma v1.0 assembly). Adjacent sequences of the SNPs were obtained from worldwideweb.phytozome.com/soybean. KASPar SNP genotyping was performed using the 'Endpoint genotyping' module of LightCycler® 480 system (worldwideweb.roche-applied-science.com). An exemplary marker shown in Table 7 describes the genomic position, target sequence, forward and reverse primers and probes used for genotyping.

TABLE 7

Exemplary TaqMan® SNP marker information for Rag3c.
Where two nucleotides shown for a position, the first nucleotide is a nucleotide found in the reference allele (Williams82) while the second is an SNP site, nucleotide substitution found in the aphid resistant germplasm.

| Marker name | Genomic position | Target sequence* | Forward Primer | Reverse Primer | Probe 1: VIC | Probe 2: FAM |
|---|---|---|---|---|---|---|
| MSU | 6,262,227 | 5'-AGAATGAGGTTTA (SEQ ID NO: 11) | 5'-TGATGTCAT | 3'-AGCCTTCA | 3'-CTTTTTCGG | 3'-TTCGGATC |
| SNP16-10 | | GATTTCATTGGGCCTTGGTTGGGCTATGTCCAAAATAGTATCCCCATTAGTTAGTATCCCATGATGTCATGAGGTGTAAACTTGTTAAGACATATCAAACTTAGGGTTTAAGTTAAC[T/C]AGATCCGAAAAAGCTGCCACTATAGNGCCTTCTCTTTGAGTATGTGGTAATTATTGATTGAAGGCTTGATTGAAGGATCATCCTCATAG-3' (SEQ ID NO: 12) | GAGGTGTAAACTTGTTAAGAC-3' (SEQ ID NO: 13) | ATCAATAATTACCACATACTCAA-5' (SEQ ID NO: 14) | ATCTAGTTAACT-5' (SEQ ID NO: 15) | TGGTTAACT-5' |

5'-3' designed from the forward strand.
3'-5' designed from the reverse strand.
*Target sequence of identified MSUSNP was submitted for custom TaqMan® SNP Genotyping Assays (website at invitrogen.com/site/us/en/home/Products-and-Services/Applications/PCR/real-time-pcr/real-time-pcr-assays/snp-genotyping-taqman-assays/custom-snp-assays.html). The company generated the assay design that included the forward and reverse primers, and the VIC/FAM labeled probes/reporter for allele discrimination. SNP assays in single tubes were shipped to the inventors, ready for use.

Exemplary SNP markers were mapped in relation to SSR markers for use in identifying regions of aphid resistant germplasm. See, examples in Tables 8 and 9.

TABLE 8

Exemplary SNP markers in relation to SSR markers for the Rag6 region obtained from soybean plant line E08934.

| Positional Location of SSR markers and SNP markers in relation to Willams82. | Start position | End position | SRR marker/ TaqMan SNP assay |
|---|---|---|---|
| Centromere end | — | — | — |
| 23,293,155 | — | — | MSUSNP08-1 |
| Sat__382 | 23,677,965 | 23,678,208 | Flanking SSR marker |
| 40,320,904 | — | — | MSUSNP08-2 |
| 41,114,696 | — | — | MSUSNP08-3 |
| Satt455 | 41,985,997 | 41,986,248 | Flanking SSR marker |
| 45,189,358 | — | — | MSUSNP08-4 |
| Telomere end | — | — | — |

An SNP marker was identified see, Table 9, which mapped near the SSR marker associated with the Rag3c region.

TABLE 9

Exemplary SNP markers in relation to SSR markers for the Rag3c region obtained from soybean plant line E08934.

| SNP position | Ref. Allele | Alter. Allele | Read Coverage | Start position | End position | TaqMan/KASP_assay ID |
|---|---|---|---|---|---|---|
| Telomere end | | | | | | |
| 6,262,227 | C* | T | 6 | | | MSUSNP16_10 |
| Satt693 | | | | 6,273,738 | 6,273,797 | |
| Sat_370 | | | | 7,054,224 | 7,054,297 | |
| Satt465 | | | | 18,741,972 | 18,742,261 | |
| Centromere end | | | | | | |

As an example, the asterisk identifying reference allele nucleotide C (above) matches an exemplary sequence reference fragment from Williams82 soybean plants:

(SEQ ID NO: 16)
GTTGGGCTATGTCCAAAATAGTATCCCCATTAGTTAGTATCCCATGAT

GTCATGAGGTGTAAACTTGTTAAGACATATCAAACTTAGGGTTTAAG

TTAA☐CAGATCCGAAAAAGCTGCCACTATAGTGCCTTCTCTTTGAGT

ATGTGGTAATTATTGATTGAAGGCTTGATTGAAGGATCATCCTCATAG

CTTAGGTTTT.

Example III

This example describes exemplary aphid resistant genes for use in stacking and/or pyramiding at least two or more aphid resistant germplasm regions in the same plant, i.e. having at least 3 aphid resistant genes in the same soybean plant for making soybean plants having enhanced aphid resistance.

Aphid resistant genes of the present inventions are contemplated to find use with other new aphid resistant genes. In some contemplated embodiments, aphid resistant genes of the present inventions are combined. In some contemplated embodiments, aphid resistant genes of the present inventions are combined with known aphid resistant genes.

TABLE 10

Aphid resistance germplasm sources for use in the present inventions. Bold denotes sources of aphid resistance germplasm and loci discovered during the development of the present inventions.

| Resistance source and maturity group | Gene | Inheritance | Location | Type of resistance | Markers | Reference |
|---|---|---|---|---|---|---|
| Dowling (PI 548663) | Rag1 | Dom. (one gene) | Chr. 7 (LG-M) | Antibiosis | Satt463 Satt540 | Hill et al. 2004 |

TABLE 10-continued

Aphid resistance germplasm sources for use in the present inventions. Bold denotes sources of aphid resistance germplasm and loci discovered during the development of the present inventions.

| Resistance source and maturity group | Gene | Inheritance | Location | Type of resistance | Markers | Reference |
|---|---|---|---|---|---|---|
| one dom gene group VIII | | | | | SNP marker 46169.7 and 21A | Hill et al. 2006 Li et al; 2007 Kim, et al. 2010 |
| Jackson, one dom germplasm/ genes (PI 548657) group VII | Rag1 allele | N/S | Chr. 7 (LG-M) | Antibiosis | N/S | Hill et al. 2004 |
| PI 567598B, group III | rag1b | rec. | Chr. 7 | Antixenosis | Satt 435-07_0295 and between a marker MSUSNP7-19 and a marker MSUSNP7-10 | |
| PI 567541B, group III | rag1c | rec. | Chr. 7 (LG-M) | Antibiosis | N/S | Mensah, Wang et al., 2008; Wang et al. 2008; Kim et al. 2008 |
| PI 243540 | Rag2 | Dom. (one gene) | Chr. 13 [formerly linkage group (LG) F]. | Antibiosis | Satt334 and Sct_033 on LG F | Kang, et al., 2008; Mian, et al., 2008 |
| PI 200538 PI 243550 | Rag2 | Dom. | Chr. 13 [formerly linkage group (LG) F]. | Antibiosis | 54-kb interval on the Williams 82 8x assembly (Glyma1) | Hill et al. 2009; Kim (Hill) et al., 2008; Kim (Hill) et al., 2010 |
| PI 567301B | near the Rag2 locus | N/S | Chr. 13 [formerly linkage group (LG) F] | Antixenosis | N/S | Jun et al, 2011 |
| PI 567543C, group III | Rag3 | Dom. Co-dom. Additive rec. | Chr. 16 (LG-J) | Antixenosis | Sat_339 and Satt414 | Zhang et al 2009b; 2010 |
| PI 567598B | rag3 | rec. | N/S | Antibiosis | N/S | |
| PI 567597C | N/S | N/S | LG J | Antixenosis | N/S | |
| **E08934, a single plant selection from a wild type soybean, *Glycine soja* accession 85-32 E00003 × E08934 (Jiyu 71 × 85-32)-mapping population | Rag3c | rec. | Chr. 16 (LG J) 4.8 to 11.3 MB and 24.6 to 28.5 MB | Antixenosis | 3.5 cM between Satt693 and Sat_370 on Chr. 16** | Not published |
| Progeny (hybrid) plants from a E08934 × | rag1c Rag3c Rag6 | | Chr. 7 (LG. M) Chr. 16 | | Satt540-a marker for rag1c | Not published |

TABLE 10-continued

Aphid resistance germplasm sources for use in the present inventions. Bold denotes sources of aphid resistance germplasm and loci discovered during the development of the present inventions.

| Resistance source and maturity group | Gene | Inheritance | Location | Type of resistance | Markers | Reference |
|---|---|---|---|---|---|---|
| E08929, an accession from PI 567541B | | | (LG. J) Chr. 8 (LG. A2) | | BARCSOYSSR_16_0371- a marker for Rag3c Satt209-a marker for Rag6 | |
| PI 567537 | rag3b | Dom. | Chr. 16 (LG-J) | Antibiosis | N/S | Not published |
| PI 567585A | rag3 loci (Rag3-1) | Co-dom. Additive | Chr. 16 (LG-J) | Antibiosis | Satt674 and Sct_065 | Not published |
| PI 567541B, group III | rag4 | Rec. | Chr. 8 | Antibiosis | N/S | Not published |
| PI 567301B | Rag5 | N/S | Chr. 8 | N/S | Between Satt437 and Satt327 | Jun et al., 2012 |
| E08934, a single plant selection from a wild type soybean, Glycine soja accession 85-32, E00003 × E08934 (Jiyu 71 × 85-32)- mapping population | Rag6 | Partially dom. Rag6 is different from that of Rag5, because the marker Satt209 closest to the peak of LOD score is 18.6 cM distance away from Satt327, based on the soybean consensus map (Song et al., 2004) | Chr. 8 (LG-A2) 38.8 to 43.9 megabase pair | Antibiosis | 13.5 cM between Sat_382 and Satt455 on Chr. 8 | Not published Provides superior aphid resistance as shown herein |

N/S = not shown.
Dom. = Dominant.
rec. = recessive.
Chr. = Chromosome.

Example IV

This example describes the discovery of aphid resistant germplasm in soybean PI 567537.

Aphid resistance loci mapping. In the greenhouse trial, the majority of PI 567537 plants were rated 1 while one plant was rated 1.5. The E00003 plants were rated 3.5. The scores of the whole mapping population ranged from 0.5 to 3.5. Seventy two lines were included in the field trial since at least one dozen plant lines did not produce seeds in the greenhouse. The average aphid resistance sore for PI 567537 in the field was 1.5 with a range of 0.5 to 2 while the E00003 plants were rated 3.5. Seven lines showed segregation of aphid resistance in the field trial. These seven lines were derived from (bred from) plants that were rated from 0.5 to 1.5 in the greenhouse trial, that indicated the aphid resistance germplasm/genes in PI 567537 soybean plants was dominant. The range of aphid resistance scores in the field trial was similar as in the greenhouse (FIG. 9A, B). However, the aphid infestation in the field trial appeared more severe than the greenhouse trial. The correlation between the greenhouse and field data was strong (0.70, $P<0.0001$). The frequency distributions of the aphid resistance scores in both trials were continuous, but showed two major peaks, indicating major genes controlling the aphid resistance in PI 567537.

A total of 804 SSR markers were tested on the two DNA pools and 51 markers showed polymorphism. These 51 markers were then genotyped on the individual lines from those two DNA pools and five markers on chromosomes 5, 8, 19, and 20 (LGs A1, A2, L, I) appeared to be associated with the aphid resistance. However, none of these markers showed significant association with aphid resistance when they were further genotyped on the whole population. In the meantime, markers closely linked with Rag1, Rag2, Rag3, rag4, were also genotyped on the whole population. For example, Satt567 on chromosome 7 (LG M) was used for Rag1 loci, Satt335 and Satt596 on chromosome 13 (LG F) used for Rag21 loci, and Satt569 on chromosome 16 (LG J) used for Rag3 loci, were also genotyped on the whole population. Satt569 was significantly ($P<0.05$) associated with the aphid resistance.

Figure 9:
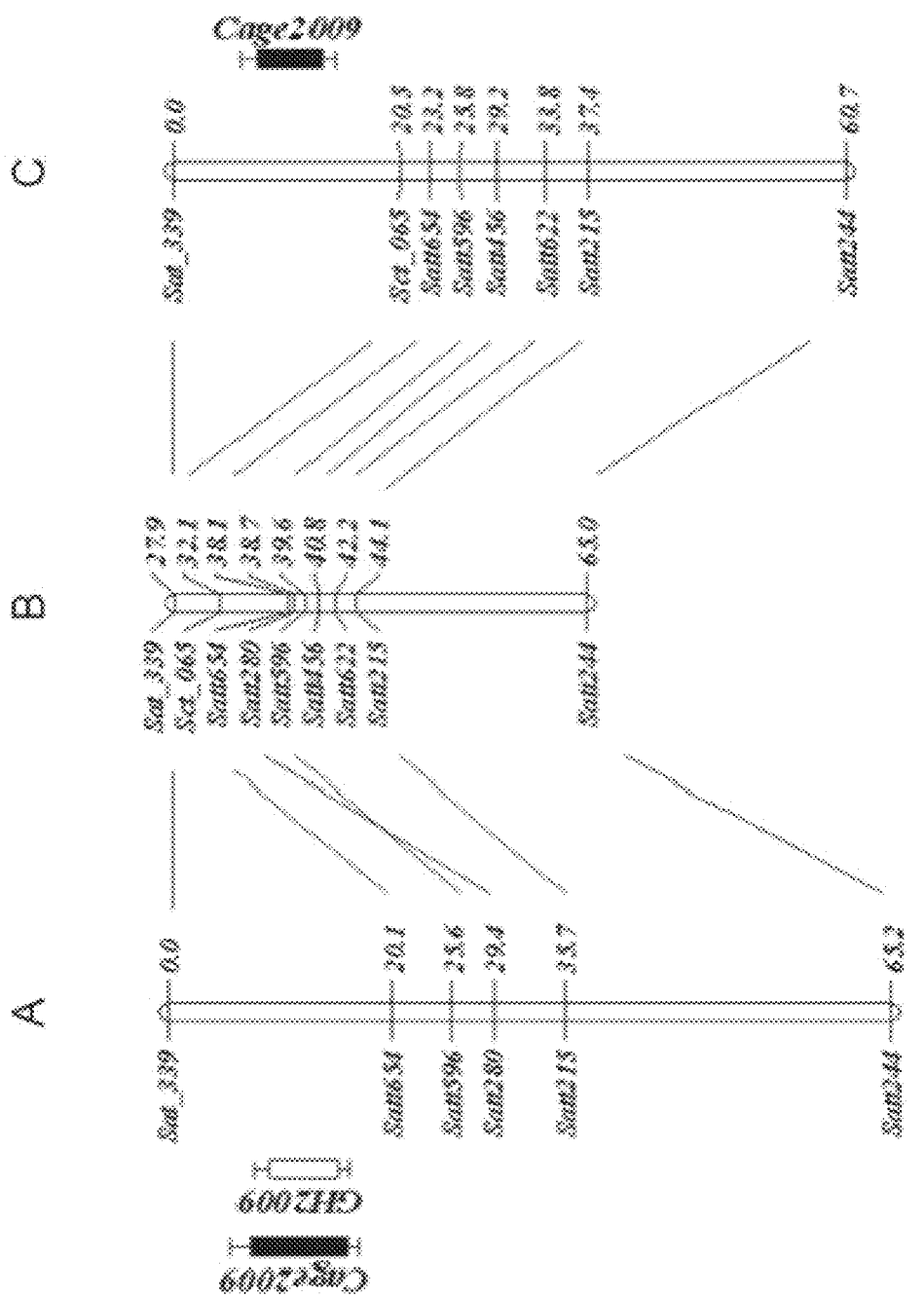
FIGS. 9A-9C illustrate locations of soybean aphid resistance loci as determined using the interval mapping method. 1-LOD and 2-LOD support intervals of each locus are marked by thick and thin bars, respectively. The unfilled bar represents loci in the year 1 greenhouse trial (GH2009) while black bars represent loci in the year 1 field cage trial (Cage2009).

Then, additional five parental polymorphic markers in this region were genotyped on the whole population. Six markers fit a 7:2:7 (homozygous female:heterozygote:homozygous male) segregation ratio (P>0.05) as expected in an $F_4$ derived population. These six markers formed one linkage group as expected and the genetic linkage map spanned a total distance of 65.2 cM (FIG. 9A), which expanded about 27 cM more compared with the consensus map of Song et al. (2004) (FIG. 9B). However, the marker order in this study was comparable with the consensus map (Song et al. 2004) except that the order of Satt596 and Satt280 was inverted (FIG. 9A). The linkage map was then used for the following QTL analysis. One QTL was consistently identified in the interval between Sat_339 and Satt654 in both trials with the Interval Mapping method (Table 11, FIG. 9). The PI 567537 allele at this locus conferred aphid resistance. This QTL explained the majority of the phenotypic variation ranging from 87.6.7% in the greenhouse trial to 78.9% in the field trial. The high percentage of phenotypic variation explained by this QTL indicates that the aphid resistance in PI 567537 may be controlled by a single gene.

Aphid resistance locus validation. In the field trial for the validation population, the average aphid resistance score for PI 567537 was 0.8 with a range of 0.5 to 1.5 while plants of the susceptible parent Skylla were rated 3.5. Among the population, the majority of plants (167 and 45) either fell into the range of resistant parent or were the same as the susceptible parent (FIG. 9C, where arrows point to the values of the parent). The remainder (21) were rated between 2 and 3. However, one was rated 2.5. The least significant difference (P<0.05) ($LSD_{0.05}$) was estimated as 0.4 based on the three replications of the two parental lines. When the resistant or susceptible categories were extended by one $LSD_{0.05}$ on the basis of scores for the parental lines, the plants with scores of 2 or less were classified as resistant while plants with scores of 3 or more were classified as susceptible. Then, the segregation ratio of resistant (181) to susceptible (51) plants in this F2 population was approximately 3:1 (P=0.29), indicating a single dominant germplasm/gene controls the aphid resistance in PI 567537.

A total of eight polymorphic SSR markers in the region containing the resistant QTL were chosen to genotype the $F_2$ population for validation. These eight markers formed one linkage group as expected and spanned a distance of 60.7 cM, inflating about 22 cM compared with the consensus map (Song et al. 2004) (FIG. 2B, C). However, the marker orders were the same as the consensus map. The QTL analysis via Interval Mapping also revealed a QTL in an interval between Sat_339 and Sct_065. This QTL position was similar to the one detected in the mapping population (Table 11, FIG. 9C). The QTL identified in the validation population also explained the majority of the phenotypic variation (86.4%). Hence, the results from the validation population confirmed the locus identified in the mapping population. The data were further analyzed with the multiple interval mapping method, which confirmed the significance of this locus's dominant effect. The dominance effect size was very similar to the additive effect at this locus, suggesting a complete dominance of this locus.

TABLE 11

Summary - aphid resistance locus in the mapping population PI 567537 × E00003 and in the validation population PI 567537 × Skylla using the composite interval mapping method with aphid damage index data.

| Population | Trials | Chr/LG[a] | Peak Pos.[b] | Flanking markers | LOD | $R^{2c}$ | $a^d$ | $d^e$ |
|---|---|---|---|---|---|---|---|---|
| PI 567537 × E00003 | Greenhouse | 16/J | 12 | Sat_339-Satt654 | 22.3 | 87.4 | 1.2 | N[f] |
|  | Field Cage | 16/J | 12 | Sat_339-Satt654 | 13.1 | 78.9 | 0.9 | N |
| PI 567537 × Skylla | Field Cage | 16/J | 10 | Sat_339-Sct_065 | 81.8 | 86.4 | 1.3 | 1.2 |

[a]Chromosome/Linkage group. The chromosome number and linkage group name are according to the SoyBase (Grant et al. 2009, herein incorporated by reference).
[b]Peak position is expressed in cM.
[c]$R^2$, percentage of phenotypic variation explained by the locus.
[d]Additive effect. The positive value implies that the PI 567537 allele decreased the phenotypic value.
[e]Dominant effect. The positive value implies that the PI 567537 allele decreased the phenotypic value.
[f]N = data not provided.

Exemplary materials and methods for discovering aphid resistance loci mapping in PI 567537 germplasm.

Plant materials and aphid resistance evaluation. A mapping population of 86 $F_4$ lines was developed from the cross of PI 567537×E00003 by single seed descent. PI 567537 plants are descended from plants that originated from Northern China (Chen et al. 2007, herein incorporated by reference) and were found during the development of the present inventions to have antibiosis resistance to the soybean aphid, while E00003 was an advanced breeding line developed at Michigan State University (MSU) and was shown susceptible to the soybean aphid.

Aphid resistance was evaluated in choice tests in both greenhouse and field trials. A greenhouse trial was conducted one spring in the Plant Science Greenhouse at MSU in East Lansing, Mich. In this trial, the $F_4$ single plant lines and its parents, as described herein, were sown in the plastic pots. The pot size was 105 mm in diameter and 125 mm deep. Eight lines were sown in each pot while each parental line was sown in one pot with eight seeds. The greenhouse was maintained at 26/15° C. day/night temperature and sodium vapor lights were also used to supplement light intensity during the day (14 h). After the completion of the aphid resistance evaluation, plants were sprayed with insecticide to allow the plants to continue their growth and produce seeds for the field trial in the following summer The field trial was conducted on the Agronomy Farm of MSU. When there were enough seeds, each line was sown with at least 11 seeds with the plant space of 5 cm and row space of 60 cm. These lines were randomized with six checks and three replications of parental lines throughout the test. Each check or parental line was sown with about ten seeds. The field trial was covered in an aphid-proof and predator-proof polypropylene cage with 0.49-mm size mesh (Redwood Empire Awning Co., Santa Rosa, Calif.).

In both types of trials, each plant was infested with two wingless aphids at the V1 stage (Fehr and Caviness 1977). The aphid biotype isolate used to infest plants for trials was collected from a naturally infested field on the Agronomy Farm of MSU the previous year and multiplied (i.e. the population was maintained) in greenhouse. The aphid rating began once the susceptible parents were heavily infested with aphids (approximately four weeks after infestation). The aphid resistance was visually rated by eye using a scale of 0 to 4 developed by Mensah et al. (2005, 2008), where 0=no aphids; 0.5=fewer than 10 aphids per plant, no colony formed; 1=11 to 100 aphids per plant, plants appear healthy; 1.5=101 to 150 aphids per plant, plants appear healthy; 2=151-300 aphids per plant, mostly on the young leaves or tender stems, plants appear healthy; 2.5=301-500 aphids per plant, plants appear healthy; 3=501-800 aphids per plant, young leaves and tender stems are covered with aphids, leaves appear slightly curly and shiny; 3.5=more than 800 aphids per plant, plants appear stunted, leaves appear curled and slightly yellow, no sooty mold and few cast skins; 4=more than 800 aphids per plant, plants appear stunted, leaves appear severely curled and yellow and are covered with sooty mold and cast skins.

DNA extraction and marker analysis. In the greenhouse trial, the non-expanded trifoliates from each single plant lines were harvested for isolating the genomic DNA before the aphid infestation. The DNA was extracted with the CTAB (hexadecyltrimethyl ammonium bromide) method as described by Kisha et al. (1997) and the concentration was determined with a ND-1000 Spectrophotometer (NanoDrop Technologies, Inc., Wilmington, Del.). The PCR was performed using the genomic DNA with simple sequence repeat (SSR) markers as described by Cregan and Quigley (1997) and was run on an MJ TETRAD™ thermal cycler (MJ Research, Waltham, Mass.). The SSR primer sequences were provided by Dr. Perry Cregan of the USDA-ARS, Beltsville, Md. The PCR products were separated on 6% non-denaturing polyacrylamide gels using an electrophoresis unit DASG-400-50 (C.B.S. Scientific Co., Del Mar, Calif.) as described by Wang et al. (2003). Gels were stained with ethidium bromide, visualized under UV light, and photographed.

In order to accelerate the identification of genomic regions associated with aphid resistance, the bulked segregant analysis method described by Michelmore et al. (1991) was used in this study. Eight resistant lines with the lowest DI values and eight susceptible lines with the highest DI values were selected to form a resistant pool and a susceptible pool, respectively. Available SSR markers on the integrated soybean map of Song et al. (2004) (excluding the ones on chromosomes 7, 13, 16) were tested on two DNA pools. The polymorphic markers between the two pools were chosen to genotype the individual lines in the two pools together with the two parents. The markers that appeared to be associated with the aphid resistance were used to genotype the remaining lines of the whole mapping population. The SSR markers associated with the resistance loci on chromosomes 7, 13, 16 found in previous studies (Li et al. 2007; Mian et al. 2008b; Zhang et al. 2009; Zhang et al. 2010) were also genotyped on the whole population. The genomic regions associated with the aphid resistance were then saturated with additional markers.

Statistical and QTL Analysis. The data from the greenhouse and field trials were analyzed separately. Pearson correlations for the aphid resistance between trials were estimated with the CORR procedure of SAS (1999). A $\chi^2$ of goodness test was performed to analyze the segregation ratio of alleles at each locus. A linkage map was constructed with JoinMap 3.0 using the Kosambi function and a LOD score of 3 (Van Ooijen and Voorrips 2001, herein incorporated by reference). Interval mapping (IM) was performed to locate aphid resistance loci using QTL Cartographer V2.5 (Wang et al. 2008, herein incorporated by reference). The walking speed chosen for IM was 2 cM. The empirical LOD threshold at the 5% probability level was determined by a 1,000-permutation test (Churchill and Doerge 1994, herein incorporated by reference). In the field trial, the mean scores for each line were used in the analysis. The maps and the locus positions were drawn using MapChart (Voorrips 2002, herein incorporated by reference).

Resistance locus validation. A population of 233 $F_2$ plants was used to validate the resistance loci identified in the mapping population. The validation population was developed from a cross between PI 567537 and 'Skylla', where Skylla is a cultivar developed at MSU and is aphid-susceptible (Wang et al. 2006, herein incorporated by reference). In the summer, the aphid resistance was evaluated for the validation population together with its parents and six checks in a field trial, which was conducted in the same way as for the mapping population. The nonexpanded trifoliates were harvested for each $F_2$ plant before the aphid infestation and DNA was extracted as for the mapping population. Polymorphic markers in the regions containing the aphid resistance loci were selected to genotype the validation population. Linkage map construction and mapping analysis were performed in the same way as for the mapping population. A $\chi^2$ of goodness test was performed to analyze the segregation ratio of resistant to susceptible plants.

Example V

This example describes the discovery of aphid resistant germplasm in soybean PI 567585A.

Figure 10A:
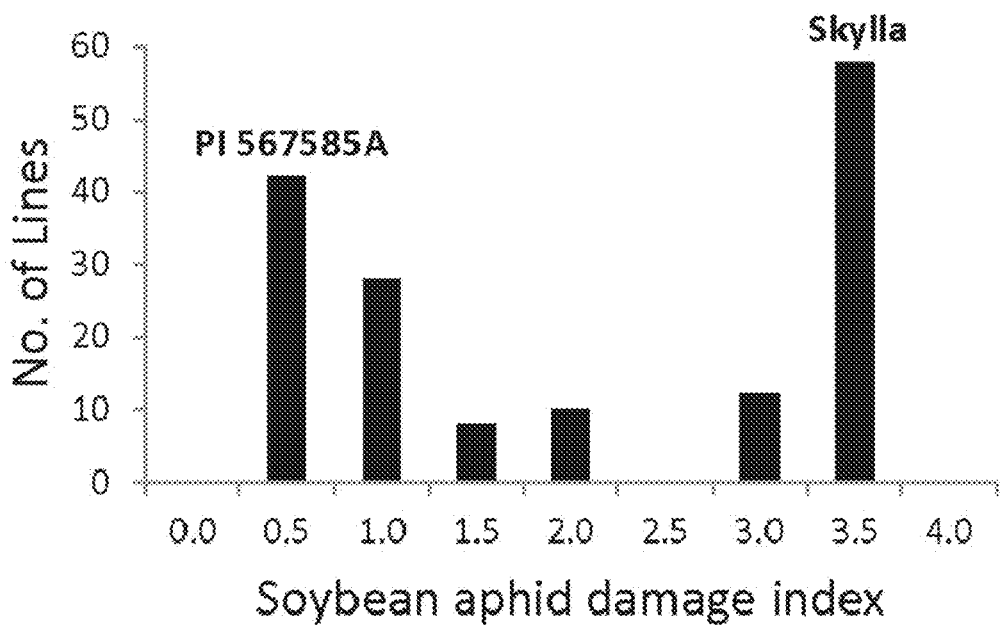
FIGS. 10A-10B show an exemplary distribution of DI scores in PI 567585A RIL populations.
Figure 10B:
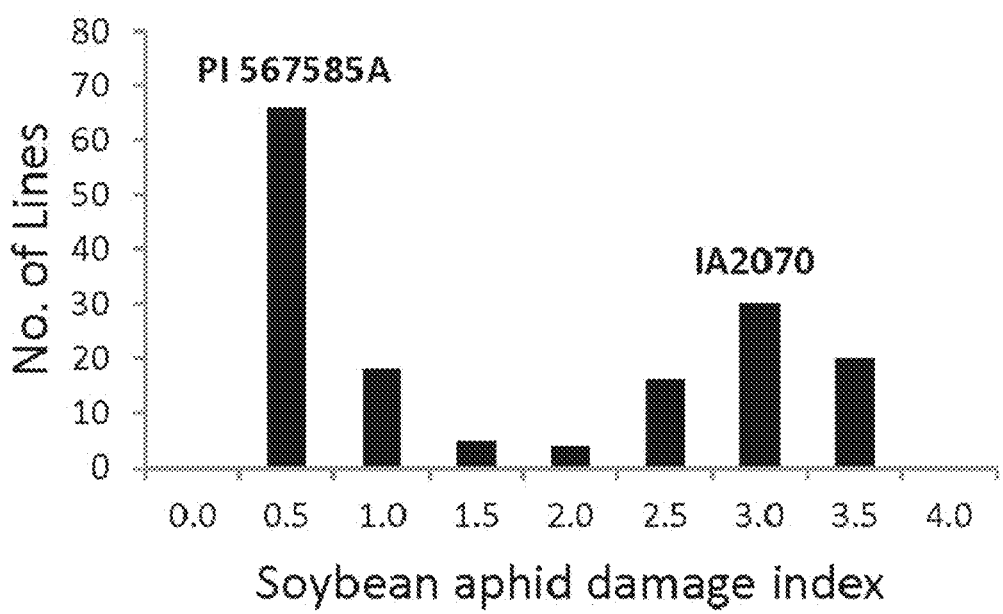

Phenotypic data analysis for mapping and validation populations. The phenotypic data for aphid damage index of mapping and validation populations, and parents in the field trial were shown in Table 12.1. Resistant parent PI 567585A had significantly (P<0.05) lower DI than susceptible parents 'Skylla' and IA2070, which were heavily infested by soybean aphids. The broad-sense heritabilities for aphid resistance were 0.96 and 0.89 for population 070082 and 070016 in the field trial, respectively (Table 12.1). This indicates that substantial variation exists among RILs within both mapping and validation populations. The DI for the two populations showed discontinuous variation and approximate bimodal distribution with a ratio of 1:1, confirming that aphid resistance was controlled by one (single) germplasm region/gene (FIG. 10).

Genetic Mapping of Aphid Resistance. A total of 313 SSR markers were polymorphic between PI 567585A and 'Skylla'. Analysis of the bulked resistant lines from the 070082-2 population indicated that the SSR markers Satt622 and Satt215 on chromosome 16 (LG J) were associated with aphid resistance. These two SSR markers were genotyped for the entire 070082 RIL population, and their associations with aphid resistance were confirmed. Five other polymorphic SSR markers within ±30 cM of Satt622 and Satt215 were genotyped for the entire mapping population. The segregation of the markers tested except Satt674 fit a 7:2:7 (homozygous SSR allele of the resistant parent: heterozygous SSR alleles from both resistant and susceptible parents:

homozygous SSR allele of the susceptible parent) segregation ratio (P>0.05) at $F_4$ generation (Table 12.2).

Figure 11:
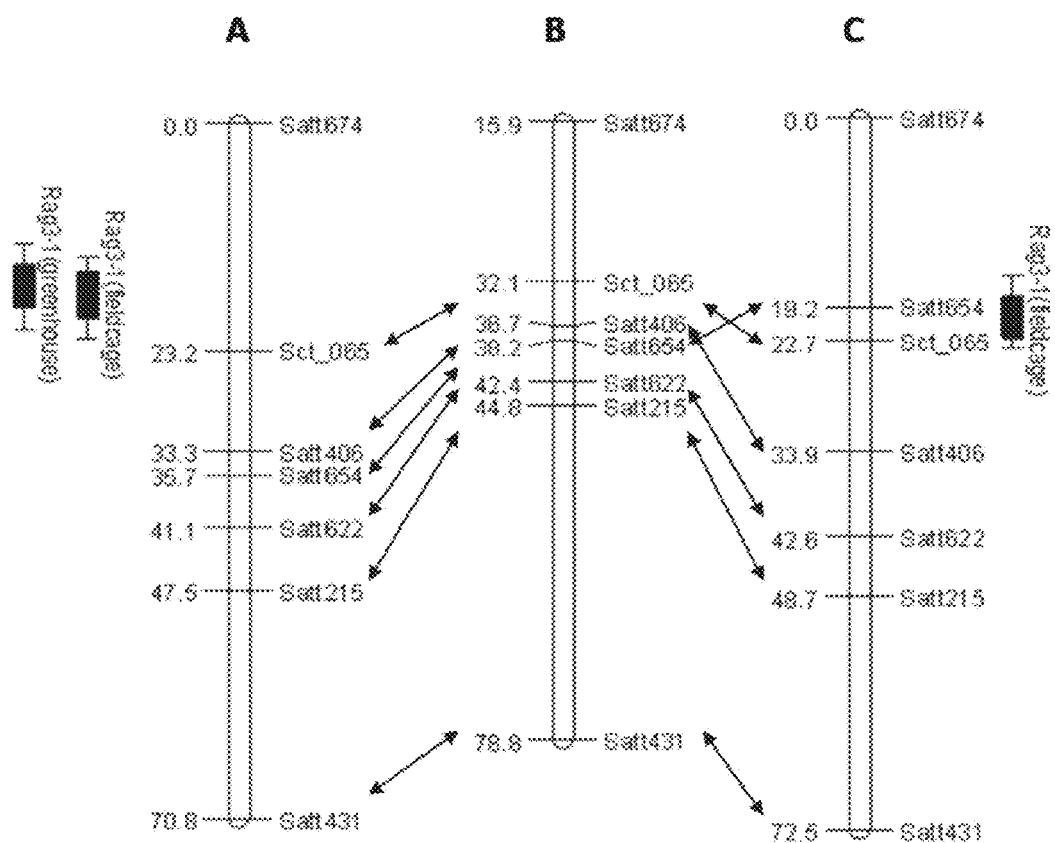
FIGS. 11A-11C illustrates linkage maps of the locations of the soybean aphid resistance genes from PI 567585A that were mapped on soybean linkage group J.

A linkage group was constructed by analyzing these seven markers with Join-Map. The marker order was highly consistent with the consensus map (Song et al., 2004), although the spanning distance was 70.2 cM, about 7.3 cM larger than the corresponding map distance of 62.9 cM (FIG. 11). The aphid resistance germplasm/genes was identified in the interval between Satt674 and Sct_065 in both greenhouse and field trials (FIG. 11 and Table 12.3). The major phenotypic variation of aphid resistance contributed by the PI 567585A germplasm/genes in the greenhouse and field trials was 93.1% and 90.1%, respectively. The additive effect of this resistance germplasm/gene region was also determined for the mapping population in both trials. The PI 567585A resistance allele decreased the soybean aphid DI value by 32.35 and 30.50 in the greenhouse and field trials, respectively (Table 12.3). In addition, the average DI value was calculated for each genotype class of Sct_065, and analyzed by ANOVA. The heterozygous class showed an intermediate level of resistance to soybean aphid between resistant and susceptible classes, which was not significantly different from the average of the two homozygous classes (Table 12.4). These results indicated that aphid resistance in PI 567585A was controlled by a single co-dominant germplasm with an additive effect, which was consistent with a genetic inheritance study of PI 567585A.

Validation of aphid resistance gene. Seven SSR markers linked to the resistance locus on LG J in the mapping population were genotyped for the validation population (070016). The segregation ratio of each marker fit the 7:2:7 ratio (Table 12.2). These seven markers were used to construct a linkage map, which was similar to the consensus map, except for the inverted order of Satt654 and Sct_065 (FIG. 11). A single aphid resistance germplasm region was identified in the interval between Satt654 and Sct_065 in the QTL analysis using the CIM analysis. This germplasm/gene region was discovered at a position of 8 cM above Sct_065, which is the same as the QTL location detected in the mapping population. Moreover, the resistance germplasm identified in the validation population explained 85.6% of the phenotypic variation in the field trial (Table 12.3). Thus, analysis of the validation population confirmed the location of the aphid resistance locus identified in the mapping population.

TABLE 12.1

Damage index of soybean aphid in summer fields for the parents: PI 567585A, Skylla, and IA2070; 158 $F_{4:5}$ RILs derived from 070082-2 validation population (PI 567585A × 'Skylla'); and 162 $F_{3:4}$ RILs derived from 070016-2 mapping population (PI 567585A × IA2070).

| Population ID | Parents | | | RILS population | | |
|---|---|---|---|---|---|---|
| | PI 567585A | IA 2070 | 'Skylla' | Mean + SE* | Range | $H^2$** |
| 70082 | 16.7$^a$ | N/D | 87.5$^b$ | 58.1 ± 8.55 | 12.5~87.5 | 95.5% |
| 70016 | 12.5$^a$ | 73.2b | N/D | 39.7 ± 12.55 | 8.3~87.5 | 88.7% |

Means followed by different letters within the same row are significantly different at P < 0.05.
$DI^\dagger$ = Σ (scale value × no. of plants in each category)/(4 × total no. of plants) × 100.
SE* = standard error.
$H^2$** = broad sense heritability.
N/P = not a parent of this line.

TABLE 12.2

$X^2$ test of segregation ratio for the aphid resistance germplasm (located within the rag3 area, i.e. Rag3-1) and seven SSR markers among 158 $F_{4:5}$ RILs from the PI 567585A × 'Skylla' mapping population and 94 $F_{3:4}$ RILs from the PI 567585A × IA 2070 validation population.

| Population ID | Locus | Number of $F_{3:4}$ RILS in each category | | | | $X^2_{7:2:7}$ | P |
|---|---|---|---|---|---|---|---|
| | | a* | b* | h* | —* | | |
| 070082 | Satt674 | 77 | 7 | 74 | 0 | 9.472 | 0.0088 |
| | Sct_065 | 75 | 22 | 62 | 0 | 1.474 | 0.4785 |
| | Satt406 | 70 | 17 | 69 | 1 | 0.374 | 0.8296 |
| | Satt654 | 75 | 18 | 62 | 3 | 1.358 | 0.5072 |
| | Satt622 | 74 | 27 | 57 | 0 | 5.132 | 0.0768 |
| | Satt215 | 68 | 26 | 64 | 0 | 2.376 | 0.3048 |
| | Satt431 | 76 | 12 | 70 | 0 | 3.736 | 0.1544 |
| | Rag3-1 | 70 | 19 | 69 | 0 | 0.040 | 0.9803 |
| 070016 | Satt674 | 36 | 6 | 52 | 0 | 6.328 | 0.0423 |
| | Sct_065 | 40 | 15 | 39 | 0 | 1.040 | 0.5947 |
| | Satt406 | 51 | 2 | 41 | 0 | 10.462 | 0.0053 |
| | Satt654 | 40 | 11 | 43 | 0 | 0.164 | 0.9212 |
| | Satt622 | 46 | 9 | 39 | 0 | 1.331 | 0.5139 |
| | Satt215 | 34 | 13 | 47 | 0 | 2.207 | 0.3318 |
| | Satt431 | 44 | 7 | 43 | 0 | 2.207 | 0.3318 |
| | Rag3-1 | 40 | 12 | 42 | 0 | 0.055 | 0.9730 | a* = homozygous SSR allele of the resistant parent, PI 567585A.
b* = homozygous SSR allele of the susceptible parent, 'Skylla' or IA 2070.
h* = heterozygous SSR alleles from both resistant and susceptible parents.
—* = missing band for SSR alleles.

TABLE 12.3

Summary for aphid resistance Rag3-1 loci detected in the mapping population and the validation population with aphid DI data using the CIM method.

| Population | Trial | LG/Chr* | Peak Pos. (cM)** | Flanking markers+ | LOD | $R^2$++ | $a^\ddagger$ |
|---|---|---|---|---|---|---|---|
| 070082 | Greenhouse | J/16 | 15.5 | Satt674~Sct_065 | 21.66 | 93.1 | 32.35 |
| | Field cage | J/16 | 16.0 | Satt674~Sct_065 | 15.66 | 90.1 | 30.50 |
| 070016 | Field cage | J/16 | 20.0 | Satt674~Sct_065 | 28.17 | 85.6 | 26.25 |

LG/Chr* = linkage group/chromosome.
Peak Pos. (cM)** = QTL peak position is expressed in cM.
Flanking markers+ = Markers flanking the peak position or the marker at the peak position.
$R^2$++ = Percentage of phenotypic variation explained by a QTL.
$a^\ddagger$ = Additive effect. The positive value implies that the PI 567585A allele decreases the DI.

TABLE 12.4

Average aphid DI for different genotypes of marker Sct_065 in the field trial for mapping and validation populations.

| Population | PI 567585A Type (a[1]) | Heterozygous Type (b[2]) | Skylla/IA 2070 Type (h[3]) | Average of PI 567585A Skylla/IA 2070 Type |
|---|---|---|---|---|
| 070082 | 39.75[a] | 53.75[b] | 81.25[c] | 60.50[b] |
| 070016 | 22.50[a] | 42.50[b] | 67.50[c] | 45.00[b] | a[1] = homozygous SSR allele of the resistant parent, PI 567585A.
b[2] = homozygous SSR allele of the susceptible parent, 'Skylla' or IA 2070 as labeled.
h[3] = heterozygous SSR alleles from both resistant and susceptible parents.

Exemplary materials and methods for discovering aphid resistant loci in PI 567585A.

Plant materials and aphid resistance evaluation. A mapping population of 158 $F_{4:5}$ lines (070082) was developed from the cross of PI 567585A×'Skylla' by single seed descent. PI 567585A possesses antibiosis resistance to the soybean aphid. The Chinese cultivar name of PI 567585A is 'Ri Zhao Huang'. The morphological and agronomic traits of PI 567585A are listed by Hill et al. (2005, herein incorporated by reference). 'Skylla' is an aphid-susceptible soybean variety (Wang et al., 2006, herein incorporated by reference).

Based on the heritability of aphid resistance shown in previous experiments (Zhang et al., 2009a, herein incorporated by reference), a single trial was carried out in the greenhouse and two replications were conducted in field. The greenhouse trial was initiated in the Plant Science Greenhouse at Michigan State University (MSU) in East Lansing, Mich. Eight seeds per line or parent were planted in a plastic pot, which were 210 mm in diameter and 125 mm deep. In a completely randomized design (CRD), two parents and the mapping population were set on the bench without replication. The temperature was maintained at 26/15° C. day/night with 14-h supplemental lighting provided by sodium vapor lamps. In the summer, the field evaluation of soybean aphid resistance was carried out in a 12.2×18.3m aphid-proof and predator-proof cage (Redwood Empire Awning Co., Santa Risa, Calif.) on the Agronomy Farm of MSU. The parental plants were planted randomly in the field, 5.1 cm apart, with two replications. Depending on the seed availability, 4 to 16 seeds per line were planted in a single row plot, 60 cm long with a row spacing of 60 cm. The average number of plants per recombinant inbred line was around nine with most plots having at least eight plants. Similarly, CRD was used to arrange the whole $F_{4:5}$ population and its parents in the field plots with two replications.

In both greenhouse and field trials, each plant was inoculated at the V2 stage with two wingless aphids. A single aphid clone was collected from a naturally infested field at the MSU Agronomy Farm in summer, and maintained in an isolation chamber in the greenhouse for the inoculation of plants in the greenhouse trial in spring. The soybean aphids used for inoculation in the field trial were collected from a naturally infested field on the MSU Agronomy Farm in the following summer The $F_{4:5}$ mapping population and parental plants were evaluated for aphid damage 3 week after inoculation using a modified 0-4 half step rating scale described by Mensah et al. (2008, herein incorporated by reference). The aphid resistance score was determined as the mean of the rated plants in each line for each replication. An aphid damage index (DI) for each line was used as an indicator of aphid resistance, ranging from 0 (no damage) to 100 (most severe damage (Mensah et al., 2005, herein incorporated by reference). DI was calculated based on the following formula: DI=Σ(scale value×no. of plants in each category)/(4× total no. of plants)×100 (Zhang et al., 2009a, herein incorporated by reference).

DNA extraction and SSR marker genotyping. In the field trial, the unopened trifoliate from each individual plant of each line ($F_{4:5}$ mapping population) and their parents were bulk harvested for the genomic DNA extraction. The CTAB (Hexadecyltrimethyl ammonium bromide) described by Kisha et al., (1997, herein incorporated by reference) was used to extract the genomic DNA. The concentration was determined with a ND-1000 Spectrophotometer (NanoDrop Technologies, Inc., Wilmington Del.).

The genomic DNA from each RIL line and parent was amplified by PCR protocol with SSR markers described by Cregan and Quigley (1997, herein incorporated by reference) on a MJ Tetrad™ thermal cycler (MJ Research Waltham, Mass.). The sequence information of SSR primers was provided by Dr. Perry Cregan (USDA-ARS, Beltsville, Md.). A total of 1056 SSR primers were used to screen for the polymorphism between PI 567585A and 'Skylla'. Bulked segregant analysis (Michelmore et al., 1991, herein incorporated by reference) was used to accelerate the identification of the aphid resistance locus. Ten resistant lines with the lowest DI scores were selected and bulked into a resistance pool for analysis. The resistant bulk and parental DNA samples were genotyped with polymorphic markers. Priority was placed on the polymorphic SSRs on chromosomes 7, 13, and 16 (LG M, F, and J) with coverage of a marker at every 10 cM because these LGs were linked to aphid resistance in other soybean accessions.

The PCR products were separated on 6% non-denaturing polyacrylamide gels with a DASG-400-50 electrophoresis unit (C.B.S. Scientific Co., Del Mar, Calif.) as described by Wang et al., (2003, herein incorporated by reference). The ethidium bromide stained gels were visualized and photographed under UV light. For polymorphic SSR markers, the PCR products of each line in the mapping population were scored as 'a' (the band of the resistant parent present), 'b' (the band of susceptible parent present) or 'h' (bands from both parents present).

Statistical and QTL analysis. The DI data from the field trial was analyzed by the analysis of variance (ANOVA) with the GLM procedure of SAS V9.1. The broad-sense heritability of DI was estimated according to the method described by Fehr (1987, herein incorporated by reference). The SSR genotyping data and the aphid resistance phenotyping data of $F_{4:5}$ RIL lines were analyzed to construct a linkage map with Join-Map 3.0 by using the Kosambi function and a LOD score of 3.0 (Van Ooijen and Voorrips, 2001, herein incorporated by reference). At each locus of potential aphid resistance, the segregation ratio of alleles was determined by $X^2$ goodness of fit to detect if the locus met the expected 7:2:7 ratio with a significance threshold of P=0.05. Composite interval mapping (CIM) was performed to detect aphid resistance loci by using QTL Cartographer V2. with a standard model Zmapqtl 6 (Wang et al., 2008, herein incorporated by reference). In order to control the genetic background, the forward and backward regression method was applied to select markers other than the interval being tested as cofactors (Zeng, 1994, herein incorporated by reference). A window size of 10 cM was chosen and the target markers interval distance was at 2 cM for CIM. The empirical LOD at 5% probability level was determined by a 1,000-permutation test (Churchill and Doerge, 1994, herein incorporated by reference). The linkage map and the aphid resistance loci were visualized by MapChart (Voorrips, 2002, herein incorporated by reference).

Resistance locus validation. A validation population of 162 $F_{3-4}$ lines (070016) was derived from the cross between PI 567585A and IA 2070 by single seed descent. IA 2070 is an aphid-susceptible soybean cultivar. In the summer, the validation population and its parents were evaluated for aphid resistance in a field trial similar to the mapping population with two replicates. Ninety four RILs were randomly selected as a subset population from the validation population. The genomic DNA of these 94 RILs was extracted by method described above. Polymorphic markers within the potential regions containing the aphid resistance locus were genotyped for the validation population. Linkage map construction and genetic mapping analysis were carried out in the same way as for the mapping population.

All publications and patents mentioned in the above specification are herein incorporated by reference. Applicants reserve the right to physically incorporate into this specification any and all materials and information from any such cited patents or publications.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a germplasm" or "a polypeptide" includes a plurality of such germplasms or polypeptides (for example, a solution of germplasm nucleic acids or polypeptides or a series of germplasm or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The following statements of the invention are intended to describe and summarize various embodiments of the invention according to the foregoing description in the specification.

Statements:

1. An aphid resistant germplasm (a) derived from soybean plant line E12902, whose seed was deposited under ATCC accession No: PTA-120715; (b) derived from soybean plant line PI 567537 chromosomal region 16 (Rag3b) region that is located between marker pair Sat_339 and Satt596; (c) derived from soybean plant cultivar PI 567585A chromosomal 16 region located between a marker pair Satt674 and Satt215; or (d) or a combination thereof 2. The aphid resistant germplasm of statement 1, wherein said aphid resistant germplasm is present in a plant that is not a wild type Glycine (G.) soja soybean plant line, a wild type soybean plant line PI 567537, a wild type soybean plant line PI 567585 A, a wild type soybean plant line PI 567598 B, a wild type soybean plant line PI 567543 C, a wild type soybean plant line PI 567541 B, or a wild type soybean plant line PI 567597 C.

3. The aphid resistant germplasm of statement 1 or 2, wherein said germplasm from E12902 comprises an aphid resistant Rag6 region on chromosome 8 located between a marker pair selected from the group consisting of Sat_382-Satt455; MSUSNP08-1(23293155_T_G)-Satt455; and Satt455-Satt209.

4. The aphid resistant germplasm of statement 1, 2 or 3, wherein said germplasm from E12902 comprises an aphid resistant Rag3c region on chromosome 16 located between a marker pair selected from the group consisting of Satt693-Sat_456; Satt693-Sat_370; Sat_370-Sat_456; MSUSNP16_10-Sat_370; MSUSNP16_10-Satt465; BARCSOYSSR_16_0383-Satt456; and BARC-SOYSSR_16_0383-Sat_370.

5. The aphid resistant germplasm of any of statements 1-4, wherein said germplasm from E12902 comprises a chromosomal 7 aphid resistant Rag1c region on located between a marker pair selected from the group consisting of Satt567-Sat_253; Satt567-Satt435; Satt540-Satt435; and Satt540-Satt435.

6. The aphid resistant germplasm of any of statements 1-5, wherein said germplasm from PI 567537 comprises a chromosomal 16 aphid resistant region located between a marker pair selected from the group consisting of Sat_339-Satt654; Sat_339-Sct_065; and Sct_065-Satt654.

7. The aphid resistant germplasm of any of statements 1-6, wherein said germplasm from PI 567585A, comprises a chromosomal 16 aphid resistant region located between a marker pair selected from the group consisting of Satt622-Satt215; Satt674-Sct_065; Satt674-Satt622; Satt674-Satt654; and Set_065-Satt622.

8. A soybean plant comprising germplasm (a) derived from soybean plant line E12902, whose seed was deposited under ATCC accession No: PTA-120715; (b) derived from soybean plant line PI 567537 chromosomal region 16 (Rag3b) region that is located between marker pair Sat_339 and Satt596; (c) derived from soybean plant cultivar PI 567585A chromosomal 16 region located between a marker pair Satt674 and Satt215; or (d) or a combination thereof; wherein said soybean plant is not a wild type Glycine (G.) soja soybean plant line, a wild type soybean PI 567537 plant, a wild type soybean PI 567585 A plant, a wild type soybean PI 567598 B plant, a wild type soybean PI 567543 C plant, a wild type soybean PI 567541 B plant, or a wild type soybean PI 567597 C plant.

9. A soybean seed comprising germplasm (a) derived from soybean plant line E12902, whose seed was deposited under ATCC accession No: PTA-120715; (b) derived from soybean plant line PI 567537 chromosomal region 16 (Rag3b) region that is located between marker pair Sat_339 and Satt596; (c) derived from soybean plant cultivar PI 567585A chromosomal 16 region located between a marker pair Satt674 and Satt215; or (d) or a combination thereof 10. A method for producing an aphid resistant soybean plant, comprising:
   a) providing aphid resistant germplasm from one or more of first soybean plants from accession PI 567585A, accession PI 567537, a germplasm of plant line E08934, or plant line E12902 whose seed was deposited under ATCC accession No. PTA-120715; and
   b) introducing said aphid resistant germplasm into a second soybean plant so as to produce an aphid resistant progeny soybean plant.
11. The method of statement 10, further comprising screening for aphid resistance to identify said aphid resistant progeny soybean plant.
12. The method of statement 10 or 11, further comprising screening for one or more molecular markers of said aphid resistant germplasm in said progeny soybean plant.
13. The method of any of statements 10-12, further comprising screening for a marker pair in said progeny soybean plant, wherein the marker pair is selected from the group consisting of Sat_339-Satt596; Satt674-Satt215; Sat_382-Satt455; MSUSNP08-1 (23293155_T_G)-Satt455; Satt455-Satt209; Satt693-Sat_456; Satt693-Sat_370; Sat_370-Sat_456; MSUSNP16_10-Sat_370; MSUSNP08-2 (40320904_A_G)-Satt209; MSUSNP16_10-Satt465; BARCSOYSSR_16_0383-Satt456; BARCSOYSSR_16_0383-Sat_370; Satt567-Sat_253; Satt567-Satt435; Satt540-Satt435; Satt540-Satt435; Sat_339-Satt654; Sat_339-Sct_065; Sct_065-Satt654; Satt622-Satt215; Satt674-Sct_065; Satt674-Satt622; Satt674-Satt654; and Set_065-Satt622.
14. The method of any of statements 10-13, further comprising one or more of a backcrossing, an outcrossing, or a self-crossing of the aphid resistant progeny soybean plant.
15. The method of any of statements 10-14, further comprising backcrossing, an outcrossing, or a self-crossing of the aphid resistant progeny soybean plant to produce aphid resistant soybean plants having homozygosity of said aphid resistant germplasm.
16. The method of any of statements 10-15, further comprising backcrossing said aphid resistant progeny soybean plant to a soybean plant of the same strain as the second soybean plant.
17. The method of any of statements 10-16, further comprising obtaining a soybean seed from the aphid resistant progeny soybean plant, or a progeny thereof.
18. The method of statement 17, wherein said soybean seed is germinated and grown into a progeny soybean plant.
19. The method of any of statements 10-18, wherein said second soybean plant is an aphid susceptible soybean plant.
20. The method of any of statements 10-19, wherein said second soybean plant is selected from the group consisting of accession PI567598B, accession PI567543C, accession PI567541B, accession PI567597C, accession PI200538, an elite soybean plant, line E06902 deposited under ATCC accession No: PTA-8794, line E00003, line IA 2070, Skylla, line E07051, E08929, E070020-19, E07906-2, and any progeny thereof.
21. The method of any of statements 10-20, wherein said second soybean plant has an agronomic trait selected from the group consisting of a desired oil content, protein content, seed protein content, seed fatty acid content, seed size, seed color, hilium color, seed coat thickness, seed sugar content, seed free amino acid content, seed germination rate, seed texture, seed fiber content, seed Vitamin E content, seed isoflavone content, seed phytate content, seed phytosterol content, seed isoflavone content, lecithin content, food-grade quality, hilium color, seed yield, plant type, plant height, lodging, shatter, herbicide resistance, disease resistance, insect resistance, nematode resistance, drought tolerance, drought resistance, water tolerance, water resistance, temperature tolerance, cold weather resistance, hot weather resistance, growth habit, maturity group, and field tolerance.
22. The method of any of statements 10-21, wherein said aphid resistant progeny soybean plant, or progeny thereof, has enhanced aphid resistance to an aphid isolate selected from the group consisting of biotype 1, biotype 2, biotype 3, biotype 4, or a combination thereof
23. The method of any of statements 10-22, wherein said aphid resistant progeny soybean plant, or progeny thereof, has an average aphid damage index of 0-9%, or is used for breeding a soybean plant line having an average aphid damage index of 0-9%.
24. The method of any of statements 10-23, wherein said aphid resistant progeny soybean plant, or progeny thereof, has a resistance score of 0.5 to 2.0, or is used for breeding a soybean plant line having a resistance score of 0.5 to 2.0.
25. The method of any of statements 10-24, further comprising: crossing said aphid resistant soybean progeny plant with a plant selected from the group consisting of accession PI567598B, accession PI567543C, accession PI567541B, accession PI567597C, line E06902 deposited under ATCC accession No: PTA-8794, line E00003, line IA 2070, Skylla, line E07051, E070020-19, E07906-2, accession PI 567585A, accession PI 567537, a progeny plant of line E08934, line E12902 whose seed was deposited under ATCC accession No. PTA-120715, and any progeny thereof so as to produce a plant having enhanced soybean aphid resistance.
26. The method of any of statements 10-25, wherein said aphid resistant progeny soybean plant is breed to generate a soybean plant line having enhanced soybean aphid resistance.
27. A plant line derived from the method of any of statements 10-26.
28. A method of identifying a marker for aphid resistance, comprising:
   a) providing,
   i) a first soybean plant germplasm, wherein said germplasm comprises nucleic acid sequences isolated from a soybean plant having a phenotype of aphid resistance selected from the group consisting of soybean plant line E12902 whose progeny seed was deposited under ATCC accession No. PTA-120715, accession PI 567585A, accession PI 567537, and progeny thereof, and
   ii) a second soybean plant germplasm, wherein said germplasm comprises nucleic acid sequences isolated from a soybean plant having less aphid resistance than the first soybean plant, and
   b) identifying a molecular marker on said first soybean plant germplasm that is not on said second soybean plant germplasm.
29. The method of statement 28, wherein said molecular marker identifies an allele located at the Rag3 loci selected from the group consisting of Rag3c, Rag3b, and Rag3-1.
30. A *Glycine max* soybean cultivar comprising aphid resistant germplasm derived from soybean plant line E12902, whose seed was deposited under ATCC accession No. PTA-120715.

31. An aphid resistant germplasm, derived from soybean plant line E12902, whose seed was deposited under ATCC accession No: PTA-120715, wherein said germplasm comprises an aphid resistant Rag6 region on chromosome 8 located between a marker pair selected from the group consisting of Sat_382;Satt455 and Satt455;Satt209.

32. An aphid resistant germplasm, derived from soybean plant line E12902, whose seed was deposited under ATCC accession No: PTA-120715, wherein said germplasm comprises an aphid resistant region on chromosome 16 located between a marker pair selected from the group consisting of Satt693;Sat_456, Satt693;Sat_370, Sat_370; Sat_456, MSUSNP16_10;Sat_370, MSUSNP16_10; Satt465, BARCSOYSSR_16_0383;Satt456, and BARCSOYSSR_16_0383;Sat_370.

34. An aphid resistant germplasm, derived from soybean plant cultivar PI 567537, wherein said germplasm comprises an aphid resistant region on chromosome 16 located between a marker pair selected from the group consisting of Sat_339;Satt654, Sat_339;Sct_065 and Set_065;Satt654.

35. An aphid resistant germplasm, derived from soybean plant cultivar PI 567585A, wherein said germplasm comprises an aphid resistant region on chromosome 16 located between a marker pair selected from the group consisting of Satt622;Satt215 and Satt674;Sct_065, Satt674;Satt622 and Set_065;Satt622.

36. A method for producing an aphid resistant soybean plant, comprising:
    a) providing aphid resistant germplasm that comprises germplasm from one or more of soybean plants accession PI 567585A, accession PI 567537, and a progeny plant of line E12902 whose seed was deposited under ATCC accession No. PTA-120715; and
    b) introducing said aphid resistant germplasm into a soybean plant so as to produce an aphid resistant soybean plant.

37. The method of Statement 36, wherein said aphid resistant soybean plant has enhanced aphid resistance.

38. The method of Statement 36 or 37, wherein said plant having enhanced soybean aphid resistance is used for breeding a soybean plant line having an average aphid damage index of 0-9%.

39. The method of any of Statements 36-38, wherein said plant having enhanced soybean aphid resistance is used for breeding a soybean plant line having a resistance score of 0.5 to 2.0.

40. The method of any of Statements 36-39, wherein enhanced soybean aphid resistance is resistance to an aphid isolate.

41. The method of any of Statements 36-40, further comprising:
    providing, aphid resistant germplasm that comprises germplasm from one or more of soybean plants selected from the group consisting of accession PI567598B, accession PI567543C, accession PI567541B, accession PI567597C, line E06902 deposited under ATCC accession No: PTA-8794, and progeny thereof, and step c) introducing said aphid resistant germplasm into said aphid resistant soybean plant so as to produce a plant having enhanced soybean aphid resistance.

42. A method for producing an aphid resistant soybean plant, comprising:
    a) providing,
    i) an aphid resistant soybean plant, comprising aphid resistant germplasm derived from one or more of soybean plants accession PI567585A, accession PI 567537, and a progeny plant of line E12902 whose seed was deposited under ATCC accession No. PTA-120715, and
    ii) an aphid susceptible soybean plant, and
    b) crossing said aphid resistant soybean plant with said aphid susceptible soybean plant so as to produce a F1 progeny soybean plant, and c) screening said F1 progeny soybean plants for selecting an F1 progeny aphid resistant soybean plant.

43. The method of Statement 42, wherein said method further comprises step (d) backcrossing said aphid resistant F1 progeny soybean plant to said susceptible soybean plant so as to produce F2 progeny aphid resistant soybean plants.

44. The method of Statement 42 or 43, wherein said method further comprises step (e) crossing said F2 progeny aphid resistant soybean plants so as to produce aphid resistant soybean plants having homozygosity of said aphid resistant germplasm.

45. A method of breeding, comprising,
    a) providing,
    i) a first soybean plant comprising aphid resistant germplasm, wherein said germplasm derives from soybean plant line E12902 whose seed was deposited under ATCC accession No. PTA-120715,
    ii) a second soybean plant comprising aphid resistant germplasm, wherein said germplasm derives from a soybean plant selected from the group consisting of accession PI567541B, line E06902 deposited under ATCC accession No: PTA-8794, line E00003, line IA 2070, Skylla, and progeny thereof, and
    b) crossing said first soybean plant to said second soybean plant for making a soybean plant having enhanced aphid resistance.

46. The method of Statement 45, wherein said enhanced aphid resistance is selected from the group consisting of a resistance score of 0.5-2.0, an average aphid damage index of 0-9% and resistance to an aphid isolate.

47. The method of Statement 45 or 46, wherein said crossing further comprises one or more of a backcrossing, an outcrossing, and a self-crossing.

48. The method of any of Statements 45-47, wherein said crossing creates a soybean seed.

49. The method of any of Statements 45-48, wherein said seed is germinated and grown into progeny soybean plants.

50. The method of Statement 48, wherein said progeny soybean plants have enhanced aphid resistance.

51. The soybean seed of Statement 49.

52. A method of breeding, comprising,
    a) providing,
    i) a first soybean plant comprising aphid resistant germplasm, wherein said germplasm derived from soybean plant line E12902 whose progeny seed was deposited under ATCC accession No. PTA-120715,
    ii) a second soybean plant comprising aphid resistant germplasm, wherein said germplasm derives from a soybean plant selected from the group consisting of accession PI567598B, accession PI567543C, accession PI567541B, accession PI567597C, line E06902 deposited under ATCC accession No: PTA-8794, line E00003, line IA 2070, Skylla, and progeny thereof, and
    b) crossing said first soybean plant to said second soybean plant for making a soybean plant having enhanced aphid resistance.

53. A method of breeding, comprising,
a) providing,
   i) a first soybean plant comprising aphid resistant germplasm, wherein said germplasm derived from soybean plant line E12902 whose progeny seed was deposited under ATCC accession No. PTA-120715,
   ii) a second soybean plant comprising aphid resistant germplasm, wherein said germplasm derives from soybean plant line E08929, and crossing said first soybean plant to said second soybean plant for making a progeny soybean plant having aphid resistance.
54. The method of Statement 52 or 53, wherein said aphid resistance is decreased aphid damage on progeny plants relative to line E08929 soybean plants.
55. The method of any of Statement 52-54, further providing, a molecular marker selected from the group consisting of Satt540, Satt209, and BARCSOYSSR_16_0371 for identifying aphid resistance germplasm, and step c) using said molecular marker for identifying said aphid resistance in said progeny aphid resistant soybean plant.
56. The method of any of Statements 52-55, wherein said progeny aphid resistance soybean plant has at least a Rag6 region.
57. The method of any of Statements 52-56, wherein said aphid resistant soybean plant is used for breeding a soybean plant line having enhanced soybean aphid resistance.
58. A method of breeding, comprising,
a) providing,
   i) a first soybean plant comprising aphid resistant germplasm is derived from soybean plant line E12902, whose seed was deposited under ATCC accession No: PTA-120715;
   ii) second soybean plant; and
   iii) a pair of molecular markers, and crossing said first soybean plant with said second soybean plant for providing a progeny soybean plant;
b) using said set of molecular marker for identifying germplasm associated with enhanced aphid resistance in said progeny soybean plant.
59. The method of Statement 58, wherein said aphid resistant germplasm is located between said pair of molecular markers.
60. The method of Statement 58 or 59, wherein said pair is a marker pair selected from the group consisting of Satt540;Satt435, Sat_382; Satt455, SNP MSUSNP08-2 (40320904_A_G);Satt209, MSUSNP08-1 (23293155 T G);Satt455, Satt693;Sat_370 and Satt693;Satt456.
61. The method of any of Statements 58-60, wherein said second soybean plant is selected from the group consisting of an elite soybean plant, line E00003, line IA 2070, Skylla, accession PI567598B, accession PI567543C, accession PI567541B, accession PI567597C, PI 567537, PI 567585A, line E06902 deposited under ATCC accession No: PTA-8794, PI 200538, and progeny thereof.
62. The method of any of Statements 58-61, wherein said progeny soybean plant has enhanced aphid resistance.
63. The method of any of Statements 58-62, wherein said progeny soybean plant is used for breeding a plant line having enhanced aphid resistance.
64. The plant line of Statement 63.
65. A method of identifying a marker for aphid resistance, comprising,
a) providing,
   i) a first soybean plant germplasm, wherein said germplasm comprises nucleic acid sequences isolated from a soybean plant having a phenotype of aphid resistance selected from the group consisting of soybean plant line E12902 whose progeny seed was deposited under ATCC accession No. PTA-120715, accession PI 567585A, accession PI 567537, and progeny thereof, and
   ii) a second soybean plant germplasm, wherein said germplasm comprises nucleic acid sequences isolated from a soybean plant having less aphid resistance than the first soybean plant, and identifying a molecular marker on said first soybean plant germplasm that is not on said second soybean plant germplasm.
66. The method of Statement 65, wherein said molecular marker identifies an allele located at the Rag3 loci selected from the group consisting of Rag3c, Rag3b, and Rag3-1.

What is claimed:

1. A soybean plant grown from seed with ATCC accession No: PTA-12075.

2. A soybean seed with ATCC accession No: PTA-12075.

* * * * *

UNITED STATES PATENT AND TRADEMARK OFFICE
CERTIFICATE OF CORRECTION

PATENT NO. : 10,253,329 B2
APPLICATION NO. : 14/099469
DATED : April 9, 2019
INVENTOR(S) : Wang et al.

Page 1 of 1

It is certified that error appears in the above-identified patent and that said Letters Patent is hereby corrected as shown below:

In Column 125, Line 2, in Claim 1, delete "PTA-12075." and insert --PTA-120715.-- therefor In Column 126, Line 1, in Claim 2, delete "PTA-12075." and insert --PTA-120715.-- therefor Signed and Sealed this
Twenty-ninth Day of December, 2020

Andrei Iancu
*Director of the United States Patent and Trademark Office*